(12) United States Patent
Liu et al.

(10) Patent No.: US 10,487,088 B2
(45) Date of Patent: Nov. 26, 2019

(54) TRICYCLIC COMPOUND SERVING AS IMMUNOMODULATOR

(71) Applicants: Chia Tai Tianqing Pharmaceutical Group Co., Ltd., Jiangsu (CN); Medshine Discovery Inc., Nanjing (CN)

(72) Inventors: Shilan Liu, Nanjing (CN); Dahai Wang, Nanjing (CN); Guibai Liang, Nanjing (CN); Guoping Hu, Nanjing (CN); Jian Li, Nanjing (CN); Shuhui Chen, Nanjing (CN)

(73) Assignees: Chia Tai Tianqing Pharmaceutical Group Co., Ltd., Beijing (CN); Medshine Discovery Inc., Nanjing (CN)

(*) Notice: Subject to any disclaimer, the term of this patent is extended or adjusted under 35 U.S.C. 154(b) by 0 days.

(21) Appl. No.: 15/999,075

(22) PCT Filed: Feb. 20, 2017

(86) PCT No.: PCT/CN2017/074141
§ 371 (c)(1),
(2) Date: Aug. 17, 2018

(87) PCT Pub. No.: WO2017/140274
PCT Pub. Date: Aug. 24, 2017

(65) Prior Publication Data
US 2019/0062338 A1 Feb. 28, 2019

(30) Foreign Application Priority Data

| Feb. 19, 2016 | (CN) | 2016 1 0094757 |
| Apr. 20, 2016 | (CN) | 2016 1 0247693 |
| May 16, 2016 | (CN) | 2016 1 0324408 |
| Sep. 13, 2016 | (CN) | 2016 1 0821994 |

(51) Int. Cl.
| *C07D 495/14* | (2006.01) |
| *C07D 487/14* | (2006.01) |
| *C07D 519/00* | (2006.01) |
| *A61K 31/5377* | (2006.01) |
| *A61K 31/407* | (2006.01) |

(52) U.S. Cl.
CPC .......... *C07D 487/14* (2013.01); *A61K 31/407* (2013.01); *A61K 31/5377* (2013.01); *C07D 495/14* (2013.01); *C07D 519/00* (2013.01); *Y02A 50/465* (2018.01)

(58) Field of Classification Search
CPC .. C07D 487/14; C07D 495/14; C07D 519/00; A61K 31/5377; A61K 31/407
See application file for complete search history.

(56) References Cited

FOREIGN PATENT DOCUMENTS

| CN | 103547579 A | 1/2014 |
| CN | 105884828 A | 8/2016 |
| WO | WO 2012/142237 A1 | 10/2012 |
| WO | WO 2014/159248 A1 | 10/2014 |
| WO | WO 2016/059412 A1 | 4/2016 |

OTHER PUBLICATIONS

Meininger, David et al., "Purification and kinetic characterization of human indoleamine 2,3-dioxygenases 1 and 2 (IDO1 and IDO2) and discovery of selective IDO1 inhibitors" Biochimica et Biophysica Acta, Jul. 2011, pp. 1947-1954, vol. 23, No. 7.
Streith, Jacques et al., "The Synthesis of Imidazol Sugars Which Mimic Cyclic Carboxonium Ions Formed During the Glycosidase-Catalysed Hydrolysis of Oligo- and Polysaccharides" European Journal of Organic Chemistry, Jan. 1999, pp. 893-898.
Supplementary European Search Report for EP 17752706 dated Nov. 27, 2018.
International Search Report for PCT/CN2017/074141 dated May 17, 2017.

*Primary Examiner* — Rebecca L Anderson
(74) *Attorney, Agent, or Firm* — Knobbe Martens Olson & Bear LLP

(57) ABSTRACT

Provided are compounds of formula I and formula II or pharmaceutically acceptable salts of the compounds and pharmaceutical compositions thereof. The compounds of formula I and formula II or the pharmaceutically acceptable salts of the compounds provide indole 2,3-dioxygenase (IDO) inhibitory activity and are capable of treating IDO-mediated immunosuppressive diseases, such as infectious diseases or cancer.

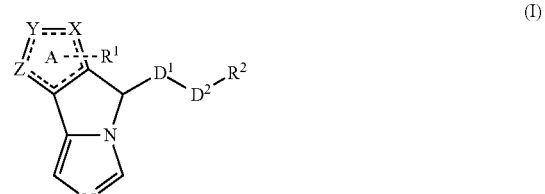

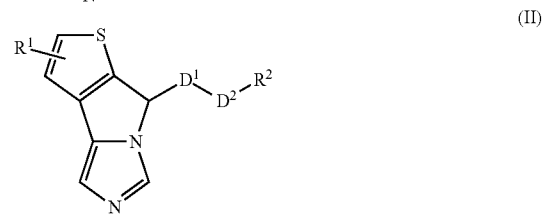

19 Claims, 1 Drawing Sheet

TRICYCLIC COMPOUND SERVING AS IMMUNOMODULATOR

CROSS REFERENCE TO RELATED APPLICATIONS

This application is a U.S. National Phase Application of PCT International Application Number PCT/CN2017/074141, filed on Feb. 20, 2017, designating the United States of America and published in the Chinese language, which is an International Application of and claims the benefit of priority to Chinese Patent Application No. 201610094757.0, filed on Feb. 19, 2016, Chinese Patent Application No. 201610247693.3, filed on Apr. 20, 2016, Chinese Patent Application No. 201610324408.3, filed on May 16, 2016 and Chinese Patent Application No. 201610821994.2, filed on Sep. 13, 2016. The disclosures of the above-referenced applications are hereby expressly incorporated by reference in their entireties.

FIELD OF THE INVENTION

The present application belongs to the field of medicine, and relates in particular to a tricyclic compound or a pharmaceutically acceptable salt thereof as an immunomodulator.

BACKGROUND OF THE INVENTION

Tryptophan (Trp) is an essential amino acid required for the biosynthesis of proteins, nicotinic acid and neurotransmitter 5-hydroxytryptamine. Indoleamine 2,3-dioxygenase (also known as INDO or IDO) catalyzes the first and rate limiting step in the degradation of L-tryptophan to N-formylkynurenine. In human cells, IFN-γ stimulation induces activation of IDO, which leads to a depletion of tryptophan, thereby arresting the growth of tryptophan-dependent intracellular pathogens such as *Toxoplasma gondii* and *Chlamydia trachomatis*. IDO activity also has an antiproliferative effect on many tumor cells, and IDO induction has been observed in vivo during rejection of aliogeneic tumors, indicating a possible role for this enzyme in the tumor rejection process.

Small molecule inhibitors of IDO can be developed to treat or prevent IDO-related diseases. For example, PCT Publication WO 99/29310 reports methods of altering T cell-mediated immunity comprising altering local extracellular concentrations of tryptophan and tryptophan metabolites, using an inhibitors of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, are methods of making antigen-presenting cells for enhancing or reducing T cell tolerance (Munn, 2003). Compounds having indoleamine-2,3-dioxygenase (IDO) inhibitory activity are further reported in WO 2004/094409, WO 2009/073620, WO 2009/132238, WO 2011/056652 and WO 2012/142237. In particular, compounds in WO 2012/142237 comprise a series of tricyclic imidazoisoindoles with potent IDO inhibitory activity, including NLG-919 having the following formula:

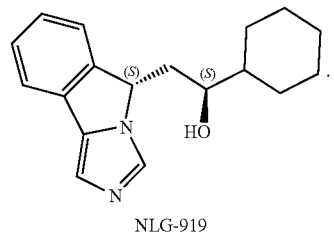

NLG-919

SUMMARY OF THE INVENTION

In one aspect, the present application provides a compound of formula I, or a pharmaceutically acceptable salt thereof,

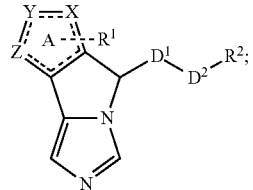

wherein, ring A is a heteroaromatic ring, X, Y and Z are each independently selected from C, O, N, S atom, and X, Y and Z are not C atom at same time, and said ring A may be optionally substituted with 1 or 2 $R^1$ groups;

$D^1$ is $(CR^{A1}R^{B1})_p$;

$D^2$ is $(CR^{A2}R^{B2})_q$, $NR^3$, O, S, SO, $SO_2$, C(O), OC(O), C(O)O, $NR^3C(O)$, $C(O)NR^3$, $NR^3SO_2$, $SO_2NR^3$, $NR^3C(O)NR^4$ or $NR^3SO_2NR^4$;

$R^2$ is selected from H, OH, $NR^3R^4$, halogen, halogenated $C_{1-6}$ alkyl, hydroxy $C_{1-6}$ alkyl, $C_{1-6}$ alkyl, $C_{1-6}$ heteroalkyl, or 3- to 12-membered saturated, partially saturated or aromatic mono-, bi-, or tri-cyclic ring, said rings may optionally contain 1, 2 or 3 heteroatoms selected from O, N, S, and said rings may be optionally substituted with 1, 2 or 3 R groups;

Each $R^1$ may be independently selected from OH, $NR^3R^4$, halogen, CN, COOH, halogenated $C_{1-6}$ alkyl, $C_{1-6}$ alkyl, $C_{2-6}$ alkenyl, $C_{2-6}$ alkynyl, $C_{1-6}$ heteroalkyl, $C_{3-6}$ cycloalkyl, halogenated $C_{3-6}$ cycloalkyl, phenyl, halogenated phenyl, 5- to 6-membered heteroaryl, or halogenated 5- to 6-membered heteroaryl;

Each R is independently selected from OH, $NR^3R^4$, halogen, oxo, CN, COOH, $C_{1-4}$ alkyl, $C_{2-4}$ alkenyl, $C_{2-4}$ alkynyl, or 6- to 12-membered aryl; said $C_{1-4}$ alkyl, $C_{2-4}$ alkenyl, $C_{2-4}$ alkynyl, or 6- to 12-membered aryl may be optionally substituted with 1 or 2 OH, halogen, $NH_2$, CN, or COOH groups;

$R^3$ and $R^4$ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynl, $C_{1-6}$ heteroalkyl, halogenated $C_{1-6}$ heteroalkyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl;

$R^{A1}$, $R^{B1}$, $R^{A2}$ and $R^{12}$ are each independently selected from H, OH, $NH_2$, halogen, halogenated $C_{1-3}$ alkyl, or $C_{1-4}$ alkyl;

p is 0, 1 or 2;

q is 0 or 1.

In an embodiment of the compound of formula I in the present application, ring A is a thiophene ring, and said thiophene ring may be optionally substituted with 1 or 2 $R^1$.

In an embodiment of the compound of formula I of the present application, ring A is a heteroaromatic ring, which may be optionally substituted with 1 or 2 $R^1$ groups; wherein, X and Y are selected from C, and Z is selected from S; or
X and Z are selected from C, and Y is selected from S; or
Y and Z are selected from C, and X is selected from S; or
X and Y are selected from C, and Z is selected from O; or
X and Z are selected from C, and Y is selected from O; or
Y and Z are selected from C, and X is selected from O; or
X and Y are selected from C, and Z is selected from N; or
X and Z are selected from C, and Y is selected from N; or
Y and Z are selected from C, and X is selected from N; or
X and Y are selected from N, and Z is selected from C; or
X and Z are selected from N, and Y is selected from C; or
Y and Z are selected from N, and X is selected from C; or
all of X, Y and Z are selected from N; or
X is selected from C, Y is selected from N, and Z is selected from O; or
X is selected from C, Y is selected from O, and Z is selected from N; or
X is selected from N, Y is selected from C, and Z is selected from O; or
X is selected from N, Y is selected from O, and Z is selected from C; or
X is selected from O, Y is selected from N, and Z is selected from C; or
X is selected from O, Y is selected from C, and Z is selected from N; or
X is selected from C, Y is selected from N, and Z is selected from S; or
X is selected from C, Y is selected from S, and Z is selected from N; or
X is selected from N, Y is selected from C, and Z is selected from S; or
X is selected from N, Y is selected from S, and Z is selected from C; or
X is selected from S, Y is selected from N, and Z is selected from C; or
X is selected from S, Y is selected from C, and Z is selected from N.

In an embodiment of the compound of formula I in the present application, ring A is a heteroaromatic ring, which may be optionally substituted with 1 or 2 $R^1$ groups; wherein, X and Y are selected from C, and Z is selected from S; or
X and Z are selected from C, and Y is selected from S; or
Y and Z are selected from C, and X is selected from S; or
X and Y are selected from N, and Z is selected from C.

In an embodiment of the compound of formula I in the present application, $D^1$ is $(CR^{A1}R^{B1})_P$, wherein P is 0 or 1.

In an embodiment of the compound of formula I in the present application, $D^1$ is $(CR^{A1}R^{B1})$.

In an embodiment of the compound of formula I in the present application, $D^1$ is $C(CH_3)_2$.

In an embodiment of the compound of formula I in the present application, $D^1$ is a single bond.

In an embodiment of the compound of formula I in the present application, $D^1$ is $(CHR^{A1})$.

In an embodiment of the compound of formula I in the present application, $D^1$ is $CH_2$.

In an embodiment of the compound of formula I in the present application, $D^2$ is a single bond, $(CR^{A2}R^{B2})$, $NR^3$, O, S, SO, $SO_2$, C(O), OC(O), C(O)O, $NR^3C(O)$, $C(O)NR^3$, $NR^3SO_2$, $SO_2NR^3$, $NR^3C(O)NR^4$ or $NR^3SO_2NR^4$.

In an embodiment of the compound of formula I in the present application, $D^2$ is a single bond, $(CR^{A2}R^{B2})$, $NR^3$, O, S, SO, $SO_2$, or C(O).

In an embodiment of the compound of formula I in the present application, $D^2$ is a single bond.

In an embodiment of the compound of formula I in the present application, $D^2$ is O.

In an embodiment of the compound of formula I in the present application, $D^2$ is —(CHR$^{A2}$)—.

In an embodiment of the compound of formula I in the present application, $D^2$ is $CH_2$, CH(OH) or $CH(CH_3)$.

In an embodiment of the compound of formula I in the present application, -$D^1$-$D^2$- is a single bond, —(CR$^{A1}$R$^{B1}$)—, —(CR$^{A1}$R$^{B1}$)—(CR$^{A2}$R$^{B2}$)— or —(CR$^{A1}$R$^{B1}$)—O—.

In an embodiment of the compound of formula I in the present application, -$D^1$-$D^2$- is a single bond, —(CHR$^{A1}$)—, —(CR$^{A1}$R$^{B1}$)(CHR$^{A2}$)—, —(CHR$^{A1}$)—(CHR$^{A2}$)— or —(CHR$^{A1}$)—O—.

In an embodiment of the compound of formula I in the present application, -$D^1$-$D^2$- is a single bond, —CH$_2$—, —CH$_2$CH$_2$—, —CH$_2$CH(OH)—, —C(CH$_3$)$_2$—CH(OH)—, —CH$_2$CH(CH$_3$)— or —CH$_2$O—.

In an embodiment of the compound of formula I in the present application, -$D^1$-$D^2$- is a single bond, —CH$_2$—, —CH$_2$CH$_2$—, —CH$_2$CH(OH)—, —CH$_2$CH(CH$_3$)—, or —CH$_2$O—.

In an embodiment of the compound of formula I in the present application, $R^2$ is selected from H, OH, $NR^3R^4$, halogen, halogenated $C_{1-6}$ alkyl, hydroxy $C_{1-6}$ alkyl, $C_{1-6}$ alkyl, or 3- to 12-membered saturated, partially saturated, or aromatic mono-, bi-, or tri-cyclic ring, said rings may optionally contain 1, 2 or 3 heteroatoms selected from O, N or S, and said rings may be optionally substituted with 1, 2 or 3 R groups.

In an embodiment of the compound of formula I in the present application, $R^2$ is selected from H; OH; methyl; ethyl; propyl; isopropyl; butyl; isobutyl; sec-butyl; tert-butyl; n-pentyl; isopentyl; neopentyl; adamantyl; cyclopropyl; cyclobutyl; cyclopentyl; cyclohexyl; cycloheptyl; cyclooctyl; or

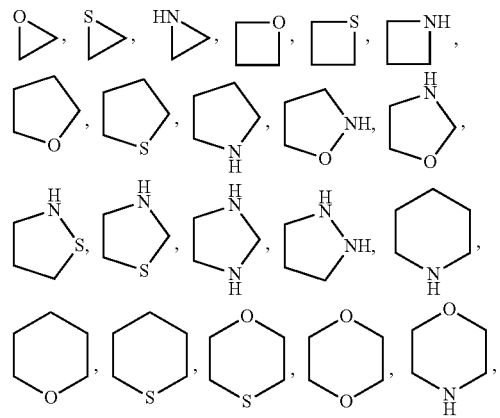

-continued

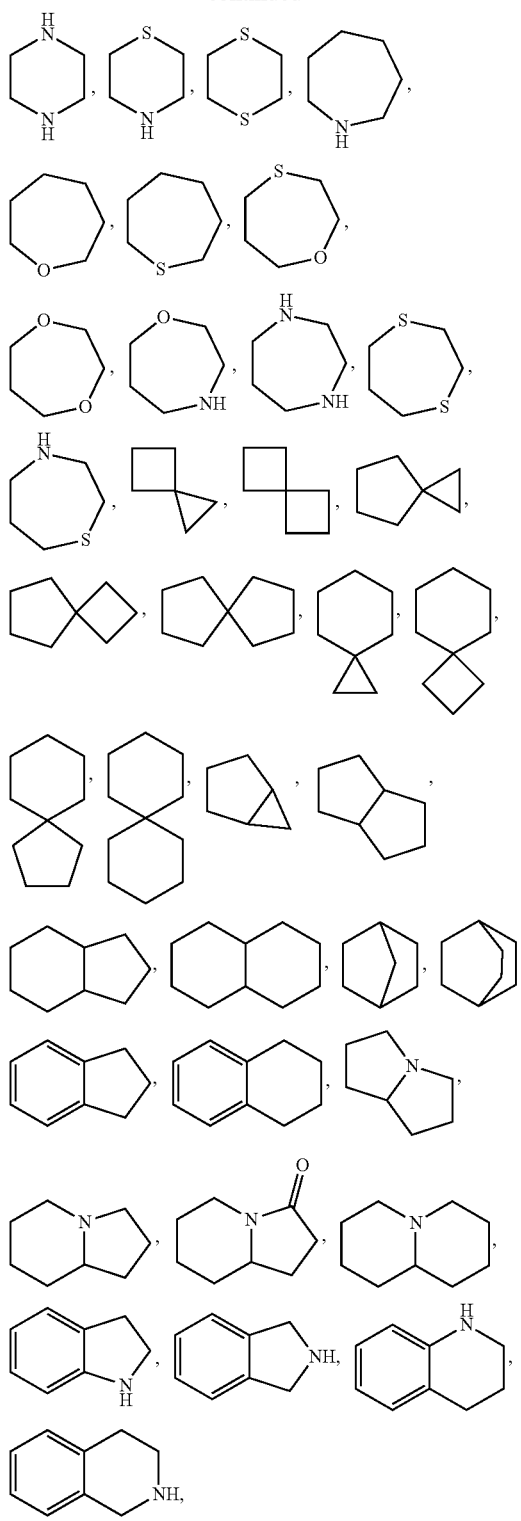

with a loss of one hydrogen atom at any position, and said rings may be optionally substituted with 1, 2 or 3 R groups.

In an embodiment of the compound of formula I in the present application, R² is selected from OH, methyl, isopropyl, tert-butyl, cyclobutyl, cyclopentyl, cyclohexyl, cycloheptyl,

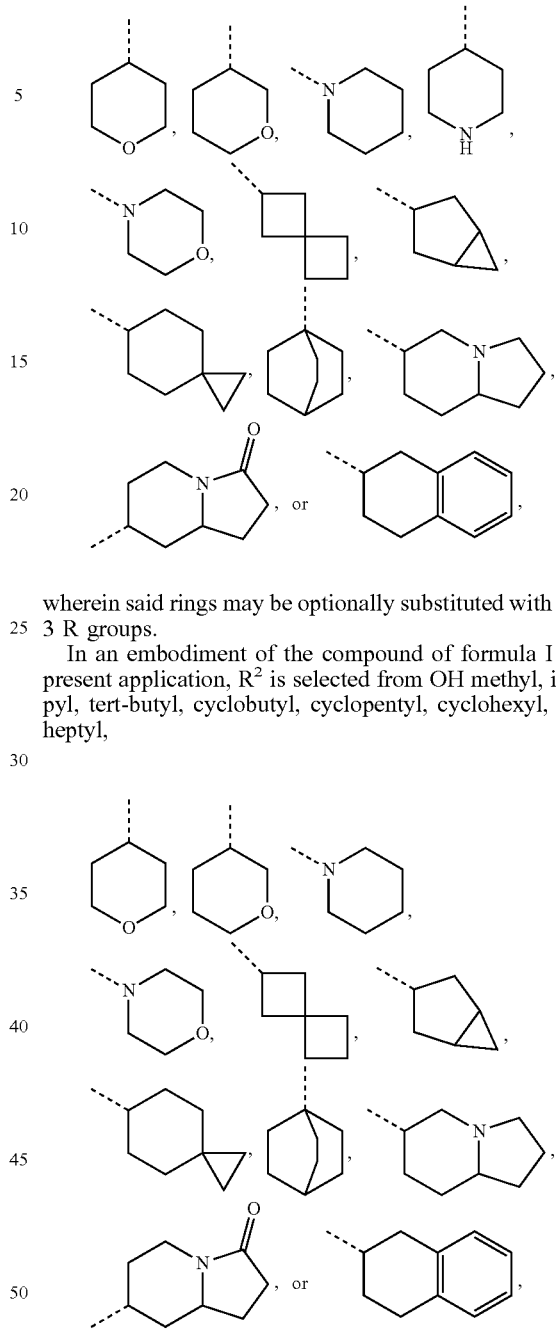

wherein said rings may be optionally substituted with 1, 2 or 3 R groups.

In an embodiment of the compound of formula I in the present application, R² is selected from OH methyl, isopropyl, tert-butyl, cyclobutyl, cyclopentyl, cyclohexyl, cycloheptyl, and said rings may be optionally substituted with 1, 2 or 3 R groups.

In an embodiment of the compound of formula I in the present application, R¹ may be independently selected from OH, NR³R⁴, halogen, halogenated $C_{1-6}$ alkyl, $C_{1-6}$ alkyl, $C_{2-6}$ alkenyl, $C_{2-6}$ alkynyl, $C_{3-6}$ cycloalkyl, halogenated $C_{3-6}$ cycloalkyl, phenyl, halogenated phenyl, 5- to 6-membered heteroaryl, or halogenated 5- to 6-membered heteroaryl.

In an embodiment of the compound of formula I in the present application, R¹ may be independently selected from halogen, halogenated $C_{1-6}$ alkyl, $C_{1-6}$ alkyl, $C_{3-6}$ cycloalkyl, halogenated $C_{3-6}$ cycloalkyl, phenyl or halogenated phenyl.

In an embodiment of the compound of formula I in the present application, R¹ may be independently selected from halogen, $C_{1-3}$ alkyl, or halogenated $C_{1-3}$ alkyl.

In an embodiment of the compound of formula I in the present application, $R^1$ may be independently selected from F, methyl or fluoro $C_{1-3}$ alkyl.

In an embodiment of the compound of formula I in the present application, $R^1$ may be independently selected from F, methyl or trifluoromethyl.

In an embodiment of the compound of formula I in the present application, $R^1$ may be independently selected from F or trifluoromethyl.

In an embodiment of the compound of formula I in the present application, R may be independently selected from OH, $NR^3R^4$, halogen, oxo, CN, COOH, $C_{1-4}$ alkyl, $C_{2-4}$ alkenyl, or $C_{2-4}$ alkynyl; and said $C_{1-4}$ alkyl, $C_{2-4}$ alkenyl or $C_{2-4}$ alkynyl may be optionally substituted with 1 or 2 OH, halogen, $NH_2$, CN or COOH groups.

In an embodiment of the compound of formula I in the present application, R may be independently selected from OH, $NR^3R^4$, halogen, oxo, CN, $C_{1-4}$ alkyl, $C_{2-4}$ alkenyl, or $C_{2-4}$ alkynyl; and said $C_{1-4}$ alkyl, $C_{2-4}$ alkenyl, or $C_{2-4}$ alkynyl may be optionally substituted with 1 or 2 OH, halogen, $NH_2$ or CN groups.

In an embodiment of the compound of formula I in the present application, R may be independently selected from OH, fluorine, chlorine, bromine, iodine, oxo, COOH, methyl, ethyl, propyl, isopropyl, butyl, isobutyl, sec-butyl, tert-butyl, phenyl or quinolinyl, wherein methyl, ethyl, propyl, isopropyl, butyl, isobutyl, sec-butyl, tert-butyl, phenyl or quinolinyl may be optionally substituted with OH.

In an embodiment of the compound of formula I in the present application, R may be independently selected from OH, fluorine, COOH, methyl, phenyl or

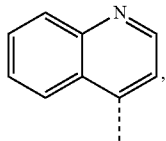

wherein methyl, phenyl or

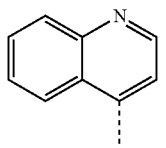

may be optionally substituted with OH.

In an embodiment of the compound of formula I in the present application, R may be independently selected from OH, fluorine, methyl, wherein methyl may be optionally substituted with OH.

In an embodiment of the compound of formula I in the present application, $R^3$ and $R^4$ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl.

In an embodiment of the compound of formula I in the present application, $R^3$ and $R^4$ are each independently selected from H, $C_{1-6}$ alkyl, $C_{2-6}$ alkenyl, $C_{2-6}$ alkynyl, $C_{3-6}$ cycloalkyl, phenyl or 5- to 6-membered heteroaryl.

In an embodiment of the compound of formula I in the present application, $R^3$ and $R^4$ are each independently selected from H, $C_{1-6}$ alkyl, $C_{3-6}$ cycloalkyl, or phenyl.

In an embodiment of the compound of formula I in the present application, $R^{A1}$, $R^{B1}$, $R^{A2}$ and $R^{B2}$ are each independently selected from H, OH, $NH_2$, halogen, or $C_{1-4}$ alkyl.

In an embodiment of the compound of formula I in the present application, $R^{A1}$ and $R^{B1}$ are each independently selected from H, OH, or $C_{1-4}$ alkyl.

In an embodiment of the compound of formula I in the present application, $R^{A1}$ and $R^{B1}$ are each independently selected from H or $C_{1-4}$ alkyl.

In an embodiment of the compound of formula I in the present application, $R^{A2}$ and $R^{B2}$ are each independently selected from H, OH, $NH_2$ or $C_{1-4}$ alkyl.

In an embodiment of the compound of formula I in the present application, $R^{A2}$ and $R^{B2}$ are each independently selected from H, OH, or $C_{1-4}$ alkyl.

In another aspect, the present application provides a compound of formula I-1, or a pharmaceutically acceptable salt thereof,

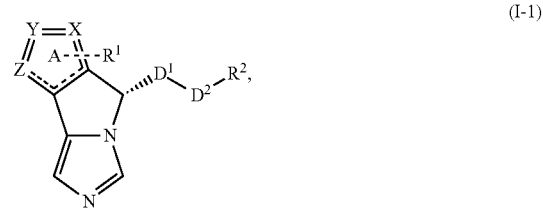

wherein the substituents are as defined in formula I.

In further another aspect, the present application provides a compound of formula I-2, or a pharmaceutically acceptable salt thereof,

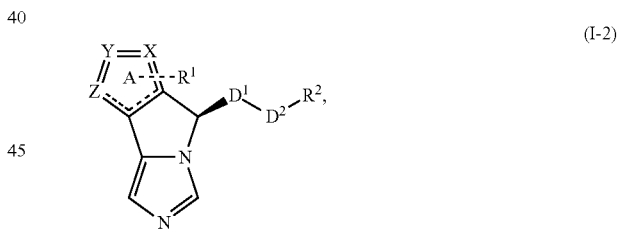

wherein the substituents are as defined in formula I.

In yet another aspect, the present application provides a compound of formula II, or a pharmaceutically acceptable salt thereof,

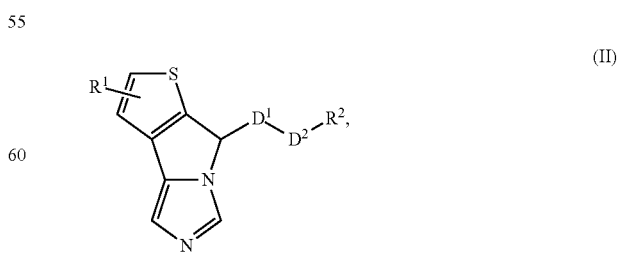

wherein, the thiophene ring may be optionally substituted with 1 or 2 $R^1$ groups; $D^1$ is $(CR^{A1}R^{B1})_p$;

D² is $(CR^{A2}R^{B2})_q$, NR³, O, S, SO, SO₂, C(O), OC(O), C(O)O, NR³C(O), C(O)NR³, NR³SO₂, SO₂NR³, NR³C(O)NR⁴ or NR³SO₂NR⁴;

R² is selected from H, OH, NR³R⁴, halogen, halogenated $C_{1-6}$ alkyl, hydroxy $C_{1-6}$ alkyl, $C_{1-6}$ alkyl, $C_{1-6}$ heteroalkyl, or 3 to 12 membered saturated, partially saturated or aromatic mono-, bi-, or tri-cyclic ring groups, which may optionally contain 1, 2 or 3 heteroatoms selected from O, N, S, and the ring may be optionally substituted with 1, 2 or 3 R groups;

Each R¹ may be independently selected from OH, NR³R⁴, halogen, CN, COOH, halogenated $C_{1-6}$ alkyl, $C_{1-6}$ alkyl, $C_{2-6}$ alkenyl, $C_{2-6}$ alkynyl, $C_{1-6}$ heteroalkyl, $C_{3-6}$ cycloalkyl, halogenated $C_{3-6}$ cycloalkyl, phenyl, halogenated phenyl, 5- to 6-membered heteroaryl, or halogenated 5- to 6-membered heteroaryl;

Each R is independently selected from OH, NR³R⁴, halogen, oxo, CN, COOH, $C_{1-4}$ alkyl, $C_{2-4}$ alkenyl, $C_{2-4}$ alkynyl, or 6- to 12-membered aryl; the above $C_{1-4}$ Alkyl, $C_{2-4}$ alkenyl, $C_{2-4}$ alkynyl or 6- to 12-membered aryl may be optionally substituted with 1 or 2 OH, halogen, NH₂, CN or COOH groups;

R³ and R⁴ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynyl, $C_{1-6}$ heteroalkyl, halogenated $C_{1-6}$ heteroalkyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl;

$R^{A1}$, $R^{B1}$, $R^{A2}$ and $R^{B2}$ are each independently selected from H, OH, NH₂, halogen, halogenated $C_{1-3}$ alkyl, or $C_{1-4}$ alkyl;

p is 0, 1 or 2;

q is 0 or 1.

In an embodiment of the compound of formula II in the present application, D¹ is $(CR^{A1}R^{B1})_P$, wherein P is 0 or 1.

In an embodiment of the compound of formula II in the present application, D¹ is $(CR^{A1}R^{B1})$.

In an embodiment of the compound of formula II in the present application, D¹ is $C(CH_3)_2$.

In an embodiment of the compound of formula II in the present application, D¹ is a single bond.

In an embodiment of the compound of formula II in the present application, D¹ is $(CHR^{A1})$.

In an embodiment of the compound of formula II in the present application, D¹ is CH₂.

In an embodiment of the compound of formula II in the present application, D² is a single bond, $(CR^{A2}R^{B2})$, NR³, O, S, SO, SO₂, C(O), OC(O), C(O)O, NR³C(O), C(O)NR³, NR³SO₂, SO₂NR³, NR³C(O)NR⁴ or NR³SO₂NR⁴.

In an embodiment of the compound of formula II in the present application, D² is a single bond, $(CR^{A2}R^{B2})$, NR³, O, S, SO, SO₂ or C(O).

In an embodiment of the compound of formula II in the present application, D² is a single bond.

In an embodiment of the compound of formula II in the present application, D² is O.

In an embodiment of the compound of formula II in the present application, D² is —(CHR^{A2})—.

In an embodiment of the compound of formula II in the present application, D² is CH₂, CH(OH) or CH(CH₃).

In an embodiment of the compound of formula II in the present application, -D¹-D²- is a single bond, —(CR^{A1}R^{B1})—, —(CR^{A1}R^{B1})—(CR^{A2}R^{B2}) or —(CR^{A1}R^{B1})—O—.

In an embodiment of the compound of formula II in the present application, -D¹-D²- is a single bond, —(CHR^{A1})—, —(CR^{A1}R^{B1})—(CHR^{A2}), —(CHR^{A1})—(CHR^{A2}), or —(CHR^{A1})—O—.

In an embodiment of the compound of formula II in the present application, -D¹-D²- is a single bond, —CH₂—, —CH₂CH₂—, —CH₂CH(OH)—, —C(CH₃)₂—CH(OH)—, —CH₂CH(CH₃)— or —CH₂O—.

In an embodiment of the compound of formula II in the present application, -D¹-D²- is a single bond, —CH₂—, —CH₂CH₂—, —CH₂CH(OH)—, —CH₂CH(CH₃)—, or —CH₂O—.

In an embodiment of the compound of formula II in the present application, R² is selected from H, OH, NR³R⁴, halogen, halogenated $C_{1-6}$ alkyl, hydroxy $C_{1-6}$ alkyl, $C_{1-6}$ alkyl, or 3- to 12-membered saturated, partially saturated or aromatic mono-, bi-, or tri-cyclic ring, said rings may optionally contain 1, 2 or 3 heteroatoms selected from O, N or S, and said rings may be optionally substituted with 1, 2 or 3 R groups.

In an embodiment of the compound of formula II in the present application, R² is selected from H; OH; methyl; ethyl; propyl; isopropyl; butyl; isobutyl; sec-butyl; tert-butyl; n-pentyl; isoamyl; neopentyl; adamantyl; cyclopropyl; cyclobutyl; cyclopentyl; cyclohexyl; cycloheptyl; cyclooctyl; or

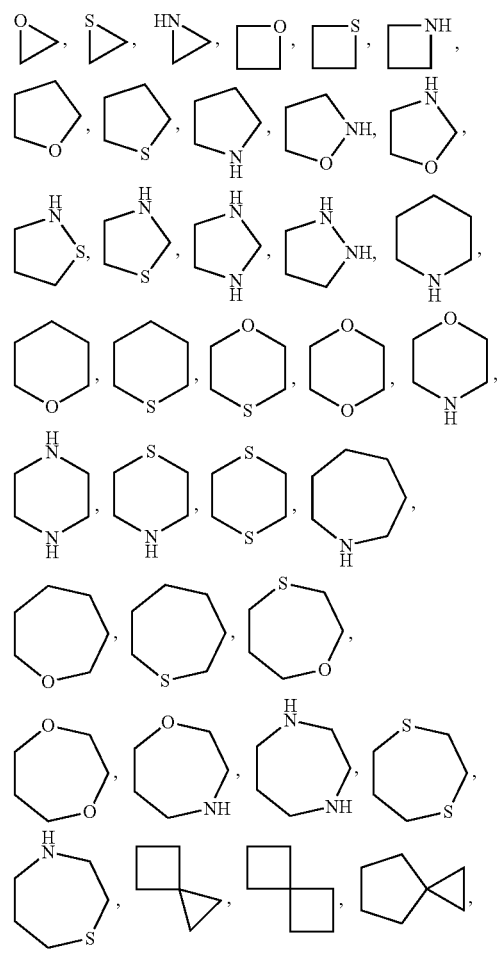

-continued

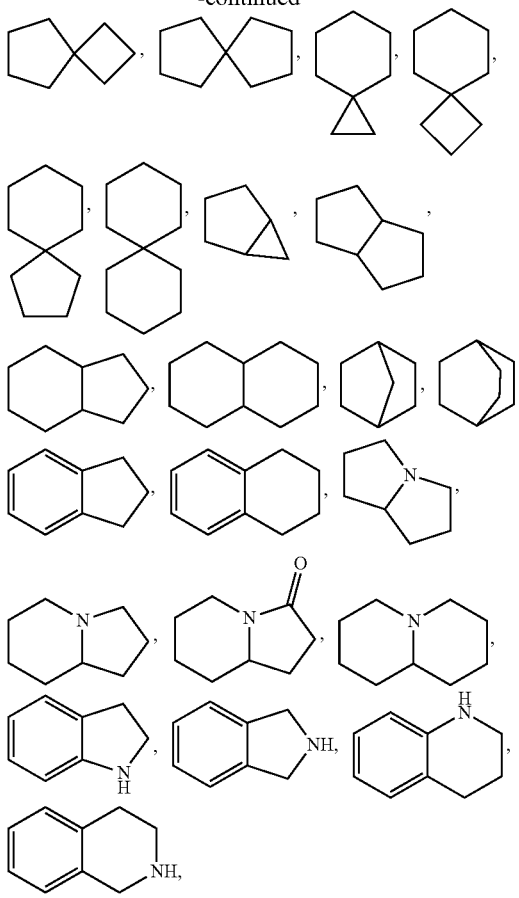

with a loss of one hydrogen atom at any position, and said rings may be optionally substituted with 1, 2 or 3 R groups.

In an embodiment of the compound of formula II in the present invention, $R^2$ is selected from OH, methyl, isopropyl, tert-butyl, cyclobutyl, cyclopentyl, cyclohexyl, cycloheptyl,

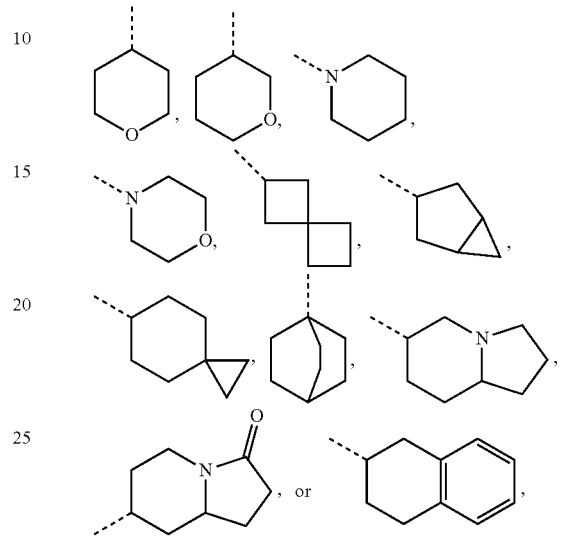

and said rings may be optionally substituted with 1, 2 or 3 R groups.

In an embodiment of the compound of formula II in the present application, $R^2$ is selected from OH, methyl, isopropyl, tert-butyl, cyclobutyl, cyclopentyl, cyclohexyl, cycloheptyl, and said rings may be optionally substituted with 1, 2 or 3 R groups.

In an embodiment of the compound of formula II in the present application, $R^1$ may be independently selected from OH, $NR^3R^4$, halogen, halogenated $C_{1-6}$ alkyl, $C_{1-6}$ alkyl, $C_{2-6}$ alkenyl, $C_{2-6}$ alkynyl, $C_{3-6}$ cycloalkyl, halogenated $C_{3-6}$ cycloalkyl, phenyl, halogenated phenyl, 5- to 6-membered heteroaryl, or halogenated 5- to 6-membered heteroaryl.

In an embodiment of the compound of formula II in the present application, $R^1$ may be independently selected from halogen, halogenated $C_{1-6}$ alkyl, $C_{1-6}$ alkyl, $C_{3-6}$ cycloalkyl, halogenated $C_{3-6}$ cycloalkyl, phenyl or halogenated phenyl.

In an embodiment of the compound of formula II in the present application, $R^1$ may be independently selected from halogen, $C_{1-3}$ alkyl, or halogenated $C_{1-3}$ alkyl.

In an embodiment of the compound of formula II in the present application, $R^1$ may be independently selected from F, methyl or fluoro $C_{1-3}$ alkyl.

In an embodiment of the compound of formula II in the present application, $R^1$ may be independently selected from F, methyl or trifluoromethyl.

In an embodiment of the compound of formula II in the present application, $R^1$ may be independently selected from F or trifluoromethyl.

In an embodiment of the compound of formula II in the present application, R may be independently selected from OH, $NR^3R^4$, halogen, oxo, CN, COOH, $C_{1-4}$ alkyl, $C_{2-4}$ alkenyl, or $C_{2-4}$ alkynyl; and the above $C_{1-4}$ alkyl, $C_{2-4}$ alkenyl or $C_{2-4}$ alkynyl may be optionally substituted with 1 or 2 OH, halogen, $NH_2$, CN or COOH groups.

In an embodiment of the compound of formula II in the present application, R may be independently selected from OH, $NR^3R^4$, halogen, oxo, CN, $C_{1-4}$ alkyl, $C_{2-4}$ alkenyl, or $C_{2-4}$ alkynyl; and the above $C_{1-4}$ alkyl, $C_{2-4}$ alkenyl, or $C_{2-4}$ alkynyl may be optionally substituted with 1 or 2 OH, halogen, $NH_2$ or CN groups.

In an embodiment of the compound of formula II in the present application, R may be independently selected from OH, fluorine, chlorine, bromine, iodine, oxo, COOH, methyl, ethyl, propyl, isopropyl, butyl, isobutyl, sec-butyl, tert-butyl, phenyl or quinolinyl, wherein methyl, ethyl, propyl, isopropyl, butyl, isobutyl, sec-butyl, tert-butyl, phenyl or quinolinyl may be optionally substituted with OH.

In an embodiment of the compound of formula II in the present application, R may be independently selected from OH, fluorine, COOH, methyl, phenyl or

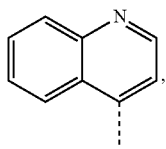

wherein methyl, phenyl or

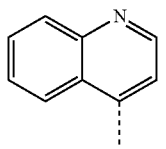

may be optionally substituted with OH.

In an embodiment of the compound of formula II in the present application, R may be independently selected from OH, fluorine, or methyl, wherein methyl may be optionally substituted with OH.

In an embodiment of the compound of formula II in the present application, $R^3$ and $R^4$ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl.

In an embodiment of the compound of formula II in the present application, $R^3$ and $R^4$ are each independently selected from H, $C_{1-6}$ alkyl, $C_{2-6}$ alkenyl, $C_{2-6}$ alkynyl, $C_{3-6}$ cycloalkyl, phenyl or 5- to 6-membered heteroaryl.

In an embodiment of the compound of formula II in the present application, $R^3$ and $R^4$ are each independently selected from H, $C_{1-6}$ alkyl, $C_{3-6}$ cycloalkyl, or phenyl.

In an embodiment of the compound of formula II in the present application, $R^{A1}$, $R^{B1}$, $R^{A2}$ and $R^{B2}$ are each independently selected from H, OH, $NH_2$, halogen, or $C_{1-4}$ alkyl.

In an embodiment of the compound of formula II in the present application, $R^{A1}$ and $R^{B1}$ are each independently selected from H, OH or $C_{1-4}$ alkyl.

In an embodiment of the compound of formula II in the present application, $R^{A1}$ and $R^{B1}$ are each independently selected from H or $C_{1-4}$ alkyl.

In an embodiment of the compound of formula II in the present application, $R^{A2}$ and $R^{B2}$ are each independently selected from H, OH, $NH_2$ or $C_{1-4}$ alkyl.

In an embodiment of the compound of formula II in the present application, $R^{A2}$ and $R^{B2}$ are each independently selected from H, OH or $C_{1-4}$ alkyl.

In further another aspect, the present application provides a compound of formula II-1, or a pharmaceutically acceptable salt thereof,

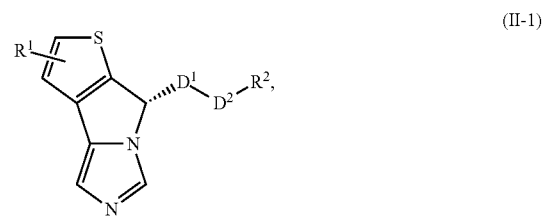

(II-1)

wherein the substituents are as defined in formula II.

In still another aspect, the present application provides a compound of formula II-2, or a pharmaceutically acceptable salt thereof,

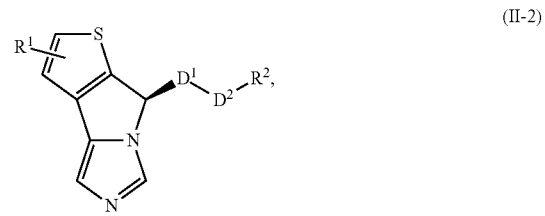

(II-2)

wherein the substituents are as defined in formula II.

In an embodiment of the present application, the compounds having the following structural formulas, or pharmaceutically acceptable salts thereof are provided:

| Compound Nos. | structural formulas |
|---|---|
| 1 | |
| 2 | |
| 3 | |

US 10,487,088 B2
15
-continued
| Compound Nos. | structural formulas |
|---|---|
| 4 | 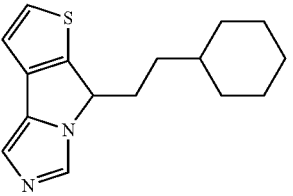 [SMILES: c1cc2c(s1)C(CCC1CCCCC1)n1cncc1-2] |
| 5 | 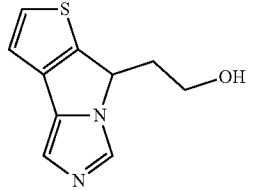 [SMILES: OCCC1c2sccc2-c2cncn21] |
| 6 | 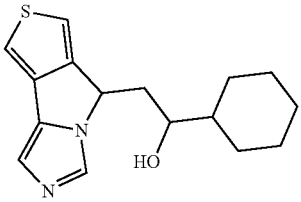 [SMILES: OC(CC1c2cscc2-c2cncn21)C1CCCCC1] |
| 7 | 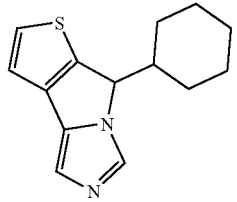 [SMILES: c1cc2c(s1)C(C1CCCCC1)n1cncc1-2] |
| 8 | 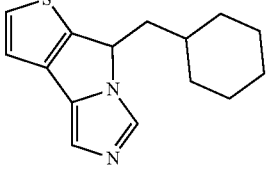 |
| 9 | 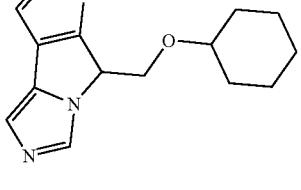 |
| 10 | 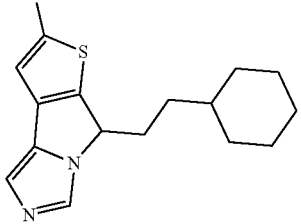 |
16
-continued
| Compound Nos. | structural formulas |
|---|---|
| 11 | 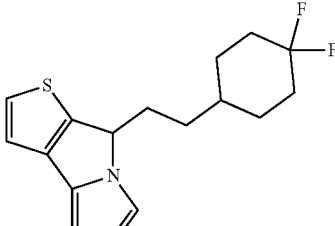 |
| 12 | 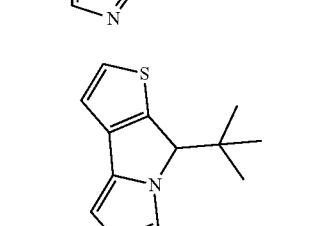 |
| 13 | 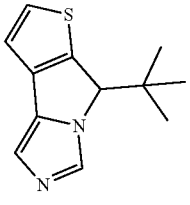 |
| 14 | 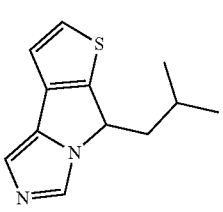 |
| 15 | 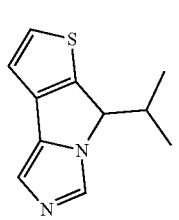 |
| 16 | 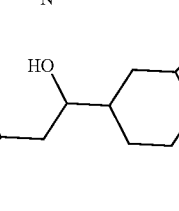 |
| 17 | 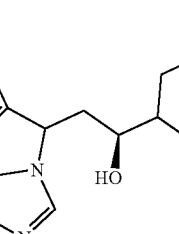 |

| Compound Nos. | structural formulas |
|---|---|
| 18 | 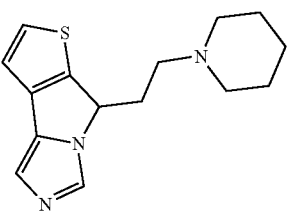 [SMILES: c1cc2c(s1)C(CCN1CCCCC1)n1cncc1-2] |
| 19 | 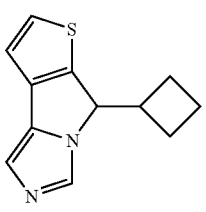 [SMILES: c1cc2c(s1)C(C1CCC1)n1cncc1-2] |
| 20 | 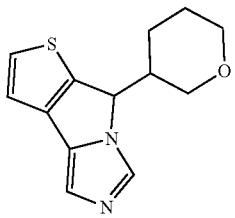 [SMILES: c1cc2c(s1)C(C1CCCOC1)n1cncc1-2] |
| 21 | 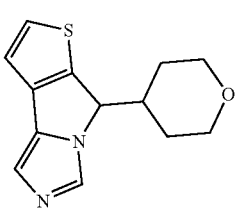 [SMILES: c1cc2c(s1)C(C1CCOCC1)n1cncc1-2] |
| 22 | 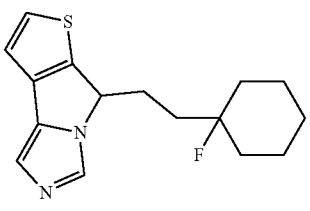 [SMILES: FC1(CCC2c3sccc3-c3cncn32)CCCCC1] |
| 23 | 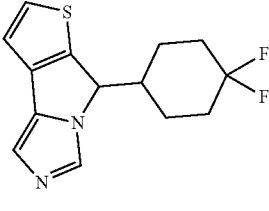 [SMILES: FC1(F)CCC(C2c3sccc3-c3cncn32)CC1] |
| 24 | 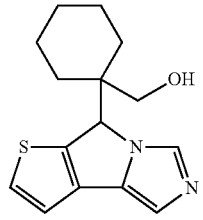 [SMILES: OCC1(C2c3sccc3-c3cncn32)CCCCC1] |
| 25 | 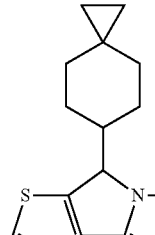 |
| 26 | 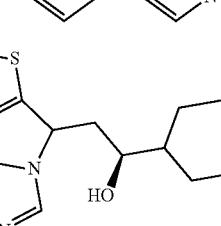 |
| 27 | 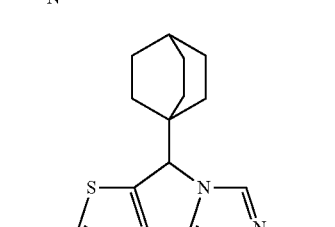 |
| 28 | 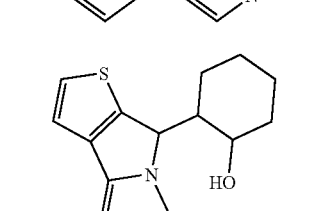 |
| 29 | 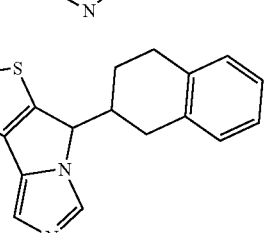 |
| 30 | 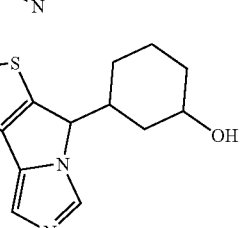 |
| 31 | 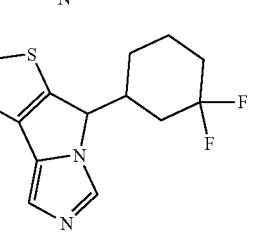 |

| Compound Nos. | structural formulas |
|---|---|
| 32 | 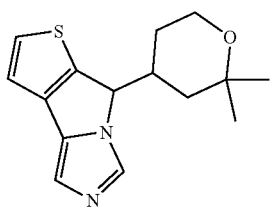 [SMILES: CC1(C)CC(C2c3sccc3-c3cncn32)CCO1] |
| 33 | 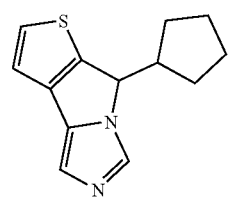 [SMILES: c1cc2c(s1)C(C1CCCC1)n1cncc1-2] |
| 34 | 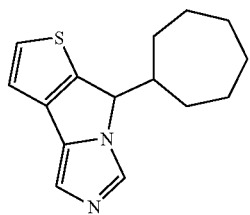 [SMILES: c1cc2c(s1)C(C1CCCCCC1)n1cncc1-2] |
| 35 | 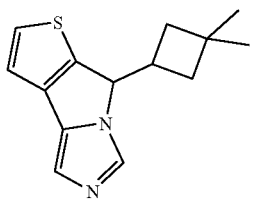 [SMILES: CC1(C)CC(C2c3sccc3-c3cncn32)C1] |
| 36 | 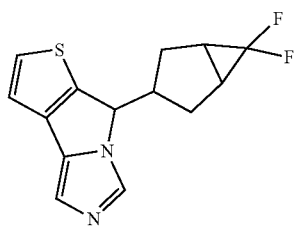 [SMILES: FC1(F)C2CC(C3c4sccc4-c4cncn43)CC21] |
| 37 | 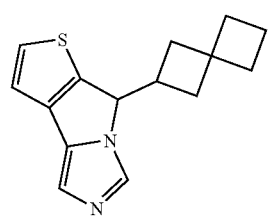 [SMILES: c1cc2c(s1)C(C1CC3(CCC3)C1)n1cncc1-2] |
| 38 | 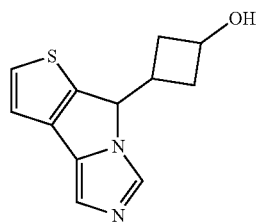 [SMILES: OC1CC(C2c3sccc3-c3cncn32)C1] |
| Compound Nos. | structural formulas |
|---|---|
| 39 | 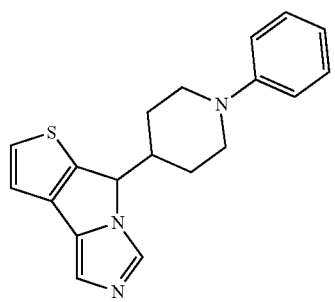 [SMILES: c1ccc(N2CCC(C3c4sccc4-c4cncn43)CC2)cc1] |
| 40 | 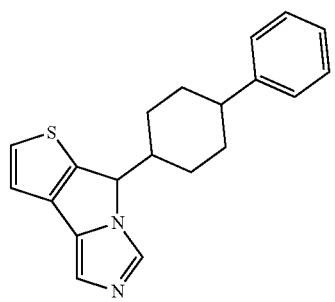 [SMILES: c1ccc(C2CCC(C3c4sccc4-c4cncn43)CC2)cc1] |
| 41 | 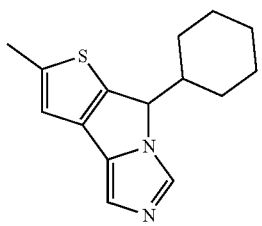 [SMILES: Cc1cc2c(s1)C(C1CCCCC1)n1cncc1-2] |
| 42 | 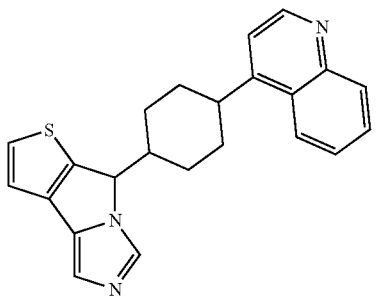 [SMILES: c1ccc2c(C3CCC(C4c5sccc5-c5cncn54)CC3)ccnc2c1] |
| 43 | 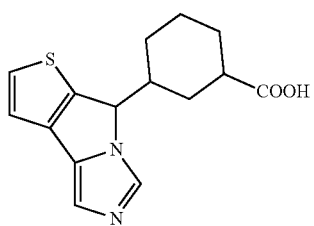 [SMILES: O=C(O)C1CCCC(C2c3sccc3-c3cncn32)C1] |

-continued
| Compound Nos. | structural formulas |
|---|---|
| 44 | |
| 45 | |
| 46 | |
| 47 | |
| 48 | |
In another embodiment of the present application, provided are the compounds having the following structural formulas, or pharmaceutically acceptable salts thereof:
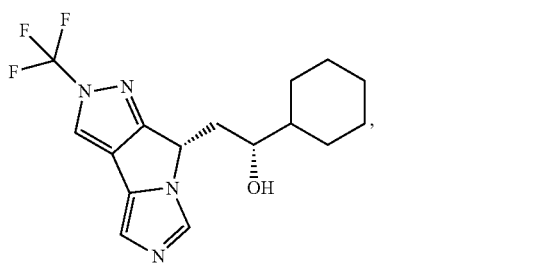

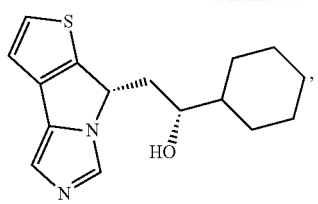,
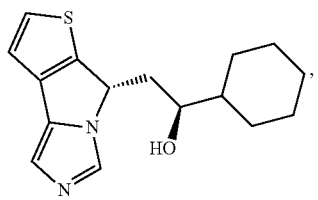,
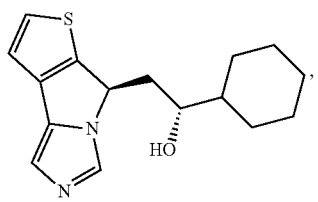,
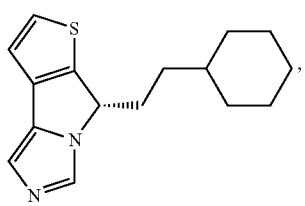,
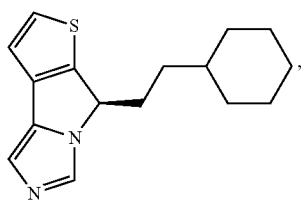,
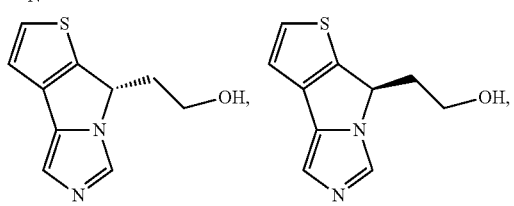
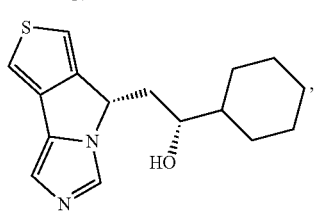,
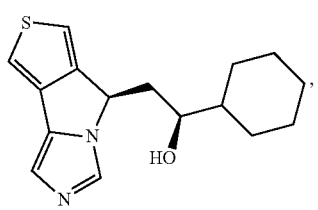,
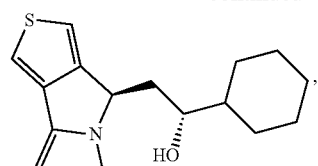,
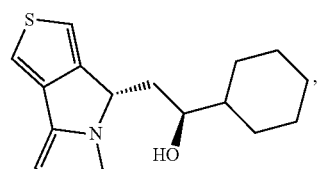,
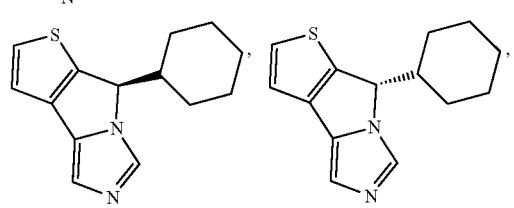
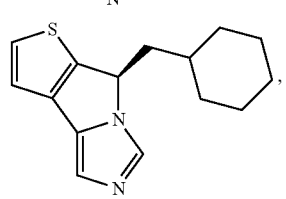,
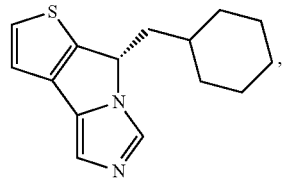,
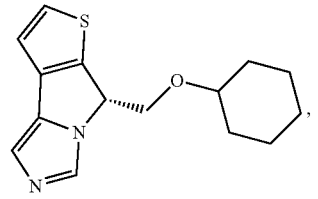,
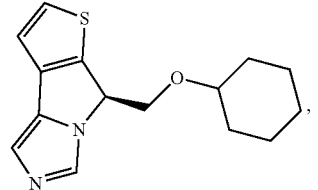,
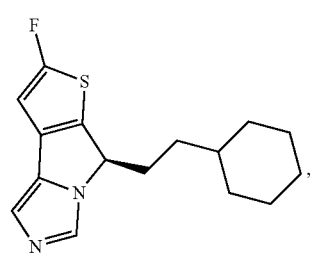,

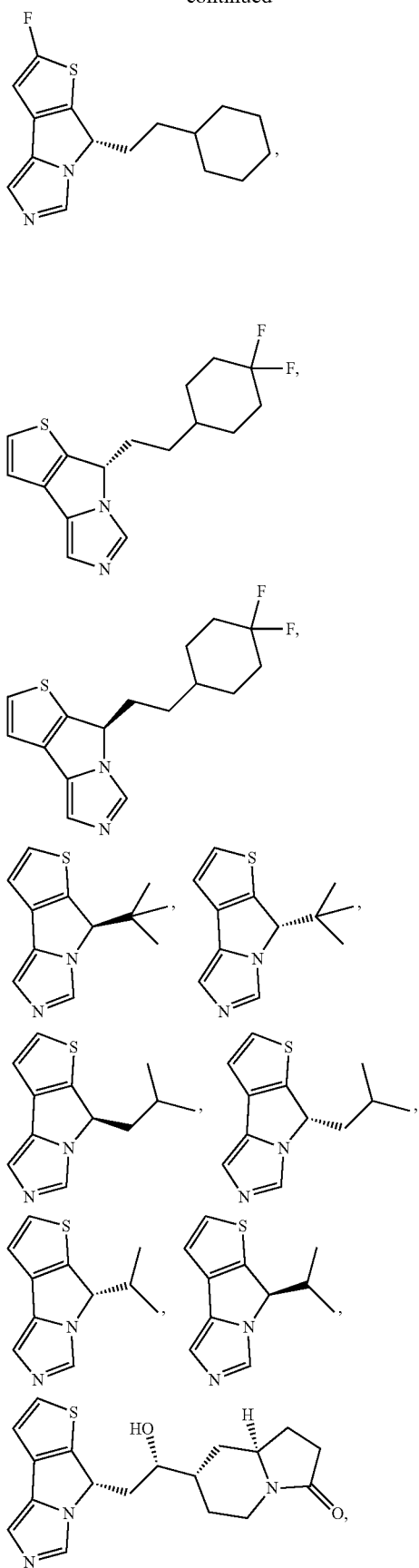
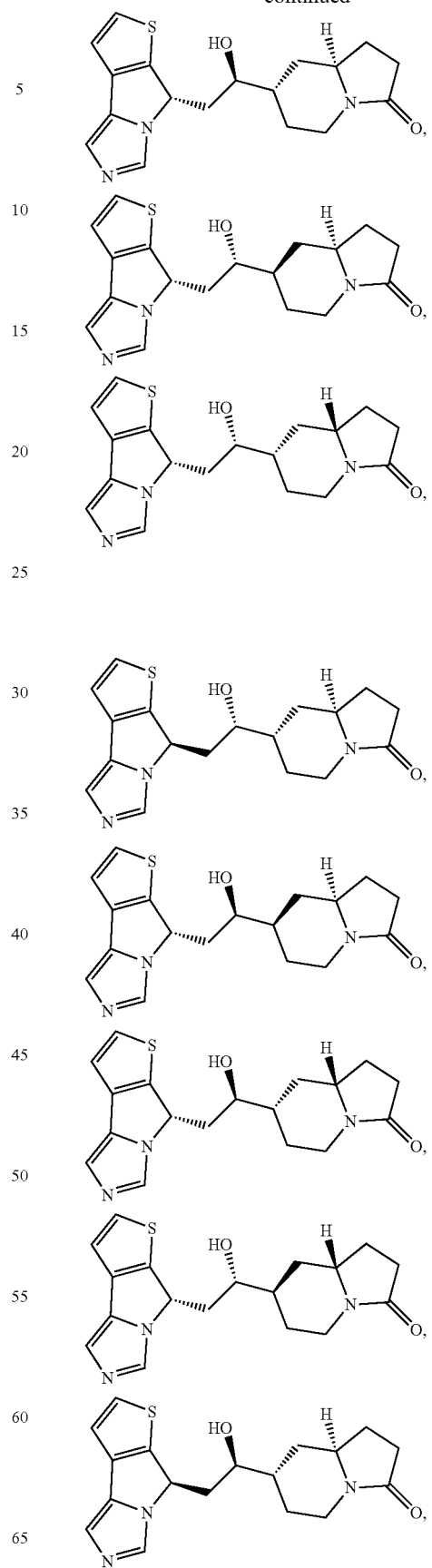

-continued
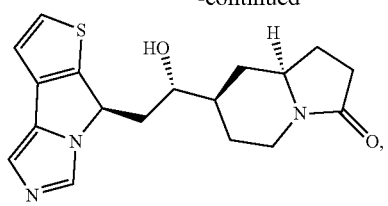

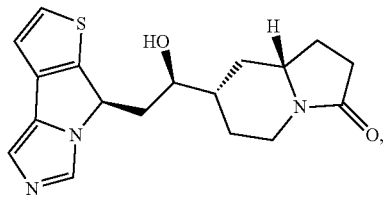
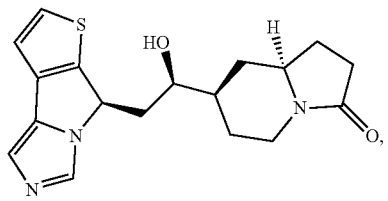

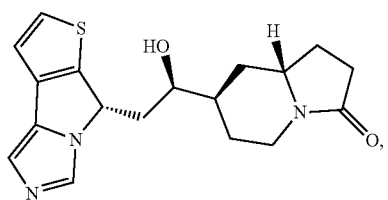
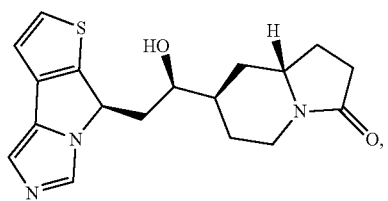
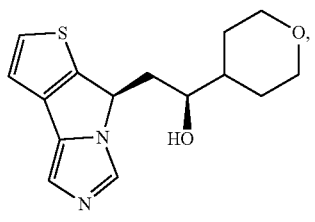
-continued
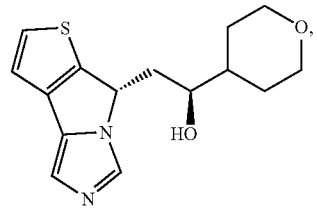
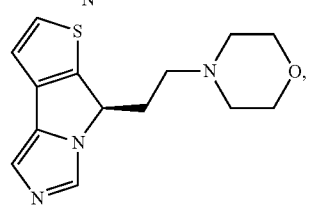
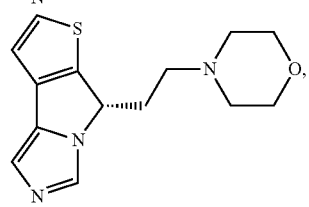
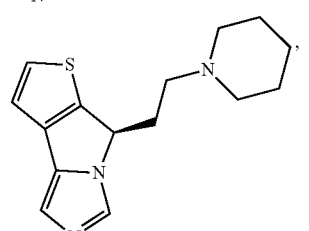
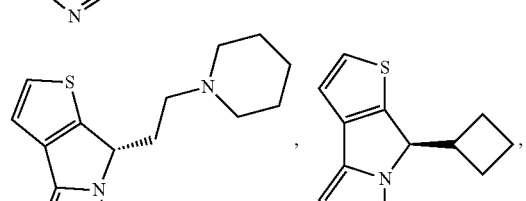
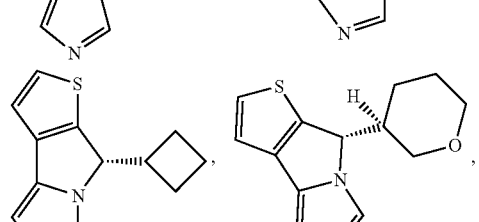
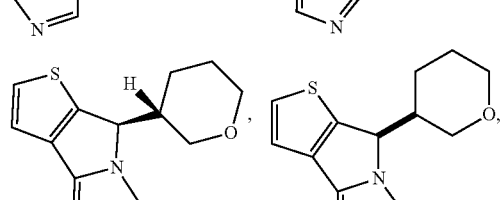
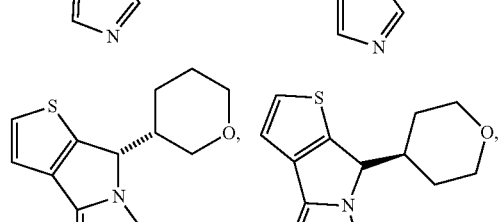

-continued
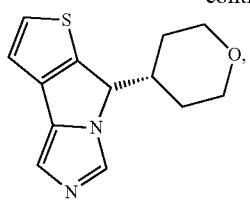
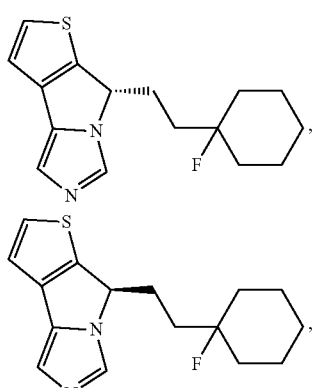
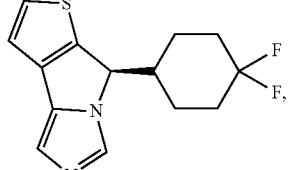
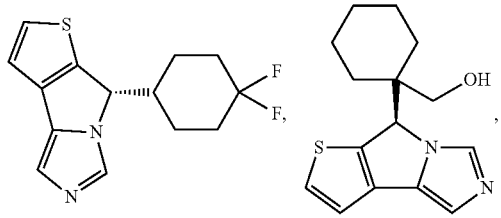
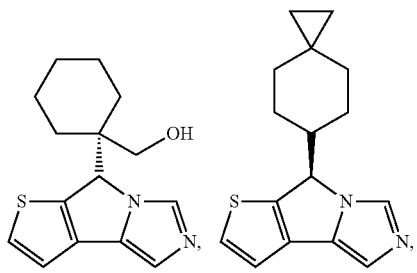
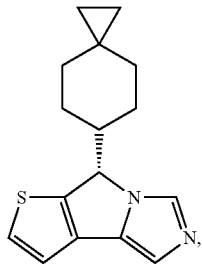
-continued
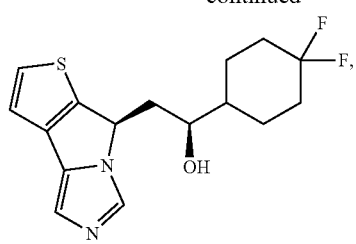
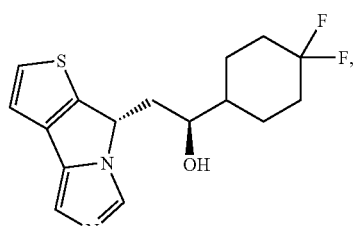
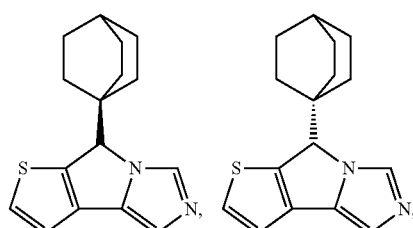
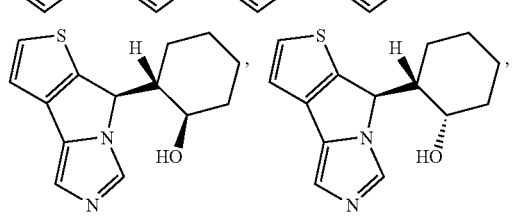
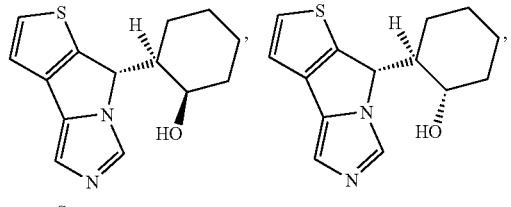
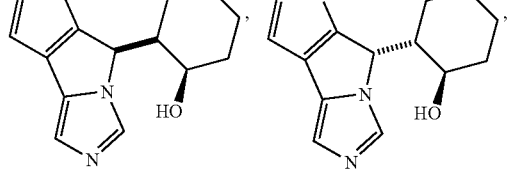
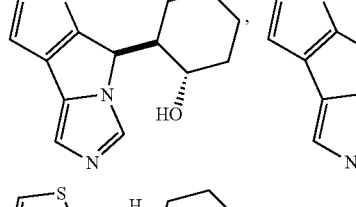
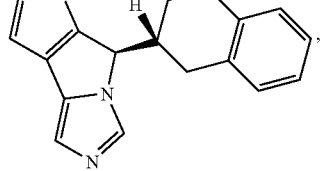

-continued
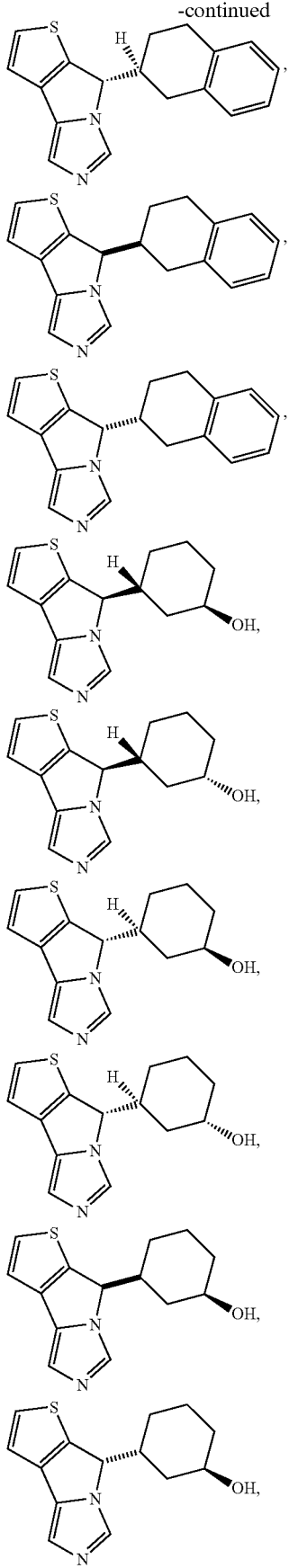
-continued
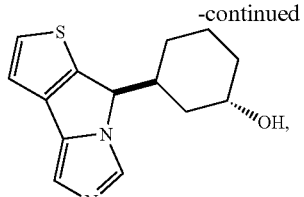
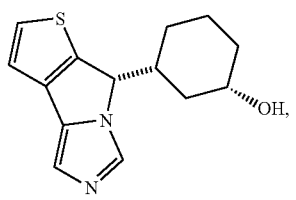
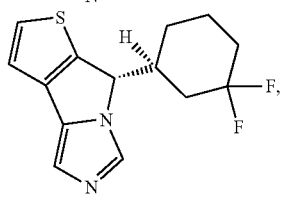
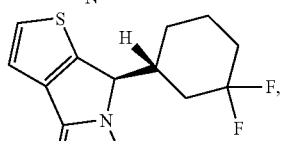
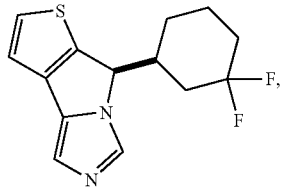
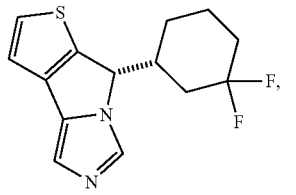
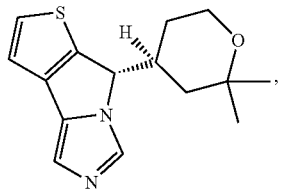
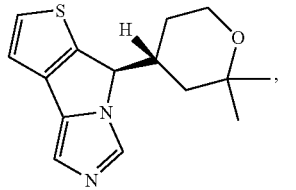
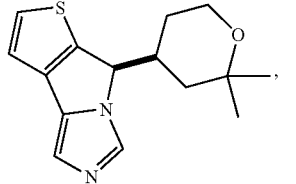

33
-continued
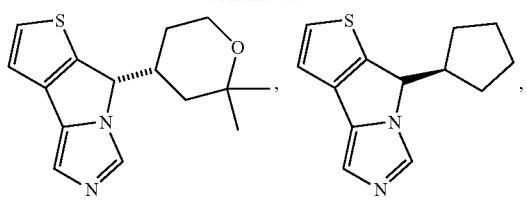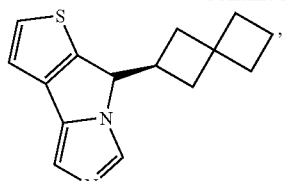
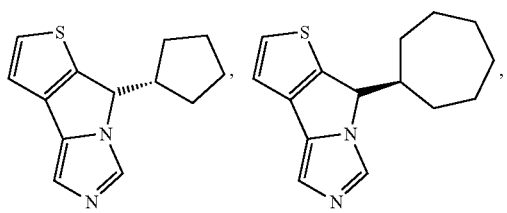
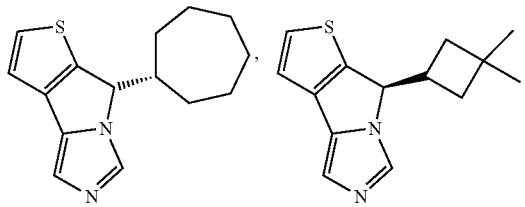
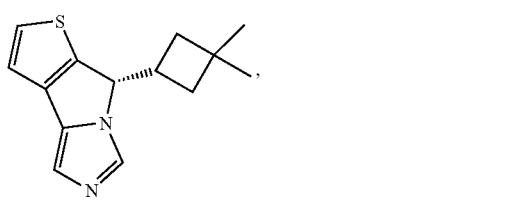
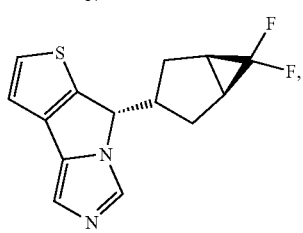
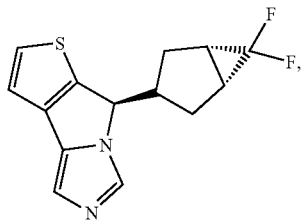
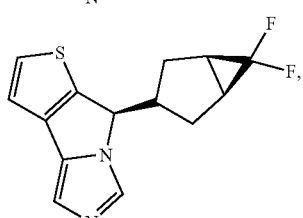
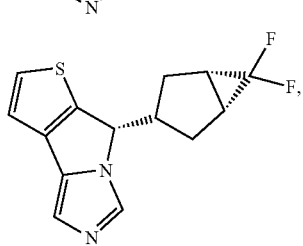
34
-continued
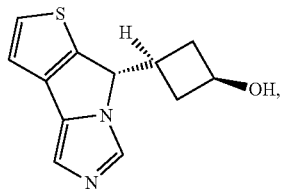
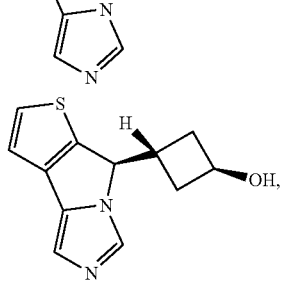
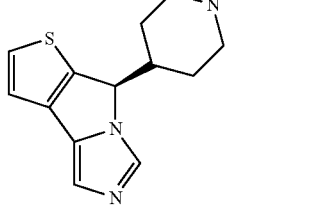

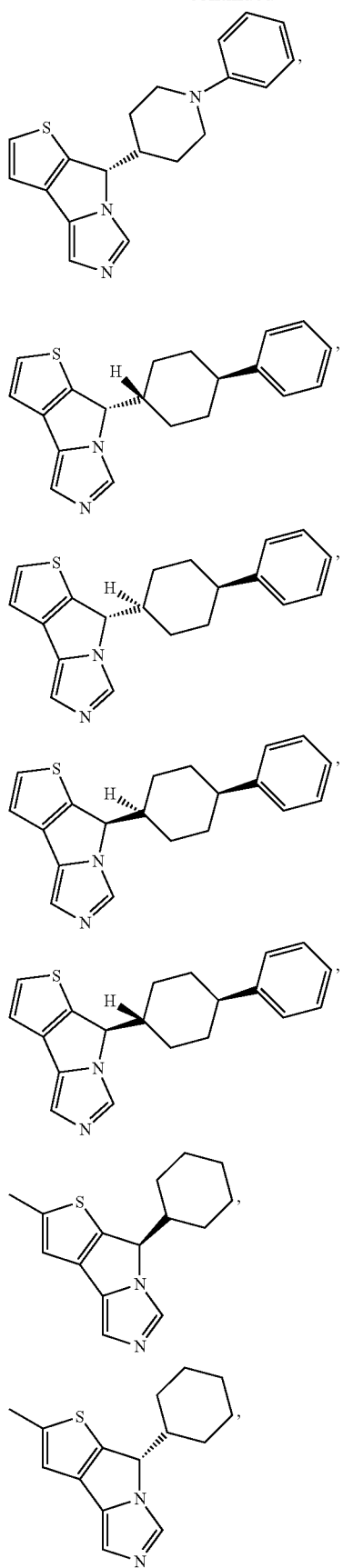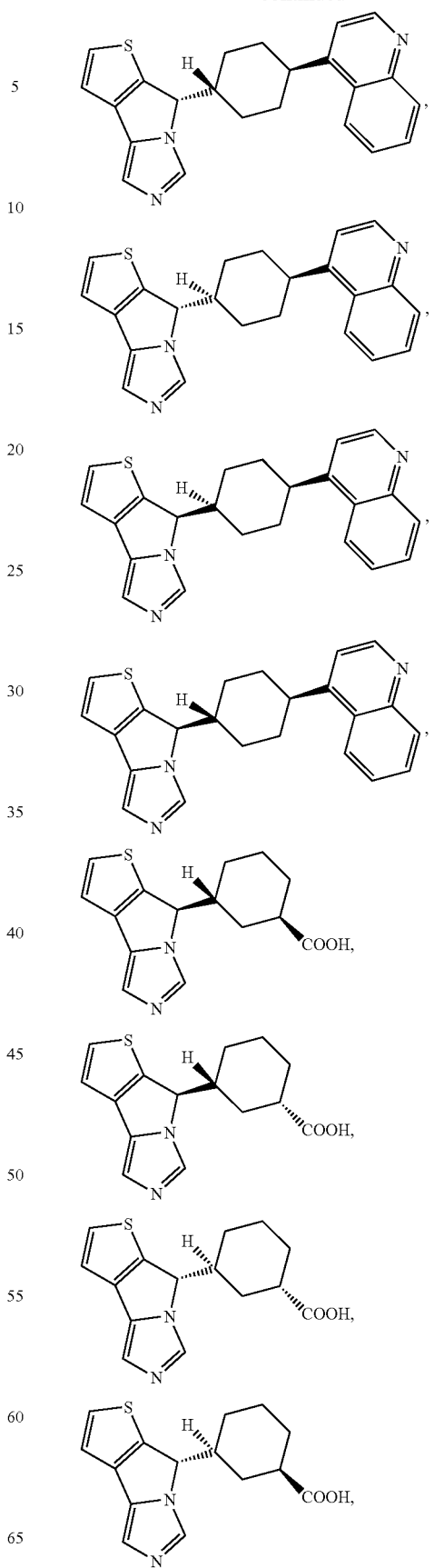

37
-continued
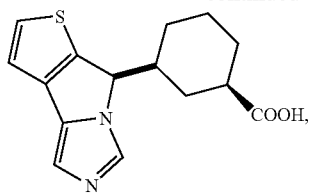
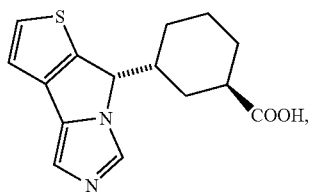
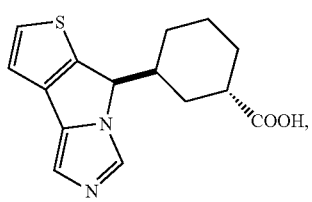
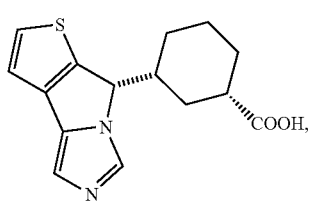
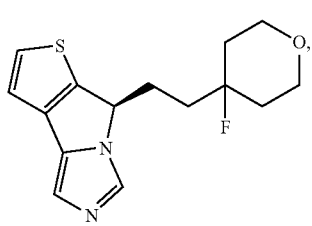
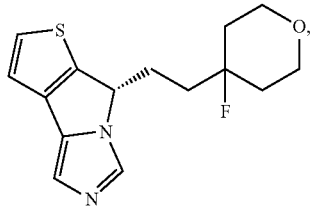
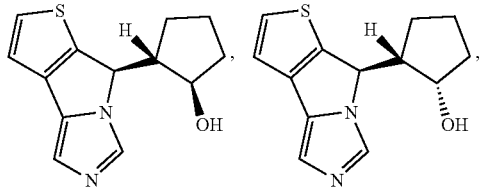
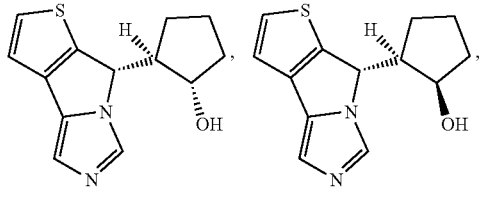
38
-continued
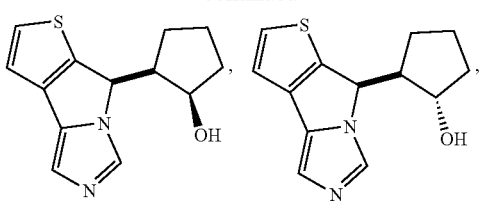
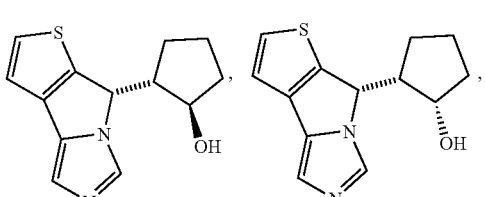
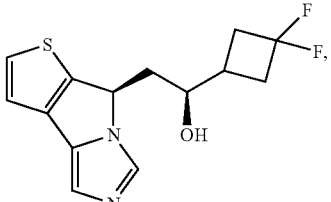
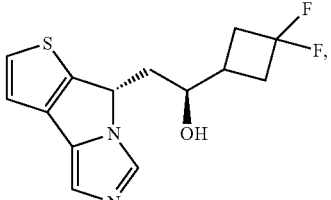
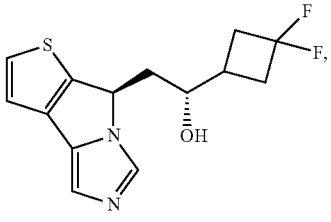
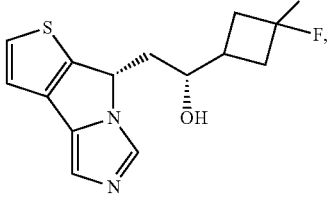
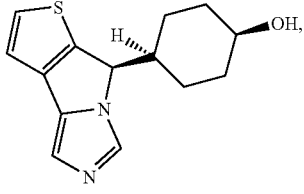
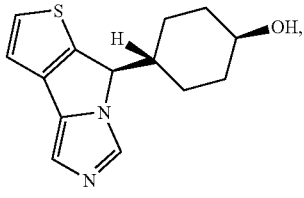

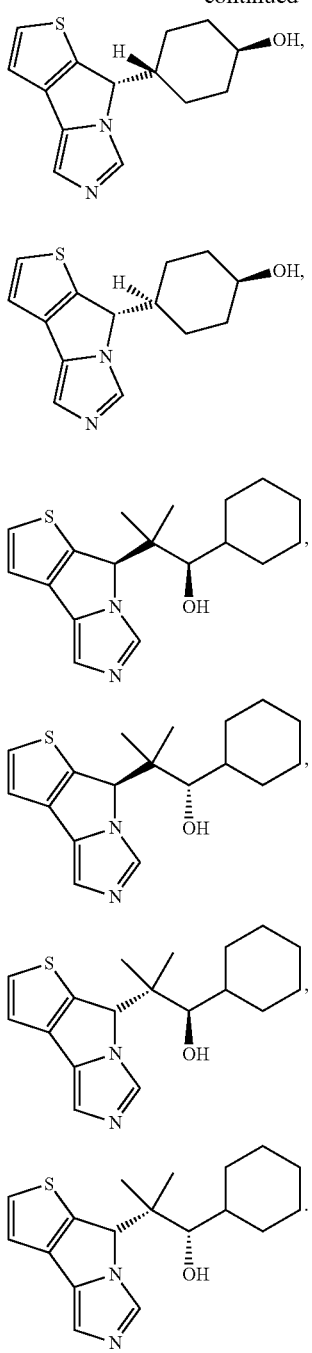

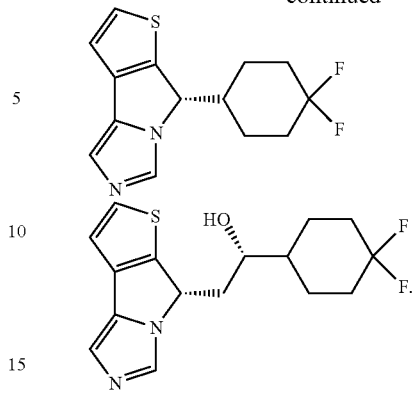

In further another aspect, the present application provides a pharmaceutical composition comprising a therapeutically effective amount of a compound of formulas I or II, or a pharmaceutically acceptable salt thereof, and one or more pharmaceutically acceptable carriers or excipients.

In still another aspect, the present application provides a method for treating indole 2,3-dioxygenase (IDO)-mediated immunosuppressive diseases, comprising administering the compound of formulas I or II or the pharmaceutically acceptable salt thereof, or the pharmaceutical composition thereof to a subject in need thereof.

In yet another aspect, the present application provides use of the compound of formulas I or II or the pharmaceutically acceptable salt thereof, or the pharmaceutical composition thereof in the manufacture of a medicament for treating indole 2,3-dioxygenase (IDO)-mediated immunosuppressive diseases.

In yet another aspect, the present application provides the compound of formulas I or II or the pharmaceutically acceptable salt thereof, or the pharmaceutical composition thereof, for use in the treatment of indole 2,3-dioxygenase (IDO)-mediated immunosuppressive diseases.

In some embodiments of the present application, the immunosuppressive diseases are associated with infectious diseases or cancer.

In some embodiments of the present application, the infectious diseases are selected from the following virus infections: influenza, hepatitis C virus (HCV), human papilloma virus (HPV), cytomegalovirus (CMV), poliovirus, herpes zoster virus, human immunodeficiency virus (HIV), epstein-barr virus (EBV) or coxsackie virus. The cancer is selected from colon cancer, pancreatic cancer, breast cancer, prostate cancer, lung cancer, brain cancer, ovarian cancer, cervical cancer, testicular cancer, kidney cancer, head or neck cancer, lymphoma, leukemia or melanoma.

Definition and Description

In the following description, certain specific details are included to provide a thorough understanding of various disclosed embodiments. However, a person skilled in the art will recognize that the embodiments of the application may be practiced without one or more of these specific details, or with other methods, components, materials, etc.

Unless otherwise required in the present application, throughout the specification and the appended claims, the expression "comprise/contain/include" and variants thereof, such as "comprises" and "comprising", should be construed as having an open-ended meaning (i.e., meaning "including, but not limited to").

In an embodiment of the present application, provided are the compounds having the following structural formulas, or pharmaceutically acceptable salts thereof:

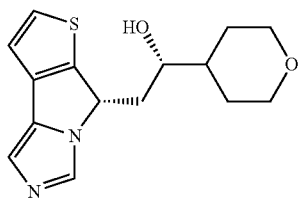

"One embodiment" or "an embodiment" or "in another embodiment" or "in certain embodiments" mentioned throughout the specification means that the specific features, structures, or characteristics related to said embodiment can be included in at least one embodiment. Thus, the appearances of phrases such as "in one embodiment" or "in an embodiment" or "in another embodiment" or "in certain embodiments" in various places throughout this specification are not necessarily referring to the same embodiment of the present application. In addition, specific features, structures, or characteristics may be combined in any suitable manner in one or more embodiments.

It should be understood that, the singular forms "a", "an", and "the", as used in the specification and the appended claims, include plural referents unless the content clearly dictates otherwise. Thus, for example, a reaction comprising "catalyst" includes a catalyst, or two or more catalysts. It should also be understood that the term "or" is generally employed in its sense including "and/or" unless the content clearly dictates otherwise.

Unless otherwise specified, the following terms and phrases as used herein have the following meanings ascribed to them. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The term "optional" or "optionally" means that the subsequently described event or circumstance may or may not occur, and that the description includes instances where said event or circumstance occurs and instances where it does not. For example, ethyl being "optionally" substituted with halogen means that, said ethyl may be unsubstituted ($CH_2CH_3$), or monosubstituted (eg, $CH_2CH_2F$), polysubstituted (eg, $CHFCH_2F$, $CH_2CHF_2$, etc.) or fully substituted ($CF_2CF_3$). As to any of the chemical moieties that contain one or more substituents, it is understood by a person skilled in the art that such moieties do not contain any substitution or substitution patterns that are sterically impractical and/or synthetically nonfeasible.

As used herein, $C_{m-n}$ refers to that said moiety has m-n carbon atoms. For example, "$C_{3-10}$ cycloalkyl" means that said cycloalkyl group has 3 to 10 carbon atoms. "$C_{0-6}$ alkylene" means that said alkylene group has 0-6 carbon atoms, where the alkylene group has 0 carbon atom, this group is a bond. It is easy to understand that where a heteroatom is contained therein, m-n represents the sum of the number of carbon atoms and heteroatoms.

The numerical ranges herein refer to include each whole integer within the range. For example, "$C_{1-10}$" means that the group may have 1, 2, 3, 4, 5, 6, 7, 8, 9 or 10 carbon atoms.

The term "substituted" means that any one or more hydrogens on the designated atom is replaced with a substituent provided that the valence of the designated atom is normal and the substitution results in a stable compound. When the substituent is a ketone group (i.e., =O) (also referred to as oxo), it means that two hydrogen atoms are substituted, and the ketone substitution will not occur on an aromatic group.

When any variable (eg, R) occurs more than one time in constituent or structure of a compound, each definition is independent. Thus, for example, if a group is showed to be substituted with 0-2R, then said group may optionally be substituted with up to two R, and R at each occurrence is selected independently from the definition of R. In addition, combinations of substituents and/or variables thereof are permissible only if such combinations result in stable compounds.

When the number of a linking group is 0, such as —(CRR)$_0$—, it means that said linking group is a single bond.

When one of the variables is selected from a single bond, it means that the two groups to which they are attached are directly linked to each other. For example, when L represents a single bond in A-L-Z, the structure is actually A-Z.

When a substituent is vacant, it means that the substituent does not exist. For example, when X is vacant in A-X, the structure is actually A. When a bond of one substituent can cross-link to two atoms on one ring, this substituent may be bonded to any atom on the ring. When it does not specify through which atom the listed substituent is linked to a compound included but not specifically mentioned in a chemical structure formula, this substituent may be bonded through any of its atoms. The combination of substituents and/or variants thereof is allowable only if such combination will result in stable compounds. For example, the structural unit

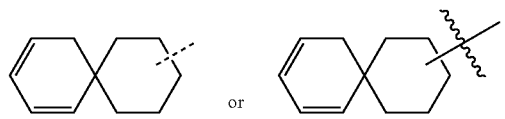

indicates that a substitution may occur at any position on cyclohexyl or cyclohexadiene.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to salts of the compounds of the present application, as the pharmaceutically acceptable salts of the compounds of formulas I or II. For example, mentioned may be metal salts, ammonium salts, salts formed with organic bases, salts formed with inorganic acids, salts formed with organic acids, salts formed with basic or acidic amino acids, etc. Non-limiting examples of metal salts include, but not limited to, alkali metal salts, such as sodium and potassium salts; alkaline earth metal salts, such as calcium, magnesium and barium salts; aluminum salts, and the like. Non-limiting examples of salts formed with organic bases include, but not limited to, salts formed with trimethylamine, triethylamine, pyridine, picoline, 2,6-dimethylpyridine, ethanolamine, diethanolamine, triethanolamine, cyclohexylamine, dicyclohexylamine and the like. Non-limiting examples of salts formed with inorganic acids include, but not limited to, the salts formed with hydrochloric acid, hydrobromic acid, nitric acid, sulfuric acid, phosphoric acid, and the like. Non-limiting examples of salts formed with organic acids include, but not limited to, the salts formed with formic acid, acetic acid, trifluoroacetic acid, fumaric acid, oxalic acid, malic acid, maleic acid, tartaric acid, citric acid, succinic acid, methanesulfonic acid, benzenesulfonic acid, p-toluenesulfonic acid, and the like. Non-limiting examples of salts formed with basic amino acids include, but not limited to, the salts formed with arginine, lysine, ornithine, and the like. Non-limiting examples of salts formed with acidic amino acids include, but not limited to, the salts formed with aspartic acid, glutamic acid, and the like.

The pharmaceutically acceptable salts of the present application can be synthesized from the parent compound containing an acid radical or a base group by conventional chemical methods. In general, such salts are prepared by the following methods: in water or an organic solvent or a mixture of both, the salts are prepared by compounds in the form of free acid or base with a stoichiometric amount of suitable base or acid. In general, non-aqueous media such as ether, ethyl acetate, ethanol, isopropanol or acetonitrile are preferred.

The compounds of formulas I or II of the present application may exist in an unsolvated or solvated form, including a hydrated form. In general, the solvated forms are equivalent to unsolvated form, and are intended to be encompassed within the scope of the present application. The compounds of formulas I or II of the present application may exist in a polymorphic or amorphous form.

The compounds of formulas I or II of the present application may have asymmetric carbon atoms (optical centers) or double bonds. Racemates, diastereomers, geometric isomers, and individual isomers are all included within the scope of the present application.

The graphic representations of racemic, ambiscalemic and scalemic or enantiomerically pure compounds herein are from Maehr, J. Chem. Ed. 1985, 62: 114-120. Unless otherwise stated, the absolute configuration of a stereocenter is represented by solid and broken wedges. When compounds of formulas I or II described herein contain olefinic double bonds or other geometric asymmetrical centers, unless otherwise specified, they include E, Z geometric isomers. Likewise, all tautomeric forms are included within the scope of the present application.

The compounds of formulas I or II of the present application may exist in specific geometric or stereoisomeric forms. All such compounds envisaged by the present application include cis and trans isomers, (−)- and (+)-enantiomer pairs, (R)- and (5)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present application is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by a fractional crystallization or chromatography method well known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compounds of formulas I or II of the present application may contain non-natural proportions of atomic isotopes on one or more atoms which constitute the compound. For example, the compound may be labeled with a radioisotope, such as tritium ($^3$H), iodine-125 ($^{125}$I) or C-14 ($^{14}$C). Any isotopic composition transformations of the compounds of formulas I or II of the present application, whether are radioactive or not, are included in the scope of the present application.

The term "pharmaceutically acceptable carrier" refers to any formulation or carrier medium capable of delivering an effective amount of the active substance of the present application, without interfering with the biological activity of the active substance and having no toxic side effects on the host or patient. Representative carriers include water, oils, vegetables and minerals, cream bases, lotion bases, ointment bases, etc. These bases include suspensions, tackifiers, transdermal enhancers, etc. Their formulations are well known to the skilled in the cosmetic field or topical drug field. Other information about carriers can refer to Remington: The Science and Practice of Pharmacy, 21$^{st}$ Ed., Lippincott, Williams & Wilkins (2005), the contents of which are incorporated herein by reference.

The term "excipient" generally refers to the carrier, diluent and/or medium which is required to formulate an effective pharmaceutical composition.

For drugs or pharmacologically active agents, the term "effective amount" or "therapeutically effective amount" refers to a sufficient amount of a drug or agent that is non-toxic but can achieve the desired effect. For the oral dosage form of the present application, the "effective amount" of one active substance in the composition means the amount needed to achieve the desired effect when used in combination with another active substance in the composition. The determination of the effective amount varies with each individual, depending on the age and general condition of the subject, as well as the specific active substance. The appropriate effective amount in each case can be determined by the skilled in the art according to a routine experiment.

The term "active ingredient", "therapeutic agent", "active substance" or "active agent" refers to a chemical entity that can effectively treat target disorders, diseases or conditions.

Unless otherwise defined, the term "halogenated" or "halogen" per se or as a part of another substituent denotes a fluorine, chlorine, bromine or iodine atom. Furthermore, the term "haloalkyl" is intended to include monohaloalkyl and polyhaloalkyl. For example, the term "halo($C_1$-$C_4$) alkyl" is intended to include, but is not limited to, trifluoromethyl, 2,2,2-trifluoroethyl, 4-chlorobutyl, 3-bromopropyl, etc. Examples of haloalkyl include, but are not limited to, trifluoromethyl, trichloromethyl, pentafluoroethyl, and pentachloroethyl.

The term "hydroxy" refers to —OH.

The term "cyano" refers to —CN.

The term "amino" refers to —NH$_2$, —NH(alkyl), and —N(alkyl)$_2$, and specific examples of an amino group include, but not limited to, —NH$_2$, —NHCH$_3$, —NHCH(CH$_3$)$_2$, —N(CH$_3$)$_2$. —NHC$_2$H$_5$, —N(CH$_3$)C$_2$H$_5$, and the like.

The term "alkyl" refers to a straight- or branched-chain saturated aliphatic hydrocarbon group consisting of carbon and hydrogen atoms, such as methyl, ethyl, propyl, butyl, pentyl, hexyl, heptyl, octyl, nonyl, decyl and the like. The specific alkyl includes all isomeric forms thereof, for example, propyl includes —CH$_2$CH$_2$CH$_3$, —CH(CH$_3$)$_2$; for example, butyl includes —CH$_2$CH$_2$CH$_2$CH$_3$, —CH(CH$_3$) (CH$_2$CH$_3$), —C(CH$_3$)$_3$, —CH$_2$CH(CH$_3$)$_2$. The term "C$_{1-8}$ alkyl" refers to an alkyl group having 1-8 carbon atoms. The term "$C_{1-6}$ alkyl" refers to an alkyl group having 1 to 6 carbon atoms. The term "$C_{1-4}$ alkyl" refers to an alkyl group having 1 to 4 carbon atoms. The term "$C_{1-3}$ alkyl" refers to an alkyl group having 1 to 3 carbon atoms. The "alkyl", "$C_{1-8}$ alkyl", "$C_{1-6}$ alkyl", "$C_{1-4}$ alkyl" or "$C_{1-3}$ alkyl" may be unsubstituted or may be substituted with one or more substituents selected from hydroxy, halogen, or amino.

The term "alkenyl" refers to a straight or branched-chain aliphatic hydrocarbon group containing 2 to 12 carbon atoms and having one or more double bonds. Examples of alkenyl groups include, but not limited to, vinyl, allyl, propenyl, 2-butenyl, and 3-hexenyl. One of carbons forming a double bond can optionally be an attachment point for a substituent in the alkenyl group.

The term "alkynyl" refers to a straight or branched-chain aliphatic hydrocarbon group containing 2 to 12 carbon atoms and having one or more triple bonds. Examples of alkynyl groups include, but not limited to, ethynyl, propargyl, and 3-hexynyl. One of carbons forming a triple bond can optionally be an attachment point for a substituent in the alkynyl group.

The term "cycloalkyl" refers to a monocyclic, saturated aliphatic hydrocarbon group consisting solely of carbon and hydrogen atoms, such as $C_{3-20}$ cycloalkyl, preferably $C_{3-6}$ cycloalkyl, such as cyclopropyl, cyclobutyl, cyclopentyl, cyclohexyl and the like. The cycloalkyl group may be unsubstituted or substituted, which the substituent includes, but not limited to, alkyl, alkyloxy, cyano, carboxyl, aryl, heteroaryl, amino, halogen, sulfonyl, sulfinyl, phosphoryl, hydroxyl and the like.

The term "alkoxy" refers to an alkyl group as defined above with a specified number of carbon atoms attached through an oxygen bridge. $C_{1-6}$ alkoxy includes $C_1$, $C_2$, $C_3$, $C_4$, $C_5$ and $C_6$ alkoxy groups. Examples of alkoxy groups include, but not limited to, methoxy, ethoxy, n-propoxy, isopropoxy, n-butoxy, sec-butoxy, tert-butoxy, n-pentoxy, and S-pentoxy.

The term "oxo" means that a substituent on a C atom is a keto group (i.e., =O).

Unless otherwise specified, the term "hetero" refers to a heteroatom or a heteroatom radical (i.e., a radical containing a heteroatom), including an atom other than carbon (C) and hydrogen (H), and a radical containing these heteroatoms, for example including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)—, or —S(=O)N(H)—.

Unless otherwise specified, a "ring" refers to a substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, a bicyclic ring, a spiro ring, a fused ring, or a bridged ring. The number of atoms in a ring is typically defined by the number of members in the rings. For example, a "5- to 7-membered ring" refers to 5 to 7 atoms arranged in a circle. Unless otherwise specified, the ring optionally contains 1 to 3 heteroatoms. Thus, a "5- to 7-membered ring" includes, for example, phenyl, pyridine, and piperidin group. In another aspect, the term "5- to 7-membered heterocycloalkyl ring" includes pyridine group and piperidin group, but not phenyl group. The term "ring" also includes a ring system containing at least one ring, in which each "ring" independently meets the above definition.

Unless otherwise specified, the term "heterocycle" or "heterocyclyl" refers to a stable mono-, bi-, or tri-cyclic ring containing a heteroatom or heteroatom radical, which may be saturated, partially unsaturated, or unsaturated (aromatic), and they contain carbon atoms and 1, 2, 3, or 4 heteroatoms independently selected from N, O, and S, wherein any of the above heterocycles may be fused to a benzene ring to form a bicyclic ring. The nitrogen and sulfur heteroatoms may be optionally oxidized (i.e., NO and S(O)$_p$, p is 1 or 2). The nitrogen atom may be substituted or unsubstituted (i.e., N or NR, wherein R is H or other substituents as already defined herein). The heterocyclic ring may be attached to its pendant group at any heteroatom or carbon atom which results in a stable structure. The heterocyclic rings described herein may be substituted on carbon or on a nitrogen atom if the resulting compound is stable. A nitrogen atom in the heterocycle is optionally be quaternized. It is preferred that when the total number of S and O atoms in the heterocycle exceeds 1, these heteroatoms are not adjacent to each another. It is preferred that the total number of S and O atoms in the heterocycle is not more than 1. As used herein, the term "aromatic heterocyclic group" or "heteroaryl" refers to a stable 5-, 6- or 7-membered monocyclic or bicyclic, or of 7-, 8-, 9- or 10-membered bicyclic aromatic heterocycle radical, which contains carbon atoms and 1, 2, 3, or 4 heteroatoms independently selected from N, O, and S. The nitrogen atom may be substituted or unsubstituted (i.e., N or NR, wherein R is H or other substituents as already defined herein). The nitrogen and sulfur heteroatoms may be optionally oxidized (i.e., NO and S(O)$_p$, and p is 1 or 2). It is to be noted that the total number of S and O atoms in the aromatic heterocycle is not more than 1. Bridged rings are also included in the definition of heterocycles. A bridged ring occurs when one or more atoms (i.e., C, O, N, or S) link two non-adjacent carbon or nitrogen atoms. Preferred bridged rings include, but not limited to, one carbon atom, two carbon atoms, one nitrogen atom, two nitrogen atoms, and a carbon-nitrogen group. It is noted that a bridge always converts a monocyclic ring into a tricyclic ring. In a bridged ring, substituents recited for the ring may also be present on the bridge.

Examples of heterocyclic compounds include, but not limited to, acridinyl, azocinyl, benzimidazolyl, benzofuranyl, benzomercaptofuranyl, benzomercaptophenyl, benzoxazolyl, benzooxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnoline decahydroquinolinyl, 2H,6H-1,5,2-dithiazinyl, dihydrofuro[2,3-b]tetrahydrofuranyl, furyl, furastanyl, imidazolidinyl, imidazolinyl, imidazolyl, 1H-indazolyl, indole alkenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazine, phenothiazine, benzoxanthinyl, phenoxazinyl, phthalazinyl, piperazinyl, piperidinyl, piperidone, 4-piperidone, piperonyl, pteridinyl, purinyl, pyranyl, pyrazinyl, pyrazolidinyl, pyrazoiinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyi, tetrazolyl, 6H-1,2,5-thiadiazinyl, 1,2,3-thiadiazolyl, 1,2,4-thiadiazolyl, 1,2,5-thiadiazolyl, 1,3,4 thiadiazolyl, thianthrenyl, thiazolyl, isothiazolylthiophenyl, thienooxazolyl, thienothiazolyl, thienoimidazolyl, thienyl, triazinyl, 1,2,3- triazolyl, 1,2,4-triazolyl, 1,2,5-triazolyl, 1,3,4-triazolyl, and xanthenyl. Fused rings and spiro compounds are also included.

Unless otherwise stated, the term "heteroalkyl" ot the specific terms (such as heteroalkyl, heteroalkenyl, heteroalkynyl, heteroaryl, etc.), by itself or in combination with another term, means a stable straight or branched chain, or cyclic hydrocarbon radical, or combinations thereof, consisting of the stated number of carbon atoms and at least one heteroatom. In some embodiments, the term "heteroalkyl", by itself or in combination with another term, means a stable straight or branched chain hydrocarbon radical, or combination thereof, consisting of the stated number of carbon atoms and at least one heteroatom. In a typical embodiment, the heteroatom is selected from B, O, N, and S, wherein the nitrogen and sulfur atoms are optionally oxidized and the nitrogen heteroatom are optionally quaternized. The heteroatom or heteroatom radical may be placed at any position of the hetero hydrocarbon radical, including the position at which the hydrocarbon radical is attached to the remainder of the molecule. Examples include, but not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two heteroatoms may be consecutive, such as —CH$_2$—NH—OCH$_3$.

The term "heteroalicyclic" refers to a monocyclic or fused ring group having in the ring(s) of 3 to 12 atoms, i.e. 3, 4, 5, 6, 7, 8, 9, 10, 11 or 12 ring atoms, in which one or two ring atoms are heteroatoms selected from N, O, or S(O)$_n$ (where n is 0, 1, or 2), the remaining atoms being C. Such rings may be saturated or unsaturated (for example having one or more double bonds), but the rings do not have a completely conjugated nT-electron system. Examples of 3-membered saturated heteroalicyclic rings include, but not limited to,

Examples of 4-membered saturated heteroalicyclic rings include, but not limited to,

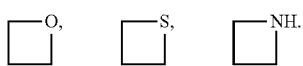

Examples of 5-membered saturated heteroalicyic rings include, but not limited to,

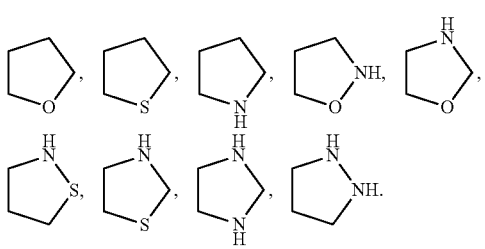

Examples of the 6-membered saturated heteroalicyclic rings include, but not limited to,

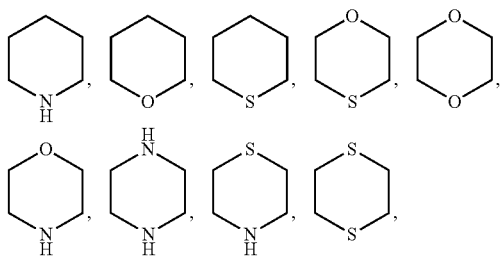

Examples of 7-membered saturated heteroalicyclic rings but not limited to,

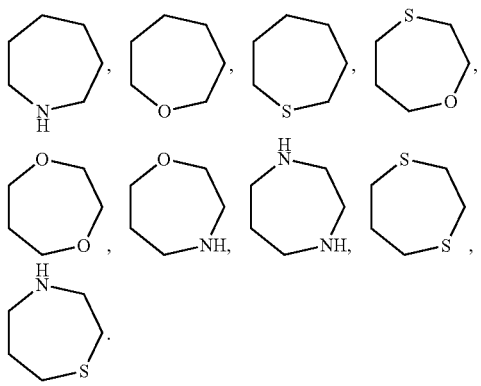

Examples of 5-membered unsaturated heteroalicyclic rings include, but not limited to,

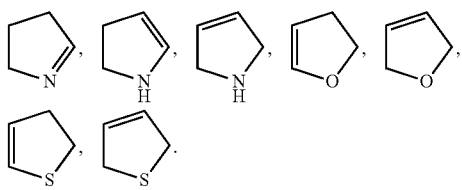

Examples of 6-membered unsaturated heteroalicyclic rings include, but not limited to,

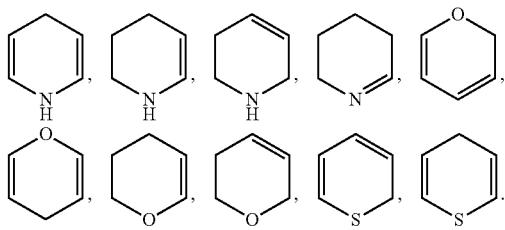

The term "heterocycloalkyl" refers to the remaining group after one hydrogen atom being removed from a "heteroalicyclic" molecule. The heterocycloalkyl may be unsubstituted or hydrogen atoms thereof may be optionally substituted by a substituent. The substituents include, but not limited to, alkyl, alkoxy, =O, aryl, arylalkyl, —COOH, —CN, amino, halogen or hydroxy.

Unless otherwise stated, the term "aryl" means a polyunsaturated, aromatic, hydrocarbon substituent which may be mono-, di-, or poly-substituted, or may be monovalent, divalent, or polyvalent, or which may be a single ring or multiple rings (such as 1 to 3 rings; at least one of which is aromatic), which are fused together or covalently linked. The term "heteroaryl" refers to an aryl group (or ring) containing one to four heteroatoms. In one illustrative example, the heteroatom is selected from B, N, O, and S, wherein the nitrogen and sulfur atoms are optionally oxidized and the nitrogen atom is optionally quaternized. A heteroaryl group can be attached to the remainder of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazole, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. The substituents for each of the above noted aryl and heteroaryl ring systems are selected from acceptable substituents described below.

Unless otherwise stated, aryl, when used in combination with other terms (e.g., aryloxy, arylthioxy, arylalkyl) includes both aryl and heteroaryl rings as defined above. Thus, the term "aralkyl" is intended to include those radicals in which an aryl groups is attached to an alkyl group (e.g., benzyl, phenethyl, pyridylmethyl, etc.), including those alkyl groups in which a carbon atom (e.g., a methylene group) has been replaced by, for example, an oxygen atom, for example phenoxymethyl, 2-pyridyloxymethyl 3-(1-naphthyloxy)propyl and the like.

DETAILED EMBODIMENTS OF THE INVENTION

Figure 1:
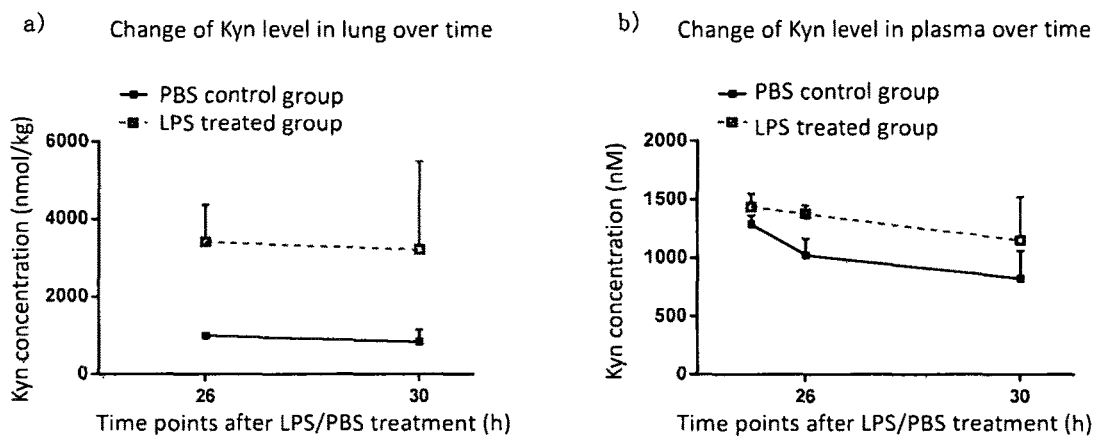
FIG. 1 shows experimental results of experimental Example 3A, and after LPS inducing, the Kyn level in lung and plasma of C57BL/6 mice were increased relative to that in the control group treated with PBS.

The compounds of the present invention may be prepared by various synthesis methods known to the person skilled in the art, including the specific embodiments listed below, the embodiments formed by combining the specific embodiments with other chemical synthesis methods, and equivalent replacements known to the person skilled in the art, and the preferred embodiments include, but not limited to, the Examples of the present invention.

Solvents used in the present invention are commercially available. The following abbreviations are used in the present invention: DMF represents N,N-dimethylformamide; DIBAL-H represents diisobutyl aluminium hydride; THF represents tetrahydrofuran; DCM represents dichloromethane; n-BuLi represents n-butyllithium; TBSOTf represents tert-butyldimethylsilyl trifluoromethanesulfonate; TLC represents thin-layer chromatography; DMAP represents 4-dimethylaminopyridine; LiHMDS represents lithium bis(trimethylsilyl)amide; CDI represents carbonyldiimidazole; NMP represents N-methylpyrrolidone; EA represents ethyl acetate; SFC represents chiral supercritical fluid chromatography; P(Cy)$_3$ represents tricyclohexylphosphine; HBTU represents O-benzotriazole-tetramethyl-uronium-hexafluorophosphate; DAST fluoroborate represents N,N-diethylamino-S,S-difluorosulfiliminium tetrafluoroborate; HATU represents O-(7-azabenzotriazol-1-yl)-N,N,N',N'-tetramethyluronium hexafluorophosphate; DIEA represents N,N-diisopropylethylamine; Ts- represents p-toluenesulfonyl; PE represents petroleum ether; DMSO represents dimethylsulfoxide; EtOAc represents ethyl acetate; Boc- represents tert-butoxycarbonyl.

Dess-Martin reagent represents 1,1,1-triacetoxy-1,1-dihydro-1,2-benziodoxol-3-(1H)-one.

The compounds are named manually or the ChemDraw® software, and the supplier's catalog names are used for the commercially available compounds.

When the compound of the Examples in the present invention has multiple chiral centers, different stereoisomers can be separated by chiral supercritical fluid chromatography, and different retention times correspond to isomers with different configurations.

The following Examples are given to describe the present application in detail, but the scope of the present invention is not limited thereto.

EXAMPLES

Examples 1 to 3: 1-cyclohexyl-2-(2-(trifluoromethyl)-2,8-dihydroimidazo[1',5':1,5]pyrrolo[3,4-c]pyrazol-8-yl)ethanol Example 1A: ethyl 4-iodo-1H-pyrazole-3-carboxylate

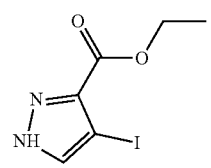

Iodine (54.33 g, 214.07 mmol) was added into a solution of ethyl 1H-pyrazole-3-carboxylate (30 g, 214.07 mmol) in acetonitrile, followed by the addition of ammonium cerium nitrate (117.36 g, 214.07 mmol). The mixture was stirred at 20° C. for 16 h, added with a cold 5% aqueous NaHSO$_3$ solution (400 mL), filtered through diatomaceous earth, and washed with water (200 mL) and ethyl acetate (500 mL). The filtrate was evaporated in a rotary evaporator to remove the organic solvent therein, and then extracted with ethyl acetate (200 mL×5). The resulting organic phase was washed with water (50 mL×2) and saturated brine (500 mL), dried over anhydrous sodium sulfate, filtered and evaporated. The residue obtained was purified by column chromatography to give the title compound as a brown liquid (40 g, 69.32%). $^1$H NMR (400 MHz, DMSO-d6) δ=7.99 (br. s., 1H), 4.29 (q, J=7.1 Hz, 2H), 1.31 (t, J=7.0 Hz, 3H).

Example 1B: ethyl 1-(bromodifluoromethyl)-4-iodo-1H-pyrazole-3-carboxylate

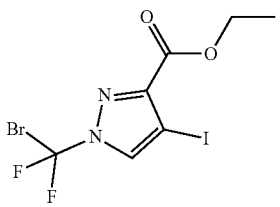

At 0° C., NaH (902.12 mg, 22.55 mmol, 60%) was added portionwise into a solution of Example 1A (5 g, 18.79 mmol) in DMF (30 mL) and stirred for 30 min. A solution of dibromodifluoromethane (9.00 g, 42.89 mmol) in DMF (30 mL) was added and stirred at 20° C. for 16 h. The reaction solution was quenched with water (100 mL) and extracted with ethyl acetate (50 mL×3). The combined organic phase was washed with brine (100 mL), dried over anhydrous sodium sulfate, filtered and evaporated to give a residue. The residue was purified by column chromatography to give the title compound as a brown liquid (2 g, 26.95%). $^1$H NMR (400 MHz, CHLOROFORM-d) δ=8.00 (s, 1H), 4.48 (q, J=7.3 Hz, 2H), 1.45 (t, J=7.2 Hz, 3H).

Example 1C: ethyl 4-iodo-1-(trifluoromethyl)-1H-pyrazole-3-formate

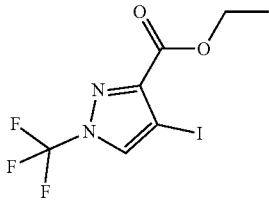

Hydrogen fluoride pyridine complex (33 g, 332.99 mmol) was added to a solution of Example 1B (6.5 g, 16.46 mmol) in isopropanol (15 mL), and then red mercuric oxide (3.57 g, 16.46 mmol) was added in portions. The mixture was stirred in a teflon sealed tank at 50° C. for 48 h. After completion, the reaction solution was poured into a 25% aqueous KF solution (300 mL), and filtered. The filtrate was extracted with ethyl acetate (3×100 mL). The combined organic phase was washed with brine (300 mL), dried over anhydrous sodium sulfate, filtered and evaporated. The residue was purified by column chromatography to give the title compound as a brown liquid (4.7 g, 86.39%). $^1$H NMR (400 MHz, CHLOROFORM-d) δ=8.01 (s, 1H), 4.49 (q, J=7.0 Hz, 2H), 1.46 (t, J=7.2 Hz, 3H).

Example 1D: 4-iodo-1-(trifluoromethyl)-1-pyrazol-3-yl)methanol

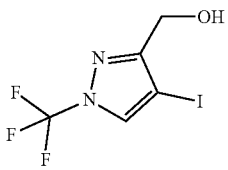 [SMILES: OCc1nn(C(F)(F)F)cc1I]

A solution of DIBAL-H (1 M, 8.97 mL) in diethyl ether was added dropwise into a solution of Example 1C (1 g, 2.99 mmol) in THF (10 mL) at −78° C., stirred for 2 h, and then warmed up to 25° C. with stirring for 14 h. The reaction solution was quenched with water (20 mL) at 0° C. and extracted with ethyl acetate (10 mL×3). The combined organic layers were washed with brine (20 mL), dried over anhydrous sodium sulfate, filtered and evaporated. The residue was purified by column chromatography to give the title compound as a yellow oil (0.6 g, 68.72%). $^1$H NMR (400 MHz, CHLOROFORM-d) δ=7.88 (s, 1H), 4.71 (d, J=6.3 Hz, 2H), 2.11 (t, J=6.3 Hz, 1H).

Example 1E: 4-iodo-1-(trifluoromethyl)-1H-pyrazole-3-carboxaldehyde

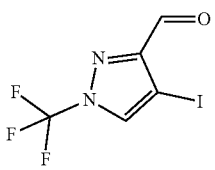

Dess-Martin reagent (870.34 mg, 2.05 mmol) was added into a solution of Example 1D (0.5 g, 1.71 mmol) in DCM (10 mL). The mixture was stirred at room temperature for 2 h, filtered, added with water (20 mL) and extracted with ethyl acetate (10 mL×3). The combined organic layers were washed with brine (20 mL), dried over anhydrous sodium sulfate, filtered and concentrated. The residue was purified by column chromatography to give the title compound as a colorless oil (0.35 g, 70.58%). $^1$H NMR (400 MHz, CHLOROFORM-d) δ=10.03 (s, 1H), 8.02 (s, 1H).

Example 1F: 1-(4-iodo-1-(trifluoromethyl)-1H-pyrazol-3-yl)ethanol

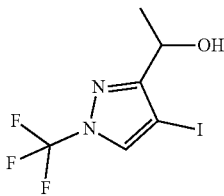

A solution of methylmagnesium iodide (3 M, 6.32 mL) in diethyl ether was added into a solution of Example 1E (5 g, 17.24 mmol) in THF (22 mL) at −70° C., with stirring for 2 h. The reaction solution was quenched with a saturated aqueous ammonium chloride solution (50 mL) and extracted with ethyl acetate (50 mL×3). The combined organic layers were washed with brine (100 mL), dried over anhydrous sodium sulfate, filtered and concentrated. The residue was purified by column chromatography to give the title compound as a colorless oil (2.8 g, 53.07%). ¹H NMR (400 MHz, CHLOROFORM-d) δ=7.86 (s, 1H), 4.96 (d, J=6.5 Hz, 1H), 2.37 (br. s., 1H), 1.61 (s, 3H).

Example 1 G: 1-(4-iodo-1-(trifluoromethyl)-1H-pyrazol-3-yl)ethanone

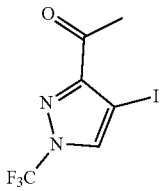

Dess-Martin reagent (4.66 g, 10.98 mmol) was added into a solution of Example 1F (2.8 g, 9.15 mmol) in DCM (12 mL). The mixture was stirred at room temperature for 3 h, and added with DCM (50 mL). After filtration, the filtrate was added with water (50 mL) and extracted with DCM (50 mL×3). The combined organic layers were washed with brine (100 mL), dried over anhydrous sodium sulfate, filtered and concentrated. The residue was purified by column chromatography to give the title compound (2.5 g, 89.87%). ¹H NMR (400 MHz, CHLOROFORM-d) δ=7.96 (s, 1H), 2.65 (s, 3H).

Example 1H: 3-cyclohexyl-3-hydroxy-1-(4-iodo-1-(trifluoromethyl)-1H-pyrazol-3-yl)propan-1-one

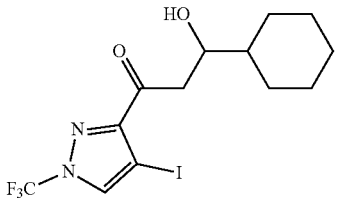 [SMILES: O=C(CC(O)C1CCCCC1)c1nn(C(F)(F)F)cc1I]

n-BuLi (2.5 M, 3.47 mL) was added dropwise into a solution of diisopropylamine (958.61 mg, 9.47 mmol, 1.33 mL) in THF (2.5 mL) at −78° C., stirred at 0° C. for 30 min, and then cooled to −30° C., and a solution of Example 1G (2.4 g, 7.89 mmol) in THF (0.5 mL) was added dropwise. After stirring for 1 h, the reaction solution was cooled to −78° C., added with cyclohexanecarbaldehyde (1.33 g, 11.84 mmol), and then warmed up to −40° C. with stirring for 2 h. The reaction solution was quenched with a saturated ammonium chloride solution (50 mL) and extracted with ethyl acetate (30 mL×3). The combined organic layers were washed with brine (50 mL), dried over anhydrous sodium sulfate, filtered and concentrated. The residue was purified by column chromatography to give the title compound as colorless oil (1.8 g, 54.88%). ¹H NMR (400 MHz, CHLOROFORM-d) δ=7.98 (s, 1H), 4.04-3.95 (m, 1H), 3.32-3.25 (mi, 1H), 3.21-3.11 (m, 1H), 2.75 (d, J=4.0 Hz, 1H), 1.91 (d, J=13.1 Hz, 1H), 1.78-1.66 (m, 4H), 1.48-1.43 (m, 1H), 1.23-1.06 (m, 5H).

Example 1I: 3-((tert-butyldimethylsilyl)oxy)-3-cyclohexyl-3-hydroxy-1-(4-iodo-1-(trifluoromethyl)-1H-pyrazol-3-yl)propan-1-one

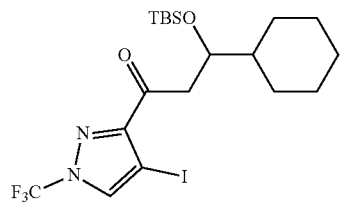 [SMILES: CC(C)(C)[Si](C)(C)OC(CC(=O)c1nn(C(F)(F)F)cc1I)C1CCCCC1]

2,6-Dimethyl pyridine (1.39 g, 12.98 mmol) and TBSOTf (2.29 g, 8.65 mmol) were added into a solution of Example 1H (1.8 g, 4.33 mmol) in DCM (1 mL) at 0° C., and stirred for 1 h. The reaction solution was quenched with water (50 mL) and extracted with ethyl acetate (30 mL×3). The combined organic layers were washed with brine (50 mL), dried over anhydrous sodium sulfate, filtered and concentrated. The residue was purified by column chromatography to give the title compound as colorless oil (1.8 g, 78.37%). ¹H NMR (400 MHz, CHLOROFORM-d) δ=7.97 (s, 1H), 4.26-4.19 (m, 1H), 3.29 (dd, J=7.3, 15.3 Hz, 1H), 3.07 (dd, J=5.1, 15.4 Hz, 1H), 1.79-1.70 (m, 4H), 1.48-1.41 (m, 1H), 1.28-1.06 (m, 6H), 0.84 (s, 9H), 0.07 (s, 3H), −0.03 (s, 3H).

Example 1J: 3-((tert-butyldimethylsilyl)oxy)-3-cyclohexyl-3-hydroxy-1-(4-iodo-1-(trifluoromethyl)-1H-pyrazol-3-yl)propan-1-ol

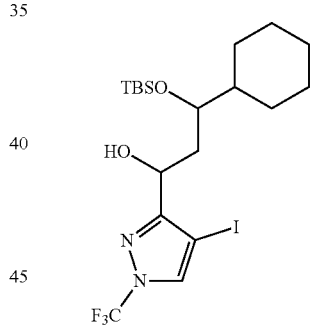

(3aS)-1-methyl-3,3-diphenyl-3a,4,5,6-tetrahydropyrrolo[1,2-c][1,3,2]oxazaborolidine (1 M, 378 µL) and BH₃-Me₂S (10 M, 189 µL) were added to a solution of Example 11 (1 g, 1.89 mmol) in THF (10 mL). The mixture was stirred at room temperature, poured into water (50 mL) and extracted with ethyl acetate (20 mL×4). The combined organic layers were washed with brine (50 mL), dried over anhydrous sodium sulfate, filtered and concentrated. The residue was purified by column chromatography to give the title compound (two isomers) as colorless oil (isomer 1: 120 mg, 11.92%; isomer 2: 250 mg, 24.84%).

Isomer 1: ¹H NMR (400 MHz, CHLOROFORM-d) δ=7.84 (s, 1H), 5.05 (d, J=9.8 Hz, 1H), 3.83 (dt, J=3.5, 6.1 Hz, 1H), 3.24 (d, J=3.8 Hz, 1H), 2.03-1.90 (m, 2H), 1.78 (d, J=8.0 Hz, 4H), 1.68 (d, J=12.5 Hz, 1H), 1.29-1.09 (m, 4H), 0.97-0.91 (m, 11H), 0.18 (s, 3H), 0.12-0.08 (m, 3H).

Isomer 2: ¹H NMR (400 MHz, CHLOROFORM-d) δ=7.85 (s, 1H), 4.93 (dd, J=3.4, 9.2 Hz, 1H), 3.88 (td, J=4.0, 8.5 Hz, 1H), 3.51 (br. s., 1H), 2.03-1.92 (m, 2H), 1.82-1.73

(m, 4H), 1.68 (d, J=11.3 Hz, 2H), 1.21-1.02 (m, 5H), 0.93 (s, 9H), 0.14 (s, 3H), 0.12-0.10 (m, 3H).

Example 1K: 3-((tert-butyldimethylsilyl)oxy)-3-cyclohexyl-1-(4-iodo-1-(trifluoromethyl)-1H-pyrazol-3-yl)propane-1-methanesulfonate

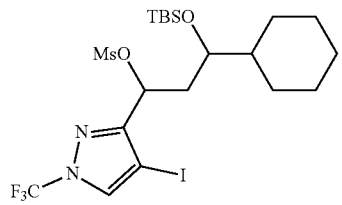 [SMILES: CC(C)(C)[Si](C)(C)OC(CC(OS(C)(=O)=O)c1nn(C(F)(F)F)cc1I)C1CCCCC1]

Triethylamine (114.03 mg, 1.13 mmol) and methanesulfonyl chloride (51.63 mg, 450.75 µmol) were added into a solution of Example 1J (200 mg, 375.62 µmol) in DCM (2 mL) at 0° C. and stirred for 1 h. The reaction was quenched with water (10 mL) and extracted with ethyl acetate (10 mL×3). The combined organic layers were washed with brine (50 mL), dried over anhydrous sodium sulfate, filtered and concentrated, to give the title compound as colorless oil (150 mg, 65.41%), which was used directly in the next step. $^1$H NMR (400 MHz, CHLOROFORM-d) δ=7.90 (s, 1H), 5.81 (dd, J=3.8, 9.5 Hz, 1H), 3.78-3.71 (m, 1H), 2.89 (s, 3H), 2.23 (ddd, J=3.1, 9.6, 14.4 Hz, 1H), 1.92 (ddd, J=3.9, 8.6, 14.4 Hz, 1H), 1.80-1.71 (m, 3H), 1.64 (d, J=12.0 Hz, 2H), 1.49-1.42 (m, 1H), 1.29-1.03 (m, 5H), 0.94 (s, 9H), 0.18 (s, 3H), 0.09 (s, 3H).

Example 1L: 3-(3-((tert-butyldimethylsilyl)oxy)-3-cyclohexyl-1-(1H-imidazol-1-yl)propyl)-4-iodo-1-(trifluoromethyl)-1H-pyrazole

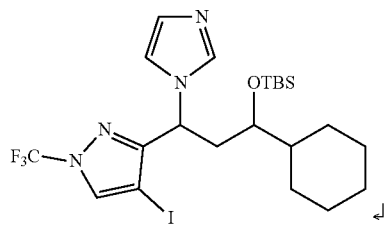 [SMILES: CC(C)(C)[Si](C)(C)OC(CC(c1nn(C(F)(F)F)cc1I)n1ccnc1)C1CCCCC1]

NaH (39.31 mg, 982.72 µmol, purity 60%) was added portionwise into a solution of imidazole (66.90 mg, 982.72 µmol) in DMF (1 mL) at 0° C. with stirring for 2 h, and then a solution of Example 1K (150 mg, 245.68 µmol) in DMF (1 mL) was added. The reaction system was stirred at 60° C. for 2 h. The reaction solution was quenched with water (20 mL) and extracted with ethyl acetate (10 mL×4). The combined organic layers were washed with water (5 mL×3) and brine (20 mL), dried over anhydrous sodium sulfate, filtered and concentrated. The residue was purified by column chromatography to give the title compound as colorless oil (120 mg, 83.85%). $^1$H NMR (400 MHz, CHLOROFORM-d) δ=7.87 (s, 1H), 7.60 (s, 1H), 7.03 (s, 1H), 6.93 (s, 1H), 5.45 (dd, J=5.1, 9.9 Hz, 1H), 3.48 (dd, J=3.9, 8.7 Hz, 1H), 2.73-2.66 (m, 1H), 2.12-2.05 (m, 1H), 1.80-1.65 (m, 5H), 1.38-1.30 (m, 1H), 1.27-1.04 (m, 5H), 0.92 (s, 9H), −0.01 (s, 3H), −0.08 (s, 3H).

Example 1M: 8-(2-((tert-butyldimethylsilyl)oxy)-2-cyclohexylethyl)-2-(trifluoromethyl)-2,8-dihydroimidazo[1',5':1,5]pyrrolo[3,4-c]pyrazole

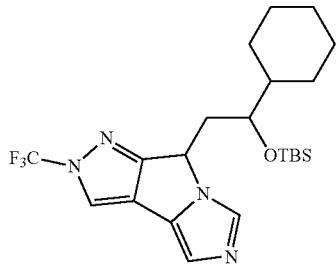 [SMILES: CC(C)(C)[Si](C)(C)OC(CC1c2nn(C(F)(F)F)cc2-c2cncn21)C1CCCCC1]

A solution of Example 1L (100 mg, 171.67 µmol), palladium acetate (3.85 mg, 17.17 µmol), tricyclohexylphosphine (9.63 mg, 34.33 µmol), pivalic acid (8.77 mg, 85.84 µmol) and potassium carbonate (71.18 mg, 515.01 µmol) in NMP (2 mL) was purged with nitrogen gas three times and reacted in a microwave reactor at 180° C. for 10 min. After the reaction was completed, the reaction solution was poured into water (20 mL) and extracted with ethyl acetate (10 mL×4). The combined organic layers were washed with brine (20 mL), dried over anhydrous sodium sulfate, filtered and concentrated to give the crude title compound (100 mg), which was used directly in the next step. LCMS (ESI) m/z: 455 (M+1).

Preparation of the Title Compounds (Examples 1 to 3)

1-cyclohexyl-2-(2-trifluoromethyl)-2,8-dihydroimidazo[1',5':1,5]pyrrolo[3,4-c]pyrazol-8-yl)ethanol

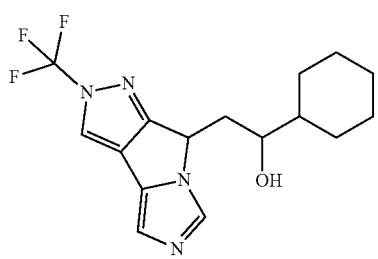 [SMILES: OC(CC1c2nn(C(F)(F)F)cc2-c2cncn21)C1CCCCC1]

Example 1M (100 mg, 219.97 mmol) was added into a 1% hydrochloric acid solution in ethanol (2 mL) and stirred at 50° C. for 2 h. The reaction solution was spin dried in a rotary evaporator to give a crude compound, and the title compound (40 mg, 44.88%) was obtained by separation with HPLC. By SFC chiral separation, a mixture of isomers 1 and 2 (Example 1), isomer 3 (Example 2) and isomer 4 (Example 3) were obtained. LCMS (ESI) m/z: 341 (M+1).

SFC chiral separation conditions: "Column: Chiralcel OD-3 150×4.6 mm I.D., 3 um; mobile phase: A: $CO_2$ B: ethanol (0.05% DEA); Gradient: 5%~40% of B in 5 min and hold 40% for 2.5 min".

Example 1: $^1$H NMR (400 MHz, METHANOL-d4) δ=9.25 (s, 0.45H), 9.16 (s, 0.55H), 8.54 (s, 1H), 7.69 (d, J=1.5 Hz, 1H), 5.91 (dd, J=3.6, 7.9 Hz, 0.55H), 5.84 (dd, J=5.8, 8.3 Hz, 0.45H), 3.96 (ddd, J=2.4, 5.7, 11.0 Hz, 0.45H), 3.45 (ddd, J=3.3, 6.2, 9.9 Hz, 0.55H), 2.49-2.40 (m, 0.6H), 2.35-2.26 (m, 1H), 2.22-2.14 (m, 0.5H), 1.89 (d, J=12.8 Hz, 1H), 1.80 (br. s., 2H), 1.70 (d, J=11.5 Hz, 2H), 1.47-1.36 (m, 1H), 1.34-1.15 (m, 3H), 1.12-0.98 (m, 2H). SFC RT=3.620, 3.981 min.

Example 2: ¹H NMR (400 MHz, METHANOL-d4) δ=9.07 (br. s., 1H), 8.52 (s, 1H), 7.64 (br. s., 1H), 5.88 (dd, J=3.5, 8.0 Hz, 1H), 3.54-3.40 (m, 1H), 2.48-2.37 (m, 1H), 2.27 (ddd, J=3.1, 8.0, 14.9 Hz, 1H), 1.89 (d, J=12.8 Hz, 1H), 1.79 (br. s., 2H), 1.70 (d, J=12.3 Hz, 2H), 1.46-1.35 (m, 1H), 1.33-1.17 (m, 3H), 1.10-0.97 (m, 2H). SFC RT=3.124 min.

Example 3: ¹H NMR (400 MHz, METHANOL-d4) δ=9.14 (br. s., 1H), 8.51 (s, 1H), 7.63 (s, 1H), 5.81 (dd, J=5.5, 8.3 Hz, 1H), 3.95 (ddd, J=2.3, 5.7, 10.9 Hz, 1H), 2.32 (ddd, J=5.5, 10.9, 13.9 Hz, 1H), 2.20-2.12 (m, 1H), 1.88 (d, J=12.0 Hz, 1H), 1.84-1.68 (m, 4H), 1.41 (ddd, J=3.0, 5.6, 11.7 Hz, 1H), 1.34-1.18 (m, 3H), 1.15-1.05 (m, 2H). SFC RT=3.655 min.

Example 4: 1-cyclohexyl-2-(4H-thieno[3,4]pyrrolo[1,5-a]imidazol-4-yl)ethanol

Example 4A: 2-bromo-3-thiophenecarboxylic acid

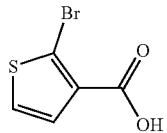

At low temperature (−78° C.), n-BuLi (24.99 g, 390.16 mmol) was slowly added dropwise to a solution of diisopropylamine (39.48 g, 390.16 mmol) in tetrahydrofuran (250 mL). After completion of addition, the reaction solution was slowly warmed up to 0° C., stirred for half an hour and then cooled to −78° C. A solution of thiophene-3-carboxylic acid (25 g, 195.08 mmol) in tetrahydrofuran (100 mL) was added dropwise. After completion of dropwise addition, the reaction solution was slowly warmed up to 20° C. with stirring for half an hour, and added with CBr₄ (64.69 g, 195.08 mmol) with stirring for 1 h. TLC showed complete reaction, the reaction solution was quenched with saturated NH₄Cl (20 mL), then added with 1N HCl (300 mL) to acidize, and extracted with DCM (300 mL×3). The organic phase was washed with saturated brine, dried over anhydrous sodium sulfate, filtered and concentrated. The residue was recrystallized in 50% ethanol (500 mL) to give the title compound (40 g, crude), which was used directly in the next step. ¹H NMR (400 MHz, DMSO-d6) δ=7.64-7.60 (m, 1H), 7.31 (d, J=5.8 Hz, 1H).

Example 4B: 2-bromo-3-thiophenecarboxylic acid-2-pyridyl ester

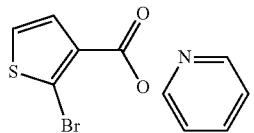

Bis(2-pyridine)carbonate (17.44 g, 80.66 mmol) and DMAP (985.38 mg, 8.07 mmol) were added into a solution of Example 4A (16.7 g, 80.66 mmol) in dichloromethane (200 mL) at room temperature. The reaction solution was stirred at room temperature for 1 h, and TLC showed completed reaction. The reaction solution was spin dried and directly purified by column chromatography (petroleum ether/ethyl acetate 10:1-5/1) to give the title compound (12 g, 42.23 mmol, yield of 52.36%, a brown liquid). ¹H NMR (400 MHz, CDCl3) δ=8.47 (dd, J=1.6, 4.8 Hz, 1H), 7.85 (dt, J=2.0, 7.6 Hz, 1H), 7.59 (d, J=5.6 Hz, 1H), 7.33-7.28 (m, 2H), 7.22 (d, J=8.0 Hz, 1H).

Example 4C: 2-bromo-3-thiophenemethyl Keone

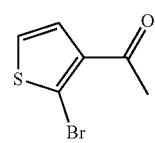

Methylmagnesium chloride (3.16 g, 42.23 mmol, 3.13 mL) was added into a solution of Example 4B (12 g, 42.23 mmol) in tetrahydrofuran at low temperature (−78° C.). The reaction solution was stirred for 1 h and slowly warmed up to 20° C. TLC showed complete reaction. The reaction solution was quenched with saturated ammonium chloride solution (100 mL), extracted with ethyl acetate (100 mL×2), washed with saturated brine (100 mL), dried over anhydrous sodium sulfate, filtered and concentrated, and purified by column chromatography (petroleum ether/ethyl acetate=10:1-5/1) to give the title compound (6 g, 29.26 mmol, yield of 69.28%, colorless oil). ¹H NMR (400 MHz, CDCl₃) δ=7.36 (d, J=5.6 Hz, 1H), 7.24 (d, J=5.6 Hz, 1H), 2.63 (s, 3H).

Example 4D: 1-(2-bromo-3-thienyl)-3-cyclohexyl-3-hydroxy-propan-1-one

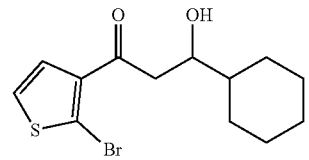 [SMILES: O=C(CC(O)C1CCCCC1)c1ccsc1Br]

Example 4C (2 g, 9.75 mmol) was added in a solution of LiHMDS (1 M, 19.50 mL) in tetrahydrofuran (20 mL) at −15° C. The reaction solution was stirred for half an hour, then added with a solution of cyclohexylcarboxaldehyde (1.20 g, 10.73 mmol, 1.29 mL) in tetrahydrofuran (10 mL), with further stirring for half an hour. The reaction solution was quenched with saturated ammonium chloride solution (20 mL), extracted with ethyl acetate (20 mL×2), washed with saturated brine (20 mL), dried over anhydrous sodium sulfate, filtered and concentrated, and then purified by column chromatography (petroleum ether/ethyl acetate=10:1-5/1) to give the title compound (500 mg, 1.58 mmol, yield of 16.21%, a colorless liquid). ¹H NMR (400 MHz, CDCl₃) δ=7.38 (d, J=6.0 Hz, 1H), 7.29 (d, J=2.0 Hz, 1H), 4.06-3.93 (m, 1H), 3.25-2.95 (m, 3H), 1.86-1.62 (m, 7H), 1.37-1.02 (m, 7H).

Example 4E: 1-(2-bromo-3-thienyl)-3-[tert-butyl (dimethyl)silyl]oxy-3-cyclohexyl-propan-1-one

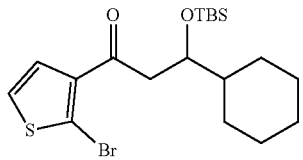 [SMILES: CC(C)(C)[Si](C)(C)OC(CC(=O)c1ccsc1Br)C1CCCCC1]

TBSOTf (4.17 g, 15.76 mmol, 3.62 mL) and 1,6-dimethyl pyridine (2.53 g, 23.64 mmol) were added to a solution of Example 4D (2.50 g, 7.88 mmol) in dichloromethane at 0° C. The reaction solution was stirred at 20° C. for 5 min, and then added with ethyl acetate (10 mL) and water (5 mL). The organic phase was washed with saturated brine (10 mL), dried over anhydrous sodium sulfate, filtered and concentrated. The title compound (2.80 g, 6.49 mmol, yield of 82.35%, a colorless liquid) was obtained by column chromatography (petroleum ether/ethyl acetate=10:1-5/1). $^1$H NMR (400 MHz, CDCl$_3$) δ=7.34 (d, J=5.8 Hz, 1H), 7.23 (d, J=5.8 Hz, 1H), 4.22 (td, J=4.0, 7.7 Hz, 1H), 3.21-3.08 (m, 1H), 2.91 (dd, J=4.5, 16.1 Hz, 1H), 1.76 (br. s., 4H), 1.50-1.38 (m, 2H), 1.26-1.04 (m, 6H), 0.87 (s, 9H), 0.28-0.25 (m, 1H), 0.05-0.00 (m, 6H).

Example 4F: 1-(2-bromo-3-thienyl)-3-[tert-butyl (dimethyl)silyl]oxy-3-cyclohexyl-propan-1-ol

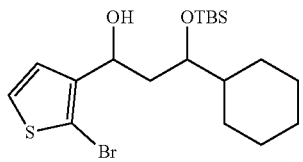 [SMILES: CC(C)(C)[Si](C)(C)OC(CC(O)c1ccsc1Br)C1CCCCC1]

NaBH$_4$ (1.23 g, 32.45 mmol) was added in a solution of Example 4E (2.8 g, 6.49 mmol) in methanol (20 mL) at 0° C. The reaction solution was stirred at 20° C. for 20 min. The reaction solution was added with saturated ammonium chloride solution (30 mL), and extracted with ethyl acetate (20 mL×2). The organic phase was washed with saturated brine (20 mL), dried over anhydrous sodium sulfate, filtered and spin dried. The title compound (2 g, crude, a colorless liquid, which was used in the next step directly) was obtained by column chromatography (petroleum ether/ethyl acetate=20: 1-10/1). $^1$H NMR (400 MHz, CDCl$_3$) δ=7.24 (d, J=5.6 Hz, 1H), 7.07 (dd, J=1.2, 5.6 Hz, 1H), 5.18-4.87 (m, 1H), 4.16-3.88 (m, 1H), 3.74-3.60 (m, 1H), 1.85-1.74 (m, 5H), 1.33-1.09 (m, 4H), 0.95 (d, J=2.4 Hz, 9H), 0.19-0.08 (m, 6H).

Example 4G: [3-(2-bromo-3-thienyl)-1-cyclohexyl-3-imidazol-1-yl-propoxy]-tert-butyl(dimethyl)silane

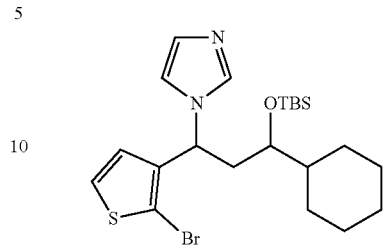

CDI (1.31 g, 8.05 mmol) was added in a solution of Example 4F (700 mg, 1.61 mmol) in acetonitrile (15 mL) at 20° C. The reaction solution was stirred at 70° C. for 40 min. After completion of reaction, the reaction solution was concentrated, and purified by column chromatography (petroleum ether/ethyl acetate=10:1-5/1) to give the title compound (750 mg, 1.27 mmol, yield of 78.99%, purity of 82%, a colorless liquid). $^1$H NMR (400 MHz, CDCl$_3$) δ=8.15-8.10 (m, 1H), 7.42 (t, J=1.3 Hz, 1H), 7.30 (t, J=5.6 Hz, 1H), 7.09-7.05 (m, 1H), 6.96 (t, J=5.8 Hz, 1H), 6.25-6.07 (m, 1H), 3.73-3.47 (m, 1H), 2.31-2.12 (m, 1H), 1.90-1.64 (m, 6H), 1.57-1.37 (m, 1H), 1.31-0.97 (m, 6H), 0.92 (s, 9H), 0.05-0.00 (m, 6H).

Example 4H: tert-butyl-[1-cyclohexyl-2-(4H-thieno[3,4]pyrrolo[1,5-a]imidazol-4-yl)ethoxy]-dimethylsilane

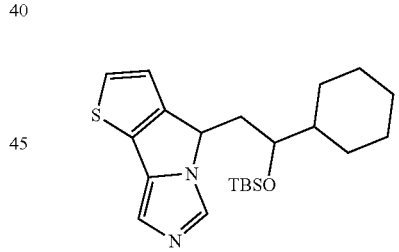

Pd(OAc)$_2$ (32.50 mg, 144.75 μmol), P(Cy)$_3$ (40.59 mg, 144.75 μmol, 46.66 μL), pivalic acid (14.78 mg, 144.75 μmol, 16.61 μL) and K$_2$CO$_3$ (200.06 mg, 1.45 mmol) were added in a solution of Example 4G (350 mg, 723.77 μmol) in NMP (2 mL). The reaction solution was reacted under microwave irradiation at 180° C. for 10 min. The reaction solution was added with EA (10 mL) and H$_2$O (20 mL). The aqueous phase was extracted with ethyl acetate (10 mL×2). The obtained organic phase was washed with saturated brine, dried over anhydrous sodium sulfate, filtered and spin dried. The title compound (20 mg, crude) was then prepared by separation. LCMS (ESI) m/z: 403 (M+1).

Preparation of the Title Compound (Example 4): 1-cyclohexyl-2-(4H-thieno[3,4]pyrrolo[1,5-a]imidazol-4-yl)ethanol

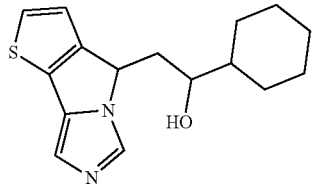 [SMILES: OC(CC1c2ccsc2-c2cncn21)C1CCCCC1]

HCl (2.14 mL, 1207.97 eq) was added in a solution of Example 4H (20 mg, 49.67 μmol) in ethanol (5 mL). The reaction solution was stirred at 60° C. for 1 h. The reaction solution was concentrated and separated to give the title compound (3.00 mg, 8.97 μmol, yield of 18.06%). $^1$H NMR (400 MHz, METHANOL-d4) δ=7.97 (d, J=12.5 Hz, 1H), 7.48-7.41 (m, 1H), 7.20-7.07 (m, 1H), 6.96 (br. s., 1H), 5.38 (ddd, J=4.5, 9.2, 19.4 Hz, 1H), 3.73-3.56 (m, 1H), 2.30-2.13 (m, 1H), 1.93-1.82 (m, 1H), 1.81-1.71 (m, 2H), 1.70-1.61 (m, 2H), 1.43-1.12 (m, 5H), 1.11-0.97 (m, 2H). LCMS (ESI) m/z: 289 (M+1).

Examples 5 to 8: cyclohexyl-2(8H-thieno[3',2':3,4]pyrrolo[1,2-c]imidazol-8-yl)ethanol Example 5A: 3-((tert-butyldimethylsilyl)oxy)-3-cyclohexyl-1-(3-iodothiophen-2-yl)propan-1-ol

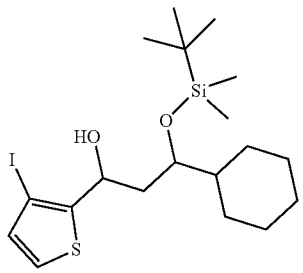 [SMILES: CC(C)(C)[Si](C)(C)OC(CC(O)c1sccc1I)C1CCCCC1]

n-BuLi (2.5 M, 10.47 mL) was added dropwise in a solution of diisopropylamine (2.65 g, 26.18 mmol) in diethyl ether at −78° C., then warmed up to 0° C. and stirred for 30 min. The reaction solution was added with 3-thiophene at −78° C. with stirring for 1 h, and then 3-((tert-butyldimethylsilyl)oxy)-3-cyclohexylpropionaldehyde was added dropwise to the above reaction solution with further stirring for 1 h. The reaction solution was quenched with saturated ammonium chloride solution (50 mL) and extracted with ethyl acetate (50 mL×3). The combined organic layers were washed with brine (100 mL), dried over anhydrous sodium sulfate, filtered and evaporated. The residue was purified by column chromatography to give the title compound (6.2 g, 54.21%). $^1$H NMR (400 MHz, CDCl$_3$) δ=7.22 (d, J=5.0 Hz, 1H), 7.02-6.98 (m, 1H), 5.04 (d, J=8.5 Hz, 1H), 4.02-3.95 (m, 1H), 2.59-2.43 (m, 1H), 1.79-1.71 (m, 7H), 1.29-1.25 (m, 6H), 0.96-0.94 (m, 9H), 0.05 (d, J=2.5 Hz, 6H).

Example 5B: 1-(3-((tert-butyldimethylsilyl)oxy)-3-cyclohexyl-1-(3-iodothiophen-2-yl)propyl)$_1$-1H-imidazole

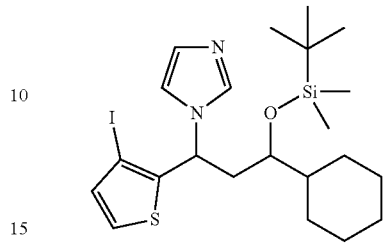

CDI (8.1 g, 390.75 mmol) was added in a solution of Example 5A (8 g, 16.65 mmol) in acetonitrile (180 mL), and heated to reflux with stirring for 3 h. The reaction solution was added with water (100 mL), concentrated to remove the solvent, and extracted with ethyl acetate (50 mL×3). The combined organic layers were washed with saturated brine (50 mL), dried over anhydrous sodium sulfate, filtered and evaporated. The residue was purified by column chromatography to give the title compound as a yellow liquid (2.7 g, 30.56%). $^1$H NMR (400 MHz, CDCl$_3$) δ=7.71-7.59 (m, 1H), 7.25 (d, J=5.3 Hz, 1H), 7.10-6.95 (m, 3H), 5.75-5.56 (m, 1H), 3.54-3.30 (m, 1H), 2.46-2.27 (m, 1H), 2.22-2.12 (m, 1H), 1.82-1.66 (m, 4H), 1.52-1.37 (m, 2H), 1.22-0.98 (m, 5H), 0.97-0.93 (m, 9H), 0.04-−0.01 (m, 6H).

Example 5C: 8-(2-((tert-butyldimethylsilyl)oxy)-2-cyclohexylethyl)-8H-thieno[3',2':3,4]pyrrolo[1,2-c]imidazole

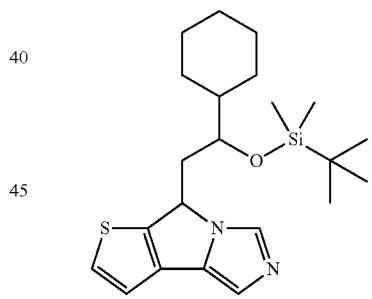

Potassium carbonate (779.50 mg, 5.64 mmol) and the solution of Example 5B (1 g, 1.88 mmol), tricyclohexylphosphine (105.44 mg, 376.00 μmol), pivalic acid (57.6 mg, 564 μmol), and palladium acetate (42.21 mg, 188 μmol) in acetonitrile (180 mL), and the mixture was added with N-methyl pyrrolidone (10 mL), purged with nitrogen gas three times, heated to 180° C. and stirred for 10 min. After cooling, the reaction solution was poured into water (100 mL) and filtered, and the filtrate was extracted with ethyl acetate (50 mL×6). The combined organic layers were washed with water (10 mL×4) and saturated brine (100 mL), dried over anhydrous sodium sulfate, filtered and evaporated. The residue was purified by column chromatography to give the title compound as a black liquid (467 mg, 61.83%). $^1$H NMR (400 MHz, CDCl$_3$) δ=7.68 (s, 1H), 7.36-7.31 (m, 1H), 7.17-7.11 (m, 1H), 6.94 (s, 1H), 5.34-5.25 (m, 1H), 3.99-3.89 (m, 1H), 2.28-2.02 (m, 1H), 1.92-

1.72 (m, 4H), 1.60-1.49 (m, 2H), 1.30-0.97 (m, 6H), 0.94-0.92 (m, 9H), 0.19-0.10 (m, 6H).

Preparation of the Title Compounds (Examples 5 to 8): cyclohexyl-2-(8H-thieno[3',2':3,4]pyrrolo[1,2-c]imidazol-8-yl)ethanol

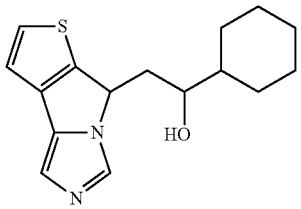 [SMILES: OC(CC1c2sccc2-c2cncn21)C1CCCCC1]

p-Toluenesulfonic acid (2.82 g, 16.38 mmol) was added into a solution of Example 5C (2.2 g, 5.46 mmol) in dichloromethane (220 mL), and stirred overnight at 20° C. The reaction solution was washed with water (10 mL×6) and saturated brine (100 mL), dried over anhydrous sodium sulfate, filtered and evaporated. The residue was purified by column chromatography to give the title compound (1.2 g, 68.58%), and then the compounds of Example 5, Example 6, Example 7, and Example 8 were obtained by chiral separation. LCMS (ESI) m/z: 289 (M+1).

SFC chiral separation conditions: Column: Chiralcel OD-3 150×4.6 mm I.D., 3 um; Mobile phase: A: $CO_2$ B: ethanol (0.05% DEA); Gradient: from 5% to 40% of B in 5 min and hold 40% for 2.5 min, then 5% of B for 2.5 min; Flow rate: 2.5 mL/min; Column temp.: 35° C.

Example 5: $^1$H NMR (400 MHz, METHANOL-d4) δ=9.12 (s, 1H), 7.69 (d, J=5.0 Hz, 1H), 7.49 (s, 1H), 7.34 (d, J=5.0 Hz, 1H), 5.87 (t, J=5.5 Hz, 1H), 3.60-3.48 (m, 1H), 2.38-2.21 (m, 2H), 1.88 (d, J=12.3 Hz, 1H), 1.78 (br. s., 2H), 1.70 (d, J=8.0 Hz, 2H), 1.40-1.16 (m, 4H), 1.11-0.97 (m, 2H). SFC RT=4.590 min.

Example 6: $^1$H NMR (400 MHz, METHANOL-d4) δ=9.17 (s, 1H), 7.70 (d, J=5.3 Hz, 1H), 7.49 (d, J=0.8 Hz, 1H), 7.36 (d, J=5.0 Hz, 1H), 5.84 (dd, J=5.5, 8.8 Hz, 1H), 3.79 (ddd, J=2.8, 5.8, 11.0 Hz, 1H), 2.37 (ddd, J=5.5, 11.0, 13.6 Hz, 1H), 1.97 (ddd, J=2.8, 8.9, 13.7 Hz, 1H), 1.89 (d, J=12.5 Hz, 1H), 1.83-1.74 (m, 2H), 1.69 (br. s., 2H), 1.42 (ddt, J=3.1, 5.8, 11.7 Hz, 1H), 1.34-1.16 (m, 3H), 1.07 (tq, J=3.5, 12.2 Hz, 2H). SFC RT=3.923 min.

Example 7: $^1$H NMR (400 MHz, METHANOL-d4) δ=7.87 (s, 1H), 7.49 (dd, J=0.8, 5.0 Hz, 1H), 7.16 (d, J=5.0 Hz, 1H), 6.86 (s, 1H), 5.48 (dd, J=5.3, 8.0 Hz, 1H), 3.74-3.64 (m, 1H), 2.12-2.03 (m, 1H), 1.92 (ddd, J=3.0, 8.2, 14.1 Hz, 2H), 1.83-1.72 (m, 2H), 1.67 (d, J=12.3 Hz, 1H), 1.42-1.30 (m, 1H), 1.29-1.14 (m, 3H), 1.13-1.00 (m, 2H). SFC RT=3.664 min.

Example 8: $^1$H NMR (400 MHz, METHANOL-d4) δ=7.90 (s, 1H), 7.52 (d, J=5.0 Hz, 1H), 7.23 (d, J=5.0 Hz, 1H), 6.89 (s, 1H), 5.49 (dd, J=4.5, 10.0 Hz, 1H), 3.73 (ddd, J=2.3, 5.8, 10.8 Hz, 1H), 2.32 (ddd, J=4.5, 10.8, 13.6 Hz, 1H), 1.90 (d, J=12.5 Hz, 1H), 1.83-1.73 (m, 3H), 1.69 (d, J=12.5 Hz, 2H), 1.45-1.35 (m, 1H), 1.34-1.17 (m, 3H), 1.13-1.02 (m, 2H). SFC RT=4.056 min.

Examples 9 to 10: 8-(2-cyclohexyl)-8H-thieno[3,4]pyrrolo[1,5-a]imidazole

Example 9A: methyl 3-cyclohexylpropanoate

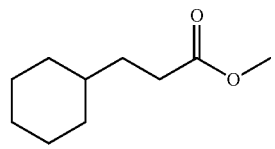

Concentrated sulfuric acid (1.84 g, 18.76 mmol, 1.00 mL) was slowly added dropwise in a solution of 3-cyclohexylpropionic acid (50.00 g, 320.06 mmol, 54.95 mL) in methanol (100 mL), heated to 70° C. and reacted for 16 h. The reaction solution was evaporated under reduced pressure to remove methanol, then diluted with ethyl acetate (200 mL), and washed successively with saturated sodium hydrogen carbonate (100 mL×3) and saturated brine (300 mL). The combined organic phase was dried over anhydrous sodium sulfate, filtered under suction and evaporated under reduced pressure, to give the title compound (52.00 g, 305.4 mmol, yield of 95.43%), which was directly used in the next step. $^1$H NMR (400 MHz, $CDCl_3$) δ=3.66 (s, 3H), 2.34-2.28 (m, 2H), 1.69 (d, J=12.3 Hz, 5H), 1.56-1.47 (m, 2H), 1.25-1.06 (m, 4H), 0.94-0.83 (m, 2H).

Example 9B: 3-cyclohexylpropanol

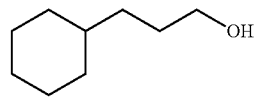

Lithium aluminum hydride was added slowly in a solution of Example 9A (10 g, 58.74 mmol) in tetrahydrofuran (100 mL) at 0° C., then warmed up to 25° C. and reacted for 2 h.

After the starting materials were completely consumed, water (2 mL), 10% NaOH solution (4 mL), and water (6 mL) were slowly added in turn to the reaction solution, and then filtered under suction. The filtrate was extracted with ethyl acetate (30 mL×3). The combined organic phase was washed with 50 mL saturated brine, dried over anhydrous sodium sulfate, filtered under suction and evaporated under reduced pressure. The crude product was purified by column chromatography to give the title compound as a colorless liquid (8 g, 56.24 mmol, 95.75%). $^1$H NMR (400 MHz, $CDCl_3$) δ=3.63 (t, J=6.7 Hz, 2H), 1.75-1.62 (m, 5H), 1.60-1.53 (m, 2H), 1.26-1.07 (m, 6H), 0.97-0.81 (m, 2H).

Example 9C: 3-cyclohexylpropionaldehyde

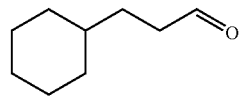

Dess-Martin reagent (35.78 g, 84.36 mmol) was slowly added to a solution of Example 9B (8 g, 56.24 mmol) in dichloromethane (80 mL) at 0° C. and reacted at 0° C. for 2 h. After completion of reaction, the reaction solution was filtered under suction and washed with dichloromethane (50 mL). The organic phase was washed with saturated sodium hydrogen carbonate (50 mL×3), extracted with ethyl acetate (50 mL×3), dried over anhydrous sodium sulfate, filtered under suction and evaporated under reduced pressure. The crude product was purified by column chromatography to give the title compound as a colorless liquid (6 g, 42.79 mmol, 76.08%). $^1$H NMR (400 MHz, CDCl$_3$) δ=9.73-9.67 (m, J=1.8, 1.8 Hz, 1H), 2.36 (dt, J=1.8, 7.7 Hz, 2H), 1.65 (br. s., 2H), 1.57 (br. s., 1H), 1.50-1.42 (m, 3H), 1.18-1.09 (m, 4H), 0.91-0.72 (m, 3H).

Example 9D: 3-cyclohexyl-1-(3-iodo-2-thienyl)propan-1-ol

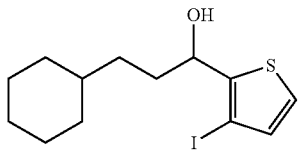 [SMILES: OC(CCC1CCCCC1)c1sccc1I]

Under protection of nitrogen gas, n-butyllithium (2.5 mol/L, 7.84 mL) was slowly added dropwise in a solution of anhydrous diisopropylamine (1.98 g, 19.61 mmol, 2.76 mL) in diethyl ether (30 mL) at −78° C., and then warmed up to 0° C. with stirring for 30 min. After cooled down to −78° C., 3-iodothiophene (3.74 g, 17.83 mmol) was added slowly dropwise and reacted at −78° C. for 30 min. Then 3-cyclohexylpropionaldehyde (3.00 g, 21.39 mmol) was slowly added dropwise, and reacted at −78° C. for 2 h. After completion of reaction, saturated ammonium chloride (50 mL) was added in the reaction system, followed by extraction with ethyl acetate (50 mL×3). The combined organic phase was washed with 50 mL saturated brine, dried over anhydrous sodium sulfate, filtered under suction and evaporated under reduced pressure. The crude product was purified by column chromatography to give the title compound as colorless oil (3 g, 8.57 mmol, 48.08%). $^1$H NMR (400 MHz, CDCl$_3$) δ=7.31 (s, 1H), 7.25 (s, 2H), 7.01 (d, J=5.3 Hz, 2H), 6.95 (s, 1H), 4.98-4.91 (m, 2H), 4.89-4.82 (m, 1H), 2.10 (d, J=3.5 Hz, 2H), 1.97 (d, J=4.3 Hz, 1H), 1.90-1.78 (m, 7H), 1.76-1.58 (m, 21H), 1.44-1.08 (m, 33H), 0.88 (dd, J=7.3, 10.5 Hz, 12H).

Example 9E: 1-[3-cyclohexyl-1-(3-iodo-2-thienyl)propyl]imidazole

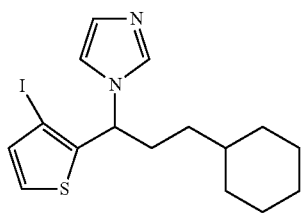 [SMILES: Ic1ccsc1C(CCC1CCCCC1)n1ccnc1]

1,1-Carbonyl-2-imidazole (6.95 g, 42.85 mmol) was added into a solution of 3-cyclohexyl-1-(3-iodo-2-thienyl)propan-1-ol (3.00 g, 8.57 mmol) in acetonitrile (35 mL), and reacted at 70° C. for 2 h. The reaction solution was added with 100 mL of water and extracted with ethyl acetate (50 mL×3). The combined organic phase was washed with 50 mL saturated brine, dried over anhydrous sodium sulfate, filtered under suction and evaporated under reduced pressure. The crude product was purified by column chromatography to give the title compound as a colorless liquid (1.40 g, 3.50 mmol, 40.81%). $^1$H NMR (400 MHz, CDCl$_3$) δ=7.69 (s, 1H), 7.32 (d, J=5.3 Hz, 1H), 7.09-7.03 (m, 3H), 5.41 (t, J=7.7 Hz, 1H), 2.25 (q, J=7.8 Hz, 2H), 1.71 (d, J=12.0 Hz, 6H), 1.24-1.07 (m, 5H), 0.95-0.84 (m, 2H).

Preparation of the Title Compounds (Examples 9 to 10): 8-(2-cyclohexyl)-8H-thieno[3,4]pyrrolo[1,5-a]imidazole

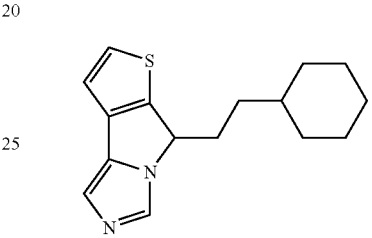

Under protection of nitrogen gas, Example 9E (0.5 g, 1.25 mmol), palladium acetate (28.04 mg, 125.00 μmol), tricyclohexylphosphine (70.05 mg, 250 μmol, 80.52 μL), potassium carbonate (517.87 mg, 3.75 mmol), pivalic acid (38.27 mg, 375.00 μmol, 43 μL), and 1-methyl-2-pyrrolidone (5 mL) were successively added in a reaction flask, and reacted at 180° C. for 10 min. After completion of reaction, the reaction solution was filtered under suction and washed with ethyl acetate (5 mL). The organic phase was added with 5 mL of water and extracted with ethyl acetate (10 mL×3). The combined organic phase was washed with 30 mL of saturated brine, dried over anhydrous sodium sulfate, filtered under suction and evaporated under reduced pressure. The crude product was purified by column chromatography to give 200 mg of racemate compounds as black brown oil. The racemate compounds were separated by chiral SFC ("Acq. Method Set: OD_3_EtOH_DEA_5_40_25 ML Vial: 2: D, 8 Channel Name: PDA Ch1 220 nm@4.8 nm—Compens. Injection Volume: 3.00 μL Proc. Chnl. Descr.: PDA Ch1 220 nm@4.8 nm—Compens. Run Time: 10.0 min"), to finally give isomer 1 (Example 9) (160 mg, 587.35 μmol, 39.96%), SFC RT=3.816 min, ee=100%; and isomer 2 (Example 10) (140 mg, 513.93 μmol, 34.96%), SFC RT=4.548 min, ee=99%. LCMS (ESI) m/z: 273 (M+1).

Example 9: $^1$H NMR (400 MHz, CDCl$_3$) δ=8.82 (br. s., 1H), 7.52 (d, J=4.8 Hz, 1H), 7.25 (d, J=5.0 Hz, 1H), 7.24 (br. s., 1H), 5.44 (br. s., 1H), 2.21 (d, J=10.8 Hz, 1H), 2.01 (d, J=10.3 Hz, 1H), 1.72 (d, J=9.3 Hz, 5H), 1.38-1.12 (m, 7H), 0.99-0.87 (m, 2H).

Example 10: $^1$H NMR (400 MHz, CDCl$_3$) δ=8.84 (s, 1H), 7.53 (d, J=5.0 Hz, 1H), 7.25 (d, J=5.0 Hz, 1H), 7.23 (s, 1H)), 5.47-5.41 (m, 1H), 2.29-2.18 (m, 1H), 2.07-1.94 (m, 1H), 1.73 (d, J=10.0 Hz, 5H), 1.40-1.06 (m, 7H), 0.92 (br. s., 2H).

Example 11: 2-(8H-thieno[3',2':3,4]pyrrolo[1,2-c]imidazol-8-yl)ethanol

Example 11A: 3-((tert-butyldimethylsilyl)oxy)propan-1-ol

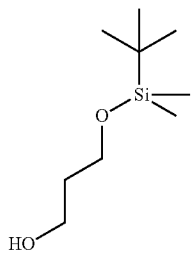

Triethylamine (13.3 g, 131.42 mmol) and TBSCl (19.81 g, 131.42 mmol) were added in a solution of 1,3-propanediol (10 g, 131.42 mmol) in DCM (200 mL) at 0° C. After stirring overnight at room temperature, the reaction solution was diluted with water (100 mL) and extracted with DCM (100 mL×3). The combined organic layers were washed with brine (300 mL), dried over anhydrous sodium sulfate, filtered and concentrated. The residue was purified by column chromatography to give the title compound as a brown liquid (20 g, 79.95%). $^1$H NMR (400 MHz, CHLOROFORM-d) δ=3.90-3.78 (m, 4H), 2.60 (br. s., 1H), 1.78 (quin, J=5.6 Hz, 2H), 0.92-0.88 (m, 9H), 0.08 (s, 6H).

Example 11B: 3-((tert-butyldimethylsilyl)oxy)propionaldehyde

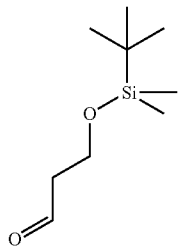

Dess-Martin reagent (12.25 g, 28.90 mmol) was added to a solution of Example 11A (5 g, 26.27 mmol) in DCM (50 mL). After stirring at room temperature for 1 h, the reaction solution was quenched with saturated aqueous NaHCO$_3$ solution (50 mL), and extracted with DCM (20 mL×3). The combined organic layers were washed with brine (50 mL), dried over anhydrous sodium sulfate, filtered and spin dried. The residue was purified by column chromatography to give the title compound, as a colorless liquid (2 g, 40.42%). $^1$H NMR (400 MHz, CHLOROFORM-d) δ=9.81 (t, J-2.1 Hz, 1H), 3.99 (t, J=6.0 Hz, 2H), 2.60 (dt, J=2.0, 6.0 Hz, 2H), 0.88 (s, 9H), 0.07 (s, 6H).

Example 11C: 3-((tert-butyldimethylsilyl)oxy)-1-(3-iodothiophen-2-yl)propan-1-ol

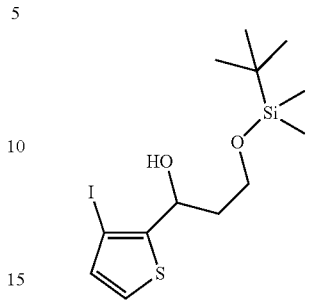

n-BuLi (2.5 M, 20.95 mL) was added dropwise into a solution of diisopropylamine (5.3 g, 52.37 mmol) in diethyl ether (100 mL) at −78° C., and the reaction mixture was warmed up to 0° C. with stirring for 30 min. Then, 3-thiophene (10 g, 47.61 mmol) was added to the reaction solution at −78° C. and stirred for 1 h. Example 11B was added dropwise to the above reaction solution, followed by stirring for another 1 hour. The reaction solution was quenched with saturated ammonium chloride solution (100 mL) and extracted with ethyl acetate (50 mL×4). The combined organic layers were washed with brine (100 mL), dried over anhydrous sodium sulfate, filtered and concentrated. The residue was purified by column chromatography to give the title compound as yellow oil (15 g, 79.08%). $^1$H NMR (400 MHz, CHLOROFORM-d) δ=7.24 (d, J=5.3 Hz, 1H), 7.02 (d, J=5.3 Hz, 1H), 5.19 (td, J=2.8, 8.5 Hz, 1H), 4.32 (d, J=2.5 Hz, 1H), 3.94 (dd, J=4.6, 6.1 Hz, 2H), 2.04-1.93 (m, 2H), 0.94 (s, 9H), 0.12 (d, J=1.3 Hz, 6H).

Example 11D: 1-(3-((tert-butyldimethylsilyl)oxy)-1-(3-iodothiophen-2-yl)-1H-imidazole

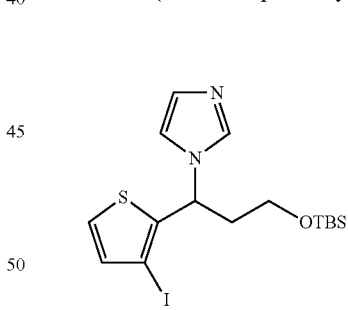

CDI (30.53 g, 188.25 mmol) was added in a solution of Example 11C (15 g, 37.65 mmol) in acetonitrile (200 mL), and heated to 80° C. with stirring for 2 h. The reaction solution was added with water (100 mL), then concentrated to remove the organic solvent, and extracted with ethyl acetate (50 mL×3). The combined organic layers were washed with saturated brine (100 mL), dried over anhydrous sodium sulfate, filtered and evaporated. The residue was purified by column chromatography to give the title compound (7 g, 41.46%). $^1$H NMR (400 MHz, CHLOROFORM-d) δ=7.68 (s, 1H), 7.30 (d, J=5.3 Hz, 1H), 7.08-7.00 (m, 3H), 5.84 (t, J=7.5 Hz, 1H), 3.62 (td, J=5.0, 10.4 Hz, 1H), 3.42 (ddd, J=5.3, 7.3, 10.5 Hz, 1H), 2.42-2.34 (m, 2H), 0.92 (s, 9H), 0.02 (d, J=4.5 Hz, 6H).

Example 11E: 8-(2-((tert-butyldimethylsilyl)oxy)-8H-thieno[3',2':3,4]pyrrolo[1,2-c]imidazole

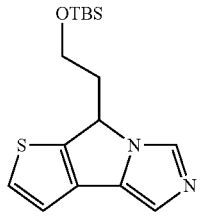 [SMILES: CC(C)(C)[Si](C)(C)OCCC1c2sccc2-c2cncn21]

A solution of Example 11D (1.5 g, 3.34 mmol), palladium acetate (75.10 mg, 334.49 μmol), tricyclohexylphosphine (187.60 mg, 668.99 μmol), pivalic acid (102.49 mg, 1 mmol) and potassium carbonate (1.39 mg, 10.03 mmol) in NMP (15 mL) was purged with nitrogen gas three times, and reacted in a microwave reactor at 180° C. for 10 min. After completion of reaction, the reaction solution was poured into water (100 mL) and ethyl acetate (30 mL) and filtered, and the filtrate was extracted with ethyl acetate (30 mL×6). The combined organic layers were washed with water (5 mL×4) and brine (50 mL), dried over anhydrous sodium sulfate, filtered and evaporated, to give the crude title compound (2 g), which was used directly in the next step. LCMS(ESI) m/z: 321 (M+1).

Preparation of the Title Compound (Example 11): 2-(8H-thieno[3',2':3,4]pyrrolo[1,2-c]imidazol-8-yl)ethanol

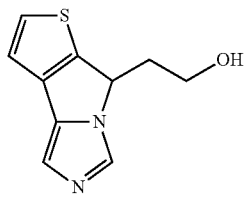 [SMILES: OCCC1c2sccc2-c2cncn21]

Example 11E (2 g, 6.24 mmol) was added to a 1% hydrochloric acid solution of in ethanol (30 mL). After stirring at 50° C. for 2 h, the reaction solution was quenched with saturated NaHCO$_3$ solution (20 mL), and concentrated to remove the organic solvent, followed by extraction with ethyl acetate (20 mL×8). The combined organic layers were washed with water (5 mL×3) and brine (50 mL), dried over anhydrous sodium sulfate, filtered and concentrated. The residue was purified by column chromatography to give the compound of Example 11 (300 mg, 23.31%). $^1$H NMR (400 MHz, CHLOROFORM-d) δ=7.72 (s, 1H), 7.35 (d, J=5.0 Hz, 1H), 7.13 (d, J=5.0 Hz, 1H), 6.94 (s, 1H), 5.43 (t, J=6.7 Hz, 1H), 3.93 (t, J=6.1 Hz, 2H), 2.25-2.14 (m, 2H), 1.93 (br. s., 1H)).

Example 12: 1-cyclohexyl-2-(5H-thieno[3',4':3,4]pyrrolo[1,2-c]imidazol-5-yl)ethanol Example 12A: 2,3,4,5-tetraiodothiophene

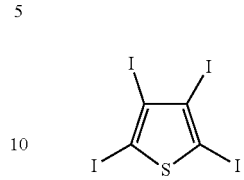

A mixed solvent of anhydrous acetic acid (30 mL), water (12 mL), concentrated sulfuric acid (600 μL) and carbon tetrachloride (6 mL) was added in a mixture of thiophene (2 g, 23.77 mmol), iodine (10.56 g, 41.60 mmol) and iodic acid (14.84 g, 84.38 mmol). The mixture was refluxed for 84 h, and additional carbon tetrachloride (12 mL) and water (6 mL) were added and refluxed for 3 h. The reaction solution was cooled down to room temperature and filtered. The filter cake was washed with water (20 mL×3), an 5% aqueous Na$_2$S$_2$O$_3$ solution (20 mL×5) and water (20 mL×2), and dried to give the title compound (12 g, 85.04%).

Example 12B: 3,4-diiodothiophene

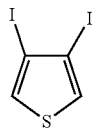

n-Butyllithium (2.5 M, 680.60 μL) was added dropwise in a solution of Example 12A (500 mg, 850.75 μmol) in diethyl ether (5 mL) at 0° C. and stirred for 30 min. The reaction solution was quenched with saturated aqueous ammonium chloride solution (10 mL) and extracted with ethyl acetate (10 mL×3). The combined organic layers were washed with brine (10 mL), dried over anhydrous sodium sulfate, filtered and evaporated to give the crude title compound as a brown liquid (150 mg). $^1$H NMR (400 MHz, CHLOROFORM-d) δ=7.42 (s, 2H).

Example 12C: 3-((tert-butyldimethylsilyl)oxy)-3-cyclohexyl-1-(4-iodothiophen-3-yl)propan-1-ol

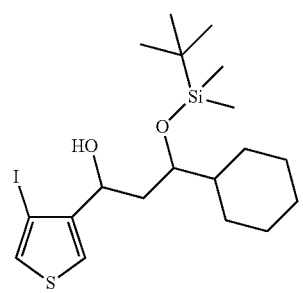 [SMILES: CC(C)(C)[Si](C)(C)OC(CC(O)c1cscc1I)C1CCCCC1]

n-Butyllithium (2.5 M, 6.55 mL) was added dropwise in a solution of Example 12B (5 g, 14.88 μmol) in diethyl ether (5 mL) at −78° C. and stirred for 1 h. 3-((tert-butyldimethylsilyl)oxy)-3-cyclohexylpropionaldehyde (4.43 g, 16.37 mmol) was added. After stirring at −78° C. for 1 h, the reaction solution was quenched with saturated aqueous ammonium chloride solution (100 mL) and extracted with ethyl acetate (50 mL×3). The combined organic layers were washed with brine (100 mL), dried over anhydrous sodium sulfate, filtered and concentrated. The residue was purified by column chromatography to give the title compound as yellow oil (5 g, 69.93%). $^1$H NMR (400 MHz, CHLOROFORM-d) δ=7.29-7.25 (m, 1H), 7.14 (t, J=3.6 Hz, 1H), 4.93-4.61 (m, 1H), 3.15 (d, J=3.3 Hz, 1H), 1.90-1.76 (m, 1H), 1.71-1.45 (m, 7H), 1.18-0.93 (m, 6H), 0.82-0.76 (m, 9H), 0.05--0.09 (m, 6H).

Example 12D: 1-(3-((tert-butyldimethylsilyl)oxy)-3-cyclohexyl-1-(4-iodothiophen-3-yl)propyl-1H-imidazole

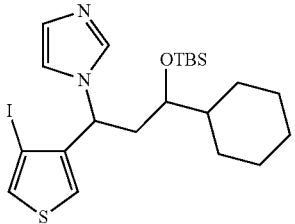 [SMILES: CC(C)(C)[Si](C)(C)OC(CC(c1cscc1I)n1ccnc1)C1CCCCC1]

CDI (8.44 g, 52.05 mmol) was added in a solution of Example 12C (5 g, 10.41 mmol) in acetonitrile (100 mL), and heated under reflux with stirring for 2 h. The reaction mixture was quenched with saturated aqueous ammonium chloride solution (50 mL), concentrated and extracted with ethyl acetate (50 mL×3). The combined organic layers were washed with saturated brine (100 mL), dried over anhydrous sodium sulfate, filtered and concentrated. The residue was purified by column chromatography to give the title compound (3.5 g, 63.37%). $^1$H NMR (400 MHz, CHLOROFORM-d) δ=8.15 (s, 1H), 7.51-7.39 (m, 2H), 7.22 (d, J=3.3 Hz, 1H), 7.08-7.03 (m, 1H), 6.16-6.03 (m, 1H), 3.74-3.49 (m, 1H), 2.28-2.22 (m, 1H), 1.75 (d, J=8.3 Hz, 3H), 1.66 (d, J=11.8 Hz, 2H), 1.47 (br. s., 1H), 1.21-1.00 (m, 5H), 0.90 (s, 10H), 0.03--0.05 (m, 6H).

Example 12E: 5-(2-((tert-butyldimethylsilyl)oxy)-2-cyclohexylethyl)-5H-thieno[3',4':3,4]pyrrolo[1,2-c]imidazole

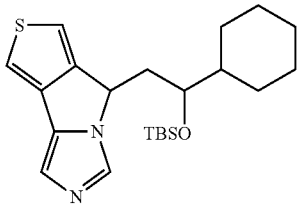 [SMILES: CC(C)(C)[Si](C)(C)OC(CC1c2cscc2-c2cncn21)C1CCCCC1]

A solution of Example 12D (0.5 g, 942.36 mmol), tricyclohexylphosphine (52.85 mg, 188.47 μmol), palladium acetate (42.21 mg, 188 μmol) and N,N-dicyclohexylmethylamine (294.53 mg, 1.51 mmol) in DMF (10 mL) was purged with nitrogen gas three times, and heated to 100° C. with stirring for 16 h. After cooling, the reaction solution was poured into water (30 mL), filtered and washed with ethyl acetate (10 mL), and the filtrate was extracted with ethyl acetate (30 mL×6). The combined organic layers were washed with water (5 mL×6) and saturated brine (50 mL), dried over anhydrous sodium sulfate, filtered and evaporated. The residue was purified by column chromatography to give the title compound as yellow oil (100 mg, 21.96%). $^1$H NMR (400 MHz, CHLOROFORM-d) δ=7.99 (s, 1H), 7.47 (d, J=8.5 Hz, 1H), 6.97-6.94 (m, 1H), 6.90 (br. s., 1H), 6.83 (s, 1H), 5.04 (dd, J=9.4, 18.7 Hz, 1H), 3.78 (d, J=8.5 Hz, 1H), 3.17-3.09 (m, 1H), 2.36 (br. s., 1H), 1.45-1.38 (m, 5H), 0.95 (d, J=3.3 Hz, 5H), 0.79-0.77 (m, 9H), 0.01--0.05 (m, 6H).

Preparation of the Title Compound (Example 12): 1-cyclohexyl-2-(5H-thieno[3',4':3,4]pyrrolo[1,2-c]imidazol-5-yl)ethanol

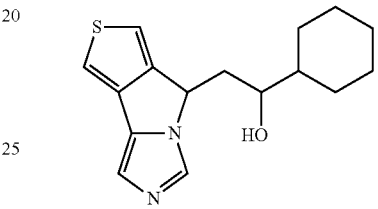

p-Toluenesulfonic acid (59.87 mg, 347.68 μmol) was added in a solution of Example 12E (70 mg, 173.84 μmol) in dichloromethane (5 mL) and stirred overnight at 20° C. The reaction solution was diluted with dichloromethane (20 mL), then washed with saturated sodium hydrogen carbonate aqueous solution (5 mL×3), dried over anhydrous sodium sulfate, filtered and evaporated. The residue was separated by high performance liquid chromatography to give the title compound (20 mg, 37.9%). $^1$H NMR (400 MHz, METHANOL-d4) δ=7.96-7.78 (m, 1H), 7.46-7.35 (m, 1H), 7.32 (s, 1H), 7.06 (br. s., 1H), 5.46-5.31 (m, 1H), 3.77-3.61 (m, 1H), 2.31-2.11 (m, 1H), 2.04-1.87 (m, 2H), 1.83-1.74 (m, 2H), 1.69 (d, J=11.3 Hz, 2H), 1.45-1.33 (m, 2H), 1.31-1.16 (m, 3H), 1.07 (q, J=12.1 Hz, 2H).

Examples 13 to 14: 8-cyclohexyl-8H-thieno[3,4]pyrrolo[1,5-a]imidazole

Example 13A: cyclohexyl-(3-iodo-2-thienyl)methanol

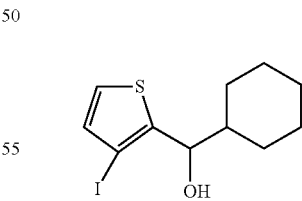

A solution of n-butyllithium (2.5 mol/L, 20.95 mL) in n-hexane was slowly added dropwise to a solution of diisopropylamine (5.30 g, 52.37 mmol, 7.36 mL) in diethyl ether (50.00 mL) at −78° C. over about 10 min, during which the temperature was maintained at −78° C. After completion of dropwise addition, the reaction solution was heated to 0° C. and stirred for 30 min. After cooling down to −78° C., 3-iodothiophene (10 g, 47.61 mmol) was added dropwise in the system, and after stirring for 30 min, cyclohexylcarboxaldehyde (6.41 g, 57.13 mmol, 6.89 mL) was added dropwise. After stirring at −78° C. for 1 h, the system was added with 50 mL of a saturated ammonium chloride solution and extracted with ethyl acetate (50 mL×3). The organic phase was combined and washed with 50 mL of saturated brine. The organic phase was dried over anhydrous sodium sulfate, filtered under suction, and evaporated under reduced pressure. The obtained crude product was purified by column chromatography to give the compound of cyclohexyl-(3-iodo-2-thienyl)methanol as a colorless liquid (8 g, 54.83 mmol, 52.15%). $^1$H NMR (400 MHz, CHLOROFORM-d) δ=7.29 (d, J=5.0 Hz, 1H), 7.01 (d, J=5.3 Hz, 1H), 4.73 (br d, J=7.8 Hz, 1H), 3.45 (d, J=6.5 Hz, 1H), 2.04-1.93 (m, 1H), 1.83-1.77 (m, 2H), 1.73-1.70 (m, 2H), 1.43 (br d, J=13.6 Hz, 1H), 1.29-1.21 (m, 4H), 0.96-0.88 (m, 1H).

Example 13B: 1-[cyclohexyl-(3-iodo-2thienyl)methyl]imidazole

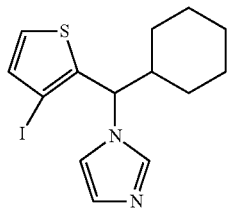 [SMILES: Ic1ccsc1C(C1CCCCC1)n1ccnc1]

1,1-Carbonyl diimidazole (9.23 g, 56.93 mmol) was added in a solution of cyclohexyl-(3-iodo-2-thienyl)methanol (4 g, 12.41 mmol) in acetonitrile (50 mL). The reaction solution was reacted at 70° C. for 2 h. After completion of reaction, the reaction solution was added with 100 mL of water, and extracted with ethyl acetate (30 mL×3). The combined organic phase was washed with 50 mL of saturated brine, dried over anhydrous sodium sulfate, filtered under suction, and evaporated under reduced pressure. The obtained crude product was purified by column chromatography to give the compound of 1-[cyclohexyl-(3-iodo-2-thienyl)methyl]imidazole as a colorless liquid (1.00 g, 2.69 mmol, 23.59%). $^1$H NMR (400 MHz, CHLOROFORM-d) δ=7.66 (s, 1H), 7.32 (d, J=5.3 Hz, 1H), 7.08-7.04 (m, 2H), 7.00 (d, J=5.3 Hz, 1H), 5.14 (d, J=11.0 Hz, 1H), 2.19-2.07 (m, 1H), 1.78 (s, 1H), 1.77-1.65 (m, 3H), 1.39 (br d, J=13.1 Hz, 1H), 1.23-1.07 (m, 3H), 1.08-0.90 (m, 2H).

Preparation of the Title Compounds (Examples 13 to 14): 8-cyclohexyl-8H-thieno[3,4]pyrrolo[1,5-a]imidazole

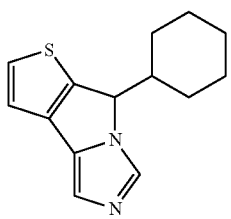 [SMILES: c1cc2c(s1)C(C1CCCCC1)n1cncc1-2]

Under protection of nitrogen gas, 1-[cyclohexyl-(3-iodo-2-thienyl)methyl]imidazole (500 mg, 1.34 mmol), palladium acetate (30.15 mg, 4.03 mmol), tricyclohexylphosphine (75.33 mg, 268.62 µmol, 86.59 µL), potassium carbonate (556.89 mg, 4.03 mmol), pivalic acid (41.15 mg, 402.93 µmol, 46.24 µL), and 1-methyl-2-pyrrolidone (5 mL) were successively added in a reaction flask, and reacted at 180° C. for 10 min. After completion of reaction, the reaction solution was filtered under suction, and washed with ethyl acetate (5 mL). The organic phase was added with 30 mL of water, and extracted with ethyl acetate (20 mL×3). The combined organic phase was washed with 20 mL of saturated brine, dried over anhydrous sodium sulfate, filtered under suction, and evaporated under reduced pressure. The crude product was purified by column chromatography to give 8-cyclohexyl-8H-thieno[3,4]pyrrolo[1,5-a]imidazole (200 mg, 818.50 µmol, 58.74%). The racemate was separated by chiral SFC (separation method: AD_3_EtOH_DEA_5_40_25 ML Vial: 1:B, 7 Channel Name: PDA Ch1 220 nm@4.8 nm—Compens. Injection Volume: 3.00 µL Proc. Chnl. Descr.: PDA Ch1 220 nm@4.8 nm—Compens. Run Time: 10.0 min), to finally give the compound of Example 13 (isomer 1) (50.00 mg, 202.78 µmol, 82.58% yield, 99.1% purity, retention time: 4.100 min, ee=99.74%) and the compound of Example 14 (isomer 2) (50 mg, 202.78 µmol, 82.58% yield, 99% purity, retention time: 4.742 min, ee=99.50%).

Example 13: $^1$H NMR (400 MHz, CHLOROFORM-d) δ=7.66 (s, 1H), 7.34 (d, J=5.0 Hz, 1H), 7.14 (d, J=4.8 Hz, 1H), 6.94 (s, 1H), 5.06 (d, J=4.3 Hz, 1H), 2.07-1.96 (m, 1H), 1.83-1.76 (m, 2H), 1.75-1.66 (m, 2H), 1.43 (br d, J=12.5 Hz, 1H), 1.38-1.04 (m, 5H), 0.88 (dq, J=3.5, 12.5 Hz, 1H), 0.08-0.08 (m, 1H).

Example 14: $^1$H NMR (400 MHz, CHLOROFORM-d) δ=7.66 (s, 1H), 7.34 (d, J=5.0 Hz, 1H), 7.14 (d, J=5.0 Hz, 1H), 6.94 (s, 1H), 5.06 (d, J=4.3 Hz, 1H), 2.06-1.96 (m, 1H), 1.87-1.76 (m, 2H), 1.73 (br s, 2H), 1.43 (br d, J=12.5 Hz, 1H), 1.38-1.05 (m, 5H), 0.88 (dq, J=3.5, 12.5 Hz, 1H).

Examples 15 to 16: 8-(cyclohexylmethyl)-8H-thieno[3,4]pyrrolo[1,5-a]imidazole

Example 15A: 2-(cyclohexyl)acetaldehyde

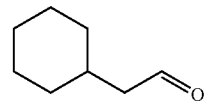

Dess-Martin oxidizing agent (24.81 g, 58.50 mmol) was slowly added to a solution of 2-(cyclohexyl)ethanol (5 g, 39 mmol) in dichloromethane (40 mL) at 0° C., and the mixture was stirred at 0° C. for 2 h. The reaction system was filtered, and the filtrate was washed with NaHCO$_3$ (50 mL×3) and brine (30 mL), dried over anhydrous sodium sulfate, filtered and concentrated. The residue was purified by silica gel column to give the title compound as a colorless liquid (3.10 g, 24.56 mmol, yield of 62.99%). $^1$H NMR (400 MHz, CHLOROFORM-d) δ=9.76 (t, J=2.1 Hz, 1H), 2.30 (dd, J=2.0, 6.8 Hz, 2H), 2.26-2.18 (m, 1H), 1.90 (dddd, J=3.5, 7.4, 10.9, 14.5 Hz, 1H), 1.37-1.24 (m, 4H), 1.22-1.12 (m, 2H), 1.07-0.93 (m, 3H).

Example 15B:
2-(cyclohexyl)-1-(3-iodo-2-thienyl)ethanol

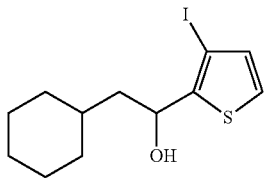 [SMILES: OC(CC1CCCCC1)c1sccc1I]

Under N₂ atmosphere, a solution of diisopropylamine (2.12 g, 20.94 mmol) in diethyl ether (30 mL) was cooled down to −78° C., and slowly added with n-butyllithium (2.5 M, 8.38 mL). The reaction system was stirred at 0° C. for 30 min and then cooled down to −78° C. 3-Iodothiophene (4 g, 19.04 mmol) was added and maintained at −78° C. with stirring for 30 min. 2-(Cyclohexyl)acetaldehyde (2.88 g, 22.85 mmol) was added, and the reaction solution was stirred at −78° C. for 2 h. The reaction solution was quenched with saturated ammonium chloride solution (50 mL), and extracted with ethyl acetate (50 mL×2). The organic phase was washed with brine (50 mL), dried over anhydrous sodium sulfate, filtered and concentrated. The residue was purified by column chromatography to give the title compound (colorless oil, 2.30 g, 6.84 mmol, yield of 35.93%). 1H NMR (400 MHz, CHLOROFORM-d) δ=7.25 (s, 1H), 7.01 (d, J=5.0 Hz, 1H), 5.14-5.07 (m, 1H), 2.11-2.02 (m, 1H), 1.89 (br d, J=13.1 Hz, 1H), 1.70-1.65 (m, 3H), 1.53-1.42 (m, 2H), 1.30-1.18 (m, 4H), 1.07-0.87 (m, 3H).

Example 15C: 1-[2-(cyclohexyl)-1-(3-iodo-2-thienyl)ethyl]imidazole

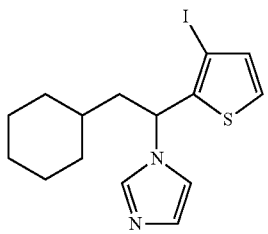 [SMILES: Ic1ccsc1C(CC1CCCCC1)n1ccnc1]

CDI (3.33 g, 20.52 mmol) was added into a solution of 2-(cyclohexyl)-1-(3-iodo-2-thienyl)ethanol (2.30 g, 6.84 mmol) in acetonitrile (25 mL), and the reaction solution was stirred at 70° C. for 2 h. The reaction solution was dispersed in water (30 mL), and extracted with ethyl acetate (30 mL×2). The organic phase was separated, washed with water (30 mL) and brine (30 mL), dried over anhydrous sodium sulfate, filtered and concentrated. The residue was purified by column chromatography to give the title compound (colorless oil, 1.17 g, 2.99 mmol, yield of 43.71%). ¹H NMR (400 MHz, CHLOROFORM-d) δ=7.69 (s, 1H), 7.30 (d, J=5.3 Hz, 1H), 7.10-7.02 (m, 3H), 5.66-5.57 (m, 1H), 2.21-2.08 (m, 2H), 1.85 (br d, J=12.8 Hz, 1H), 1.76-1.63 (m, 5H), 1.17 (br d, J=8.0 Hz, 3H), 1.10-0.95 (m, 2H).

Preparation of the Title Compounds (Examples 15 to 16): 8-(cyclohexylmethyl)-8H-thieno[3,4]pyrrolo[1,5-a]imidazole

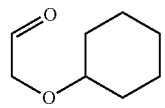

Under protection of nitrogen gas, a mixture of 1-[2-(cyclohexyl)-1-(3-iodo-2-thienyl)ethyl]imidazole (0.7 g, 1.81 mmol), palladium acetate (40.64 mg, 181 μmol), tricyclohexylphosphine (101.52 mg, 362 μmol), potassium carbonate (500.32 mg, 3.62 mmol) and a solution of 2,2-dimethylpropanoic acid (55.46 mg, 543 μmol) in NMP (3.50 mL) was stirred at 180° C. for 10 min. The reaction solution was dispersed in water (30 mL) and ethyl acetate (30 mL), filtered, and extracted with ethyl acetate (20 mL×4). The organic phase was washed with water (5 mL×4) and brine (50 mL), dried over anhydrous sodium sulfate, filtered and concentrated. The residue was purified by column chromatography to give the title compound (270 mg, yield of 42.25%) as a racemate. The racemate was subjected to chiral separation (chiral separation conditions: "Column: Chiralpak AD-3 150×4.6 mm I.D., 3 um; Mobile phase: A: CO2 B: ethanol (0.05% DEA); Gradient: from 5% to 40% of B in 5 min and hold 40% for 2.5 min, then 5% of B for 2.5 min; Flow rate: 2.5 mL/min; Column temp.: 35° C."), and high performance liquid chromatography, to give Example 15 (isomer 1, 100 mg, SFC Rt=4.223 min) and Example 16 (isomer 2, 100 mg, SFC Rt=4.959 min) were prepared by HPLC.

Example 15: ¹H NMR (400 MHz, METHANOL-d4) δ=9.21 (s, 1H), 7.71 (d, J=5.0 Hz, 1H), 7.53 (s, 1H), 7.38 (d, J=5.0 Hz, 1H), 5.84 (dd, J=5.8, 8.5 Hz, 1H), 5.02 (br s, 3H), 3.35-3.31 (m, 1H), 2.20 (ddd, J=5.8, 8.0, 13.6 Hz, 1H), 1.97-1.88 (m, 1H), 1.86-1.61 (m, 6H), 1.44-1.09 (m, 5H).

Example 16: ¹H NMR (400 MHz, METHANOL-d4) δ=9.21 (s, 1H), 7.71 (br t, J=4.9 Hz, 1H), 7.44-7.28 (m, 1H), 5.83 (br d, J=5.3 Hz, 1H), 2.20 (ddd, J=5.9, 8.0, 13.7 Hz, 1H), 1.97-1.62 (m, 7H), 1.48-1.02 (m, 5H).

Examples 17 to 18: 8-((cyclohexyloxy)methyl)-8H-thieno[3',2':3,4]pyrrolo[1,2-c]imidazole Example 17A: 2-(cyclohexyloxy)acetaldehyde Dimethyl sulfoxide (4.88 g, 62.40 mmol) was slowly added dropwise to a solution of oxalyl chloride (4.75 g, 37.44 mmol) in dichloromethane (40.00 mL) at −60° C., and the mixture was stirred for 20 min. A solution of 2-(cyclohexyloxy)ethanol (4.50 g, 31.20 mmol) in dichloromethane (10.00 mL) was slowly added dropwise. After reaction for 10 min, triethylamine (15.79 g, 156.00 mmol) was slowly added. After 30 min, the reaction solution was slowly warmed up to room temperature. The reaction was quenched with water (100 mL) and the aqueous layer was extracted with ethyl acetate (100 mL×3). The combined organic phase was washed with brine (100 mL×3), dried over anhydrous sodium sulfate, filtered and evaporated, to give the crude title compound (a yellow liquid, 4.3 g), which can be used directly in the next step without further purification.

Example 17B:
2-(cyclohexyloxy)-1-(3-iodo-2-thienyl)ethanol

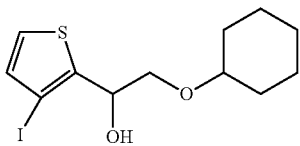 [SMILES: OC(COC1CCCCC1)c1sccc1I]

A solution of n-butyllithium (2.5 M, 13.20 mL) in diethyl ether (60 mL) was cooled down to −78° C., and added with diisopropylamine (3.64 g, 35.99 mmol). After 1 hour, 3-iodothiophene (6.30 g, 29.99 mmol) was added and maintained at −78° C. with further stirring for 1 hour. 2-(Cyclohexyloxy)acetaldehyde (4.26 g, 29.99 mmol) was added, and the reaction solution was stirred at −78° C. for 1 h. The reaction solution was quenched with ammonium chloride solution (100 mL), diluted with water (100 mL) and extracted with ethyl acetate (100 mL×3). The organic phase was washed with brine (100 mL), dried over anhydrous sodium sulfate, filtered and evaporated. The residue was purified by column chromatography to give the title compound (colorless oil, 3.2 g, yield of 30.29%). $^1$H NMR (400 MHz, CHLOROFORM-d) δ=7.27 (d, J=5.0 Hz, 1H), 7.03 (d, J=5.0 Hz, 1H), 5.12 (td, J=2.8, 8.5 Hz, 1H), 3.77 (dd, J=3.1, 9.7 Hz, 1H), 3.46-3.36 (m, 2H), 3.14 (d, J=2.5 Hz, 1H), 1.93 (br d, J=9.0 Hz, 2H), 1.79-1.71 (m, 2H), 1.57-1.51 (m, 1H), 1.40-1.32 (m, 2H), 1.31-1.24 (m, 3H).

Example 17C: 1-[2-(cyclohexyloxy)-1-(3-iodo-2-thienyl)ethyl]imidazole

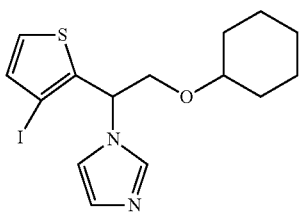 [SMILES: Ic1ccsc1C(COC1CCCCC1)n1ccnc1]

CDI (7.36 g, 45.40 mmol) was added into a solution of 2-(cyclohexyloxy)-1-(3-iodo-2-thienyl)ethanol (3.20 g, 9.08 mmol) in acetonitrile (35.00 mL), and the reaction solution was stirred at 70° C. for 4 h. The reaction solution was dispersed in ethyl acetate (200 mL) and water (100 mL). The organic phase was separated, washed with brine (100 mL×3), dried over anhydrous sodium sulfate, filtered and evaporated. The residue was purified by column chromatography to give the title compound (colorless oil, 2.50 g, yield of 68.44%). MS-ESI (m/z): 403 (M+H)$^+$. $^1$H NMR (400 MHz, CHLOROFORM-d) δ=7.73 (s, 1H), 7.32 (d, J=5.3 Hz, 1H), 7.09 (s, 1H), 7.06 (d, J=5.3 Hz, 1H), 7.03 (s, 1H), 5.66 (dd, J=4.0, 5.8 Hz, 1H), 4.04-3.94 (m, 2H), 3.38-3.28 (m, 1H), 1.83 (br d, J=7.0 Hz, 2H), 1.69 (br d, J=4.8 Hz, 2H), 1.55-1.45 (m, 1H), 1.43-1.32 (m, 2H), 1.29-1.23 (m, 3H).

Preparation of the Title Compounds (Examples 17 to 18): 8-(cyclohexyloxymethyl)-8H-thieno[3,4]pyrrolo[1,5-a]imidazole

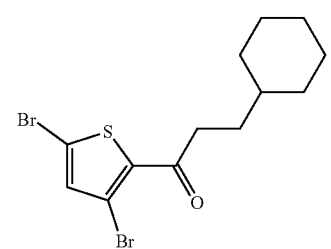 [SMILES: O=C(CCC1CCCCC1)c1sc(Br)cc1Br]

Under protection of nitrogen gas, a mixture solution of 1-[2-(cyclohexyloxy)-1-(3-iodo-2-thienyl)ethyl]imidazole (1.00 g, 2.49 mmol), palladium acetate (55.81 mg, 248.58 μmol), tricyclohexylphosphine (139.42 mg, 497.15 μmol), potassium carbonate (687.12 mg, 4.97 mmol) in xylene (10.00 mL) was stirred at 140° C. for 16 h. The reaction solution was dispersed in ethyl acetate (100 mL) and water (100 mL). The organic phase was separated, washed with brine (100 mL×3), dried over anhydrous sodium sulfate, filtered and evaporated. The residue was purified by column chromatography to give the title compound (290 mg, 37.35%) as a racemate. The racemate was subjected to chiral separation (separation conditions: ChiralCel OD-H 150×4.6 mm I.D., 5 μm; mobile phase: A: carbon dioxide B: ethanol (0.05% diethylamine)), to give Example 17 (isomer 1, 89 mg, yield of 42.46%) (retention time: 3.758 min) and Example 18 (isomer 2, 93 mg, yield of 45.04%) (retention time: 4.462 min).

Example 17: $^1$H NMR (400 MHz, METHANOL-d4) δ=9.03 (s, 1H), 7.71 (br d, J=5.0 Hz, 1H), 7.51 (s, 1H), 7.37 (br d, J=5.0 Hz, 1H), 5.90-5.79 (m, 1H), 4.17-4.06 (m, 1H), 3.71 (br t, J=8.8 Hz, 1H), 3.44 (br s, 1H), 1.98-1.80 (m, 2H), 1.72 (br s, 2H), 1.54 (br d, J=6.3 Hz, 1H), 1.42-1.25 (m, 5H).

Example 18: $^1$H NMR (400 MHz, METHANOL-d4) δ=9.03 (s, 1H), 7.72 (d, J=5.0 Hz, 1H), 7.52 (s, 1H), 7.37 (d, J=5.0 Hz, 1H), 5.89-5.81 (m, 1H), 4.12 (dd, J=4.8, 9.8 Hz, 1H), 3.70 (t, J=8.9 Hz, 1H), 3.49-3.39 (m, 1H), 1.99-1.83 (m, 2H), 1.72 (br s, 2H), 1.54 (br d, J=6.0 Hz, 1H), 1.46-1.22 (m, 5H).

Examples 19 to 20: 8-(2-cyclohexylethyl)-2-fluoro-8H-thieno[3',2':3,4]pyrrolo[1,2-c]imidazole Example 19A:
3-cyclohexyl-1-(3,5-dibromo-2-thienyl)propan-1-one Under protection of nitrogen gas, a solution of 2,4-dibromothiophene (1 g, 4.13 mmol) in CS$_2$ (10.00 mL) was added in one portion with AlCl$_3$ (826.04 mg, 6.20 mmol), cooled down to 0° C., and slowly added dropwise with cyclohexylpropionyl chloride (1.12 g, 6.40 mmol). The reaction solution was stirred at room temperature for 16 h. The reaction mixture was poured into 50 mL of ice water and extracted with dichloromethane (2×50 mL). The combined organic phase was washed with water and 5% sodium hydrogen carbonate (50 mL), dried over anhydrous sodium sulfate, filtered and evaporated. The residue was purified by column chromatography to give the title compound (1.4 g, yield of 89.17%). $^1$H NMR (400 MHz, CHLOROFORM-d) δ=7.09 (s, 1H), 3.06-2.91 (m, 2H), 1.81-1.66 (m, 5H), 1.64-1.59 (m, 2H), 1.32-1.13 (m, 4H), 0.99-0.89 (m, 2H).

Example 19B: 2-(2-cyclohexylethyl)-2-(3,5-dibromo-2-thienyl)-1,3-dioxolane

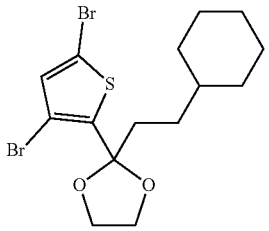

Under protection of nitrogen gas, a mixture solution of 3-cyclohexyl-1-(3,5-dibromo-2-thienyl)propan-1-one (1.40 g, 3.68 mmol), ethylene glycol (913.67 mg, 14.72 mmol) and p-toluenesulfonic acid (35 mg, 184 μmol) in toluene (30 mL), which was connected to a water separator, was stirred at 120° C. for 16 h. The reaction solution was dispersed in ethyl acetate (100 mL) and water (50 mL). The organic phase was separated, washed with brine (50 mL×3), dried over anhydrous sodium sulfate, filtered and evaporated. The residue was purified by column chromatography to give the title compound (yellow oil, 1.5 g, yield of 96.09%). $^1$H NMR (400 MHz, CHLOROFORM-d) δ=7.27 (s, 1H), 6.92 (s, 1H), 4.08-4.02 (m, 2H), 3.99-3.92 (m, 2H), 2.16-2.09 (m, 2H), 1.71-1.60 (m, 6H), 1.27-1.17 (m, 5H), 0.93-0.82 (m, 2H).

Example 19C: 2-(3-bromo-5-fluoro-2-thienyl)-2-(2-cyclohexylethyl)-1,3-dioxolane

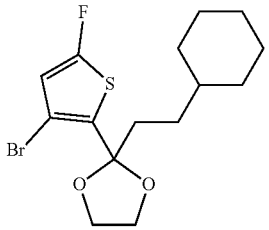 [SMILES: Fc1cc(Br)c(C2(CCC3CCCCC3)OCCO2)s1]

Under protection of nitrogen gas, n-butyllithium (2.5 mol, 1.59 mL) was added dropwise to a solution of 2-(2-cyclohexylethyl)-2-(3,5-dibromo-2-thienyl)-1,3-dioxolane (1.3 g, 3.06) in tetrahydrofuran (10 mL), maintained at −78° C. and stirred for 1 h. A solution of NFSI (1.25 g, 3.98 mmol) in tetrahydrofuran (2 mL) was then added dropwise, and the reaction was stirred at −78° C. for 2 h. The reaction solution was added with saturated ammonium chloride solution (50 mL) to quench, diluted with water (50 mL), and extracted with ethyl acetate (50 mL×3). The organic phase was washed with brine (50 mL×3), dried over anhydrous sodium sulfate, filtered and evaporated. The residue was purified by column chromatography to give the title compound (colorless oil, 400 mg, yield of 35.98%). $^1$H NMR (400 MHz, CHLOROFORM-d) δ=6.40 (d, J=1.0 Hz, 1H), 4.05-4.01 (m, 2H), 3.99-3.95 (m, 2H), 2.16-2.10 (m, 2H), 1.74-1.63 (m, 6H), 1.25-1.16 (m, 5H), 0.87 (br d, J=10.8 Hz, 2H).

Example 19D: 1-(3-bromo-5-fluoro-2-thienyl)-3-cyclohexyl-propan-1-one

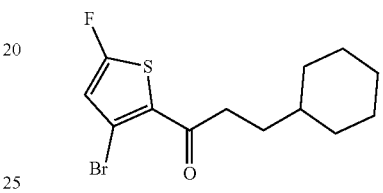

Hydrogen chloride (3 mol, 1.24 mL) solution was added into a solution of 2-(3-bromo-5-fluoro-2-thienyl)-2-(2-cyclohexylethyl)-1,3-dioxolane (450 mg, 1.24 mmol) in tetrahydrofuran (5 mL), and the reaction mixture was stirred at 70° C. for 4 h. The reaction solution was added with saturated sodium hydrogen carbonate solution (30 mL) to quench, diluted with water (20 mL), and extracted with ethyl acetate (30 mL×3). The organic phase was washed with brine (30 mL×3), dried over anhydrous sodium sulfate, filtered and evaporated. The residue was purified by column chromatography to give the title compound (colorless oil, 300 mg, yield of 75.79%). $^1$H NMR (400 MHz, CHLOROFORM-d) δ=6.58 (s, 1H), 3.05-2.95 (m, 2H), 1.74 (br t, J=13.1 Hz, 4H), 1.66-1.57 (m, 3H), 1.32-1.14 (m, 4H), 0.99-0.89 (m, 2H).

Example 19E: 1-(3-bromo-5-fluoro-2-thienyl)-3-cyclohexyl-propan-1-ol

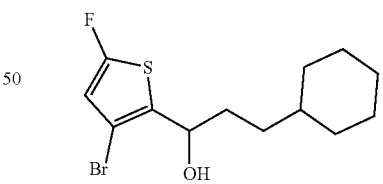

Sodium borohydride (35.55 mg, 939.76 μmol) was added into a solution of 1-(3-bromo-5-fluoro-2-thienyl)-3-cyclohexyl-propan-1-one (200 mg, 626.51 μmol) in methanol (5 mL) at 0° C., and the reaction mixture was stirred at 0° C. for 2 h. The reaction solution was added with 1 mol hydrochloric acid (20 mL) to quench, diluted with water (20 mL), and extracted with ethyl acetate (20 mL×3). The organic phase was washed with brine (20 mL×3), dried over anhydrous sodium sulfate, filtered and evaporated. The residue was purified by column chromatography to give the title compound (colorless oil, 280 mg, yield of 92.75%). $^1$H NMR (400 MHz, CHLOROFORM-d) δ=6.35 (s, 1H), 4.95

(br s, 1H), 2.15 (s, 1H), 1.83-1.61 (m, 7H), 1.35 (dt, J=6.0, 11.3 Hz, 1H), 1.28-1.10 (m, 5H), 0.94-0.84 (m, 2H).

Example 19F: 1-[1-(3-bromo-5-fluoro-2-thienyl)-3-cyclohexyl-propyl]imidazole

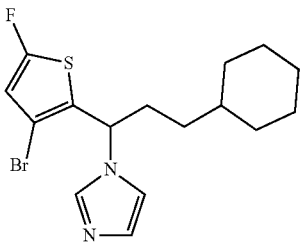 [SMILES: Fc1cc(Br)c(C(CCC2CCCCC2)n2ccnc2)s1]

CDI (706.65 mg, 4.36 mmol) was added into a solution of 1-(3-bromo-5-fluoro-2-thienyl)-3-cyclohexyl-propan-1-ol (280 mg, 871.60 µmol) in acetonitrile (5 mL), and the reaction solution was stirred at 70° C. for 4 h. The reaction solution was dispersed into ethyl acetate (50 mL) and water (50 mL). The organic phase was separated, washed with brine (50 mL×3), dried over anhydrous sodium sulfate, filtered and evaporated. The residue was purified by column chromatography to give the title compound (colorless oil, 200 mg, 61.80%). MS-ESI (m/z): 372 (M+H)$^+$. $^1$H NMR (400 MHz, CHLOROFORM-d) δ=7.62 (s, 1H), 7.07 (s, 1H), 6.99 (s, 1H), 6.38 (s, 1H), 5.40 (dt, J=3.0, 7.8 Hz, 1H), 2.19-2.07 (m, 2H), 1.74-1.60 (m, 5H), 1.28-1.10 (m, 6H), 0.94-0.79 (m, 2H).

Preparation of the Title Compounds (Examples 19 to 20): 8-(2-cyclohexylethyl)-2-fluoro-8H-thieno[3,4]pyrrolo[1,5-a]imidazole

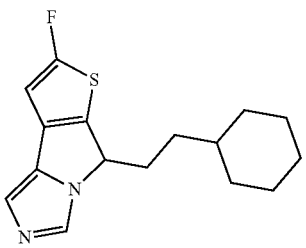 [SMILES: Fc1cc2c(s1)C(CCC1CCCCC1)n1cncc1-2]

Under protection of nitrogen gas, a mixture solution of 1-[1-(3-bromo-5-fluoro-2-thienyl)-3-cyclohexyl-propyl]imidazole (120 mg, 323.18 µmol), palladium acetate (7.26 mg, 32.32 µmol), tricyclohexylphosphine (18.13 mg, 64.64 µmol), and potassium carbonate (89.33 mg, 646.36 µmol) in xylene (5 mL) was stirred at 140° C. for 16 h. The reaction solution was dispersed in ethyl acetate (50 mL) and water (50 mL). The organic phase was separated, washed with brine (50 mL×3), dried over anhydrous sodium sulfate, filtered and evaporated. The residue was purified by column chromatography to give the title compound (a racemate, 32 mg, yield of 34.10%). The racemate (300 mg) was subjected to chiral separation (column: ChiralPak AD-3 150×4.6 mm I.D., 3 µm; mobile phase: A: carbon dioxide B: methanol (0.05% diethylamine)), to give Example 19 (retention time: 3.938 min, 135 mg, yield of 63.85%) and Example 20 (retention time: 4.312 min, 129.00 mg, yield of 61.38%).

Example 19: $^1$H NMR (400 MHz, METHANOL-d4) δ=9.20 (s, 1H), 7.48 (s, 1H), 7.01 (d, J=1.0 Hz, 1H), 5.72 (t, J=5.9 Hz, 1H), 2.28 (tdd, J=4.7, 11.8, 14.0 Hz, 1H), 2.16-2.02 (m, 1H), 1.75-1.62 (m, 5H), 1.32-1.16 (m, 5H), 1.15-1.08 (m, 1H), 0.96-0.84 (m, 2H).

Example 20: $^1$H NMR (400 MHz, METHANOL-d4) δ=9.19 (s, 1H), 7.47 (s, 1H), 7.00 (d, J 15=1.0 Hz, 1H), 5.72 (t, J=5.9 Hz, 1H), 2.28 (tdd, J=4.8, 11.8, 14.0 Hz, 1H), 2.15-2.01 (m, 1H), 1.75-1.62 (m, 5H), 1.31-1.16 (m, 5H), 1.14-1.07 (m, 1H), 0.95-0.84 (m, 2H).

Examples 21 to 22: 8-(2-(4,4-difluorocyclohexyl)ethyl)-8H-thieno[3',2':3,4]pyrrolo[1,2-c]imidazole Example 21A: methyl 4,4-difluorocyclohexanecarboxylate

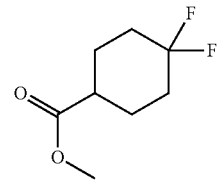

Concentrated sulfuric acid (2.09 g, 21.32 mmol) was slowly added dropwise to a solution of 4,4-difluorocyclohexylcarbamic acid (7 g, 42.64 mmol) in methanol (70 mL) at 0° C., and the reaction solution was stirred at 70° C. for 16 h. The reaction solution was adjusted to pH=7 with a saturated sodium hydrogen carbonate solution, and extracted with ethyl acetate (100 mL×2). The combined organic phase was washed with brine (100 mL), dried over anhydrous sodium sulfate, filtered and evaporated. The residue was purified by column chromatography to give the title compound (yellow oil, 6.90 g, yield of 90.82%). $^1$H NMR (400 MHz, CHLOROFORM-d) δ=3.70 (s, 2H), 2.48-2.37 (m, 1H), 2.16-2.06 (m, 2H), 2.03-1.94 (m, 2H), 1.92-1.69 (m, 4H).

Example 21B: (4,4-difluorocyclohexyl)methanol

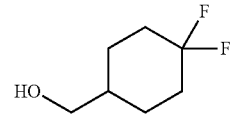

Under protection of nitrogen gas, LiAlH$_4$ (2.9 g, 76.32 mmol) was added slowly into a solution of methyl 4,4-difluorocyclohexanecarboxylate (3.40 g, 19.08 mmol) in tetrahydrofuran (40 mL) at 0° C., and then the reaction solution was stirred at 20° C. for 2 h. The reaction solution was quenched with water (50 mL) and 1 mol/L sodium hydroxide solution (20 mL), and then filtered. The filtrate was extracted with ethyl acetate (50 mL×2). The combined organic phase was washed with brine (50 mL), dried over anhydrous sodium sulfate, filtered and evaporated. The residue was purified by column chromatography to give the title compound (yellow oil, 2.05 g, yield of 71.55%). $^1$H NMR (400 MHz, CHLOROFORM-d) δ=3.53 (d, J=6.5 Hz, 2H), 2.21-2.07 (m, 2H), 1.86 (br d, J=13.6 Hz, 2H), 1.81-1.64 (m, 2H), 1.58 (br d, J=3.5 Hz, 1H), 1.43-1.27 (m, 3H).

Example 21C: (4,4-difluorocyclohexal)carboxaldehyde

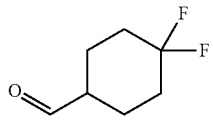

At 0° C., Dess-Martin reagent (8.47 g, 19.98 mmol) was slowly added in a solution of (4,4-difluorocyclohexyl)methanol (2.00 g, 13.32 mmol) in dichloromethane (20 mL), and then the reaction solution was stirred at 0° C. for 2 h. The reaction solution was filtered, and the filtrate was washed with saturated sodium hydrogen carbonate (20 mL×3) and 20 mL of brine. The organic phase was dried over anhydrous sodium sulfate, filtered and evaporated. The residue was purified by column chromatography to give the title compound (yellow oil, 1.80 g, yield of 91.22%). $^1$H NMR (400 MHz, CHLOROFORM-d) δ=9.68 (s, 1H), 2.35 (br d, J=8.0 Hz, 1H), 2.11 (br d, J=2.3 Hz, 1H), 2.01 (br s, 2H), 1.94-1.71 (m, 5H).

Example 21D: ethyl (E)-3-(4,4-difluorocyclohexyl)acrylate

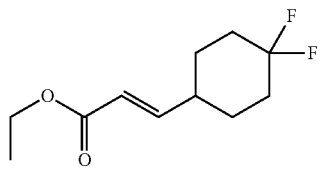

Sodium hydrogen (728.99 mg, 18.23 mmol) was slowly added in a solution of ethyl 2-diethoxy phosphate (4.09 g, 18.23 mmol) in tetrahydrofuran (20 mL) at 0° C., and the reaction solution was stirred at 0° C. for 30 min. 4,4-Difluorocyclohexylcarboxaldehyde (1.8 g, 12.15 mmol) was then added at 0° C., and the reaction solution was further stirred at 20° C. for 2 h. The reaction mixture was poured slowly into water (50 mL) and extracted with ethyl acetate (50 mL×2). The combined organic phase was washed with brine (50 mL), dried over anhydrous sodium sulfate, filtered and evaporated. The residue was purified by column chromatography to give the title compound (colorless oil, 1 g, yield of 37.71%). $^1$H NMR (400 MHz, CHLOROFORM-d) δ=6.90 (dd, J=6.8, 15.8 Hz, 1H), 5.83 (dd, J=1.0, 15.8 Hz, 1H), 4.20 (q, J=7.3 Hz, 2H), 2.25 (br d, J=6.3 Hz, 1H), 2.18-2.07 (m, 2H), 1.91-1.68 (m, 4H), 1.61-1.52 (m, 2H), 1.30 (t, J=7.0 Hz, 3H).

Example 21E: ethyl 3-(4,4-difluorocyclohexyl)propanoate

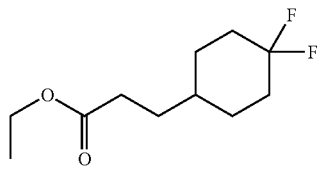

Under protection of nitrogen gas, wet palladium carbon (350 mg) was added in a solution of ethyl (E)-3-(4,4-difluorocyclohexyl)acrylate (1 g, 4.58 mmol) in ethanol (20 mL), and then the reaction solution was purged with hydrogen gas three times, and reacted under a hydrogen pressure (45 psi) at 20° C. for 19 h. The reaction solution was filtered through diatomaceous earth, and the filtrate was concentrated. The residue was purified by column chromatography to give the title compound (colorless oil, 980 mg, yield of 97.15%). $^1$H NMR (400 MHz, CHLOROFORM-d) δ=4.17-4.11 (m, 2H), 4.07-4.07 (m, 1H), 2.33 (t, J=7.7 Hz, 2H), 2.14-2.05 (m, 2H), 1.81-1.57 (m, 6H), 1.26 (t, J=7.2 Hz, 5H).

Example 21F: 3-(4,4-difluorocyclohexyl)propan-1-ol

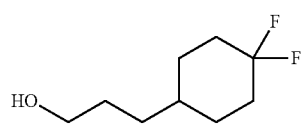 [SMILES: OCCCC1CCC(F)(F)CC1]

Under protection of nitrogen gas, LiAlH$_4$ (337.7 mg, 8.90 mmol) was added slowly in a solution of ethyl 3-(4,4-difluorocyclohexyl)propanoate (980 mg, 4.45 mmol) in tetrahydrofuran (20 mL) at 0° C. The reaction solution was then stirred at 20° C. for 2 h. The reaction solution was quenched with water (20 mL) and 2 mol/l sodium hydroxide (4 mL), followed by filtering. The filtrate was extracted with ethyl acetate (20 mL×2). The combined organic phase was washed with brine (20 mL), dried over anhydrous sodium sulfate, filtered and evaporated. The residue was purified by column chromatography to give the title compound (colorless oil, 680 mg, yield of 85.74%). $^1$H NMR (400 MHz, CHLOROFORM-d) δ=3.65 (t, J=6.5 Hz, 2H), 2.15-2.06 (m, 2H), 1.84-1.55 (m, 6H), 1.37-1.23 (m, 5H).

Example 21G: 3-(4,4-difluorocyclohexyl)propionaldehyde

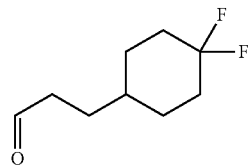 [SMILES: O=CCCC1CCC(F)(F)CC1]

Dimethyl sulfoxide (964.46 mg, 12.34 mmol) was slowly added dropwise to a solution of oxalyl chloride (939.79 mg, 7.40 mmol) in dichloromethane (10 mL) at −60° C., and then stirred for 40 min. A solution of 3-(4,4-difluorocyclohexyl)propan-1-ol (1.10 g, 6.17 mmol) in dichloromethane (2 mL) was added and stirred for 20 min, followed by slowly adding triethylamine (3.12 g, 30.85 mmol). After 1 hour, the reaction solution was warmed up to 12° C. The reaction solution was dispersed into dichloromethane (50 mL) and water (50 mL). The separated organic phase was washed with water (30 mL×3), dried over anhydrous sodium sulfate, filtered and evaporated. The residue was purified by column chromatography to give the title compound (colorless oil, 500 mg, yield of 45.99%). $^1$H NMR (400 MHz, CHLORO- FORM-d) δ=9.78 (t, J=1.5 Hz, 1H), 2.48 (dt, J=1.5, 7.5 Hz, 2H), 2.10-2.03 (m, 2H), 1.80-1.73 (m, 3H), 1.65-1.58 (m, 3H), 1.33-1.22 (m, 3H).

Example 21H: 3-(4,4-difluorocyclohexyl)-1-(3-iodo-2-thienyl)propan-1-ol

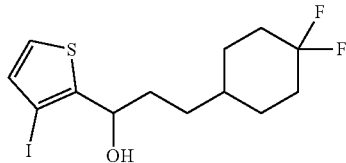 [SMILES: OC(CCC1CCC(F)(F)CC1)c1sccc1I]

A solution of n-butyllithium (2.5 M, 1.26 mL) in diethyl ether (10 mL) was cooled down to −78° C., and added slowly with diisopropylamine (347.28 mg, 3.43 mmol). After 1 hour, 3-iodothiophene (600 mg, 2.86 mmol) was added, and maintained at −78° C. with stirring for 1 h. 3-(4,4-Difluorocyclohexyl)propionaldehyde (500 mg, 2.86 mmol) was further added, and the reaction solution was stirred at −78° C. for 1 h. The reaction solution was added with ammonium chloride solution (30 mL) to quench, diluted with water (30 mL), and extracted with ethyl acetate (30 mL×3). The organic phase was washed with brine (30 mL×3), dried over anhydrous sodium sulfate, filtered and evaporated. The residue was purified by column chromatography to give the title compound (colorless oil, 500 mg, yield of 45.10%). $^1$H NMR (400 MHz, CHLOROFORM-d) δ=7.27 (d, J=5.0 Hz, 1H), 7.02 (d, J=5.3 Hz, 1H), 4.99-4.92 (m, 1H), 2.21 (br d, J=3.0 Hz, 1H), 2.10-2.06 (m, 2H), 1.90-1.80 (m, 3H), 1.71-1.58 (m, 3H), 1.52-1.45 (m, 1H), 1.36-1.28 (m, 3H).

Example 21I: 1-[3-(4,4-difluorocyclohexyl)-1-(3-iodo-2-thienyl)propyl]imidazole

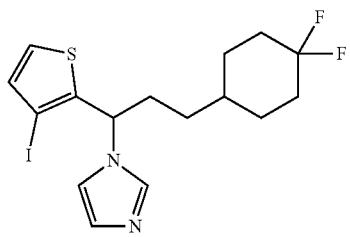 [SMILES: FC1(F)CCC(CCC(c2sccc2I)n2ccnc2)CC1]

CDI (1.05 g, 6.45 mmol) was added in a solution of 3-(4,4-difluorocyclohexyl)-1-(3-iodo-2-thienyl)propan-1-ol (500 mg, 1.29 mmol) in acetonitrile (5 mL), and the reaction solution was stirred at 70° C. for 4 h. The reaction solution was dispersed in ethyl acetate (30 mL) and water (30 mL). The organic phase was separated, washed with brine (30 mL×3), dried over anhydrous sodium sulfate, filtered and evaporated. The residue was purified by column chromatography to give the title compound (yellow oil, 300 mg, yield of 53.30%). MS-ESI (m/z): 437 (M+H)$^+$. $^1$H NMR (400 MHz, CHLOROFORM-d) δ=7.67 (s, 1H), 7.31 (d, J=5.3 Hz, 1H), 7.07 (s, 1H), 7.06-7.01 (m, 2H), 5.41 (t, J=7.8 Hz, 1H), 2.24 (q, J=7.9 Hz, 2H), 2.13-2.06 (m, 2H), 1.80-1.72 (m, 3H), 1.71-1.58 (m, 2H), 1.26 (br t, J=7.2 Hz, 4H).

Preparation of the Title Compounds (Examples 21 to 22): 8-[2-(4,4-difluorocyclohexyl)ethyl]-8H-thieno[3,4]pyrrolo[1,5-a]imidazole

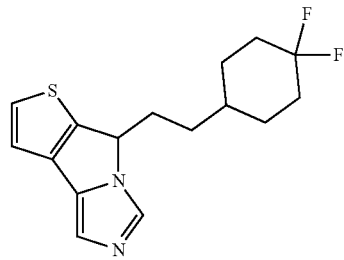 [SMILES: FC1(F)CCC(CCC2c3sccc3-c3cncn32)CC1]

Under protection of nitrogen gas, a mixture solution of 1-[3-(4,4-difluorocyclohexyl)-1-(3-iodo-2-thienyl)propyl] imidazole (250 mg, 0.573 mmol), palladium acetate (12.86 mg, 57.3 μmol), tricyclohexylphosphine (32.14 mg, 114.60 μmol), potassium carbonate (158.39 mg, 1.15 mmol) in xylene (5.00 mL) was stirred at 140° C. for 16 h. The reaction solution was dispersed into ethyl acetate (30 mL) and water (30 mL). The organic phase was separated, washed with brine (30 mL×3), dried over anhydrous sodium sulfate, filtered and evaporated. The residue was purified by column chromatography to give the title compound (a racemate, 110 mg, yield of 45.65%). MS-ESI (m/z): 309 (M+H)$^+$ (Acq Method: 5-95 AB_1.5 min; Rt: 0.728 min). The racemate was subjected to chiral separation (column: ChiralPak AD-3 150×4.6 mm I.D., 3 μm; mobile phase: A: carbon dioxide B: ethanol (0.05% diethylamine)), to give Example 21 (retention time: 4.181 min, 29.00 mg, yield of 38.49%) and Example 22 (retention time: 4.791 min, 26.00 mg, yield of 34.51%).

Example 21: $^1$H NMR (400 MHz, METHANOL-d4) δ=9.19 (s, 1H), 7.73 (d, J=5.0 Hz, 1H), 7.52 (d, J=0.8 Hz, 1H), 7.38 (d, J=5.0 Hz, 1H), 5.81-5.76 (m, 1H), 2.41-2.30 (m, 1H), 2.17-2.08 (m, 1H), 2.07-1.97 (m, 2H), 1.85-1.67 (m, 4H), 1.48-1.39 (m, 1H), 1.38-1.31 (m, 2H), 1.30-1.24 (m, 2H).

Example 22: $^1$H NMR (400 MHz, METHANOL-d4) δ=9.20 (s, 1H), 7.73 (d, J=5.0 Hz, 1H), 7.53 (s, 1H), 7.38 (d, J=5.0 Hz, 1H), 5.82-5.77 (m, 1H), 2.41-2.31 (m, 1H), 2.17-2.08 (m, 1H), 2.02 (br dd, J=4.0, 7.0 Hz, 2H), 1.82 (br d, J=11.0 Hz, 3H), 1.75-1.67 (m, 1H), 1.45 (br s, 1H), 1.40-1.31 (m, 2H), 1.25 (m, 2H).

Example 23: 8-(tert-butyl)-8H-thieno[3',2':3,4]pyrrolo[1,2-c]imidazole

Example 23A: 1-(3-iodo-2-thienyl)-2,2-dimethylpropan-1-ol

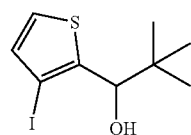

A solution of n-butyllithium (2.5 M, 4.19 mL) in diethyl ether (20 mL) was cooled down to −78° C., and added slowly with diisopropylamine (1.16 g, 11.43 mmol). After 1 hour, 3-iodothiophene (2 g, 9.52 mmol) was added, followed by stirring at −78° C. for 1 h. 2,2-Dimethylpropanol (863.11 mg, 9.52 mmol) was added, and the reaction solution was stirred at −78° C. for 1 h. The reaction solution was added with ammonium chloride solution (50 mL) to quench, diluted with water (50 mL), and extracted with ethyl acetate (50 mL×3). The organic phase was washed with brine (50 mL×3), dried over anhydrous sodium sulfate, filtered and evaporated. The residue was purified by column chromatography to give the title compound (colorless oil, 1.1 g, yield of 39.01%). $^1$H NMR (400 MHz, CHLOROFORM-d) δ-7.31-7.25 (m, 1H), 7.04-6.89 (m, 1H), 4.93-4.50 (m, 1H), 2.20-1.58 (m, 1H), 1.07-0.95 (m, 9H).

Example 23B: 1-[1-(3-iodo-2-thienyl)-2,2-dimethyl-propyl]imidazole

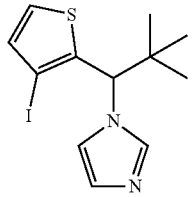 [SMILES: CC(C)(C)C(c1sccc1I)n1ccnc1]

CDI (3.01 g, 18.55 mmol) was added in a solution of 1-(3-iodo-2-thienyl)-2,2-dimethyl-propan-1-ol (1.10 g, 3.71 mmol) in acetonitrile (10 mL), and the reaction solution was stirred at 70° C. for 16 h. The reaction solution was dispersed in ethyl acetate (30 mL) and water (30 mL). The organic phase was separated and washed with brine (30 mL×3), dried over anhydrous sodium sulfate, filtered and evaporated. The residue was purified by column chromatography to give the title compound (400 mg, yield of 31.14%). MS-ESI (m/z): 347 (M+H)$^+$. $^1$H NMR (400 MHz, CHLOROFORM-d) δ=7.66 (s, 1H), 7.37 (dd, J=0.8, 5.3 Hz, 1H), 7.14-7.12 (m, 1H), 7.06 (d, J=5.3 Hz, 1H), 7.03 (s, 1H), 6.97-6.94 (m, 1H), 5.47 (s, 1H), 1.11 (s, 9H).

Preparation of the Title Compound (Example 23): 8-tert-butyl-8H-thieno[3,4]pyrrolo[1,5-a]imidazole

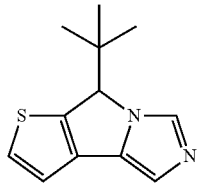

Under protection of nitrogen gas, a mixture solution of 1-[1-(3-iodo-2-thienyl)-2,2-dimethyl-propyl]imidazole (400 mg, 1.16 mmol), palladium acetate (25.94 mg, 115.53 μmol), tricyclohexylphosphine (64.80 mg, 231.06 μmol) and potassium carbonate (319.35 mg, 2.31 mmol) in xylene (5 mL) was stirred at 140° C. for 16 h. The reaction solution was dispersed in ethyl acetate (40 mL) and water (40 mL). The organic phase was separated, washed with brine (40 mL×3), dried over anhydrous sodium sulfate, filtered and evaporated. The residue was purified by preparative chromatography to give the title compound (colorless oil, 190 mg, yield of 74.80%). MS-ESI (m/z): 219 (M+H)$^+$. $^1$H NMR (400 MHz, METHANOL-d4) δ=9.22 (s, 1H), 7.69 (d, J=4.8 Hz, 1H), 7.54 (s, 1H), 7.37 (d, J=5.0 Hz, 1H), 5.57 (s, 1H), 1.11 (s, 9H).

Example 24: 8-isobutyl-8H-thieno[3',2':3,4]pyrrolo[1,2-c]imidazole Example 24A: 1-(3-iodothiophen-2-yl)-3-methylbutan-1-ol

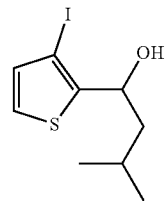

n-BuLi (2.5 M, 4.19 mL) was added dropwise in a solution of diisopropylamine (1.06 g, 10.47 mmol) in diethyl ether at −78° C., and warmed up to 0° C. with stirring for 30 min. The reaction solution was further cooled down to −78° C., and 3-iodothiophene (2 g, 9.25 mmol) was added dropwise, with stirring for 1 h. Isovaleraldehyde (983.95 mg, 11.42 mmol) was added dropwise to the reaction solution at −78° C., and then the reaction mixture was stirred at −78° C. for 2 h. The reaction mixture was quenched with saturated aqueous ammonium chloride solution (50 mL) and extracted with ethyl acetate (20 mL×3). The combined organic layers were washed with brine (50 mL), dried over anhydrous sodium sulfate, filtered and evaporated. The residue was purified by column chromatography to give the title compound (1.2 g, 42.56%). $^1$H NMR (400 MHz, CHLOROFORM-d) δ=7.18 (d, J=5.8 Hz, 1H), 6.94 (d, J=5.3 Hz, 1H), 5.02-4.96 (m, 1H), 2.02 (d, J=3.3 Hz, 1H), 1.75-1.68 (m, 2H), 1.60-1.52 (m, 1H), 0.93 (dd, J=6.4, 9.7 Hz, 6H).

Example 24B: 1-(1-(3-iodothiophen-2-yl)-3-methyl-butyl)-1H-imidazole

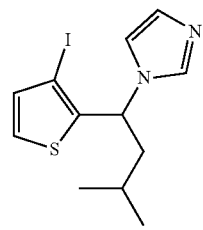 [SMILES: CC(C)CC(c1sccc1I)n1ccnc1]

CDI (1.97 g, 12.15 mmol) was added in a solution of 1-(3-iodothiophen-2-yl)-3-methylbutan-1-ol (1.2 g, 4.05 mmol) in acetonitrile (20 mL), heated to 80° C. and stirred for 3 h. The reaction solution was added with saturated aqueous ammonium chloride solution (30 mL), and extracted with ethyl acetate (10 mL×3). The combined organic layers were washed with saturated brine (50 mL), dried over anhydrous sodium sulfate, filtered and evaporated. The residue was purified by column chromatography to give the title compound (a colorless liquid, 700 mg, 49.92%). $^1$H NMR (400 MHz, CHLOROFORM-d) δ=7.70 (s, 1H), 7.31 (d, J=5.3 Hz, 1H), 7.09-7.03 (m, 3H), 5.62-5.54 (m, 1H), 2.22-2.07 (m, 2H), 1.49 (quind, J=6.7, 13.6 Hz, 1H), 1.01 (dd, J=6.8, 18.3 Hz, 6H).

Preparation of the Title Compound (Example 24): 8-isobutyl-8H-thieno[3',2':3,4]pyrrolo[1,2-c]imidazole

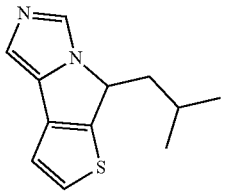

N-methylpyrrolidone (3 mL) was added to a mixture of 1-(1-(3-iodothiophen-2-yl)-3-methylbutyl)-1H-imidazole (500 mg, 1.44 mmol), tricyclohexylphosphine (80.76 mg, 288.00 μmol), pivalic acid (44.12 mg, 432 μmol), palladium acetate (3233 mg, 144 μmol) and potassium carbonate (398.04 mg, 2.88 mmol), then purged with nitrogen gas three times, heated to 180° C. and stirred for 10 min. After cooling, the reaction solution was poured into water (20 mL) and ethyl acetate (10 mL), and filtered. The filtrate was extracted with ethyl acetate (10 mL×4). The combined organic layers were washed with water (5 mL×4) and saturated brine (20 mL), dried over anhydrous sodium sulfate, filtered and evaporated. The residue was purified by high performance liquid chromatography to give the title compound (2.2 g, 61.83%). $^1$H NMR (400 MHz, METHANOL-d4) δ=7.87 (s, 1H), 7.53 (d, J=5.0 Hz, 1H), 7.22 (d, J=5.0 Hz, 1H), 6.89 (s, 1H), 5.46-5.38 (m, 1H), 2.05-1.91 (m, 2H), 1.81-1.69 (m, 1H), 1.09 (d, J=6.3 Hz, 3H), 1.01 (d, J=6.5 Hz, 3H). MS-ESI (m/z): 219 (M+H)$^+$.

Example 25: 8-isopropyl-8H-thieno[3,4]pyrrolo[1,5-a]imidazole

Example 25A: 1-(3-iodo-2-thienyl)-2-methyl-propan-2-ol

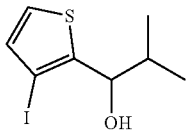

At −78° C., a solution of n-butyllithium (2.5 mol/L, 12.71 mL) in n-hexane was slowly added dropwise in a solution of diisopropylamine (3.22 g, 31.78 mmol, 4.47 mL) in diethyl ether (20 mL) over about 10 min, while the temperature was controlled at −78° C. After completion of dropwise addition, the mixture was warmed up to 0° C. and stirred for 30 min. The system was cooled down to −78° C. and then added dropwise with 3-iodothiophene (6.07 g, 28.89 mmol). After stirring for 30 min, isopropyl formaldehyde (2.50 g, 34.67 mmol, 3.16 mL) was added dropwise. After completion of reaction, the system was added with 30 mL of a saturated ammonium chloride solution, and extracted with ethyl acetate (30 mL×3). The organic phases were combined and washed with 40 mL saturated brine, and the organic phase was dried over anhydrous sodium sulfate, filtered under suction and evaporated under reduced pressure. The crude compound was purified by column chromatography to give the title compound (colorless oil, 4 g, 14.18 mmol, yield of 49.07%). $^1$H NMR (400 MHz, CHLOROFORM-d) δ=7.27 (d, J=5.3 Hz, 1H), 7.01 (d, J=5.3 Hz, 1H), 4.70 (br d, J=7.0 Hz, 1H), 2.13-2.05 (m, 2H), 1.09 (d, J=6.8 Hz, 3H), 0.90 (d, J=6.8 Hz, 3H).

Example 25B: 1-[1-(3-iodo-2-thienyl)-2-methyl-propyl]imidazole

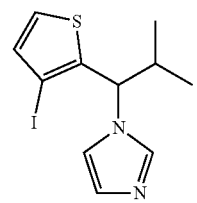

1,1-Carbonyldiimidazole (5.75 g, 35.45 mmol) was added in a solution of 1-(3-iodo-2-thienyl)-2-methyl-propan-2-ol (2 g, 7.09 mmol) in acetonitrile (20 mL). The reaction solution was reacted at 70° C. for 2 h. The reaction solution was added with 100 mL of water, and extracted with ethyl acetate (50 mL×3). The combined organic phase was washed with 50 mL of saturated brine, dried over anhydrous sodium sulfate, filtered under suction and evaporated under reduced pressure. The crude product was purified by column chromatography to give the title compound (colorless oil compound, 2 g, 6.02 mmol, yield of 42.45%). $^1$H NMR (400 MHz, CHLOROFORM-d) δ=7.67 (s, 1H), 7.34-7.30 (m, 1H), 7.07-7.04 (m, 2H), 7.01 (d, J=5.3 Hz, 1H), 5.10-5.03 (m, 1H), 2.51 (quind, J=6.5, 10.8 Hz, 1H), 0.98 (d, J=6.5 Hz, 3H), 0.89 (d, J=6.3 Hz, 3H).

Preparation of the Title Compound (Example 25): 8-isopropyl-8H-thieno[3,4]pyrrolo[1,5-a]imidazole

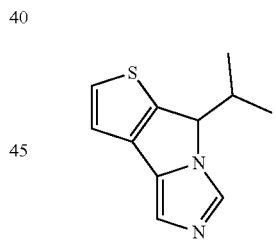

Under protection of nitrogen gas, 1-[1-(3-iodo-2-thienyl)-2-methyl-propyl]imidazole (200 mg, 602.05 μmol), palladium acetate (13.52 mg, 60.20 μmol), tricyclohexylphosphine (33.77 mg, 120.47 μmol), potassium carbonate (249.63 mg, 1.81 mmol), pivalic acid (18.45 mg, 180.61 μmol) and 1-methyl-2-pyrrolidone (1 mL) were successively added in a reaction flask, and reacted at 180° C. for 10 min. After completion of reaction, the reaction solution was filtered under suction, and washed with ethyl acetate (5 mL). The organic phase was added with 5 mL of water, extracted with ethyl acetate (20 mL×3). The combined organic phase was washed with 20 mL of saturated brine, dried over anhydrous sodium sulfate, filtered under suction and evaporated under reduced pressure. The crude product was purified by column chromatography to give the title compound (100 mg, 489.50 μmol, yield of 81.31%). $^1$H NMR (400 MHz, CHLOROFORM-d) δ=8.90 (s, 1H), 7.52 (d, J=5.0

Hz, 1H), 7.25 (d, J=1.3 Hz, 2H), 5.41 (d, J=4.0 Hz, 1H), 2.62-2.50 (m, 1H), 1.17 (d, J=6.8 Hz, 3H), 0.74 (d, J=6.8 Hz, 3H).

Examples 26 to 27: (7S,8aS)-7-(1-hydroxy-2-(8H-thieno[3',2':3,4]pyrrolo[1,2-c]imidazol-8-yl)ethyl) hexahydroindolizine-3(2H)-one Example 26A:
1-(butyl-3-ene-1-yl)pyrrolidine-2,5-dione

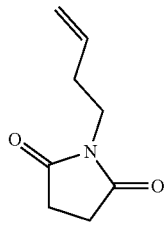

Under protection of nitrogen gas, pyrrolidine-2,5-dione (100 g, 1.01 mol) was dissolved in DMF (1 L), and sodium hydride (48.48 g, 1.21 mol, purity of 60%) was added thereto at 0° C., followed by stirring at 20° C. for 1 h. 4-Bromo-1-butene (163.49 g, 1.21 mol) was added dropwise at 20° C., and the mixture was warmed up to 50° C. to react for 16 h. The reaction solution was poured into brine (6 L) to quench, and extracted with ethyl acetate (1 L×5). The organic phase was dried over anhydrous sodium sulfate and filtered. The residue was purified by column chromatography to give the title compound (130 g, 848.67 mmol, yield of 84%). $^1$H NMR (400 MHz, CHLOROFORM-d) δ=5.72 (tdd, J=7.0, 10.1, 17.0 Hz, 1H), 5.14-4.92 (m, 2H), 3.58 (t, J=7.2 Hz, 2H), 2.68 (s, 4H), 2.43-2.26 (m, 2H).

Example 26B: 1-(butyl-3-ene-1-yl)-5-hydroxypyrrolidin-2-one

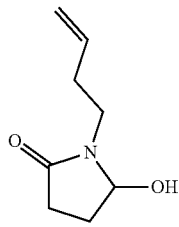

Under protection of nitrogen gas, 1-(butyl-3-ene-1-yl) pyrrolidine-2,5-dione (20 g, 130.57 mmol) was dissolved in methanol (150 mL), and sodium borohydride (7.41 g, 195.86 mmol) was added portionwise at 15° C. After stirring at 20° C. for 1 hour, the reaction solution was quenched with water (200 mL) and extracted with dichloromethane (200 mL×3). The combined organic phase was dried over anhydrous sodium sulfate, filtered and evaporated. The residue was purified by column chromatography to give the title compound (54 g, yield of 38%, collected from 7 batches in parallel), as a yellow liquid. $^1$H NMR (400 MHz, CHLOROFORM-d) δ=5.77 (tdd, J=6.9, 10.2, 17.1 Hz, 1H), 5.27-5.17 (m, 1H), 5.13-4.98 (m, 2H), 3.61-3.49 (m, 2H), 3.25 (td, J=7.0, 13.7 Hz, 1H), 2.63-2.46 (m, 1H), 2.43-2.19 (m, 4H), 1.94-1.84 (m, 1H).

Example 26C:
(7S,8aS)-3-oxodecahydroindolizin-7-yl-formate

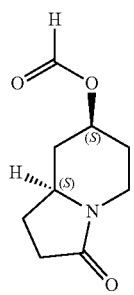

A solution of 1-(butyl-3-ene-1-yl)-5-hydroxypyrrolidin-2-one (36 g, 231.97 mmol) in formic acid (360 mL) was stirred at 20° C. for 16 h. The reaction solution was concentrated to give the title compound (35 g, crude, yellow oil), which was directly used in the next step without further purification.

Example 26D:
(7S,8aS)-7-hydroxyhexahydroindolizin-3(2H)-one

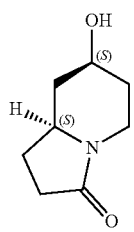

Lithium hydroxide monohydrate (16.03 g, 382.1 mmol) was added in a solution of (7S,8aS)-3-oxodecahydroindolizin-7-yl-formate (35 g, 191 mmol) in methanol (150 mL) and water (50 mL). The reaction solution was stirred at 20° C. for 2 h. The reaction was quenched with 1N hydrochloric acid to pH=8-9. The reaction solution was concentrated, and the residue with that from the last batch was purified by column chromatography to give the title compound (45.8 g, 295.12 mmol), as a colorless liquid. $^1$H NMR (400 MHz, CHLOROFORM-d)=4.17-4.02 (m, 1H), 3.81-3.66 (m, 1H), 3.49 (dtd, J=3.3, 7.3, 11.2 Hz, 1H), 3.13 (br. s., 1H), 2.63 (dt, J=3.4, 13.2 Hz, 1H), 2.43-2.09 (m, 5H), 2.00-1.90 (m, 1H), 1.69-1.56 (m, 1H), 1.37-1.24 (m, 1H), 1.15 (q, J=11.5 Hz, 1H).

Example 26E: (7S,8aS)-3-oxodecahydroindolizin-7-yl-4-methylbenzenesulfonate

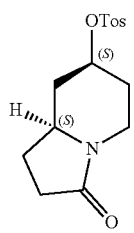

Triethylamine (59.73 g, 590.24 mmol) and DMAP (3.61 g, 29.51 mmol) were added in a solution of (7S,8aS)-7-hydroxyhexahydroindolizin-3(2H)-one (45.80 g, 295.12 mmol) in dichloromethane (700 mL), and then cooled down to 0° C. The reaction solution was added with p-methylbenzenesulfonyl chloride (67.52 g, 354.14 mmol), and stirred at 20° C. for 16 h. The reaction was quenched with 1N HCl to pH=6, followed by extraction with ethyl acetate (200 mL×4). The combined organic phase was washed with brine, dried and concentrated to give the crude title compound (85 g), which was directly used in the next step without further purification. $^1$H NMR (400 MHz, CHLOROFORM-d)=7.80 (d, J=8.5 Hz, 2H), 7.36 (d, J=8.0 Hz, 2H), 4.57 (tt, J=4.3, 11.4 Hz, 1H), 4.23-4.04 (m, 1H), 3.48 (dtd, J=3.1, 7.3, 11.0 Hz, 1H), 2.61 (dt, J=3.4, 13.2 Hz, 1H), 2.46 (s, 3H), 2.42-2.33 (m, 2H), 2.29-2.15 (m, 2H), 1.98-1.87 (m, 1H), 1.70-1.60 (m, 1H), 1.53 (dd, J=5.4, 11.7 Hz, 1H), 1.46-1.34 (m, 1H).

Example 26F: (7R,8aS)-3-oxodecahydroindolizine-7-carbonitrile

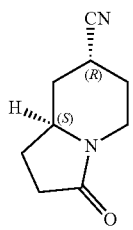

Sodium cyanide (15.45 g, 315.15 mmol) was added in a solution of (7S,8aS)-3-oxodecahydroindolizin-7-yl-4-methylbenzenesulfonate (65 g, 210.1 mmol) in dimethyl sulfoxide (700 mL), and the reaction solution was warmed up to 80° C. with stirring for 16 h. The reaction solution was quenched with water (4 L) and extracted with ethyl acetate (500 mL×10). The combined organic phase was dried, filtered and concentrated. The residue was purified by column chromatography to give the title compound (32 g, yield of 92.76%), a yellow oil. $^1$H NMR (400 MHz, CHLOROFORM-d)=4.18 (dd, J=4.6, 13.9 Hz, 1H), 3.81 (dtd, J=3.3, 7.4, 11.1 Hz, 1H), 3.16 (br. s., 1H), 3.07-2.93 (m, 1H), 2.48-2.25 (m, 3H), 2.17 (dd, J=1.8, 13.3 Hz, 1H), 1.99 (d, J=13.6 Hz, 1H), 1.69-1.55 (m, 2H), 1.50-1.37 (m, 1H).

Example 26G: (7S,8aS)-3-oxodecahydroindolizine-7-carboxaldehyde

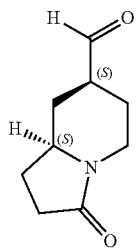

Under protection of nitrogen gas, 1 M diisobutyl aluminum hydride solution (60.69 mL, 60.69 mmol) was added dropwise in a solution of (7R,8aS)-3-oxodecahydroindolizine-7-carbonitrile (5 g, 30.45 mmol) in dichloromethane (50 mL) at −70° C. The reaction solution was stirred at −70° C. for 2 h. The reaction solution was quenched with water (5 mL) and was adjusted to pH of 5 with 1 equivalent of dilute hydrochloric acid. The reaction solution was extracted with dichloromethane (50 mL×3). The combined organic phase was washed with brine (100 mL), dried, filtered and concentrated. The concentrate was purified by column chromatography to give the crude title compound (2 g), as yellow oil. $^1$H NMR (400 MHz, CHLOROFORM-d) δ=9.82 (s, 1H), 4.18 (dd, J=4.8, 13.8 Hz, 1H), 4.06 (dd, J=5.1, 13.7 Hz, 1H), 3.88-3.73 (m, 1H), 3.51 (dtd, J=3.5, 7.3, 11.2 Hz, 1H), 3.15 (br s, 1H), 3.08-2.93 (m, 1H), 2.75 (br t, J=5.4 Hz, 1H), 2.67 (dt, J=3.0, 13.4 Hz, 1H), 2.49-2.11 (m, 9H), 2.11-1.88 (m, 1H), 1.81-1.51 (m, 5H), 1.50-1.36 (m, 3H).

Example 26H: (7S,8aS)-7-((S)-1-hydroxybutyl-3-ene-1-yl)hexahydroindolizine-3(2H)-one

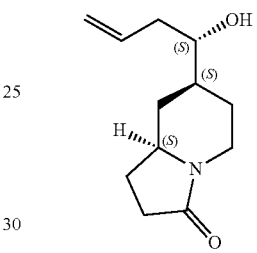

Under protection of nitrogen gas, indium (686.62 mg, 5.98 mmol), (1S,2R)-2-amino-1,2-diphenyl-ethanol (637.69 mg, 2.99 mmol) and pyridine (473.02 mg, 5.98 mmol) were added in a solution of bromopropene (723.46 mg, 5.98 mmol) in tetrahydrofuran (30 mL) at 15° C. The reaction solution was stirred for 3 h until it became clear. (7S,8aS)-3-oxodecahydroindolizine-7-carboxaldehyde (500.00 mg, 2.99 mmol) in tetrahydrofuran (10 mL) was added to the above reaction solution after cooled down to −70° C., and then stirred for 3 h. The reaction solution was warmed up to 16° C. and further stirred for 10 h. The reaction solution was adjusted to pH of 4 with 1 equivalent of dilute hydrochloric acid, and then extracted with ethyl acetate (50 mL×3). The combined organic phase was washed with brine (100 mL), dried, filtered and concentrated. The concentrate was purified by column chromatography to give the crude title compound (300 mg, yield of 48%), as yellow oil.

Example 26I: (7S,8aS)-7-((S)-1-((tert-butyldimethylsilyl)oxy)butyl-3-ene-1-yl)hexahydroindolizine-3(2H)-one

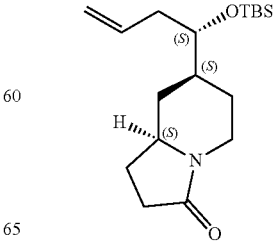

Under protection of nitrogen gas, 2,6-dimethylpyridine (4.61 g, 42.99 mmol), tert-butyldimethylsilyl trifluoromethanesulfonate (5.68 g, 21.5 mmol) were added in a solution of (7S,8aS)-7-((S)-1-hydroxybutyl-3-ene-1-yl)hexahydroindolizine-3(2H)-one (3 g, 14.33 mmol) in dichloromethane (50 mL) at 0° C. The reaction solution was stirred at 15° C. for 2 h. The reaction solution was adjusted to pH of 6 with 1 mol/L dilute hydrochloric acid, and then extracted with ethyl acetate (100 mL×3). The combined organic phase was washed with brine (150 mL), dried, filtered and concentrated. The concentrate was purified by column chromatography to give the title compound (1.5 g, yield of 32.3%), as yellow oil.

Example 26J: (7S,8aS)-7-((S)-1-((tert-butyldimethylsilyl)oxy)butyl-3-ene-1-yl)hexahydroindolizine-3(2H)-one

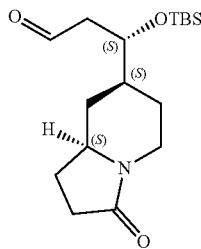

At −78° C., ozone was introduced into a mixture solution of (7S,8aS)-7-((S)-1-((tert-butyldimethylsilyl)oxy)butyl-3-ene-1-yl)hexahydroindolizine-3(2H)-one (1.5 g, 4.64 mmol) in dichloromethane (20 mL) and methanol (5 mL), until the reaction solution turned blue. Nitrogen gas gas was then introduced for 5 min, and dimethyl sulfide (2.88 g, 46.4 mmol) was added at −70° C. The reaction solution was stirred at 15° C. for 10 h. The reaction mixture was concentrated, and the concentrate was purified by column chromatography to give the title compound (0.85 g, yield of 56.28%), as brown oil. $^1$H NMR (400 MHz, CHLOROFORM-d) δ=9.87 (dd, J=2.1, 4.9 Hz, 1H), 4.54-4.33 (m, 1H), 4.25-4.02 (m, 1H), 3.98-3.81 (m, 1H), 3.77-3.35 (m, 1H), 2.79-2.51 (m, 2H), 2.43-2.31 (m, 2H), 2.29-2.10 (m, 2H), 2.05-1.90 (m, 1H), 0.98-0.79 (m, 10H), 0.16-0.04 (m, 6H).

Example 26K: (7S,8aS)-7-((1S)-1-((tert-butyldimethylsilyl)oxy)-3-hydroxy-3-(3-iodothiophen-2-yl)propyl)hexahydroindolizine-3(2H)-one

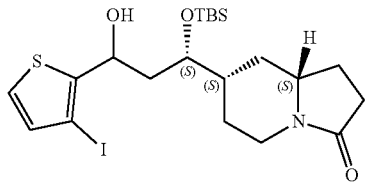

Under protection of nitrogen gas, 2.5 M n-butyllithium solution (294.91 µL) was added dropwise to a solution of diisopropylamine (74.61 mg, 737.28 µmol) in diethyl ether (5 mL) at −70° C. After stirring at 0° C. for 30 min, the mixture was cooled down to −70° C. and added with 3-iodothiophene (154.86 mg, 737.28 µmol), and the reaction solution was stirred for 1 h. A solution of (7S,8aS)-7-((S)-1-((tert-butyldimethylsilyl)oxy)butyl-3-ene-1-yl)hexahydroindolizine-3(2H)-one (200.00 mg, 614.40 µmol) in diethyl ether (5 mL) was added dropwise to the reaction solution, which was then stirred at −70° C. for 2 h. The reaction solution was quenched with saturated aqueous ammonium chloride solution (50 mL), and extracted with ethyl acetate (30 mL×3). The combined organic phase was washed with brine (50 mL), dried, filtered and concentrated. The concentrate was purified by column chromatography to give the title compound (0.15 g, yield of 38.3%), as yellow oil. $^1$H NMR (400 MHz, CHLOROFORM-d) δ=7.08-6.89 (m, 1H), 5.10 (br t, J=9.9 Hz, 1H), 4.54-3.42 (m, 7H), 3.17-2.49 (m, 3H), 2.45-1.75 (m, 17H), 1.43 (s, 4H), 0.92 (s, 9H), 0.27-0.03 (m, 12H).

Example 26L: (7S,8aS)-7-((1S)-1-((tert-butyldimethylsilyl)oxy)-3-(1H-imidazol-1-yl)-3-(3-iodothiophen-2-yl)propyl)hexahydroindolizine-3(2H)-one

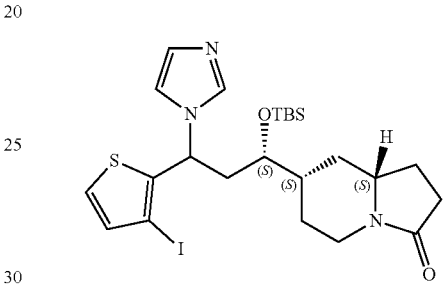

Under protection of nitrogen gas, carbonyldiimidazole (4.9 g, 30.25 mmol) was added in a solution of (7S,8aS)-7-((1S)-1-((tert-butyldimethylsilyl)oxy)-3-hydroxy-3-(3-iodothiophen-2-yl)propyl)hexahydroindolizine-3(2H)-one (3.24 g, 6.05 mmol) in acetonitrile (5 mL). The reaction solution was stirred at 80° C. for 2 h, then quenched with saturated aqueous ammonium chloride solution (50 mL), and extracted with ethyl acetate (30 mL). The organic phase was washed with brine (50 mL), dried, filtered and concentrated. The concentrate was purified by column chromatography to give the title compound (2 g, yield of 56.5%), as brown oil. $^1$H NMR (400 MHz, CHLOROFORM-d) δ=7.87-7.64 (m, 1H), 7.32 (dd, J=5.3, 8.3 Hz, 1H), 7.14-6.93 (m, 3H), 5.97-5.58 (m, 1H), 4.01-3.29 (m, 4H), 3.09-2.82 (m, 1H), 2.63-2.07 (m, 7H), 1.95-1.49 (m, 10H), 1.01-0.72 (m, 14H), 0.19-−0.08 (m, 7H).

Example 26M: (7S,8aS)-7-((1S)-1-((tert-butyldimethylsilyl)oxy)-2-(8H-thieno[3',2':3,4]pyrrolo[1,2-c]imidazol-8-yl)ethyl)hexahydroindolizine-3(2H)-one

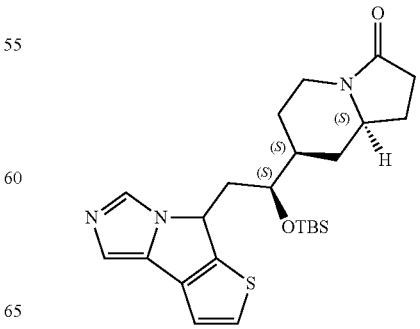

Under protection of nitrogen gas, potassium carbonate (354 mg, 2.56 mmol), palladium acetate (19.17 mg, 85.38 µmol), tricyclohexylphosphine (47.89 mg, 170.76 µmol) and pivalic acid (26.16 mg, 256.14 µmol) were added in a solution of (7S,8aS)-7-((1S)-1-(((tert-butyldimethylsilyl)oxy)-3-(1H-imidazol-1-yl)-3-(3-iodothiophen-2-yl)propyl)hexahydroindolizine-3(2H)-one (0.5 g, 0.854 mmol) in N-methylpyrrolidone (2 mL). The reaction solution was stirred at 180° C. for 10 min. The reaction solution was filtered, and the filtrate was poured into water (50 mL) and extracted with ethyl acetate (30 mL×3). The combined organic phase was washed with brine (100 mL), dried, filtered and concentrated. The concentrate was purified by column chromatography to give the title compound (400 mg, yield of 51.2%), as brown oil.

Example 26N: (7S,8aS)-7-((1S)-1-hydroxy-2(8H-thieno[3',2':3,4]pyrrolo[1,2-c]imidazol-8-yl)ethyl)hexahydroindolizine-3(2H)-one

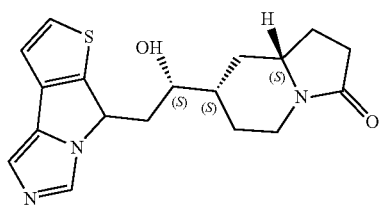

Under protection of nitrogen gas, p-toluenesulfonic acid (263.4 mg, 1.53 mmol) was added in a solution of (7S,8aS)-7-((1S)-1-((tert-butyldimethylsilyl)oxy)-2-(8H-thieno[3',2':3,4]pyrrolo[1,2-c]imidazol-8-yl)ethyl) hexahydroindolizine-3(2H)-one (350 mg, 0.765 mmol) in dichloromethane (3 mL). The reaction solution was stirred at 10° C. for 16 h, and then concentrated. The concentrate was purified by a preparative chromatographic column to give the title compound (200 mg, yield of 69.3%), as brown oil.

Preparation of the Title Compounds (Examples 26 to 27): (7S,8aS)-7-((1S)-1-hydroxy-2(8H-thieno[3',2':3,4]pyrrolo[1,2-c]imidazol-8-yl)ethyl)hexahydroindolizine-3(2H)-one Example 26

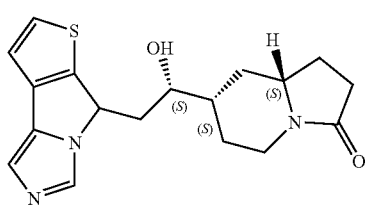

A mixture of isomers 1, 2 and 3

Example 27

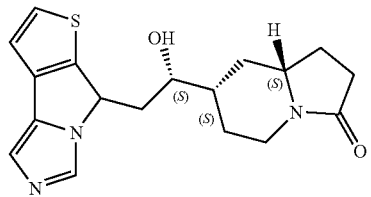

A mixture of isomers 4, 5 and 6

(7S,8aS)-7-((1S)-1-hydroxy-2(8H-thieno[3',2':3,4]pyrrolo[1,2-c]imidazol-8-yl)ethyl)hexahydroindolizine-3(2H)-one (200 mg, 0.582 mmol) was subjected to chiral separation (column: AD (250 mm*30 mm, 5 µm); mobile phase: [alkaline-ethanol]; B %: 35%-%, minutes) to give Example 26 (RT=3.837 min, 3.931 min, 4.024 min, 20 mg, yield of 10%) and Example 27 (RT=4.406 min, 4.54 min, 4.630 min, 20 mg, yield of 10%).

Example 26: $^1$H NMR (400 MHz, CHLOROFORM-d) δ=8.02-7.57 (m, 1H), 7.38-7.23 (m, 1H), 7.13-7.00 (m, 1H), 6.82 (br s, 1H), 5.62-5.39 (m, 1H), 4.32-4.09 (m, 1H), 3.93-3.67 (m, 2H), 3.44-3.30 (m, 1H), 2.95 (br t, J=12.3 Hz, 1H), 2.87-2.62 (m, 1H), 2.45-1.96 (m, 5H), 1.61-1.14 (m, 6H).

Example 27: $^1$H NMR (400 MHz, CHLOROFORM-d) δ=8.06-7.61 (m, 1H), 7.26 (br dd, J=4.9, 11.2 Hz, 1H), 7.05 (t, J=6.2 Hz, 1H), 6.83 (br s, 1H), 5.60-5.36 (m, 1H), 4.17 (br t, J=10.5 Hz, 1H), 3.91-3.51 (m, 3H), 3.42-2.52 (m, 2H), 2.43-1.67 (m, 7H), 1.47 (br dd, J=4.6, 6.7 Hz, 9H).

Example 28: (1S)-1-(tetrahydro-2H-pyran-4-yl)-2-((R)-8H-thieno[3',2':3,4]pyrrolo[1,2-c]imidazol-8-yl)ethanol Example 29: (1S)-1-(tetrahydro-2H-pyran-4-yl)-2-((S)-8H-thieno[3',2':3,4]pyrrolo[1,2-c]imidazol-8-yl)ethanol Example 28A: (S)-1-(tetrahydro-2H-pyran-4-yl)but-3-en-1-ol

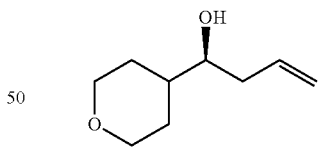

A mixture of pyridine (1.39 g, 17.52 mmol), 3-bromo-1-propene (2.12 g, 17.52 mmol), (1S,2R)-2-amino-1,2-diphenyl-ethanol (1.87 g 8.76 mmol) and tetrahydrofuran (100 mL) was purged with nitrogen gas three times, and indium (2.01 g, 17.52 mmol) was added portionwise thereto at 10° C. Tetrahydropyran-4-carboxaldehyde (1 g, 8.76 mmol) was added dropwise to the mixture at −78° C. with stirring for 1 h, then cooled down to 0° C. and stirred for another 2 h. The reaction solution was quenched with saturated ammonium chloride solution (20 mL), filtered, and washed with petroleum ether (100 mL). The filtrate was washed twice with brine (50 mL), dried over anhydrous sodium sulfate, filtered and evaporated. The residue was purified by column chromatography to give the title compound as colorless oil (1.2 g, yield of 87.69%). ¹H NMR (400 MHz, CHLOROFORM-d) δ=5.94-5.77 (m, 1H), 5.22-5.12 (m, 2H), 4.01 (td, J=5.8, 11.2 Hz, 2H), 3:43-3.31 (m, 3H), 2.37 (dddd, J=1.8, 3.3, 4.5, 14.0 Hz, 1H), 0.2.12 (td, J=8.4, 14.1 Hz, 1H), 1.77 (br dd, J=1.4, 13.2 Hz, 1H), 1.63-1.51 (m, 2H), 1.49-1.37 (m, 2H).

Example 28B: (S)-tert-butyldimethyl((1-(tetrahydro-2H-pyran-4-yl)but-3-ene-1-yl)oxy)silane

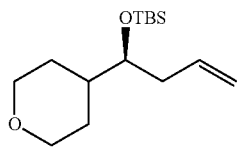 [SMILES: C=CC[C@H](O[Si](C)(C)C(C)(C)C)C1CCOCC1]

2,6-Dimethylpyridine (2.74 g, 25.6 mmol) and TBSOTf (5.08 g, 19.2 mmol) were added in a solution of (S)-1-(tetrahydro-2H-pyran-4-yl)bul-3-en-1-ol (2 g, 12.8 mmol) in dichloromethane (20 mL) at 0° C. and stirred at 0° C. for 2 h. The reaction solution was diluted with dichloromethane (50 mL), washed with water (30 mL) and saturated brine (50 mL), dried over anhydrous sodium sulfate, filtered and evaporated. The residue was purified by column chromatography to give the title compound as colorless oil (2.5 g, yield of 72.21%). ¹H NMR (400 MHz, CHLOROFORM-d) S=5.88-5.67 (m, 1H), 5.08-4.95 (m, 2H), 4.00-3.87 (m, 2H), 3.44 (q, J=5.4 Hz, 1H), 3.36-3.21 (m, 2H), 2.26-2.14 (m, 2H), 1.66-1.54 (m, 2H), 1.43-1.30 (m, 3H), 0.85 (s, 9H), 0.01 (d, J=5.3 Hz, 6H).

Example 28C: (S)-3-(tert-butyldimethylsilyl)oxy)-3-(tetrahydro-2H-pyran-4-yl)propionaldehyde

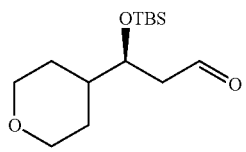 [SMILES: CC(C)(C)[Si](C)(C)O[C@@H](CC=O)C1CCOCC1]

Ozone was introduced into a mixture solution of (S)-tert-butyldimethyl((1-(tetrahydro-2H-pyran-4-yl)but-3-ene-1-yl)oxy)silane (2.5 g, 9.24 mmol) in dichloromethane (15 mL) and methanol (15 mL) at −78° C. until the reaction solution turned blue, and the excess ozone was blown off with nitrogen gas. Dimethyl sulfide (5.74 g, 92.4 mmol) was then added to the reaction solution, and stirred for 2 h. The reaction solution was warmed slowly to room temperature and stirred overnight. The reaction solution was evaporated in a rotary evaporator to remove the solvent, then diluted with ethyl acetate (50 mL), washed with water (15 mL) and brine (50 mL), dried over anhydrous sodium sulfate, filtered and evaporated. The residue was purified by column chromatography to give the title compound as colorless oil (1.5 g, 59.58%). ¹H NMR (400 MHz, CHLOROFORM-d) δ=9.84 (t, J=2.4 Hz, 1H), 4.05-3.95 (m, 3H), 3.40-3.30 (m, 2H), 2.56 (dt, J=1.5, 3.4 Hz, 2H), 1.68-1.52 (m, 3H), 1.47-1.32 (m, 2H), 0.88 (s, 8H), 0.07 (d, J=8.0 Hz, 6H).

Example 28D: (3S)-3-(tert-butyldimethylsilyl)oxy)-1-(3-iodothiophen-2-yl)-3-(tetra hydro-2H-pyran-4-yl)propan-1-ol

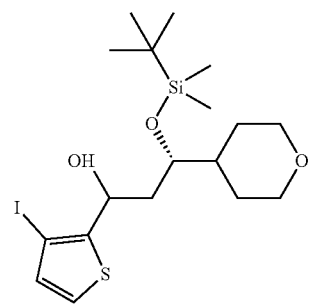 [SMILES: CC(C)(C)[Si](C)(C)O[C@@H](CC(O)c1sccc1I)C1CCOCC1]

n-BuLi (2.5 M, 1.05 mL) was added dropwise to a solution of diisopropylamine (289 mg, 2.86 mmol) in diethyl ether (5 mL) at −78° C., and warmed up to 0° C. with stirring for 30 min. 3-Thiophene (500 mg, 3.38 mmol) was then added to the reaction solution at −78° C. and stirred for 1 h. 3-((Tert-butyldimethylsilyl)oxy)-3-cyclohexylpropionaldehyde was added dropwise to the above reaction solution, and stirred for another 1 h. The reaction solution was quenched with saturated ammonium chloride solution (50 mL) and extracted with ethyl acetate (50 mL×3). The combined organic layers were washed with brine (100 mL), dried over anhydrous sodium sulfate, filtered and evaporated. The residue was purified by column chromatography to give the title compound as yellow oil (6.2 g, yield of 54.21%). ¹H NMR (400 MHz, CHLOROFORM-d) δ=7.09 (d, J=5.0 Hz, 1H), 6.86 (dd, J=5.1, 9.2 Hz, 1H), 5.20-4.88 (m, 1H), 5.06 (br d, J=5.8 Hz, 1H), 3.86 (br d, J=5.5 Hz, 2H), 3.22-3.12 (m, 2H), 2.44-2.37 (m, 1H), 1.78-1.67 (m, 3H), 1.56 (br s, 1H), 1.27-1.19 (m, 2H), 0.80 (d, J=4.8 Hz, 9H), 0.06--0.03 (m, 6H).

Example 28E: 1-((3S)-3-((tert-butyldimethylsilyl)oxy)-1-(3-iodothiophen-2-yl)-3-(tetrahydro-2H-pyran-4-yl)propyl)-1H-imidazole

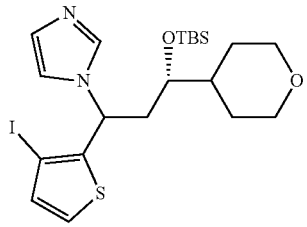 [SMILES: CC(C)(C)[Si](C)(C)O[C@@H](CC(c1sccc1I)n1ccnc1)C1CCOCC1]

CDI (201.64 mg, 1.24 mmol) was added in a solution of (3S)-3-(tert-butyldimethylsilyl)oxy)-1-(3-iodothiophen-2-yl)-3-(tetrahydro-2H-pyran-4-yl)propan-1-ol (200 mg, 414.52 μmol) in acetonitrile (5 mL), and warmed up to 80° C. with stirring for 3 h. The reaction solution was added with water (10 mL), and extracted with ethyl acetate (10 mL×3). The combined organic layers were washed with saturated brine (20 mL), dried over anhydrous sodium sulfate, filtered and evaporated. The residue was purified by column chromatography to give the title compound as a yellow liquid (500 mg, yield of 56.62%). $^1$H NMR (400 MHz, CHLOROFORM-d) δ=7.72-7.61 (m, 1H), 7.31-7.24 (m, 1H), 7.07-6.94 (m, 3H), 5.72-5.59 (m, 1H), 3.99 (br dd, J=3.1, 10.7 Hz, 2H), 3.41-3.21 (m, 3H), 2.48-2.32 (m, 1H), 2.28-2.14 (m, 1H), 1.55-1.45 (m, 2H), 1.44-1.33 (m, 3H), 0.96-0.90 (m, 9H), 0.05--0.01 (m, 6H).

Example 28F: 8-((S)-2-((tert-butyldimethylsilyl)oxy)-2-(tetrahydro-2H-pyran-4-yl)-8H-thieno[3',2':3,4]pyrrolo[1,2-c]imidazole

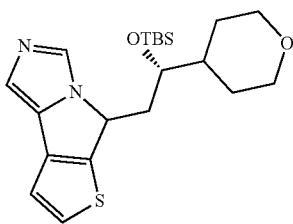 [SMILES: CC(C)(C)[Si](C)(C)O[C@@H](CC1c2sccc2-c2cncn21)C1CCOCC1]

N-methylpyrrolidone (4 mL) was added in a mixture of 1-((3S)-3-((tert-butyldimethylsilyl)oxy)-1-(3-iodothiophen-2-yl)-3-(tetrahydro-2H-pyran-4-yl)propyl)-1H-imidazole (0.4 g, 751.1 μmol), tricyclohexylphosphine (42.13 mg, 150.22 μmol), palladium acetate (16.86 mg, 75.11 μmol), pivalic acid (23.01 mg, 225.33 μmol) and potassium carbonate (207.62 mg, 1.5 mmol), then purged with nitrogen gas three times, heated to 180° C. and stirred for 10 min. After cooling, the reaction solution was poured into water (20 mL) and filtered, and then the filtrate was extracted with ethyl acetate (20 mL×4). The combined organic layers were washed with water (5 mL×4) and saturated brine (30 mL), dried over anhydrous sodium sulfate, filtered and evaporated. The residue was purified by column chromatography to give the crude title compound as a black liquid (200 mg).

Preparation of the Title Compound (Example 28)

(1S)-1-(tetrahydro-2H-pyran-4-yl)-2-((R)-8H-thieno[3',2':3,4]pyrrolo[1,2-c]imidazol-8-yl)ethanol

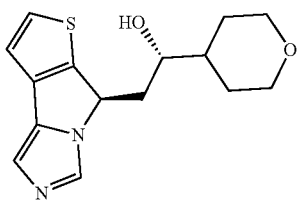 [SMILES: O[C@@H](C[C@@H]1c2sccc2-c2cncn21)C1CCOCC1]

Preparation of the Title Compound (Example 29)

(1S)-1-(tetrahydro-2H-pyran-4-yl)-2-((S)-8H-thieno[3',2':3,4]pyrrolo[1,2-c]imidazol-8-yl)ethanol

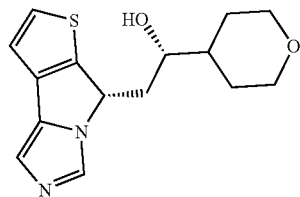 [SMILES: O[C@@H](C[C@H]1c2sccc2-c2cncn21)C1CCOCC1]

p-Toluenesulfonic acid (255.34 mg, 1.48 mmol) was added in a solution of the crude of 8-((S)-2-((tert-butyldimethylsilyl)oxy)-2-(tetrahydro-2H-pyran-4-yl)-8H-thieno[3',2':3,4]pyrrolo[1,2-c]imidazole (200 mg) in dichloromethane (4 mL), and stirred at 15° C. for 32 h. The reaction solution was diluted with dichloromethane (100 mL), washed with saturated aqueous sodium hydrogen carbonate solution (5 mL×4) and saturated brine (50 mL), dried over anhydrous sodium sulfate, filtered and evaporated. The residue was purified by high performance liquid chromatography to give the title compound (110 mg, yield of 53.38%). The title compound was subjected to chiral separation (SFC separation conditions: AD_MEOH(DEA)_5_40_2, 8 ML_8 min. MColumn: Chiralpak AD-3 100×4.6 mm I.D., 3 um; Mobile phase: A: CO$_2$ B: Methanol (0.05% DEA); Gradient: from 5% to 40% of B in 4.5 min and hold 40% for 2.5 min, then 5% of B for 1 min; Flow rate: 2.8 mL/min; Column temperature: 40° C.) to give two isomers. MS-ESI (m/z): 291 (M+H)$^+$.

Example 28: (isomer 1, SFC RT=3.575 min)$^1$H NMR (400 MHz, METHANOL-d4) δ=9.19 (s, 1H), 7.72 (d, J=5.0 Hz, 1H), 7.51 (d, J=0.8 Hz, 1H), 7.38 (d, J=5.0 Hz, 1H), 5.88 (dd, J=5.8, 8.5 Hz, 1H), 4.06-3.91 (m, 2H), 3.82 (ddd, J=2.8, 6.2, 10.9 Hz, 1H), 3.49-3.37 (m, 2H), 2.40 (ddd, J=5.6, 11.0, 13.7 Hz, 1H), 2.03 (ddd, J=2.8, 8.7, 13.7 Hz, 1H), 1.80 (br d, J=13.1 Hz, 1H), 1.74-1.63 (m, 1H), 1.60-1.52 (m, 1H), 1.51-1.37 (m, 2H).

Example 29: (isomer 2, SFC RT=3.842 min)$^1$H NMR (400 MHz, METHANOL-d4) δ=9.13 (s, 1H), 7.70 (d, J=5.0 Hz, 1H), 7.50 (d, J=0.8 Hz, 1H), 7.34 (d, J=5.0 Hz, 1H), 5.89 (t, J=5.9 Hz, 1H), 3.98 (dt, J=3.6, 12.0 Hz, 2H), 3.57 (ddd, J=3.3, 6.4, 9.9 Hz, 1H), 3.40 (dt, J=2.3, 11.8 Hz, 2H), 2.37-2.23 (m, 2H), 1.82-1.74 (m, 1H), 1.68-1.52 (m, 2H), 1.39 (dq, J=4.4, 12.5 Hz, 2H).

Example 30: 4-(8H-thieno[3',2':3,4]pyrrolo[1,2-c]imidazol-8-yl)ethyl)morpholine

Example 30A: 3-((tert-butyldimethylsilyl)oxy)propan-1-ol

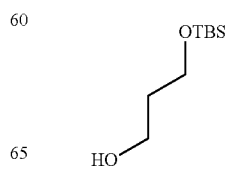

Triethylamine (13.3 g, 131.42 mmol) and tert-butyldimethylsilyl chloride (19.81 g, 131.42 mmol) were added in a solution of 1,3-propanediol (10 g, 131.42 mmol) in dichloromethane (200 mL) at 0° C., and stirred at 25° C. for 16 h. The reaction solution was diluted with water (100 mL), and then extracted with dichloromethane (100 mL×3). The combined organic layers were washed with brine (300 mL), dried over anhydrous sodium sulfate, filtered and evaporated. The residue was purified by column chromatography to give the title compound as a yellow liquid (20 g, yield of 79.95%). $^1$H NMR (400 MHz, CHLOROFORM-d) δ=3.90-3.78 (m, 4H), 2.60 (br. s., 1H), 1.78 (quin, J=5.6 Hz, 2H), 0.92-0.88 (m, 9H), 0.08 (s, 6H).

Example 30B: 3-((tert-butyldimethylsilyl)oxy)propionaldehyde

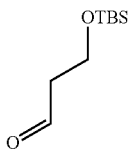 [SMILES: CC(C)(C)[Si](C)(C)OCCC=O]

Dess-Martin reagent (12.25 g, 28.09 mmol) was added dropwise into a solution of 3-((tert-butyldimethylsilyl)oxy)propan-1-ol (5 g, 26.27 mmol) in dichloromethane and stirred at 20° C. for 1 h. The reaction solution was quenched with saturated NaHCO$_3$ solution (50 mL), and extracted with dichloromethane (20 mL×3). The combined organic layers were washed with brine (50 mL), dried over anhydrous sodium sulfate, filtered and evaporated. The residue was purified by column chromatography to give the title compound as colorless oil (2 g, yield of 40.42%). $^1$H NMR (400 MHz, CHLOROFORM-d) δ=9.81 (t, J=2.1 Hz, 1H), 3.99 (t, J=6.0 Hz, 2H), 2.60 (dt, J=2.0, 6.0 Hz, 2H), 0.88 (s, 9H), 0.07 (s, 6H).

Example 30C: 3-((tert-butyldimethylsilyl)oxy)-1-(3-iodothiophen-2-yl)propan-1-ol

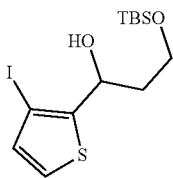 [SMILES: CC(C)(C)[Si](C)(C)OCCC(O)c1sccc1I]

n-BuLi (2.5 M, 10.47 mL) was added dropwise in a solution of diisopropylamine (5.3 g, 52.37 mmol) in diethyl ether (100 mL) at −78° C., then warmed up to 0° C. and stirred for 30 min. 3-Thiophene (10.00 g, 47.61 mmol) was then added to the reaction solution at −78° C. and stirred for 1 h, followed by addition of 3-((tert-butyldimethylsilyl)oxy)propionaldehyde (10.76 q, 57.13 mmol) with stirring for another 1 h. The reaction solution was quenched with saturated ammonium chloride solution (100 mL), and extracted with ethyl acetate (50 mL×4). The combined organic layers were washed with brine (100 mL), dried over anhydrous sodium sulfate, filtered and evaporated. The residue was purified by column chromatography to give the title compound as yellow oil (15 g, yield of 79.08%). $^1$H NMR (400 MHz, CHLOROFORM-d) δ=7.24 (d, J=5.3 Hz, 1H), 7.02 (d, J=5.3 Hz, 1H), 5.19 (td, J=2.8, 8.5 Hz, 1H), 4.32 (d, J=2.5 Hz, 1H), 3.94 (dd, J=4.6, 6.1 Hz, 2H), 2.04-1.93 (m, 2H), 0.94 (s, 9H), 0.12 (d, J=1.3 Hz, 6H).

Example 30D: 1-(3-((tert-butyldimethylsilyl)oxy)-1-(3-iodothiophen-2-yl)propyl)-1-H-imidazole

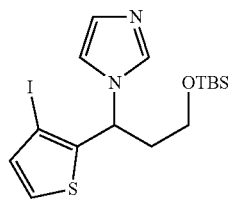 [SMILES: CC(C)(C)[Si](C)(C)OCCC(c1sccc1I)n1ccnc1]

CDI (30.53 g, 188.25 mmol) was added in a solution of 3-((tert-butyldimethylsilyl)oxy)-1-(3-iodothiophen-2-yl)propan-1-ol (15 g, 37.65 mmol) in acetonitrile (200 mL), and heated to reflux with stirring for 2 h. The reaction solution was added with water (100 mL), and extracted with ethyl acetate (50 mL×3). The combined organic layers were washed with saturated brine (100 mL), dried over anhydrous sodium sulfate, filtered and evaporated. The residue was purified by column chromatography to give the title compound as a yellow liquid (7 g, yield of 41.46%). $^1$H NMR (400 MHz, CHLOROFORM-d) δ=7.68 (s, 1H), 7.30 (d, J=5.3 Hz, 1H), 7.08-7.00 (m, 3H), 5.84 (t, J=7.5 Hz, 1H), 3.62 (td, J=5.0, 10.4 Hz, 1H), 3.42 (ddd, J=5.3, 7.3, 10.5 Hz, 1H), 2.42-2.34 (m, 2H), 0.92 (s, 9H), 0.02 (d, J=4.5 Hz, 6H).

Example 30E: 8-(2-((tert-butyldimethylsilyl)oxy)ethyl)-8H-thieno[3',2':3,4]pyrrolo[1,2-c]imidazole

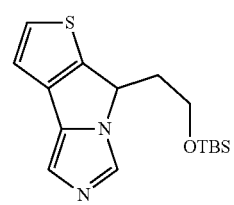 [SMILES: CC(C)(C)[Si](C)(C)OCCC1c2sccc2-c2cncn21]

N-methylpyrrolidone (15 mL) was added to a mixture of 1-(3-((tert-butyldimethylsilyl)oxy)-1-(3-iodothiophen-2-yl)propyl)-1-H-imidazole (1.5 g, 3.34 mmol), tricyclohexylphosphine (187.6 mg, 668.99 μmol), pivalic acid (102.49 mg, 1 mmol), palladium acetate (75.10 mg, 334.49 μmol) and potassium carbonate (1.39 mg, 10.03 mmol), purgd with nitrogen gas three times, and heated to 180° C. with stirring for 10 min. After cooling, the reaction solution was poured into water (100 mL) and ethyl acetate (30 mL), and filtered. The filtrate was extracted with ethyl acetate (30 mL×6). The combined organic layers were washed with water (5 mL×4) and saturated brine (50 mL), dried over anhydrous sodium sulfate, filtered and evaporated. The residue (2 g) as a crude was used directly in the next step. MS-ESI (m/z): 321 (M+H)$^+$.

Example 30F: 2(8H-thieno[3',2':3,4]pyrrolo[1,2-c]imidazol-8-yl)ethanol

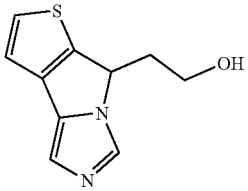 [SMILES: OCCC1c2sccc2-c2cncn21]

p-Toluenesulfonic acid (1.29 g, 7.5 mmol) was added in a solution of 8-(2-((tert-butyldimethylsilyl)oxy)ethyl)-8H-thieno[3',2':3,4]pyrrolo[1,2-c]imidazole (800 mg, 2.5 mmol) in dichloromethane (10 mL), and stirred at 15° C. for 32 h. The reaction solution was washed with dichloromethane (40 mL), saturated aqueous sodium hydrogen carbonate solution (5 mL×4) and saturated brine (20 mL), dried over anhydrous sodium sulfate, filtered and evaporated. The residue was purified by column chromatography to give the title compound (400 mg, yield of 77.57%). MS-ESI (m/z): 289 (M+H)$^+$; $^1$H NMR (400 MHz, DMSO-d6) δ=7.89 (s, 1H), 7.63 (d, J=5.0 Hz, 1H), 7.24 (d, J=5.0 Hz, 1H), 6.84 (s, 1H), 5.43 (t, J=6.8 Hz, 1H), 4.95 (t, J=4.9 Hz, 1H), 3.71-3.63 (m, 2H), 2.26-2.13 (m, 1H), 1.97-1.85 (m, 1H).

Example 30G: 2-(8H-thieno[3',2':3,4]pyrrolo[1,2-c]imidazol-8-yl)ethylmethanesulfonate

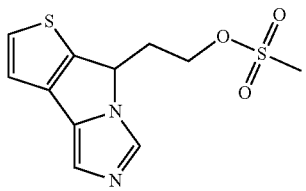 [SMILES: CS(=O)(=O)OCCC1c2sccc2-c2cncn21]

Triethylamine (98.12 mg, 969.64 µmol) and methanesulfonyl chloride (83.30 mg, 727.23 µmol) were added in a solution of 2(8H-thieno[3',2':3,4]pyrrolo[1,2-c]imidazol-8-yl)ethanol (100 mg, 484.82 µmol) in dichloromethane (2 mL) at 0° C. The mixture was stirred at 0° C. for 2 h. The reaction solution was diluted with dichloromethane (20 mL), then washed with saturated sodium hydrogen carbonate solution (20 mL) and brine (20 mL), dried over anhydrous sodium sulfate, filtered and evaporated to give a crude product (130 mg).

Preparation of the Title Compound (Example 30): 4-(8H-thieno[3',2':3,4]pyrrolo[1,2-c]imidazol-8-yl)ethyl)morpholine

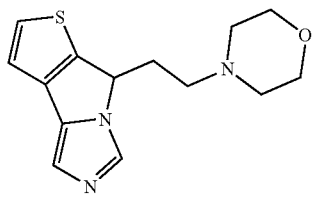 [SMILES: c1cc2c(s1)C(CCN1CCOCC1)n1cncc1-2]

Morpholine (76.6 mg, 879.2 µmol) was added in a solution of 2-(8H-thieno[3',2':3,4]pyrrolo[1,2-c]imidazol-8-yl)ethylmethanesulfonate (50 mg, 175.84 µmol) in acetonitrile (2 mL). The mixture was stirred at 80° C. for 4 h. The residue obtained by concentration and drying of the reaction solution was separated by high performance liquid chromatography to give the title compound (20 mg, yield of 41.18%). $^1$H NMR (400 MHz, METHANOL-d4) δ=7.90 (s, 1H), 7.54 (d, J=4.8 Hz, 1H), 7.21 (d, J=5.0 Hz, 1H), 6.89 (s, 1H), 5.48 (dd, J=4.6, 7.2 Hz, 1H), 3.70 (t, J=4.8 Hz, 4H), 2.57-2.44 (m, 5H), 2.44-2.35 (m, 2H), 2.15-2.06 (m, 1H).

Example 31: 8-(2-(piperidin-1-yl)ethyl)-8H-thieno[3',2':3,4]pyrrolo[1,2-c]imidazole

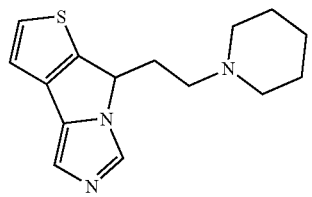 [SMILES: c1cc2c(s1)C(CCN1CCCCC1)n1cncc1-2]

Piperidine (149.73 mg, 1.76 mmol) was added in a solution of 2-(8H-thieno[3',2':3,4]pyrrolo[1,2-c]imidazol-8-yl)ethylmethanesulfonate (50 mg, 175.84 µmol) in acetonitrile (2 mL). The mixture was stirred at 80° C. for 3 h. The residue obtained by concentration and drying of the reaction solution was separated by high performance liquid chromatography, to give the title compound (20 mg, yield of 41.18%). $^1$H NMR (400 MHz, METHANOL-d4) δ=7.89 (s, 1H), 7.52 (d, J=5.0 Hz, 1H), 7.20 (d, J=5.0 Hz, 1H), 6.87 (s, 1H), 5.52-5.37 (m, 1H), 2.52-2.24 (m, 7H), 2.19-2.02 (m, 1H), 1.60 (quin, J=5.6 Hz, 4H), 1.47 (br d, J=5.3 Hz, 2H).

Example 32: 8-cyclobutyl-8-hydro-thieno[3,4]pyrrolo[1,5-a]imidazole Example 32A: cyclobutyl-(3-iodo-2-thienyl)methanol

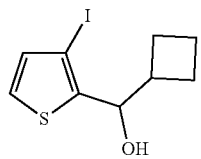 [SMILES: OC(c1sccc1I)C1CCC1]

A solution of N-butyllithium (2.5 mol/L, 10.46 mL) in n-hexane was slowly added dropwise in a solution of diisopropylamine (2.65 g, 26.16 mmol, 3.68 mL) in diethyl ether (40 mL) at −78° C. over about 10 min, during which the temperature was controlled at −78° C. After completion of dropwise addition, the mixture was warmed up to 0° C. and stirred for 30 min. The reaction system was then cooled down to −78° C., and added with 3-iodothiophene (5.49 g, 26.16 mmol). After stirring for 30 min, cyclobutylcarboxaldehyde (2 g, 23.78 mmol) was added dropwise, and stirred at −78° C. for 2 h. The system was added with 50 mL of saturated ammonium chloride solution, and then extracted with ethyl acetate (50 mL×3). The organic phase was combined and washed with 50 mL of saturated brine. The organic phase was dried over anhydrous sodium sulfate, filtered under suction and evaporated under reduced pressure. The crude compound obtained was purified by column chromatography to give the compound of cyclobutyl-(3-iodo-2-thienyl)methanol as a colorless liquid (3 g, 10.20 mmol, yield of 42.89%). $^1$H NMR (400 MHz, CHLOROFORM-d) δ=7.26-7.23 (m, 1H), 7.01 (d, J=5.3 Hz, 1H), 4.94 (d, J=7.8 Hz, 1H), 2.84-2.71 (m, 1H), 2.15-2.07 (m, 3H), 1.91-1.87 (m, 3H).

Example 32B: 1-[cyclobutyl-(3-iodo-2-thienyl)methyl]imidazole

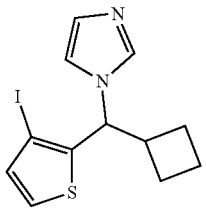 [SMILES: Ic1ccsc1C(C1CCC1)n1ccnc1]

1,1-Carbonyldiimidazole (8.27 g, 51 mmol) was added in a solution of cyclobutyl-(3-iodo-2-thienyl)methanol (3 g, 10.20 mmol) in acetonitrile (30 mL). The reaction solution was reacted at 70° C. for 4 h. The reaction solution was added with 50 mL of water, and extracted with ethyl acetate (30 mL×3). The combined organic phase was washed with 50 mL of saturated brine, dried over anhydrous sodium sulfate, filtered under suction and evaporated under reduced pressure. The crude product obtained was purified by column chromatography to give the compound of 1-[cyclobutyl-(3-iodo-2-thienyl)methyl]imidazole (2.80 g, 8.13 mmol, yield of 79.75%), as colorless oil. $^1$H NMR (400 MHz, CHLOROFORM-d) δ=7.56 (s, 1H), 7.24 (d, J=5.3 Hz, 1H), 6.97 (d, J=5.3 Hz, 2H), 6.88 (t, J=1.1 Hz, 1H), 5.32 (d, J=10.8 Hz, 1H), 3.12 (quind, J=7.8, 10.6 Hz, 1H), 2.08-1.99 (m, 2H), 1.94-1.87 (m, 1H), 1.87-1.80 (m, 2H), 1.77-1.65 (m, 1H).

Preparation of the Title Compound (Example 32): 8-cyclobutyl-8-hydro-thieno[3,4]pyrrolo[1,5-a]imidazole

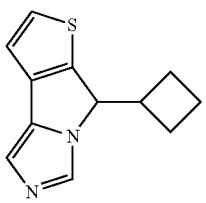 [SMILES: c1cc2c(s1)C(C1CCC1)n1cncc1-2]

Under protection of nitrogen gas, 1-[cyclobutyl-(3-iodo-2-thienyl)methyl]imidazole (1 g, 2.91 mmol), palladium acetate (65.33 mg, 291 μmol), tricyclohexylphosphine (163.21 mg, 582.00 μmol), potassium carbonate (804.38 mg, 5.82 mmol) and o-xylene (10 mL) were added successively in a reaction flask, followed by reaction at 140° C. for 16 h. The reaction solution was filtered under suction, and washed with ethyl acetate (5 mL). The organic phase was washed with 30 mL of water, and extracted with ethyl acetate (20 mL×3). The combined organic phase was washed with 20 mL of saturated brine, dried over anhydrous sodium sulfate, filtered under suction, and evaporated under reduced pressure. The crude product was purified by column chromatography to give 8-cyclobutyl-8-hydro-thieno[3,4]pyrrolo[1,5-a]imidazole (220 mg, 1.02 mmol, yield of 35.05%). $^1$H NMR (400 MHz, METHANOL-d4) δ=7.84 (s, 1H), 7.52 (dd, J=0.8, 5.0 Hz, 1H), 7.22 (d, J=5.0 Hz, 1H), 6.88 (s, 1H), 5.36 (d, J=7.5 Hz, 1H), 2.84-2.72 (m, 1H), 2.26-2.16 (m, 1H), 2.13-2.04 (m, 2H), 2.03-1.94 (m, 1H), 1.95-1.87 (m, 1H), 1.95-1.87 (m, 1H).

Examples 33 to 36: 8-(tetrahydro-2H-pyran-3-yl)-8H-thieno[3',2':3,4]pyrrolo[1,2-c]imidazole Example 33A: N-methoxy-N-methyltetrahydro-2H-pyran-3-carboxamide

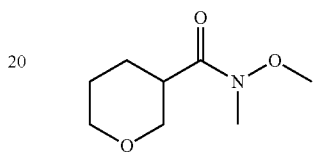

Triethylamine (5.36 g, 53.01 mmol), N-methoxy methylamine hydrochloride (1.8 g, 19.44 mmol) and HBTU (7.37 g, 19.44 mmol) were added in a solution of tetrahydropyran-3-carboxylic acid (2.3 g, 17.67 mmol) in DMF (25 mL), and the mixture was stirred overnight at room temperature. The reaction solution was diluted with water (100 mL) and extracted with ethyl acetate (50 mL×5). The combined organic layers were washed with water (10 mL×4) and saturated brine (20 mL), dried over anhydrous sodium sulfate, filtered and evaporated. The residue was purified by column chromatography to give the title compound as a colorless liquid (2.6 g, yield of 84.95%). $^1$H NMR (400 MHz, CHLOROFORM-d) δ=4.05-3.91 (m, 2H), 3.73 (s, 3H), 3.55-3.37 (m, 2H), 3.18 (s, 3H), 3.02 (br d, J=11.5 Hz, 1H), 1.99-1.92 (m, 1H), 1.86-1.67 (m, 3H).

Example 33B: tetrahydro-2H-pyran-3-carboxaldehyde

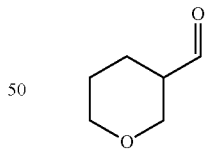

A solution of DIBAL-H (1M, 19.05 mL) in toluene was added dropwise to a solution of N-methoxy-N-methyltetrahydro-2H-pyran-3-carboxamide (3 g, 17.32 mmol) in THF (30 mL) at −78° C. The mixture was stirred at −78° C. for 3 h. The reaction solution was quenched with saturated sodium potassium tartrate solution (30 mL), and extracted with (20 mL×4). The combined organic layers were washed with saturated brine (50 mL), dried over anhydrous sodium sulfate, filtered and evaporated. The residue was purified by column chromatography to give the title compound as a colorless liquid (1.2 g, yield of 51.86%). $^1$H NMR (400 MHz, CHLOROFORM-d) δ=9.79-9.63 (m, 1H), 3.98 (dd, J=3.6, 11.7 Hz, 1H), 3.82 (dd, J=6.9, 11.7 Hz, 1H), 3.77-3.67

(m, 1H), 3.61-3.52 (m, 1H), 2.52-2.42 (m, 1H), 2.01-1.92 (m, 1H), 1.90-1.79 (m, 1H), 1.77-1.66 (m, 1H), 1.65-1.60 (m, 1H).

Example 33C: (3-iodothiophen-2-yl)(tetrahydro-2H-pyran-3-yl)methanol

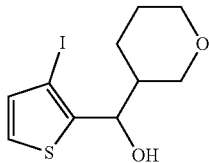 [SMILES: OC(c1sccc1I)C1CCCOC1]

n-BuLi (2.5 M, 2 mL) was added dropwise to a solution of diisopropylamine (529.94 mg, 5.24 mmol) in diethyl ether (10 mL) at −78° C., and the mixture was warmed up to 0° C. and stirred for 30 min. 3-Iodothiophene (1 g, 4.76 mmol) was then added in the reaction solution at −78° C. and stirred for 1 hour, followed by dropwise addition of tetrahydro-2H-pyran-3-carboxaldehyde (188.98 mg, 4.28 mmol) to the above reaction mixture and further stirring for 1 h. The reaction solution was quenched with saturated ammonium chloride solution (20 mL), with extracted with ethyl acetate (10 mL×4). The combined organic layers were washed with brine (20 mL), dried over anhydrous sodium sulfate, filtered and evaporated. The residue was purified by column chromatography to give the title compound as yellow oil (0.3 g, yield of 19.44%). $^1$H NMR (400 MHz, CHLOROFORM-d) δ=7.33 (d, J=5.3 Hz, 1H), 7.05-7.02 (m, 1H), 4.88 (dd, J=3.4, 8.9 Hz, 1H), 4.20 (dd, J=3.8, 11.3 Hz, 1H), 3.89-3.81 (m, 2H), 3.62-3.51 (m, 2H), 2.15-2.08 (m, 1H), 2.03-1.86 (m, 1H), 1.70-1.61 (m, 2H), 1.40-1.32 (m, 1H).

Example 33D: 1-((3-iodothiophen-2-yl)(tetrahydro-2H-pyran-3-yl)methyl)-1H-imidazole

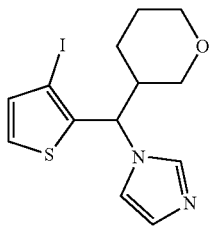 [SMILES: Ic1ccsc1C(C1CCCOC1)n1ccnc1]

CDI (450.17 mg, 2.78 mmol) was added in a solution of (3-iodothiophen-2-yl)(tetrahydro-2H-pyran-3-yl)methanol (300 mg, 925.41 μmol) in acetonitrile (5 mL), and heated to 80° C. with stirring for 4 h. The reaction solution was added with water (10 mL), and extracted with ethyl acetate (5 mL×4). The combined organic layers were washed with saturated brine (20 mL), dried over anhydrous sodium sulfate, filtered and evaporated. The residue was purified by column chromatography to give the title compound as yellow oil (200 mg, yield of 57.75%). $^1$H NMR (400 MHz, CHLOROFORM-d) δ=7.69 (s, 1H), 7.35 (dd, J=0.8, 5.3 Hz, 1H), 7.11-7.06 (m, 2H), 7.02 (d, J=5.3 Hz, 1H), 5.52-5.30 (m, 1H), 3.86-3.70 (m, 2H), 3.63-3.45 (m, 2H), 2.47 (dq, J=3.5, 7.8 Hz, 1H), 1.80-1.68 (m, 1H), 1.53-1.33 (m, 3H).

Preparation of the Title Compounds (Examples 33 to 36): 8-(tetrahydro-2H-pyran-3-yl)-8H-thieno[3',2':3,4]pyrrolo[1,2-c]imidazole

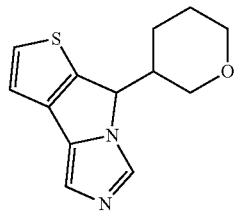 [SMILES: c1cc2c(s1)C(C1CCCOC1)n1cncc1-2]

A mixture of 1-((3-iodothiophen-2-yl)(tetrahydro-2H-pyran-3-yl)methyl)-1H-imidazole (0.18 g, 481 μmol), tricyclohexylphosphine (26.9 mg, 96.2 μmol), palladium acetate (11 mg, 48 μmol) and potassium carbonate (133 mg, 962 μmol) was added with o-Xylene (2 mL), purged with nitrogen gas three times, and heated to 140° C. with stirring for 16 h. After cooling, the reaction solution was poured into water (20 mL) and filtered, and the filtrate was extracted with ethyl acetate (10 mL×4). The combined organic layers were washed with saturated brine (20 mL), dried over anhydrous sodium sulfate, filtered and evaporated. The residue was purified by column chromatography to give the title compound as yellow oil (60 mg, yield of 39.33%). The obtained compound was subjected to chiral separation to give four isomers (separation method: OD_ETOH(DEA)_5_40_2, 8 ML_8 min. M Column: Chiralcel OD-3 100×4.6 mm I.D., 3 um; Mobile phase: A: $CO_2$ B: ethanol (0.05% DEA); Gradient: from 5% to 40% of B in 4.5 min and hold 40% for 2.5 min, then 5% of B for 1 min; Flow rate: 2.8 mL/min; Column temperature: 40° C.).

Example 33: (isomer 1, SFC RT=3.240 min)$^1$H NMR (400 MHz, METHANOL-d4) δ=7.93 (s, 1H), 7.57 (d, J=5.0 Hz, 1H), 7.23 (d, J=5.0 Hz, 1H), 6.91 (s, 1H), 5.35 (d, J=4.0 Hz, 1H), 3.87 (br d, J=11.0 Hz, 1H), 3.61-3.53 (m, 1H), 3.32-3.25 (m, 1H), 3.10 (t, J=11.0 Hz, 1H), 2.43 (qt, J=3.9, 11.2 Hz, 1H), 1.93 (td, J=1.7, 12.7 Hz, 1H), 1.75-1.66 (m, 2H), 1.54-1.41 (m, 1H).

Example 34: (isomer 2, SFC RT=3.508 min)$^1$H NMR (400 MHz, METHANOL-d4) δ=7.81 (s, 1H), 7.45 (d, J=5.0 Hz, 1H), 7.11 (d, J=5.0 Hz, 1H), 6.80 (s, 1H), 5.23 (d, J=4.3 Hz, 1H), 3.75 (br d, J=11.3 Hz, 1H), 3.50-3.42 (m, 1H), 3.20-3.12 (m, 1H), 2.98 (t, J=10.9 Hz, 1H), 2.31 (qt, J=3.9, 11.2 Hz, 1H), 1.81 (td, J=1.6, 12.8 Hz, 1H), 1.63-1.54 (m, 2H), 1.42-1.29 (m, 1H).

Example 35: (isomer 3, SFC RT=4.564 min)$^1$H NMR (400 MHz, METHANOL-d4) δ=7.91 (s, 1H), 7.57 (d, J=4.8 Hz, 1H), 7.23 (d, J=5.0 Hz, 1H), 6.91 (s, 1H), 5.34 (d, J=4.3 Hz, 1H), 4.03 (td, J=1.9, 9.3 Hz, 1H), 3.88 (br d, J=11.3 Hz, 1H), 3.41-3.35 (m, 1H), 2.46-2.35 (m, 1H), 1.68-1.49 (m, 3H), 1.26-1.12 (m, 1H).

Example 36: (isomer 4, SFC RT=7.277 min)$^1$H NMR (400 MHz, METHANOL-d4) δ=7.93 (br s, 1H), 7.57 (d, J=5.0 Hz, 1H), 7.24 (d, J=5.0 Hz, 1H), 6.92 (br s, 1H), 5.34 (d, J=4.5 Hz, 1H), 4.08-3.98 (m, 1H), 3.88 (br d, J=11.0 Hz, 1H), 3.42-3.35 (m, 1H), 2.46-2.35 (m, 1H), 1.67-1.49 (m, 3H), 1.27-1.16 (m, 1H).

Examples 37 to 38: 8-tetrahydropyran-4-8H-thieno[3,4]pyrrolo[1,5-a]imidazole

Example 37A: (3-iodo-2-thienyl)-tetrahydropyran-4-methanol

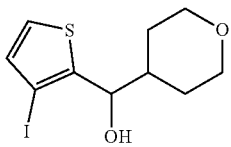 [SMILES: OC(c1sccc1I)C1CCOCC1]

A solution of n-butyllithium (2.5 mol/L, 3.85 mL) in n-hexane was slowly added dropwise to a solution of diisopropylamine (975.07 mg, 9.64 mmol, 1.35 mL) in diethyl ether (20 mL) at −78° C. over about 10 min, during which the temperature was controlled at −78° C. After completion of dropwise addition, the mixture was warmed up to 0° C. and stirred for 30 min. The system was cooling down to −78° C. and added dropwise with 3-iodothiophene (2.21 g, 10.51 mmol), and after stirring for 30 min, tetrahydropyran-4-carboxaldehyde (1.00 g, 8.76 mmol) was added dropwise thereto and stirred at −78° C. for 2 h: The reaction system was added with 50 mL of saturated ammonium chloride solution, and extracted with ethyl acetate (50 mL×3). The organic phase was combined and washed with 50 mL of saturated brine. The organic phase was dried over anhydrous sodium sulfate, filtered under suction and evaporated under reduced press. The obtained crude product was purified by column chromatography to give the compound of (3-iodo-2-thienyl)-tetrahydropyran-4-methanol (1.10 g, 3.39 mmol, yield of 38.73%), as light yellow oil. $^1$H NMR (400 MHz, CHLOROFORM-d) δ=7.30 (d, J=5.3 Hz, 1H), 7.02 (d, J=5.0 Hz, 1H), 4.76 (d, J=7.5 Hz, 1H), 4.03 (dd, J=4.3, 11.5 Hz, 1H), 3.94 (br dd, J=3.4, 11.4 Hz, 1H), 3.36 (dtd, J=2.1, 11.8, 20.0 Hz, 2H), 2.02-1.92 (m, 2H), 1.62-1.56 (m, 1H), 1.56-1.43 (m, 2H).

Example 37B: 1-[(3-iodo-2-thienyl)-tetrahydropyran-4-methyl]imidazole

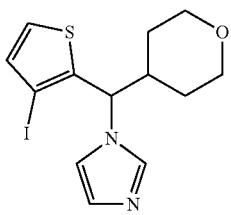 [SMILES: Ic1ccsc1C(C1CCOCC1)n1ccnc1]

1,1-Carbonyldiimidazole (2.75 g, 16.97 mmol) was added in a solution of (3-iodo-2-thienyl)-tetrahydropyran-4-methanol (1.10 g, 3.39 mmol) in acetonitrile (20.00 mL). The reaction solution was reacted at 70° C. for 4 h. The reaction solution was added with 50 mL of water, and extracted with ethyl acetate (30 mL×3). The combined organic phase was washed with 50 mL of saturated brine, dried over anhydrous sodium sulfate, filtered under suction and evaporated under reduced press. The obtained crude product was purified by column chromatography to give the compound of 1-[(3-iodo-2-thienyl)-tetrahydropyran-4-methyl]imidazole (500 mg, 1.34 mmol, yield of 39.41%). $^1$H NMR (400 MHz, CHLOROFORM-d) δ=7.68 (s, 1H), 7.37-7.33 (m, 1H), 7.35 (dd, J=0.8, 5.3 Hz, 1H), 7.09-7.06 (m, 2H), 7.03 (d, J=5.0 Hz, 1H), 5.19 (d, J=11.0 Hz, 1H), 3.96 (td, J=2.0, 11.7 Hz, 2H), 3.36 (ddt, J=2.4, 9.1, 11.7 Hz, 2H), 2.37 (tq, J=3.8, 11.2 Hz, 1H), 1.53-1.46 (m, 1H), 1.45-1.32 (m, 2H), 1.30-1.23 (m, 1H).

Preparation of the Title Compounds (Examples 37 to 38): 8-tetrahydropyran-4-8H-thieno[3,4]pyrrolo[1,5-a]imidazole

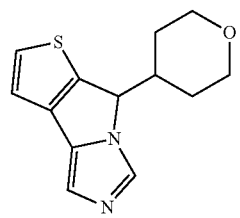 [SMILES: c1cc2c(s1)C(C1CCOCC1)n1cncc1-2]

Under protection of nitrogen gas, 1-[(3-iodo-2-thienyl)-tetrahydropyran-4-methyl]imidazole (200 mg, 534.42 mmol), palladium acetate (12 mg, 53.44 μmol), tricyclohexylphosphine (29.97 mg, 106.88 μmol), potassium carbonate (147.72 mg, 1.07 mmol), and o-xylene (4 mL) were successively added in a reaction flask, and followed by reaction at 140° C. for 16 h. The reaction solution was filtered under suction, and washed with ethyl acetate (5 mL). The organic phase was added with 30 mL of water and extracted with ethyl acetate (20 mL×3). The combined organic phase was washed with 20 mL of saturated brine, dried over anhydrous sodium sulfate, filtered under suction and evaporated under reduced press. The crude product was purified by column chromatography to give 8-tetrahydropyran-4-8H-thieno[3,4]pyrrolo[1,5-a]imidazole (110.00 mg, a racemate). The racemate was subjected to SFC chiral separation (SFC separation conditions: Acq. Method Set: OD_3_EtOH_DEA_5_40_25 ML Vial: 1:F, 2 Channel Name: PDA Ch1 220 nm@4.8 nm—Compens. Injection Volume: 3.00 μL Proc. Chnl. Descr.: PDA Ch1 220 nm@4.8 nm—Compens. Run Time: 10.0 min), and further purified by preparative chromatography to give Example 37 (isomer 1, trifluoroacetate) (30.00 mg, 83.25 μmol, 39.96% yield, RT=4.298 min, ee=100%) and Example 38 (isomer 2, trifluoroacetate) (30 mg, 83.25 μmol, yield of 17.09%, RT=4.996 min, ee=99.4%).

Example 37: $^1$H NMR (400 MHz, METHANOL-d$_4$) δ=7.92 (s, 1H), 7.56 (d, J=5.0 Hz, 1H), 7.25 (d, J=5.0 Hz, 1H), 6.91 (s, 1H), 5.36 (d, J=4.3 Hz, 1H), 4.02 (dd, J=4.4, 11.2 Hz, 1H), 3.93-3.87 (m, 1H), 3.51-3.37 (m, 2H), 2.44 (qt, J=4.1, 11.9 Hz, 1H), 1.77 (br d, J=10.5 Hz, 2H), 1.63-1.53 (m, 1H), 1.26-1.14 (m, 2H).

Example 38: $^1$H NMR (400 MHz, METHANOL-d4) δ=9.13 (s, 1H), 7.64 (d, J=5.0 Hz, 1H), 7.45 (s, 1H), 7.30 (d, J=5.0 Hz, 1H), 5.66 (d, J=4.3 Hz, 1H), 3.94 (dd, J=4.3, 11.5 Hz, 1H), 3.80 (dd, J=3.9, 11.4 Hz, 1H), 3.44-3.26 (m, 2H)), 2.52 (qt, J=3.9, 12.1 Hz, 1H), 1.70 (br dd, J=1.5, 12.8 Hz, 1H), 1.50 (dq, J=4.6, 12.3 Hz, 1H), 1.18-1.11 (m, 1H), 1.10-0.99 (m, 1H)

Example 39: 8-(2-(1-fluorocyclohexyl)ethyl)-8H-thieno[3',2':3,4]pyrrolo[1,2-c]imidazole

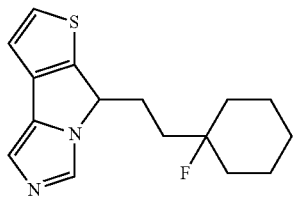 [SMILES: FC1(CCC2c3sccc3-c3cncn32)CCCCC1]

A solution of Example 8 (150 mg, 520 μmol) in dichloromethane (2 mL) was added in a solution of DAST fluoroborate (595.5 mg, 2.6 mmol) in dichloromethane (2 mL), followed by addition of triethylamine hydrogen fluoride complex (167.7 mg, 1.04 μmol). The mixture was stirred at room temperature for 32 h. After quench with water (20 mL), the reaction solution was extracted with dichloromethane (10 mL×3). The combined organic layers were washed with saturated brine (20 mL), dried over anhydrous sodium sulfate, filtered and evaporated. The residue was purified by high performance liquid chromatography to give the title compound (50 mg, 23.77%). $^1$H NMR (400 MHz, METHANOL-d4) δ=9.24 (s, 1H), 7.73 (d, J=5.0 Hz, 1H), 7.53 (s, 1H), 7.38 (d, J=5.0 Hz, 1H), 5.88-5.78 (m, 1H), 2.48 (tdd, J=5.4, 11.1, 13.8 Hz, 1H), 2.25-2.13 (m, 1H), 1.89-1.78 (m, 2H), 1.72-1.24 (m, 10H).

Examples 40 to 41: 8-(4,4-difluorocyclohexyl)-8H-thieno[3,4]pyrrolo[1,5-a]imidazole

Example 40A: 4,4 difluoro-N-methoxy-N-methyl-cyclohexanecarboxamide

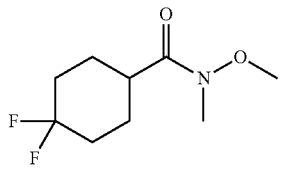

N-methoxymethylamine (653.42 mg, 6.70 mmol), HATU (2.55 g, 6.70 mmol) and DIEA (1.57 g, 12.18 mmol, 2.13 mL) were added in a solution of 4,4-difluorocyclohexanecarboxylic acid (1 g, 6.09 mmol) in DMF (10 mL) at 16° C., and the mixture was attired for 16 h. The reaction solution was dispersed in ethyl acetate (30 mL) and water (30 mL). The organic phase was separated, washed with brine (30 mL×3), dried over anhydrous sodium sulfate, filtered and evaporated. The residue was purified by column chromatography to give the title compound (colorless oil, 1.2 g, yield of 95.09%). $^1$H NMR (400 MHz, CHLOROFORM-d) δ=3.69 (s, 3H), 3.17 (s, 3H), 2.72 (br d, J=5.8 Hz, 1H), 2.22-2.09 (m, 2H), 1.87-1.77 (m, 5H), 1.76-1.65 (m, 1H).

Example 40B: 4,4-difluorocyclohexanecarboxaldehyde

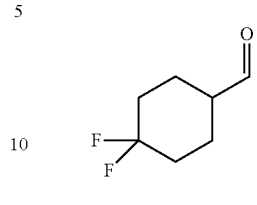

Under protection of nitrogen gas, DIBAL-H (1 M, 12.74 mL) was slowly added in a solution of 4,4-difluoro-N-methoxy-N-methyl-cyclohexanecarboxamide (1.20 g, 5.79 mmol) in tetrahydrofuran (12.00 mL) at −78° C. The reaction solution was then stirred at −78° C. for 4 h. The reaction solution was quenched with 1N hydrochloric acid (5 mL), diluted with water (20 mL) and extracted with ethyl acetate (20 mL×3). The combined organic phase was washed with brine (20 mL×3), dried over anhydrous sodium sulfate, filtered and evaporated to give the title compound (yellow oil, 780 mg, crude). $^1$H NMR (400 MHz, CHLOROFORM-d) δ=9.66 (s, 1H), 2.39-2.28 (m, 1H), 2.07-1.98 (m, 4H), 1.84-1.73 (m, 4H).

Example 40C: (3-bromo-2-thienyl)-(4,4-difluorocyclohexyl)methanol

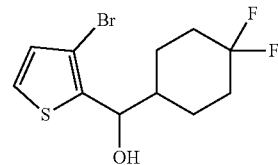 [SMILES: OC(c1sccc1Br)C1CCC(F)(F)CC1]

A solution of n-butyllithium (2.5 M, 2.29 mL) in diethyl ether (10.00 mL) was cooled down to −78° C. and slowly added with diisopropylamine (663.06 mg, 6.26 mmol), and 3-bromothiophene (850 mg, 5.21 mmol) was added after 1 hour. The mixture was maintained at −78° C. and stirred for 1 h. 4,4-Difluorocyclohexanecarboxaldehyde (772.37 mg, 5.21 mmol) was further added, and the reaction solution was stirred at −78° C. for 1 h. The reaction solution was quenched with ammonium chloride solution (30 mL), diluted with water (30 mL) and extracted with ethyl acetate (30 mL×3). The organic phase was washed with brine (30 mL×3), dried over anhydrous sodium sulfate, filtered and evaporated. The residue was purified by column chromatography to give the title compound (colorless oil, 700 mg, yield of 43.18%). $^1$H NMR (400 MHz, CHLOROFORM-d) δ=7.30 (d, J=5.3 Hz, 1H), 6.94 (d, J=5.3 Hz, 1H), 4.86 (dd, J=2.4, 7.9 Hz, 1H), 2.29 (d, J=3.0 Hz, 1H), 2.19-2.07 (m, 3H), 1.82-1.63 (m, 4H), 1.52-1.46 (m, 2H).

Example 40D: 1-[(3-bromo-2-thienyl)-(4,4-difluoro-cyclohexyl)methyl]imidazole

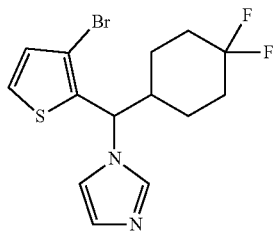 [SMILES: FC1(F)CCC(C(c2sccc2Br)n2ccnc2)CC1]

CDI (1.82 g, 11.25 mmol) was added in a solution of (3-bromo-2-thienyl)-(4,4-difluorocyclohexyl)methanol (700 mg, 2.25 mmol) in acetonitrile (10 mL), and the reaction solution was stirred at 80° C. for 16 h. The reaction solution was dispersed in ethyl acetate (20 mL) and water (20 mL). The organic phase was separated, washed with brine (20 mL×3), dried over anhydrous sodium sulfate, filtered and evaporated. The residue was purified by column chromatography to give the title compound (colorless oil, 460 mg, yield of 56.59%). MS-ESI (m/z): 361/363 (M+H)$^+$(Acq Method: 10-80 AB_2 min; Rt: 0.830 mixtures). $^1$H NMR (400 MHz, CHLOROFORM-d) δ=7.65 (s, 1H), 7.34 (d, J=5.3 Hz, 1H), 7.08 (d, J=5.0 Hz, 2H), 6.95 (d, J=5.3 Hz, 1H), 5.28 (d, J=11.0 Hz, 1H), 2.21 (br d, J=11.5 Hz, 1H), 2.14-2.06 (m, 2H), 1.83-1.59 (m, 4H), 1.42-1.30 (m, 2H).

Preparation of the Title Compound (Example 40)

(R)-8-(4,4-difluorocyclohexyl)-8H-thieno[3,4]pyrrolo[1,5-a]imidazole

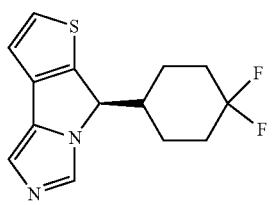 [SMILES: FC1(F)CCC([C@@H]2c3sccc3-c3cncn32)CC1]

Preparation of the Title Compound (Example 41)

(S)-8-(4,4-difluorocyclohexyl)-8H-thieno[3,4]pyrrolo[1,5-a]imidazole

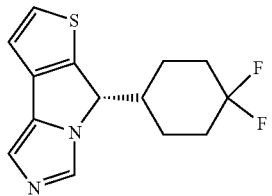 [SMILES: FC1(F)CCC([C@H]2c3sccc3-c3cncn32)CC1]

Under protection of nitrogen gas, a mixture solution of 1-[(3-bromo-2-thienyl)-(4,4-difluorocyclohexyl)methyl]imidazole (460 mg, 1.27 mmol), palladium acetate (28.51 mg, 127.00 μmol), tricyclohexylphosphine (71.23 mg, 254.00 μmol), potassium carbonate (351.05 mg, 2.54 mmol) in o-xylene (5.00 mL) was stirred at 140° C. for 16 h. The reaction solution was dispersed in ethyl acetate (20 mL) and water (20 mL). The organic phase was separated, washed with brine (20 mL×3), dried over anhydrous sodium sulfate, filtered and evaporated. The residue was purified by preparative chromatography to give the title compound (a racemate, 190 mg, yield of 53.37%). MS-ESI (m/z): 281 (M+H)$^+$. The racemate of 8-(4,4-difluorocyclohexyl)-8H-thieno[3,4]pyrrolo[1,5-a]imidazole (190.00 mg, 677.75 μmol) was subjected to chiral separation (Chiral separation conditions: ChiralPak AD-3 150×4.6 mm I.D., 3 μm; mobile phase: A: carbon dioxide B: ethanol (0.05% diethylamine)), to give Example 40 (isomer 1, 40.00 mg, yield of 29.93%, RT=3.996 min) and Example 41 (isomer 2, 53.00 mg, yield of 39.66%, RT=4.619 min).

Example 40: $^1$H NMR (400 MHz, METHANOL-d4) δ=9.21 (s, 1H), 7.72 (d, J=5.0 Hz, 1H), 7.54 (s, 1H), 7.38 (d, J=5.3 Hz, 1H), 5.80 (d, J=3.8 Hz, 1H), 2.50 (dt, J=3.0, 12.2 Hz, 1H), 2.23-2.10 (m, 1H), 2.04-1.96 (m, 2H), 1.95-1.68 (m, 2H), 1.65-1.51 (m, 1H), 1.37-1.24 (m, 1H), 1.06 (dq, J=3.4, 13.0 Hz, 1H).

Example 41: $^1$H NMR (400 MHz, METHANOL-d4) δ=9.21 (s, 1H), 7.72 (d, J=5.0 Hz, 1H), 7.53 (s, 1H), 7.38 (d, J=5.0 Hz, 1H), 5.80 (d, J=3.8 Hz, 1H), 2.50 (dt, J=3.0, 12.2 Hz, 1H), 2.23-2.11 (m, 1H), 2.04-1.96 (m, 2H), 1.95-1.68 (m, 2H), 1.65-1.52 (m, 1H), 1.36-1.26 (m, 1H), 1.05 (dq, J=3.4, 13.1 Hz, 1H).

Examples 42 to 43: [1-(8H-thieno[3,4]pyrrolo[1,5-a]imidazol-8-yl)cyclohexyl]methanol Example 42A: ethyl cyclohexane-1,1-dicarboxylate

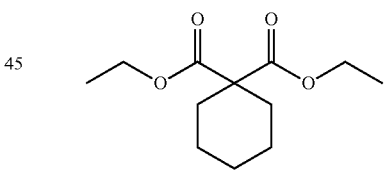

Diethyl malonate (8.36 g, 52.19 mmol, 7.89) and 1,5-dibromopentane (8.00 g, 34.79 mmol) were dissolved in ethanol (80.00 mL), a solution of sodium ethoxide (9.47 g, 139.16 mmol) in ethanol (60.00 mL) was slowly added thereto, and the reaction solution was stirred at 14° C. for 16 h. The reaction solution was quenched with water (100 mL) and extracted with ethyl acetate (50 mL×3). The combined organic phase was washed with brine (50 mL×3), dried over anhydrous sodium sulfate, filtered and evaporated. The residue was purified by column chromatography to give the title compound (colorless oil, 3.7 g, yield of 46.59%). $^1$H NMR (400 MHz, CHLOROFORM-d) δ=4.18 (q, J=7.0 Hz, 4H), 2.00-1.93 (m, 4H), 1.56-1.48 (m, 4H), 1.46-1.38 (m, 2H), 1.25 (t, J=7.0 Hz, 6H).

Example 42B: [1-(hydroxymethyl)cyclohexyl]methanol

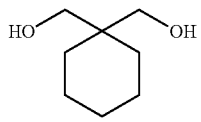

Under protection of nitrogen gas, LiAlH4 (1.35 g, 35.66 mmol) was slowly added in a solution of ethyl cyclohexane-1,1-dicarboxylate (3.7 g, 16.21 mmol) in tetrahydrofuran (15.00 mL), and then the reaction solution stirred at 15° C. for 1 h. The reaction solution was quenched with saturated ammonium chloride solution (30 mL) and 5 mol HCl (30 mL), then filtered and extracted with ethyl acetate (50 mL×3). The combine organic phase was washed with brine (30 mL×3), dried over anhydrous sodium sulfate, filtered and evaporated, to give the title compound (2.00 g, 85.56%). $^1$H NMR (400 MHz, CHLOROFORM-d) δ=3.62 (s, 4H), 2.68 (br s, 2H), 1.45 (br s, 6H), 1.38-1.33 (m, 4H).

Example 42C: [1-[[tert-butyl(dimethyl)silyl]oxymethyl]cyclohexyl]methanol

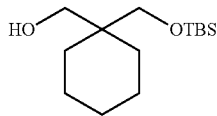 [SMILES: CC(C)(C)[Si](C)(C)OCC1(CO)CCCCC1]

Imidazole (1.13 g, 16.64 mmol) and TBSCl (2.30 g, 15.26 mmol) were added in a solution of [1-(hydroxymethyl)cyclohexyl]methanol (2 g, 13.87 mmol) in dichloromethane (20 mL), and the mixture was stirred at 15° C. for 16 h. The reaction solution was dispersed in dichloromethane (50 mL) and water (50 mL). The separated organic phase was washed with water (50 mL×3), dried over anhydrous sodium sulfate, filtered and evaporated. The residue was purified by column chromatography to give the title compound (colorless oil, 2.7 g, yield of 75.31%). $^1$H NMR (400 MHz, CHLOROFORM-d) δ=3.58 (s, 2H), 3.55 (s, 2H), 3.09 (br s, 1H), 1.49-1.36 (m, 8H), 1.29-1.20 (m, 2H), 0.90 (s, 9H), 0.07 (s, 6H).

Example 42D: [1-[[tert-butyl(dimethyl)silyl]oxymethyl]cyclohexyl]carboxaldehyde

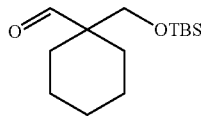 [SMILES: CC(C)(C)[Si](C)(C)OCC1(C=O)CCCCC1]

Dimethyl sulfoxide (1.21 g, 15.48 mmol) was slowly added dropwise to a solution of oxalyl chloride (1.18 g, 9.29 mmol) in dichloromethane (20 mL) at −78° C., and after stirring for 30 min, a solution of [1-[[tert-butyl(dimethyl)silyl]oxymethyl]cyclohexyl]methanol (2 g, 7.74 mmol) in dichloromethane (5 mL) and stirred for another 30 min, followed by slowly adding triethylamine (3.92 g, 38.70 mmol). After 30 min, the reaction system was warmed up to 12° C. The reaction solution was dispersed in dichloromethane (50 mL) and water (50 mL). The separated organic phase was washed with water (50 mL×3), dried over anhydrous sodium sulfate, filtered and evaporated. The residue was purified by column chromatography to give the title compound (colorless oil, 1.30 g, yield of 65.49%). $^1$H NMR (400 MHz, CHLOROFORM-d) δ=9.55 (s, 1H), 9.58-9.52 (m, 1H), 3.56 (s, 2H), 1.97-1.83 (m, 2H), 1.53 (br d, J=5.8 Hz, 3H), 1.35-1.21 (m, 5H), 0.84 (s, 9H), 0.00 (s, 6H).

Example 42E: (3-bromo-2-thienyl)-[1-[[tert-butyl(dimethyl)silyl]oxymethyl]cyclohexyl]methanol

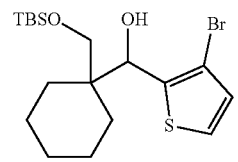 [SMILES: CC(C)(C)[Si](C)(C)OCC1(C(O)c2sccc2Br)CCCCC1]

A solution of n-butyllithium (2.5 M, 2.16 mL) in diethyl ether (10 mL) was cooled down to −78° C., and diisopropylamine (595.82 mg, 5.89 mmol) was slowly added thereto. After 1 h, 3-bromothiophene (800 mg, 4.91 mmol) was added and stirred at −78° C. for 1 h. [1-[[Tert-butyl(dimethyl)silyl]oxymethyl]cyclohexyl]carboxaldehyde (1.26 g, 4.91 mmol) was further added, and the reaction solution was stirred at −78° C. for 1 h. The reaction solution was quenched with ammonium chloride solution (50 mL), diluted with water (50 mL), and extracted with ethyl acetate (50 mL×3). The organic phase was washed with brine (50 mL×3), dried over anhydrous sodium sulfate, filtered and evaporated. The residue was purified by column chromatography to give the title compound (colorless oil, 2.00 g, yield of 64.77%). $^1$H NMR (400 MHz, CHLOROFORM-d) δ=7.14 (d, J=5.3 Hz, 1H), 6.76 (d, J=5.3 Hz, 1H), 4.90 (d, J=6.3 Hz, 1H), 4.66 (d, J=6.3 Hz, 1H), 3.88 (d, J=10.3 Hz, 1H), 3.59 (d, J=10.3 Hz, 1H), 1.76-1.69 (m, 1H), 1.45 (br dd, J=4.8, 8.5 Hz, 3H), 1.29-1.23 (m, 2H), 1.23-1.17 (m, 2H), 1.11-1.05 (m, 2H), 0.81 (s, 9H), 0.01 (d, J=7.3 Hz, 6H).

Example 42F: [1-[(3-bromo-2-thienyl)-imidazol-1-yl-methyl]cyclohexyl]methoxy-tert-butyl-dimethyl-silane

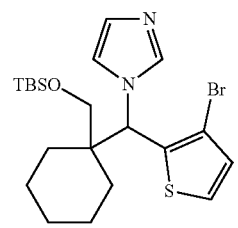 [SMILES: CC(C)(C)[Si](C)(C)OCC1(C(c2sccc2Br)n2ccnc2)CCCCC1]

CDI (1.93 g, 11.90 mmol) was added in a solution of (3-bromo-2-thienyl)-[1-[[tert-butyl(dimethyl)silyl]oxymethyl]cyclohexyl]methanol (2 g, 4.76 mmol) in acetonitrile (10 mL) and the reaction solution was stirred at 80° C. for 16 h. The reaction solution was dispersed in ethyl acetate (50 mL) and water (50 mL). The organic phase was separated, washed with brine (50 mL×3), dried over anhydrous sodium sulfate, filtered and evaporated. The residue was purified by column chromatography to give the title compound (1.50 g, yield of 67.02%). MS-ESI (m/z): 469/471 (M+H)⁺. ¹H NMR (400 MHz, CHLOROFORM-d) δ=7.64 (s, 1H), 7.33 (d, J=5.5 Hz, 1H), 7.10 (s, 1H), 6.98 (s, 1H), 6.97 (d, J=5.3 Hz, 1H), 6.21 (s, 1H), 3.75 (d, J=10.3 Hz, 1H), 3.06 (d, J=10.3 Hz, 1H), 1.93-1.76 (m, 2H), 1.64 (br s, 2H), 1.52 (br t, J=14.3 Hz, 2H), 1.36-1.24 (m, 2H), 1.15-1.00 (m, 2H), 0.98 (s, 9H), 0.08 (d, J=2.0 Hz, 6H).

Example 42G: tert-butyl-dimethyl-[[1-(8H-thieno[3,4]pyrrolo[1,5-a]imidazol-8-yl)cyclohexyl]methoxy]silane

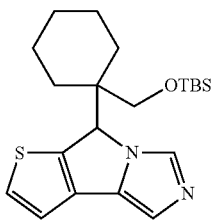 [SMILES: CC(C)(C)[Si](C)(C)OCC1(C2c3sccc3-c3cncn32)CCCCC1]

Under protection of nitrogen gas, a mixture solution of [1-[(3-bromo-2-thienyl)-imidazol-1-yl-methyl]cyclohexyl]methoxy-tert-butyl-dimethyl-silane (1.40 g, 2.98 mmol), palladium acetate (66.94 mg, 298 μmol), tricyclohexylphosphine (167.22 mg, 596.00 μmol), potassium carbonate (824.17 mg, 5.86 mmol) in o-xylene (14 mL) was stirred at 140° C. for 16 hour. The reaction solution was dispersed in ethyl acetate (50 mL) and water (50 mL). The organic phase was separated, washed with brine (50 mL×3), dried over anhydrous sodium sulfate, filtered and evaporated. The residue was purified by column chromatography to give the title compound (900.00 mg, yield of 77.71%). MS-ESI (m/z): 389 (M+H)⁺. ¹H NMR (400 MHz, CHLOROFORM-d) δ=7.71 (s, 1H), 7.33 (d, J=5.0 Hz, 1H), 7.14 (d, J=5.0 Hz, 1H), 6.93 (s, 1H), 5.26 (s, 1H), 3.95-3.87 (m, 1H), 3.81-3.75 (m, 1H), 1.67-1.57 (m, 3H), 1.51 (br d, J=12.5 Hz, 1H), 1.42-1.32 (m, 2H), 1.31-1.25 (m, 2H), 1.21-1.09 (m, 2H), 0.93 (s, 9H), 0.14 (d, J=2.0 Hz, 6H).

Preparation of the Title Compounds (Examples 42 to 43): [1-(8H-thieno[3,4]pyrrolo[1,5-a]imidazol-8-yl)cyclohexyl]methanol

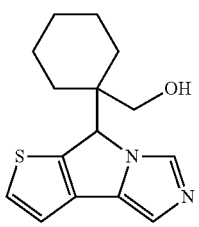 [SMILES: OCC1(C2c3sccc3-c3cncn32)CCCCC1]

TsOH.H₂O (1.32 g, 6.96 mmol) was added in a solution of tert-butyl-dimethyl-[[1-(8H-thieno[3,4]pyrrolo[1,5-a]imidazol-8-yl)cyclohexyl]methoxy]silane (900 mg, 2.32 mmol) in dichloromethane (10 mL), and the mixture was stirred at 18° C. for 16 h. The reaction solution was dispersed in dichloromethane (30 mL) and water (30 mL). The organic phase was separated, washed with water (30 mL×3), dried over anhydrous sodium sulfate, filtered and evaporated. The residue was purified by column chromatography to give the title compound (a racemate, 600 mg, yield of 75.41%). MS-ESI (m/z): 275 (M+H)⁺.

[1-(8H-thieno[3,4]pyrrolo[1,5-a]imidazol-8-yl)cyclohexyl]methanol (600 mg, 2.19 μmol) was subjected to chiral separation (chiral separation conditions: Chiralpak AD-3 100×4.6 mm I.D., 3 μm; mobile phase: A: carbon dioxide B: isopropanol (0.05% diethylamine)) to give Example 42 (isomer 1, 215 mg, yield of 50.20%, retention time: 4.312 min) and Example 43 (isomer 3, 235 mg, yield of 55.26%, retention time: 4.893 min).

Example 42: ¹H NMR (400 MHz, METHANOL-d4) δ=9.05 (s, 1H), 7.70 (d, J=5.0 Hz, 1H), 7.49 (s, 1H), 7.38 (d, J=5.3 Hz, 1H), 5.72 (s, 1H), 3.91 (d, J=12.0 Hz, 1H), 3.49 (d, J=11.8 Hz, 1H), 1.88 (br d, J=11.8 Hz, 1H), 1.76-1.65 (m, 2H), 1.63-1.49 (m, 3H), 1.42-1.31 (m, 2H), 1.28-1.15 (m, 2H).

Example 43: ¹H NMR (400 MHz, METHANOL-d4) δ=9.06 (s, 1H), 7.71 (d, J=5.3 Hz, 1H), 7.50 (s, 1H), 7.38 (d, J=5.0 Hz, 1H), 5.73 (s, 1H), 3.92 (d, J=12.0 Hz, 1H), 3.50 (d, J=12.0 Hz, 1H), 1.89 (br d, J=12.0 Hz, 1H), 1.77-1.66 (m, 2H), 1.65-1.50 (m, 3H), 1.43-1.32 (m, 2H), 1.29-1.16 (m, 2H).

Examples 44 to 45: 8-spiro[2.5]octan-6-yl-8H-thieno[3,4]pyrrolo[1,5-a]imidazole

Example 44A: spiro[2.5]octane-6-carboxaldehyde

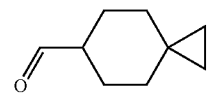

Dimethyl sulfoxide (668.64 mg, 8.56 mmol) was slowly added dropwise in a solution of oxalyl chloride (651.76 mg, 5.13 mmol) in dichloromethane (5 mL) at −78° C., and then stirred for 30 min. A solution of spiro[2.5]octane-6-methanol (600 mg, 4.28 mmol) in dichloromethane (2 mL) was added thereto, followed by further stirring for 30 min. Triethylamine (2.16 g, 21.39 mmol) was slowly added. After 30 min, the reaction solution was warmed up to 16° C. The reaction solution was dispersed in dichloromethane (20 mL) and water (20 mL). The separated organic phase was washed with water (20 mL×3), dried over anhydrous sodium sulfate, filtered and evaporated, to give the title compound (yellow oil, 600 mg, crude). ¹H NMR (400 MHz, CHLOROFORM-d) δ=9.67 (d, J=1.0 Hz, 1H), 2.34-2.20 (m, 1H), 1.95-1.85 (m, 2H), 1.68-1.51 (m, 4H), 1.11-1.03 (m, 2H), 0.32-0.27 (m, 2H), 0.23-0.18 (m, 2H).

Example 44B: (3-bromo-2-thienyl)-spiro[2.5]octan-6-yl-methanol

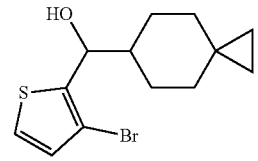 [SMILES: OC(c1sccc1Br)C1CCC2(CC1)CC2]

A solution of n-butyllithium (2.5 M, 1.89 mL) in diethyl ether (7 mL) was cooled down to −78° C., and diisopropylamine (520.93 mg, 5.15 mmol) was slowly added thereto. After 1 h, 3-bromothiophene (700 mg, 4.29 mmol) was added, and the reaction system was maintained at −78° C. and stirred for 1 h. Spiro[2.5]octane-6-carboxaldehyde (593.39 mg, 4.29 mmol) was further added, and the reaction solution was stirred at −78° C. for 1 h. The reaction solution was quenched with ammonium chloride solution (10 mL), diluted with water (20 mL) and extracted with ethyl acetate (20 mL×3). The organic phase was washed with brine (20 mL×3), dried over anhydrous sodium sulfate, filtered and evaporated. The residue was purified by column chromatography to give the title compound (colorless oil, 600 mg, yield of 46.43%). $^1$H NMR (400 MHz, CHLOROFORM-d) δ=7.07 (d, J=5.0 Hz, 1H), 6.72 (d, J=5.3 Hz, 1H), 4.66 (d, J=7.8 Hz, 1H), 1.89-1.83 (m, 1H), 1.60-1.44 (m, 3H), 1.28-1.18 (m, 1H), 1.17-1.04 (m, 2H), 0.78-0.63 (m, 2H), 0.13--0.06 (m, 4H).

Example 44C: 1-[(3-bromo-2-thienyl)-spiro[2.5]octan-6-yl-methyl]imidazole

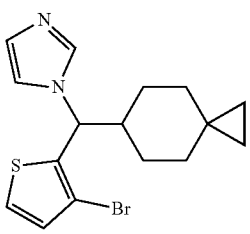 [SMILES: Brc1ccsc1C(C1CCC2(CC1)CC2)n1ccnc1]

CDI (1.61 g, 9.55 mmol) was added in a solution of (3-bromo-2-thienyl)-spiro[2.5]octan-6-yl-methanol (600 mg, 1.99 mmol) in acetonitrile (6 mL), and the reaction solution was stirred at 80° C. for 16 h. The reaction solution was dispersed in ethyl acetate (20 mL) and water (20 mL). The organic phase was separated, washed with brine (20 mL×3), dried over anhydrous sodium sulfate, filtered and evaporated. The residue was purified by column chromatography to give the title compound (480 mg, yield of 68.66%). MS-ESI (m/z): 351/353 (M+H)$^+$. $^1$H NMR (400 MHz, CHLOROFORM-d) δ=7.63 (s, 1H), 7.29 (d, J=5.3 Hz, 1H), 7.08-7.02 (m, 2H), 6.91 (d, J=5.5 Hz, 1H), 5.26 (d, J=11.0 Hz, 1H), 2.13 (tq, J=3.4, 11.0 Hz, 1H), 1.72-1.57 (m, 3H), 1.38-1.30 (m, 1H), 1.22-1.09 (m, 2H), 0.93-0.84 (m, 2H), 0.31-0.25 (m, 2H), 0.21-0.14 (m, 2H).

Preparation of the Title Compounds (Examples 44 to 45): 8-spiro[2.5]octan-6-yl-8H-thieno[3,4]pyrrolo[1,5-a]imidazole

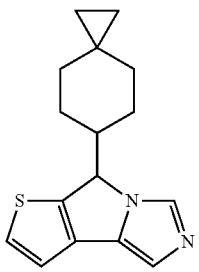 [SMILES: c1cc2c(s1)C(C1CCC3(CC1)CC3)n1cncc1-2]

Under protection of nitrogen gas, a mixture solution of 1-[(3-bromo-2-thienyl)-spiro[2.5]octan-6-yl-methyl]imidazole (500 mg, 1.42 mmol), palladium acetate (31.88 mg, 142.00 μmol), tricyclohexylphosphine (79.64 mg, 284.00 μmol), potassium carbonate (392.52 mg, 2.84 mmol) in o-xylene (5 mL) was stirred at 140° C. for 16 h. The reaction solution was dispersed in ethyl acetate (20 mL) and water (20 mL). The organic phase was separated, washed with brine (20 mL×3), dried over anhydrous sodium sulfate, filtered and evaporated. The residue was purified by column chromatography to give the title compound (a racemate, 40 mg, yield of 10.42%). MS-ESI (m/z): 271 (M+H)$^+$.

The racemate of 8-spiro[2.5]octan-6-yl-8H-thieno[3,4]pyrrolo[1,5-a]imidazole (40 mg, 147.93 μmol) was subjected to chiral separation (chiral separation conditions: Chiralcel OD-3 100×4.6 mm I.D., 3 μm; mobile phase: A: carbon dioxide B: ethanol (0.05% diethylamine)) to give Example 44 (isomer 1, 9 mg, yield of 30.17%, retention time: 2.632 min) and Example 45 (isomer 2, 9 mg, yield of 31.65%, retention time: 2.947 min).

Example 44: $^1$H NMR (400 MHz, METHANOL-d4) δ=8.98 (s, 1H), 7.53-7.47 (m, 1H), 7.30 (d, J=1.0 Hz, 1H), 7.16 (d, J=5.3 Hz, 1H), 5.52 (d, J=4.0 Hz, 1H), 2.16 (tdd, J=3.4, 12.3, 15.7 Hz, 1H), 1.75-1.63 (m, 2H), 1.61-1.53 (m, 1H), 1.34-1.21 (m, 1H), 1.07-0.98 (m, 1H), 0.81-0.71 (m, 2H), 0.65-0.58 (m, 1H), 0.11-0.05 (m, 2H), 0.02--0.04 (m, 1H), 0.05--0.11 (m, 1H).

Example 45: $^1$H NMR (400 MHz, METHANOL-d4) δ=8.98 (s, 1H), 7.50 (d, J=5.0 Hz, 1H), 7.30 (s, 1H), 7.16 (d, J=5.0 Hz, 1H), 5.52 (d, J=3.8 Hz, 1H), 2.21-2.09 (m, 1H), 1.75-1.61 (m, 2H), 1.61-1.51 (m, 1H), 1.33-1.20 (m, 1H), 1.04-0.95 (m, 1H), 0.83-0.68 (m, 2H), 0.66-0.57 (m, 1H), 0.13-0.04 (m, 2H), 0.01--0.04 (m, 1H), 0.05--0.11 (m, 1H).

Example 46: (1S)-1-(4,4-difluorocyclohexyl)-2-((S)-8H-thieno[3,4]pyrrolo[1,5-a]imidazol-8-yl)ethanol Example 47: (1S)-1-(4,4-difluorocyclohexyl)-2-((R)-8H-thieno[3,4]pyrrolo[1,5-a]imidazol 8-yl)ethanol Example 46A: 4,4-difluoro-N-methoxy-N-methyl-cyclohexanecarboxamide

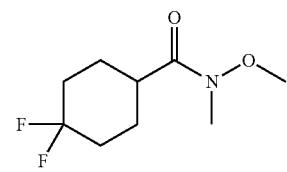

N-methoxymethylamine (5.88 g, 60.31 mmol), HATU (22.93 g, 60.31 mmol) and DIEA (14.17 g, 109.66 mmol, 19.15 mL) were add in a solution of 4,4-difluorocyclohexanecarboxylic acid (9 g, 54.83 mmol) in DMF (90 mL) at 16° C., and the mixture was stirred for 16 h. The reaction solution was dispersed in ethyl acetate (100 mL) and water (100 mL). The organic phase was separated, washed with brine (100 mL×3), dried over anhydrous sodium sulfate, filtered and evaporated. The residue was purified by column chromatography to give the title compound (colorless oil, 11.00 g, yield of 96.82%). $^1$H NMR (400 MHz, CHLORO- FORM-d) δ=3.70 (s, 3H), 3.17 (s, 3H), 2.72 (br d, J=6.0 Hz, 1H), 2.25-2.07 (m, 2H), 1.88-1.77 (m, 5H), 1.75-1.66 (m, 1H).

Example 46B: 4,4-difluorocyclohexylcarboxaldehyde

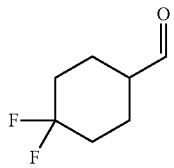

Under protection of nitrogen gas, DIBAL-H (1 M, 106.16 mL) was slowly added in a solution of 4,4-difluoro-N-methoxy-N-methyl-cyclohexanecarboxamide (11.00 g, 53.08 mmol) in tetrahydrofuran (110.00 mL) at −78° C., and the reaction solution was then stirred at −78° C. for 4 h. The reaction solution was quenched with 1N HCl (50 mL), diluted with water (100 mL) and extracted with ethyl acetate (100 mL×3). The combined organic phase was washed with brine (100 mL×3), dried over anhydrous sodium sulfate, filtered and evaporated. The residue was purified by column chromatography to give the title compound (colorless oil, 5.50 g, yield of 69.93%). $^1$H NMR (400 MHz, CHLOROFORM-d) δ=9.67 (s, 1H), 2.38-2.28 (m, 1H), 2.07-1.98 (m, 4H), 1.85-1.75 (m, 4H).

Example 46C: (1S)-1-(4,4-difluorocyclohexyl)but-3-en-1-ol

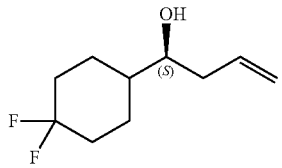

Under protection of nitrogen gas, the mixture solution of allyl bromide (5.72 g, 47.25 mmol), indium (5.43 g, 47.25 mmol), (1S,2R)-2-amino-1,2-diphenyl-ethanol (5.04 g, 23.62 mmol) and pyridine (3.74 g, 47.25 mmol) in tetrahydrofuran (50.00 mL) was stirred at 18° C. for 3 h. The reaction solution was cooled down to −78° C., and 4,4-difluorocyclohexylcarboxaldehyde (3.50 g, 23.62 mmol) was slowly added. The reaction solution was controlled at −78° C. and stirred for 2 h. The reaction solution was added with saturated ammonium chloride solution (100 mL) to quench reaction, and filtered, and the filtrate was extracted with ethyl acetate (100 mL×3). The combined organic phase was dried over anhydrous sodium sulfate, filtered and evaporated. The residue was purified by column chromatography to give the title compound (yellow oil, 3.55 g, yield of 60.78%). $^1$H NMR (400 MHz, CHLOROFORM-d) δ=5.89-5.75 (m, 1H), 5.22-5.12 (m, 2H), 3.51-3.42 (m, 1H), 2.41-2.30 (m, 1H), 2.13 (td, J=8.5, 13.8 Hz, 3H), 1.99-1.90 (m, 1H), 1.74 (br dd, J=4.1, 7.2 Hz, 2H), 1.68-1.62 (m, 2H), 1.49-1.35 (m, 3H).

Example 46D: tert-butyl-[(1S)-1-(4,4-difluorocyclohexyl)but-3-enoxy]-dimethyl-silane

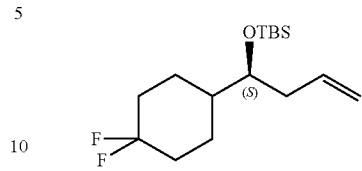

2,6-Dimethylpyridine (2.96 g, 27.60 mmol, 3.22 mL) and TBSOTf (5.84 g, 22.08 mmol) were added in a solution of (1S)-1-(4,4-difluorocyclohexyl)but-3-en-1-ol (3.50 g, 18.40 mmol) in dichloromethane (35.00 mL), and the mixture was stirred at 22° C. for 16 h. The reaction solution was dispersed in dichloromethane (50 mL) and water (50 mL). The organic phase was separated, washed with water (50 mL×3), dried over anhydrous sodium sulfate, filtered and evaporated. The residue was purified by column chromatography to give the title compound (colorless oil, 4.7 g, yield of 83.89%). $^1$H NMR (400 MHz, CHLOROFORM-d) δ=5.88-5.74 (m, 1H), 5.09-5.00 (m, 2H), 3.53 (q, J=5.5 Hz, 1H), 2.27-2.20 (m, 2H), 2.16-2.03 (m, 2H), 1.87-1.77 (m, 1H), 1.76-1.59 (m, 3H), 1.47-1.29 (m, 3H), 0.90-0.86 (m, 9H), 0.05-0.01 (m, 6H).

Example 46E: (3S)-3-[tert-butyl(dimethyl)silyl]oxy-3-(4,4-difluorocyclohexyl)propionaldehyde

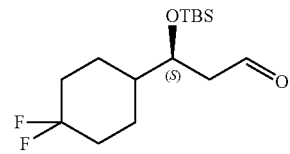

Ozone was introduced into a solution of tert-butyl-[(1S)-1-(4,4-difluorocyclohexyl)but-3-enoxy]-dimethyl-silane (4.70 g, 15.44 mmol) in dichloromethane (20.00 mL) and methanol (20.00 mL) at −78° C. (5 min), and the excess ozone was blown off with nitrogen gas. Dimethyl sulfide (9.16 g, 147.43 mmol) was added, and the mixture was stirred at 22° C. for 16 h. The reaction solution was evaporated. The residue was purified by preparative chromatography to give the title compound (colorless oil, 4.20 g, yield of 88.76%). $^1$H NMR (400 MHz, CHLOROFORM-d) δ=9.83-9.80 (m, 1H), 4.07 (q, J=5.3 Hz, 1H), 2.63-2.46 (m, 2H), 2.18-2.07 (m, 2H), 1.81-1.74 (m, 2H), 1.72-1.58 (m, 2H), 1.55-1.45 (m, 1H), 1.43-1.28 (m, 2H), 0.87 (s, 9H), 0.07 (s, 3H), 0.05 (s, 3H).

Example 46F: (3S)-1-(3-bromo-2-thienyl)-3-[tert-butyl(dimethyl)silyl]oxy-3-(4,4-difluorocyclohexyl)propan-1-ol

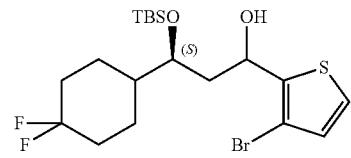

A solution of diisopropylamine (1.66 g, 16.44 mmol) in diethyl ether (10.00 mL) was cooled down to −78° C., and n-butyllithium (2.5 M, 6.03 mL) was slowly added. After 1 h, 3-,bromothiophene (2.23 g, 13.70 mmol) was added, and the reaction was maintained at −78° C. and stirred for 1 h. (3S)-3-[tert-butyl(dimethyl)silyl]oxy-3-(4,4-difluorocyclohexyl)propionaldehyde (4.20 g, 13.70 mmol) was added and the reaction solution was stirred at −78° C. for 1 h. The reaction solution was added with ammonium chloride solution (50 mL) to quench, diluted with water (50 mL), and extracted with ethyl acetate (50 mL×3). The organic phase was washed with brine (50 mL×3), dried over anhydrous sodium sulfate, filtered and evaporated. The residue was purified by column chromatography to give the title compound (colorless oil, 4.00 g, yield of 62.19%). $^1$H NMR (400 MHz, CHLOROFORM-d) δ=7.25-7.21 (m, 1H), 6.95-6.89 (m, 1H), 5.36-5.08 (m, 1H), 4.03-3.81 (m, 1H), 3.58-3.26 (m, 1H), 2.15 (br s, 2H), 1.97-1.83 (m, 3H), 1.73-1.61 (m, 3H), 1.46-1.25 (m, 3H), 0.95-0.93 (m, 9H), 0.19-0.16 (m, 3H), 0.14-0.12 (m, 2H), 0.10 (d, J=2.0 Hz, 1H).

Example 46G: [(1S)-3-(3-bromo-2-thienyl)-1-(4,4-difluorocyclohexyl)-3-imidazol-1-yl-propoxy]-tert-butyl-dimethyl-silane

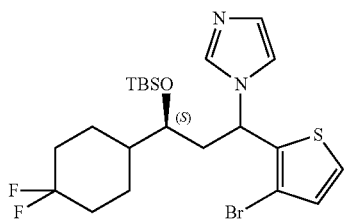

CDI (6.91 g, 42.60 mmol) was added in a solution of (3S)-1-(3-bromo-2-thienyl)-3-[tert-butyl(dimethyl)silyl] oxy-3-(4,4-difluorocyclohexyl)propan-1-ol (4.00 g, 8.52 mmol) in acetonitrile (40 mL), and the reaction solution was stirred at 80° C. for 16 h. The reaction solution was dispersed in ethyl acetate (100 mL) and water (100 mL). The organic phase was separated, washed with brine (100 mL×3), dried over anhydrous sodium sulfate, filtered and evaporated. The residue was purified by column chromatography to give the title compound (colorless oil, 3.20 g, yield of 72.29%). MS-ESI (m/z): 519/521 (M+H)$^+$. $^1$H NMR (400 MHz, CHLOROFORM-d) δ=7.66-7.57 (m, 1H), 7.31 (d, J=5.5 Hz, 1H), 7.24 (d, J=5.3 Hz, 1H), 7.05 (d, J=16.1 Hz, 1H), 7.01-6.97 (m, 1H), 6.97-6.90 (m, 1H), 5.82-5.66 (m, 1H), 3.60-3.55 (m, 1H), 3.44 (td, J=2.9, 9.3 Hz, 1H), 2.39-2.16 (m, 2H), 1.91-1.68 (m, 3H), 1.63-1.44 (m, 3H), 1.38-1.25 (m, 3H), 0.94-0.91 (m, 9H), 0.04-−0.02 (m, 6H).

Example 46H: tert-butyl-[(1S)-1-(4,4-difluorocyclohexyl)-2-(8H-thieno[3,4]pyrrolo[1,5-a]imidazol-8-yl)ethoxy]-dimethyl-silane

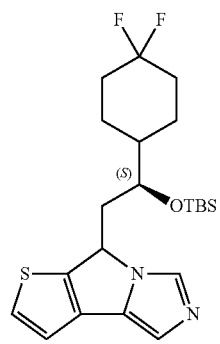

Under protection of nitrogen gas, the mixture solution of [(1S)-3-(3-bromo-2-thienyl)-1-(4,4-difluorocyclohexyl)-3-imidazol-1-yl-propoxy]-tert-butyl-dimethyl-silane (3.10 g, 5.97 mmol), palladium acetate (133.96 mg, 596.66 μmol), tricyclohexylphosphine (33.64 mg, 1.19 mmol), potassium carbonate (1.65 g, 11.93 mmol) in o-xylene (40.00 mL) was stirred at 140° C. for 16 h. The reaction solution was dispersed in ethyl acetate (60 mL) and water (60 mL). The organic phase was separated, washed with brine (60 mL×3), dried over anhydrous sodium sulfate, filtered and evaporated. The residue was purified by preparative chromatography to give the title compound (1.60 g, yield of 61.10%). MS-ESI (m/z): 439 (M+H)$^+$. $^1$H NMR (400 MHz, METHANOL-d4) δ=7.93 (d, J=7.0 Hz, 1H), 7.55 (d, J=5.0 Hz, 1H), 7.23 (dd, J=5.0, 8.0 Hz, 1H), 6.90 (d, J=1.5 Hz, 1H), 5.46-5.39 (m, 1H), 4.04-3.95 (m, 1H), 2.40-2.25 (m, 1H), 2.07-1.95 (m, 2H), 1.89 (ddd, J=4.5, 9.0, 13.6 Hz, 1H), 1.76-1.54 (m, 5H), 1.52-1.44 (m, 1H), 1.38-1.25 (m, 1H), 0.94 (s, 5H), 0.90 (s, 4H), 0.17 (d, J=1.3 Hz, 4H), 0.10 (s, 1H), 0.02 (s, 1H).

Preparation of the Title Compound (Example 46)

(1S)-1-(4,4-difluorocyclohexyl)-2-((S)-8H-thieno[3,4]pyrrolo[1,5-a]imidazol-8-yl)ethanol

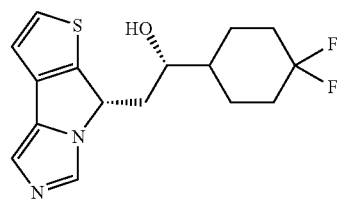 [SMILES: O[C@@H](C[C@H]1c2sccc2-c2cncn21)C1CCC(F)(F)CC1]

Preparation of the Title Compound (Example 47)

(1S)-1-(4,4-difluorocyclohexyl)-2-((R)-8H-thieno[3,4]pyrrolo[1,5-a]imidazol-8-yl)ethanol

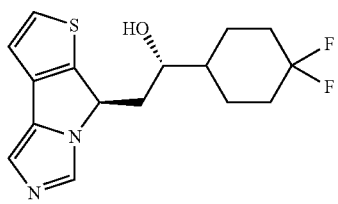 [SMILES: O[C@@H](C[C@@H]1c2sccc2-c2cncn21)C1CCC(F)(F)CC1]

TsOH.H$_2$O (2.08 g, 10.95 mmol) was added in a solution of tert-butyl-[(1S)-1-(4,4-difluorocyclohexyl)-2-(8H-thieno[3,4]pyrrolo[1,5-a]imidazol-8-yl)ethoxy]-dimethyl-silane (1.60 g, 3.65 mmol) in dichloromethane (20.00 mL), and the mixture was stirred at 24° C. for 16 h. The reaction solution was dispersed in dichloromethane (50 mL) and water (50 mL). The organic phase was separated, washed with water (50 mL×3), dried over anhydrous sodium sulfate, filtered and evaporated. The residue was purified by preparative chromatography to give the title compound (a racemate, 0.98 g, yield of 81.03%). MS-ESI (m/z): 325 (M+H)$^+$.

The racemate (980 mg, 3.02 μmol) was subjected to chiral separation (column: Chiralcel OD-3 100×4.6 mm I.D., 3 μm; mobile phase: A: carbon dioxide B: isopropanol (0.05% diethylamine)), to give Example 46 (210 mg, yield of 20.94%) (retention time: 2.946 min) and Example 47 (380 mg, yield of 28.30%) (retention time: 3.824 min).

Example 46: $^1$H NMR (400 MHz, METHANOL-d4) δ=7.91 (s, 1H), 7.52 (d, J=5.0 Hz, 1H), 7.19 (d, J=5.0 Hz, 1H), 6.89 (s, 1H), 5.51 (dd, J=5.5, 7.8 Hz, 1H), 3.86-3.73 (m, 1H), 2.21-1.91 (m, 5H), 1.88-1.60 (m, 3H), 1.56-1.32 (m, 3H).

Example 47: $^1$H NMR (400 MHz, METHANOL-d4) δ=9.18 (s, 1H), 7.72 (d, J=5.5 Hz, 1H), 7.51 (d, J=1.0 Hz, 1H), 7.38 (d, J=5.0 Hz, 1H), 5.87 (dd, J=5.8, 8.5 Hz, 1H), 3.90 (ddd, J=2.8, 5.5, 10.9 Hz, 1H), 2.42 (ddd, J=5.8, 11.0, 13.6 Hz, 1H), 2.14-1.94 (m, 4H), 1.86-1.67 (m, 3H), 1.58-1.37 (m, 3H).

Examples 48 to 49: 8-(4-bicyclo[2.2.2]octyl)-8H-thieno[3,4]pyrrolo[1,5-a]imidazole Example 48A: N-methoxy-N-methyl-bicyclo[2.2.2]octane-4-carboxamide

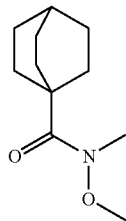

N-methoxymethylamine (632.51 mg, 6.48 mmol), HATU (2.71 g, 7.13 mmol) and DIEA (1.67 g, 12.96 mmol, 2.26 mL) were added in a solution of bicyclo[2.2.2]octane-4-carboxylic acid (1.00 g, 6.48 mmol) in DMF (10.00 ml) at 20° C., and the mixture was stirred for 16 h. The reaction solution was dispersed in ethyl acetate (50 mL) and water (50 mL). The organic phase was separated, washed with brine (50 mL×3), dried over anhydrous sodium sulfate, filtered and evaporated. The residue was purified by column chromatography to give the title compound (colorless oil, 800.00 mg, yield of 62.58%). $^1$H NMR (400 MHz, CHLOROFORM-d) δ=3.64 (s, 3H), 3.14 (s, 3H), 1.86-1.79 (m, 6H), 1.62-1.51 (m, 7H).

Example 48B: bicyclo[2.2.2]octane-4-carboxaldehyde

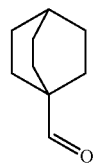

Under protection of nitrogen gas, DIBAL-H (1 M, 8.12 mL) was slowly added in a solution of N-methoxy-N-methyl-bicyclo[2.2.2]octane-4-carboxamide (800 mg, 4.06 mmol) in tetrahydrofuran (10 mL) at −78° C., and then the reaction solution was stirred at −78° C. for 3 h. The reaction solution was quenched with saturated sodium potassium tartrate (10 mL), diluted with water (10 mL), and extracted with ethyl acetate (10 mL×3). The combined organic phase was washed with brine (10 mL×3), dried over anhydrous sodium sulfate, filtered and evaporated. The residue was purified by column chromatography to give the title compound (colorless oil, 300.00 mg, yield of 53.46%). $^1$H NMR (400 MHz, CHLOROFORM-d) δ=9.39 (s, 1H), 1.59 (s, 13H).

Example 48C: 4-bicyclo[2.2.2]octyl-(3-bromo-2-thienyl)methanol

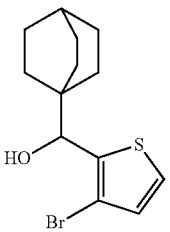

A solution of diisopropylamine (152.50 mg, 2.58 mmol) in diethyl ether (5 mL) was cooled down to −78° C., and slowly added with n-butyllithium (2.5 M, 0.946 mL). After 1 hour, 3-bromothiophene (350 mg, 2.15 mmol) was added thereto and the mixture was maintained at −78° C. and stirred for 1 hour. Bicyclo[2.2.2]octane-4-carboxaldehyde (297.15 mg, 2.15 mmol) was further added, and the reaction solution was stirred at −78° C. for 1 h. The reaction solution was added with ammonium chloride solution (5 mL) to quench the reaction, diluted with water (10 mL) and extracted with ethyl acetate (10 mL×3). The organic phase was washed with brine (10 mL×3), dried over anhydrous sodium sulfate, filtered and evaporated. The residue was purified by column chromatography to give the title compound (colorless oil, 240 mg, yield of 37.06%). $^1$H NMR (400 MHz, CHLOROFORM-d) δ=7.28 (d, J=5.3 Hz, 1H), 6.91 (d, J=5.3 Hz, 1H), 4.79 (s, 1H), 1.72-1.62 (m, 3H), 1.59-1.50 (m, 7H), 1.46-1.37 (m, 3H).

Example 48D: 1-[4-bicyclo[2.2.2]octyl-(3-bromo-2-thienyl)methyl]imidazole

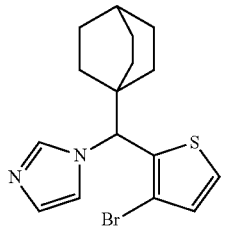 [SMILES: Brc1ccsc1C(n1ccnc1)C12CCC(CC1)CC2]

CDI (645.93 mg, 3.98 mmol) was added in a solution of 4-bicyclo[2.2.2]octyl-(3-bromo-2-thienyl)methanol (240 mg, 796.71 μmol) in acetonitrile (5 mL), and the reaction solution was stirred at 80° C. for 16 h. The reaction solution was dispersed in ethyl acetate (30 mL) and water (30 mL). The organic phase was separated, washed with brine (30 mL×3), dried over anhydrous sodium sulfate, filtered and evaporated. The residue was purified by column chromatography to give the title compound (210 mg, yield of 75.03%). $^1$H NMR (400 MHz, CHLOROFORM-d) δ=7.59 (s, 1H), 7.35-7.32 (m, 1H), 7.07 (t, J=1.3 Hz, 1H), 7.01 (s, 1H), 6.95 (d, J=5.3 Hz, 1H), 5.42 (s, 1H), 1.62-1.59 (m, 2H), 1.58-1.52 (m, 8H), 1.51-1.42 (m, 3H).

Preparation of the Title Compounds (Examples 48 to 49): 8-(4-bicyclo[2.2.2]octyl)-8H-thieno[3,4]pyrrolo[1,5-a]imidazole

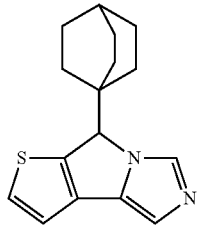

Under protection of nitrogen gas, a mixture solution of 1-[4-bicyclo[2.2.2]octyl-(3-bromo-2-thienyl)methyl]imidazole (210 mg, 597.78 μmol), palladium acetate (13.42 mg, 59.78 μmol), tricyclohexylphosphine (33.53 mg, 119.56 μmol), potassium carbonate (165.24 mg, 1.20 mmol) in o-xylene (5.00 mL) was stirred at 140° C. for 16 h. The reaction solution was dispersed in ethyl acetate (50 mL) and water (50 mL). The organic phase was separated, washed with brine (50 mL×3), dried over anhydrous sodium sulfate, filtered and evaporated. The residue was purified by preparative chromatography to give the title compound (a racemate, brown oil, 120 mg, yield of 67.71%). MS-ESI (m/z): 271 (M+H)$^+$.

The racemate of 8-(4-bicyclo[2.2.2]octyl)-8H-thieno[3,4]pyrrolo[1,5-a]imidazole (120 mg, 443.80 μmol) was subjected to chiral separation (chiral separation conditions: Column: Lux Cellulose-2 150×4.6 mm I.D., 3 μm; mobile phase: A: carbon dioxide B: ethanol (0.05% diethylamine)) to give Example 48 (48 mg, yield of 56.27%) (retention time: 6.805 min) and Example 49 (48 mg, yield of 56.27%) (retention time: 8.477 min).

Example 48: $^1$H NMR (400 MHz, METHANOL-d4) δ=9.16 (s, 1H), 7.70 (d, J=5.3 Hz, 1H), 7.51 (s, 1H), 7.36 (d, J=5.0 Hz, 1H), 5.43 (s, 1H), 1.66 (br d, J=3.5 Hz, 7H), 1.60-1.54 (m, 6H).

Example 49: $^1$H NMR (400 MHz, METHANOL-d4) δ=9.16 (s, 1H), 7.70 (d, J=5.0 Hz, 1H), 7.51 (s, 1H), 7.36 (d, J=5.0 Hz, 1H), 5.43 (s, 1H), 1.66 (br d, J=3.0 Hz, 7H), 1.60-1.53 (m, 6H).

Examples 50 to 53: 2-(8H-thieno[3,4]pyrrolo[1,5-a]imidazol-8-yl)cyclohexanol

Example 50A: ethyl 2-hydroxycyclohexanecarboxylate

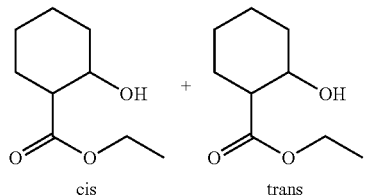

Sodium borohydride (889.00 mg, 23.50 mmol) was slowly added in a solution of ethyl 2-cyclohexanone formate (10.00 g, 58.75 mmol, 8.43 mL) in ethanol (100.00 mL) at 0° C., and the reaction solution was stirred at 0° C. for 4 h. The reaction system was added with 50 mL of water at room temperature to quench the reaction, and extracted with ethyl acetate (30 mL×3). The organic phase was combined, washed with brine (50 mL), dried over anhydrous sodium sulfate, filtered under suction and evaporated under reduced pressure. The obtained crude product was purified by column chromatography to give ethyl cis-2-hydroxycyclohexanecarboxylate (4.80 g, 27.87 mmol, yield of 47.44%) and ethyl trans-2-hydroxycyclohexanecarboxylate (2.60 g, 15.10 mmol, yield of 25.70%), both as a colorless liquid.

Ethyl cis-2-hydroxycyclohexanecarboxylate: $^1$H NMR (400 MHz, CHLOROFORM-d) δ=4.19-4.08 (m, 3H), 3.20 (br s, 1H), 2.50-2.42 (m, 1H), 1.94-1.81 (m, 2H), 1.75-1.62 (m, 3H), 1.51-1.37 (m, 2H), 1.26 (t, J=7.2 Hz, 4H).

Ethyl trans-2-hydroxycyclohexanecarboxylate: $^1$H NMR (400 MHz, CHLOROFORM-d) δ=4.17 (q, J=7.3 Hz, 2H), 3.76 (dt, J=4.5, 10.2 Hz, 1H), 2.85 (br s, 1H), 2.24 (ddd, J=3.8, 9.8, 12.3 Hz, 1H), 2.08-2.05 (m, 1H), 2.04-1.99 (m, 1H), 1.82-1.68 (m, 2H), 1.40-1.31 (m, 1H), 1.29-1.22 (m, 6H).

Example 50B: ethyl 2-[tert-butyl(dimethyl)silyl]oxycyclohexanecarboxylate

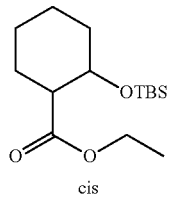 [SMILES: CCOC(=O)C1CCCCC1O[Si](C)(C)C(C)(C)C]

t-Butyldimethylsilyl trifluoromethanesulfonate (8.84 g, 33.44 mmol, 7.69 mL) and 2,6-dimethylpyridine (4.48 g, 41.81 mmol, 4.87 mL) were slowly added dropwise in ethyl cis-2-hydroxycyclohexanecarboxylate (4.80 g, 27.87 mmol) in dichloromethane (40.00 mL). The reaction solution was stirred at 0° C. for 2 h. After completion, the reaction system was added with 200 mL of water at room temperature to quench the reaction, and extracted with ethyl acetate (50 mL×3). The organic phase was combined and washed with 50 mL of saturated brine. The organic phase was dried over anhydrous sodium sulfate, filtered under suction and evaporated under reduced pressure. The obtained crude product was purified by column chromatography to give the compound of ethyl 2-[tert-butyl(dimethyl)silyl]oxycyclohexanecarboxylate (6.80 g, 23.74 mmol, yield of 85.17%) as a colorless liquid. $^1$H NMR (400 MHz, CHLOROFORM-d) δ=4.39 (br s, 1H), 4.19-4.10 (m, 1H), 4.03 (qd, J=7.1, 10.8 Hz, 1H), 2.34-2.28 (m, 1H), 1.88 (dq, J=3.6, 12.8 Hz, 1H), 1.76 (dt, J=3.1, 8.3 Hz, 2H), 1.70-1.60 (m, 2H), 1.46-1.34 (m, 2H), 1.25 (t, J=7.2 Hz, 3H), 1.22-1.12 (m, 1H), 0.86 (s, 9H), 0.03 (s, 3H), −0.02 (s, 3H).

Example 50C: {2-[tert-butyl(dimethyl)silyl]oxycyclohexyl}methanol

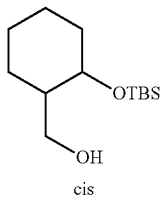

A solution of diisobutylaluminium hydride in 1M methylbenzene (1 mol/L, 54.45 mL) was slowly added dropwise into a solution of ethyl 2-[tert-butyl(dimethyl)silyl]oxycyclohexanecarboxylate (5.20 g, 18.15 mmol) in dichloromethane (50 mL). The reaction solution was stirred at −78° C. for 2 h. After completion of reaction, the reaction system was added with 50 mL of saturated sodium potassium tartrate solution at room temperature to quench the reaction, and extracted with dichloromethane (50 mL×3). The organic phase was combined, washed with 50 mL of saturated brine, dried over anhydrous sodium sulfate, filtered under suction and evaporated under reduced pressure. The obtained crude product was purified by column chromatography to give the compound of {2-[tert-butyl(dimethyl)silyl]oxycyclohexyl}methanol (1.10 g, 4.50 mmol, yield of 24.79%) as a colorless liquid. $^1$H NMR (400 MHz, CHLOROFORM-d) δ=4.04 (td, J=2.9, 5.6 Hz, 1H), 3.76 (dd, J=7.8, 10.5 Hz, 1H), 3.52 (dd, J=4.6, 10.7 Hz, 1H), 2.40-1.93 (m, 1H), 1.78-1.63 (m, 3H), 1.62-1.51 (m, 2H), 1.50-1.34 (m, 3H), 1.30-1.19 (m, 1H), 0.90 (s, 8H), 0.07 (d, J=1.0 Hz, 6H). {2-[Tert-butyl(dimethyl)silyl]oxycyclohexyl}methanol (3.30 g, 13.61 mmol, yield of 75.00%) as a colorless liquid was obtained at the same time. $^1$H NMR (400 MHz, CHLOROFORM-d) δ=9.71 (s, 1H), 4.46-4.35 (m, 1H), 2.23 (td, J=3.2, 10.5 Hz, 1H), 1.95-1.85 (m, 1H), 1.77-1.69 (m, 2H), 1.66 (br d, J=2.0 Hz, 1H), 1.55-1.49 (m, 1H), 1.46-1.40 (m, 1H), 1.33-1.23 (m, 2H), 0.86 (s, 9H), 0.06-0.06 (m, 1H), 0.06 (s, 3H), 0.03 (s, 3H).

Example 50D: {2-[tert-butyl(dimethyl)silyl]oxycyclohexyl}carboxaldehyde

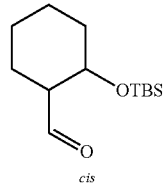

IBX (3.89 g, 13.90 mmol) was slowly added dropwise in a solution of {2-[tert-butyl(dimethyl)silyl]oxycyclohexyl}methanol (1.70 g, 6.95 mmol) in ethyl acetate (20.00 mL). The reaction solution was stirred at 78° C. for 10 h. After completion of reaction, the reaction solution was filtered under suction and evaporated under reduced pressure. The obtained crude compound was purified by column chromatography to give a compound of {2-[tert-butyl(dimethyl)silyl]oxycyclohexyl}carboxaldehyde (1.10 g, 4.50 mmol, yield of 65.29%) as a colorless liquid. $^1$H NMR (400 MHz, CHLOROFORM-d) δ=9.71 (s, 1H), 4.45-4.35 (m, 1H), 2.24 (td, J=3.3, 10.3 Hz, 1H), 1.91-1.84 (m, 1H), 1.91-1.84 (m, 1H), 1.77-1.73 (m, 1H), 1.66 (br d, J=2.3 Hz, 1H), 1.64-1.60 (m, 1H), 1.55-1.51 (m, 1H), 1.42 (br dd, J=3.9, 8.4 Hz, 1H), 1.31-1.24 (m, 2H), 0.86 (s, 9H), 0.06 (s, 3H), 0.03 (s, 3H).

Example 50E: {2-[tert-butyl(dimethyl)silyl]oxycyclohexyl}-(3-iodo-2-thienyl)methanol

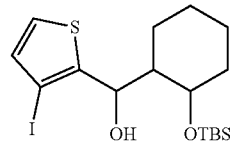 [SMILES: CC(C)(C)[Si](C)(C)OC1CCCCC1C(O)c1sccc1I]

A solution of n-butyllithium (2.5 mol/L, 7.08 mL) in n-hexane was slowly added dropwise to a solution of diisopropylamine (1.79 g, 17.70 mmol, 2.49 mL) in diethyl ether (40.00 mL) at −78° C. over about 10 min, during which the temperature was maintained at −78° C. After completion of dropwise addition, the mixture was warmed up to 0° C. and stirred for 30 min. The system was cooled down to −78° C., and added dropwise with 3-iodothiophene (4.06 g, 19.31 mmol), and after stirring for 30 min, {2-[tert-butyl(dimethyl)silyl]oxycyclohexyl}carboxaldehyde (3.90 g, 16.09 mmol) was added dropwise thereto and stirred at −78° C. for 2 h. After completion of reaction, the system was added with 50 mL of saturated ammonium chloride solution, and extracted with ethyl acetate (50 mL×3). The organic phase was combined and washed with 50 mL of saturated brine, and the obtained organic phase was dried over anhydrous sodium sulfate, filtered under suction and evaporated under reduced pressure. The obtained crude compound was purified by column chromatography to give the compound of {2-[tert-butyl(dimethyl)silyl]oxycyclohexyl}-(3-iodo-2-thienyl)methanol (3.20 g, 7.07 mmol, yield of 43.96%) as a colorless liquid. $^1$H NMR (400 MHz, CHLOROFORM-d) δ=7.21 (d, J=5.3 Hz, 1H), 7.02 (d, J=5.0 Hz, 1H), 5.10 (s, 1H), 4.38 (br s, 1H), 4.09 (s, 1H), 1.88-1.81 (m, 2H), 1.78-1.73 (m, 2H), 1.50 (br d, J=2.5 Hz, 1H), 1.40 (br s, 1H), 1.33-1.25 (m, 1H), 1.16-1.09 (m, 1H), 0.96 (s, 8H), 0.18 (d, J=10.5 Hz, 6H).

Example 50F: tert-butyl-{[2-imidazolyl(3-iodothienyl)methyl]cyclohexyl}-dimethylsilane

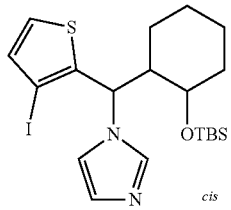 [SMILES: CC(C)(C)[Si](C)(C)OC1CCCCC1C(c1sccc1I)n1ccnc1]

1,1-Carbonyldiimidazole (899.93 mg, 5.55 mmol) was added in a solution of {2-[tert-butyl(dimethyl)silyl]oxycyclohexyl}-(3-iodo-2-thienyl)methanol (500 mg, 1.11 mmol) in acetonitrile (5.00 mL). The reaction solution was reacted at 70° C. for 4 h. After completion of reaction, the reaction solution was added with 50 mL of water, and extracted with ethyl acetate (30 mL×3). The combined organic phase was washed with 50 mL of saturated brine, dried over anhydrous sodium sulfate, filtered under suction and evaporated under reduced pressure. The crude product was purified by column chromatography to give the compound of tert-butyl-{[2-imidazolyl(3-iodothienyl)methyl]cyclohexyl}-dimethylsilane (500 mg, 994.97 μmol, yield of 89.64%) as colorless oil. $^1$H NMR (400 MHz, CHLOROFORM-d) δ=7.71-7.59 (m, 1H), 7.34-7.27 (m, 1H), 7.08-7.05 (m, 1H), 7.04-6.84 (m, 2H), 5.66-5.27 (m, 1H), 2.24-2.13 (m, 1H), 1.83 (br d, J=13.8 Hz, 1H), 1.67 (br s, 2H), 1.58-1.54 (m, 1H), 1.47-1.34 (m, 3H), 1.24-1.06 (m, 2H), 1.02-0.95 (m, 9H), 0.00-−0.17 (m, 6H).

Example 50G: tert-butyl-methyl-[2-(8H-thieno[3,4]pyrrolo[1,5-a]imidazol-8-yl)cyclohexylsilane

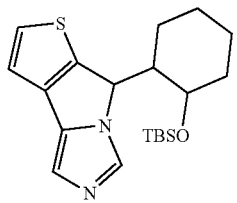 [SMILES: CC(C)(C)[Si](C)(C)OC1CCCCC1C1c2sccc2-c2cncn21]

Under protection of nitrogen gas, tert-butyl-{[2-imidazolyl(3-iodothienyl)methyl]cyclohexyl}-dimethylsilane (2.70 g, 5.37 mmol), palladium acetate (120.63 mg, 537.00 μmol), tricyclohexylphosphine (30.34 mg, 1.07 mmol), potassium carbonate (1.48 g, 10.74 mmol), and o-xylene (50.00 mL) were successively added in a reaction flask, followed by reaction at 140° C. for 16 h. After completion of reaction, the reaction solution was filtrated under suction, and washed with ethyl acetate (30 mL). The organic phase was added with 50 mL of water, and extracted with ethyl acetate (30 mL×3). The combined organic phase was washed with 20 mL of saturated brine, dried over anhydrous sodium sulfate, filtered under suction and evaporated under reduced pressure. The crude product was purified by column chromatography to give the compound of tert-butyl-methyl-[2-(8H-thieno[3,4]pyrrolo[1,5-a]imidazol-8-yl)cyclohexyl-silane (600 mg, 1.60 mmol, yield of 29.83%) as yellow oil. $^1$H NMR (400 MHz, METHANOL-d4) δ=7.84 (d, J=18.1 Hz, 1H), 7.51 (d, J=5.0 Hz, 1H), 7.20 (t, J=5.4 Hz, 1H), 6.88 (d, J=6.0 Hz, 1H), 5.25-5.19 (m, 1H), 4.51 (brd, J=19.3 Hz, 1H), 2.03-1.94 (m, 1H), 1.89-1.77 (m, 3H), 1.75-1.68 (m, 1H), 1.55 (br d, J=14.8 Hz, 1H), 1.36-1.23 (m, 2H), 0.96 (d, J=15.1 Hz, 8H), 0.19 (dd, J=10.9, 16.4 Hz, 6H).

Preparation of the Title Compounds (Examples 50 to 53): 2-(8H-thieno[3,4]pyrrolo[1,5-a]imidazol-8-yl)cyclohexanol

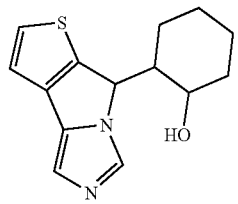 [SMILES: OC1CCCCC1C1c2sccc2-c2cncn21]

p-Toluenesulfonic acid monohydrate (838.87 mg, 4.41 mmol) was added in a solution of tert-butyl-methyl-[2-(8H-thieno[3,4]pyrrolo[1,5-a]imidazol-8-yl)cyclohexylsilane (550 mg, 1.47 mmol) in 1,2-dichloroethane (6 mL). The reaction solution was reacted at 85° C. for 16 h. The reaction solution was then added with 25 mL of a saturated sodium hydrogen carbonate solution, and extracted with ethyl acetate (30 mL×3). The combined organic phase was washed with 50 mL of saturated brine, dried over anhydrous sodium sulfate, filtered under suction and evaporated under reduced pressure. The crude product was purified by column chromatography to give 2-(8H-thieno[3,4-a]pyrrolo[1,5-a]imidazol-8-yl)cyclohexanol (a racemate, 380 mg, 1.46 mmol, yield of 99.29%). $^1$H NMR (400 MHz, METHANOL-d4) δ=8.02-7.86 (m, 1H), 7.48 (dd, J=5.0, 16.1 Hz, 1H), 7.16 (dd, J=2.8, 5.0 Hz, 1H), 6.85 (s, 1H), 5.33-5.19 (m, 1H), 4.37-4.29 (m, 1H), 3.95-3.69 (m, 1H), 1.96-1.89 (m, 1H), 1.73 (br d, J=3.0 Hz, 1H), 1.62-1.35 (m, 5H), 1.33-1.23 (m, 1H).

The racemate was subjected to chiral SFC separation (separation conditions: "Acq. Method Set: OD_3_EtOH_DEA_5_40_25 ML Vial: 1:F, 2 Channel Name: PDA Ch1 220 nm@4.8 nm—Compens. Injection Volume: 3.00 μL Proc. Chnl. Descr.: PDA Ch1 220 nm@4.8 nm—Compens. Run Time: 10.0 min"), to give Example 50 (isomer 1, 50 mg, 192.05 μmol, RT=4.651 min), Example 51 (isomer 2, 50 mg, 192.05 μmol, RT=5.265 min, ee=97%), Example 52 (isomer 3, 80 mg, 307.28 μmol, RT=5.766 min), and Example 53 (isomer 4, 80 mg, 307.28 μmol, RT=6.155 min).

Example 50: $^1$H NMR (400 MHz, METHANOL-d4) δ=7.88 (s, 1H), 7.46 (d, J=5.0 Hz, 1H), 7.16 (d, J=5.0 Hz, 1H), 6.85 (s, 1H), 5.24 (d, J=6.3 Hz, 1H), 4.32 (br d, J=2.5 Hz, 1H), 1.96-1.82 (m, 2H), 1.79-1.65 (m, 2H), 1.62-1.40 (m, 4H), 1.33-1.22 (m, 1H).

Example 51: $^1$H NMR (400 MHz, METHANOL-d4) δ=8.00 (s, 1H), 7.50 (d, J=5.0 Hz, 1H), 7.17 (d, J=5.0 Hz, 1H), 6.85 (s, 1H), 5.29 (d, J=5.8 Hz, 1H), 5.33-5.25 (m, 1H), 4.35 (br d, J=2.3 Hz, 1H), 1.89 (br d, J=13.3 Hz, 1H), 1.84-1.69 (m, 3H), 1.60-1.45 (m, 4H), 1.26-1.13 (m, 1H), 1.26-1.13 (m, 1H).

Example 52: $^1$H NMR (400 MHz, METHANOL-d4) δ=8.03 (s, 1H), 7.50 (d, J=5.0 Hz, 1H), 7.17 (d, J=5.0 Hz, 1H), 6.86 (s, 1H), 5.30 (d, J=5.8 Hz, 1H), 4.35 (br d, J=2.3 Hz, 1H), 1.94-1.86 (m, 1H), 1.84-1.67 (m, 3H), 1.60-1.45 (m, 4H), 1.27-1.18 (m, 1H), 1.27-1.18 (m, 1H).

Example 53: ¹H NMR (400 MHz, METHANOL-d4) δ=7.90 (s, 1H), 7.46 (d, J=5.0 Hz, 1H), 7.16 (d, J=5.0 Hz, 1H), 6.86 (s, 1H), 5.24 (d, J=6.3 Hz, 1H), 4.31 (br d, J=2.5 Hz, 1H), 1.95-1.84 (m, 2H), 1.79-1.67 (m, 2H), 1.61-1.47 (m, 3H), 1.44-1.38 (m, 1H), 1.33-1.32 (m, 1H), 1.32-1.23 (m, 1H).

Examples 54 to 57: 8-tetrahydronaphthalen-2-yl-8H-thieno[3,4]pyrrolo[1,5-a]imidazole Example 54A:
N-methoxy-N-methyl-tetrahydronaphthalene-2-amide

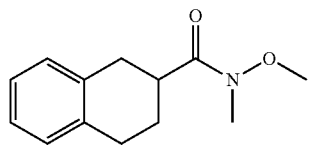 [SMILES: CON(C)C(=O)C1CCc2ccccc2C1]

N-methoxymethylamine hydrochloride (664.83 mg, 6.82 mmol), HATU (2.37 g, 6.24 mmol) and diisopropylethylamine (1.47 g, 11.35 mmol, 1.98 mL) were added in a solution of tetrahydronaphthalene-2-carboxylic acid (1.00 g, 5.68 mmol) in N,N-dimethylformamide (10 mL). The reaction solution was stirred at 20° C. for 16 h. The reaction system was added with 100 mL of water at room temperature to quench the reaction, and extracted with ethyl acetate (20 mL×5). The organic phases were combined and washed with 50 mL of saturated brine. The organic phase was dried over anhydrous sodium sulfate, filtered under suction and evaporated under reduced pressure. The obtained crude compound was purified by column chromatography to give the compound of N-methoxy-N-methyl-tetrahydronaphthalene-2-amide (1.00 g, 4.56 mmol, yield of 80.29%) as colorless oil. ¹H NMR (400 MHz, CHLOROFORM-d) δ=7.11 (d, J=1.0 Hz, 4H), 3.71 (s, 3H), 3.24 (s, 3H), 3.17-2.98 (m, 2H), 2.94-2.83 (m, 3H), 2.12-2.02 (m, 1H), 1.94-1.82 (m, 1H).

Example 54B:
tetrahydronaphthalene-2-carboxaldehyde

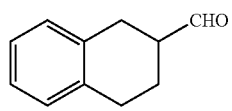 [SMILES: O=CC1CCc2ccccc2C1]

A solution of 1 M diisobutylaluminum hydride in toluene (1 mol/L, 9.12 mL) was slowly added dropwise in a solution of N-methoxy-N-methyl-tetrahydronaphthalene-2-amide (1.00 g, 4.56 mmol) in dichloromethane (10.00 mL). The reaction solution was stirred at −78° C. for 4 h. The reaction system was added with 30 mL of a saturated sodium potassium tartrate solution at room temperature to quench the reaction, and extracted with dichloromethane (30 mL×3). The organic phase was combined and washed with 50 mL of saturated brine. The organic phase was dried over anhydrous sodium sulfate, filtered under suction and evaporated under reduced pressure. The obtained crude compound was purified by column chromatography to give the compound of tetrahydronaphthalene-2-carboxaldehyde (600.00 mg, 3.75 mmol, yield of 82.13%) as a colorless liquid. ¹H NMR (400 MHz, CHLOROFORM-d) δ=9.80 (d, J=1.0 Hz, 1H), 7.16-7.09 (m, 4H), 3.01-2.96 (m, 2H), 2.71 (dtdd, J=1.1, 3.4, 6.9, 15.5 Hz, 1H), 2.60 (s, 2H), 2.29-2.16 (m, 1H), 1.80 (dddd, J=6.5, 9.6, 10.4, 13.2 Hz, 1H).

Example 54C:
(3-iodo-2-thienyl)-tetrahydronaphthyl-2-methanol

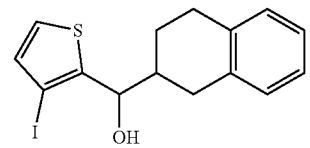 [SMILES: OC(c1sccc1I)C1CCc2ccccc2C1]

A solution of n-butyllithium (2.5 mol/L, 1.65 mL) in n-hexane was slowly added dropwise to a solution of diisopropylamine (417.41 mg, 4.13 mmol, 579.73 μL) in diethyl ether (10.00 mL) at −78° C. over about 10 min, during which the temperature thereof was controlled at −78° C. After completion of dropwise addition, the mixture was warmed up to 0° C. and stirred for 30 min. The system was cooled down to −78° C., and added dropwise with 3-iodothiophene (945.18 mg, 4.50 mmol). After stirring for 30 min, tetrahydronaphthalene-2-carboxaldehyde (600.00 mg, 3.75 mmol) was added dropwise thereto, with stirring at −78° C. for 2 h. After completion of reaction, the reaction system was added with 20 mL of a saturated ammonium chloride solution, and then extracted with ethyl acetate (30 mL×3). The organic phases were combined and washed with 50 mL of saturated brine. The organic phase was dried over anhydrous sodium sulfate, filtered under suction and evaporated under reduced pressure. The obtained crude compound was purified by column chromatography to give the compound of (3-iodo-2-thienyl)-tetrahydronaphthyl-2-methanol (500.00 mg, 1.35 mmol, yield of 36.01%) as a colorless liquid. ¹H NMR (400 MHz, CHLOROFORM-d) δ=7.32 (t, J=4.5 Hz, 1H), 7.12-7.03 (m, 1H), 7.12-7.03 (m, 4H), 4.90 (br dd, J=8.0, 13.3 Hz, 1H), 2.96-2.75 (m, 3H), 2.66-2.51 (m, 1H), 2.34-2.16 (m, 2H), 0.93-0.81 (m, 1H).

Example 54D: 1-[(3-iodo-2-thienyl)tetrahydronaphthalen-2-yl-methyl]imidazole

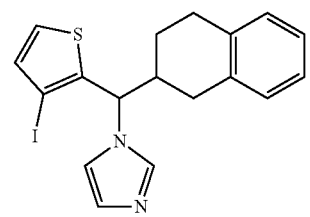 [SMILES: Ic1ccsc1C(C1CCc2ccccc2C1)n1ccnc1]

1,1-Carbonyldiimidazole (1.09 g, 6.75 mmol) was added in a solution of (3-iodo-2-thienyl)-tetrahydronaphthalenyl-2-methanol (500.00 mg, 1.35 mmol) in acetonitrile (5.00 mL). The reaction solution was reacted at 70° C. for 4 h. The reaction solution was added with 50 mL of water, and extracted with ethyl acetate (30 mL×3). The combined organic phase was washed with 50 mL of saturated brine, dried over anhydrous sodium sulfate, filtered under suction and evaporated under reduced pressure. The crude product was purified by column chromatography to give 1-[(3-iodo-2-thienyl)tetrahydronaphthalen-2-yl-methyl]imidazole (450.00 mg, 1.07 mmol, yield of 79.31%). $^1$H NMR (400 MHz, CHLOROFORM-d) δ=7.75-7.68 (m, 1H), 7.39-7.34 (m, 1H), 7.16-7.07 (m, 5H), 7.05 (dd, J=3.3, 5.3 Hz, 1H), 6.96 (br t, J=8.0 Hz, 1H), 5.31 (dd, J=2.6, 11.2 Hz, 1H), 2.87-2.47 (m, 5H), 1.98-1.80 (m, 1H), 1.62-1.46 (m, 1H).

Preparation of the Title Compounds (Examples 54 to 57): 8-tetrahydronaphthalen-2-yl-8H-thieno[3,4]pyrrolo[1,5-a]imidazole

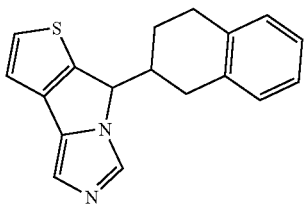 [SMILES: c1ccc2c(c1)CCC(C1c3sccc3-c3cncn31)C2]

Under protection of nitrogen gas, 1-[(3-iodo-2-thienyl)tetrahydronaphthalen-2-yl-methyl]imidazole (400.00 mg, 951.68 μmol), palladium acetate (21.37 mg, 95.17 μmol), tricyclohexylphosphine (53.38 mg, 190.34 μmol), potassium carbonate (263.06 mg, 1.90 mmol), and o-xylene (8.00 mL) were successively added in a reaction flask, followed by reaction at 140° C. for 16 h. After completion of reaction, the reaction solution was filtered under suction, and washed with ethyl acetate (10 mL). The organic phase was added with 20 mL of water, and extracted with ethyl acetate (20 mL×3). The combined organic phase was washed with 20 mL of saturated brine, dried over anhydrous sodium sulfate, filtered under suction and evaporated under reduced pressure. The crude product was purified by column chromatography to give 8-tetrahydronaphthalen-2-yl-8H-thieno[3,4]pyrrolo[1,5-a]imidazole (a racemate, 220.00 mg, 753.39 μmol, yield of 79.06%) as yellow oil. $^1$H NMR (400 MHz, CHLOROFORM-d) δ=7.78 (br s, 1H), 7.38-7.35 (m, 1H), 7.18 (d, J=4.8 Hz, 1H), 7.09 (br d, J=8.3 Hz, 4H), 7.00 (d, J=6.3 Hz, 1H), 5.60 (dd, J=2.0, 6.0 Hz, 2H), 3.99-3.95 (m, 3H), 2.40 (br s, 1H), 2.15 (s, 1H), 1.49-1.47 (m, 1H).

The crude product as the racemate was subjected to chiral SFC separation (Column: Chiralcel OJ-3 150×4.6 mm I.D., 3 um; Mobile phase: A: $CO_2$ B: ethanol (0.05% DEA); Gradient: from 5% to 40% of B in 5 min and hold 40% for 2.5 min, then 5% of B for 2.5 min; Flow rate: 2.5 mL/min; Column temp.: 35° C.) and further purified by acidic HPLC (TFA), to finally give:

Example 54 (a single isomer, 7.00 mg, 17.22 μmol, yield of 2.29%, trifluoroacetate, RT=4.287 min, ee=90%). $^1$H NMR (400 MHz, METHANOL-d4) δ=9.22 (s, 1H), 7.72 (d, J=5.0 Hz, 1H), 7.58 (s, 1H), 7.42 (d, J=5.0 Hz, 1H), 7.13-7.05 (m, 2H), 7.05-6.98 (m, 1H), 6.90 (d, J=7.3 Hz, 1H), 5.93 (d, J=4.0 Hz, 1H), 2.96 (br dd, J=3.6, 8.4 Hz, 2H), 2.87-2.75 (m, 1H), 2.47-2.37 (m, 1H), 2.30-2.14 (m, 2H), 1.73 (tt, J=8.8, 12.1 Hz, 1H).

Example 55 (a single isomer, 8.00 mg, 19.68 μmol, yield of 2.62%, trifluoroacetate, RT=4.514 min, ee=85%). $^1$H NMR (400 MHz, METHANOL-d4) δ=9.22 (s, 1H), 7.73 (d, J=5.0 Hz, 1H), 7.59-7.53 (m, 1H), 7.41 (d, J=5.3 Hz, 1H), 7.14-7.02 (m, 4H), 5.92 (br d, J=2.5 Hz, 1H), 3.06-2.94 (m, 1H), 2.85-2.67 (m, 4H), 1.62 (br d, J=13.1 Hz, 1H), 1.38-1.23 (m, 1H).

Example 56 (a single isomer, 30.00 mg, 73.82 μmol, yield of 9.81%, trifluoroacetate, RT=5.297 min, ee=90%). $^1$H NMR (400 MHz, METHANOL-d4) δ=9.22 (s, 1H), 7.73 (d, J=5.0 Hz, 1H), 7.56 (s, 1H), 7.42 (d, J=5.0 Hz, 1H), 7.12-7.03 (m, 4H), 5.92 (d, J=3.0 Hz, 1H), 3.07-2.94 (m, 1H), 2.86-2.61 (m, 4H), 1.68-1.58 (m, 1H), 1.39-1.24 (m, 1H).

Example 57 (a single isomer, 8.00 mg, 19.68 μmol, yield of 2.62%, trifluoroacetate, RT=5.478 min, ee=90%). $^1$H NMR (400 MHz, METHANOL-d4) δ=9.22 (s, 1H), 7.73 (d, J=5.3 Hz, 1H), 7.58 (s, 1H), 7.42 (d, J=5.0 Hz, 1H), 7.12-6.99 (m, 3H), 6.90 (d, J=7.3 Hz, 1H), 5.93 (d, J=4.3 Hz, 1H), 2.96 (br dd, J=3.6, 8.4 Hz, 2H), 2.90-2.77 (m, 1H), 2.46-2.36 (m, 1H), 2.30-2.15 (m, 2H), 1.81-1.66 (m, 1H).

Examples 58 to 61: 3-(8H-thieno[3,4]pyrrolo[1,5-a]imidazol-8-yl)cyclobutanol

Example 58A: ethyl 3-carbonylcyclobutylformate

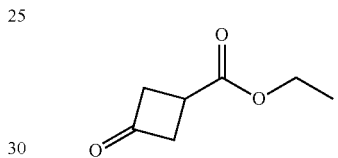

Trimethyl orthoformate (77.93 g, 525.84 mmol, 87.56 mL) was added in a solution of 3-carbonylcyclobutylcarboxylic acid (20.00 g, 175.28 mmol) in toluene (150.00 mL). The reaction solution was stirred at 110° C. for 5 h, and TLC showed that the starting materials were completely reacted and a new product was formed. After completion of reaction, the system was added with 50 mL of 1 mol/L of dilute hydrochloric acid, washed with an excess of saturated sodium hydrogen carbonate to become alkaline and then extracted with ethyl acetate (40 mL×3). The organic phase was combined and washed with 50 mL of saturated brine. The obtained organic phase was dried over anhydrous sodium sulfate, filtered under suction and evaporated under reduced pressure. The obtained crude compound was purified by column chromatography to give the compound of ethyl 3-carbonylcyclobutylformate (11.30 g, 79.49 mmol, yield of 45.35%) as a colorless liquid. $^1$H NMR (400 MHz, CHLOROFORM-d) δ=4.24-4.17 (m, 1H), 4.21 (q, J=7.2 Hz, 1H), 3.45-3.35 (m, 2H), 3.33-3.16 (m, 3H), 1.29 (t, J=7.2 Hz, 3H).

Example 58B: ethyl 3-hydroxycyclobutylformate

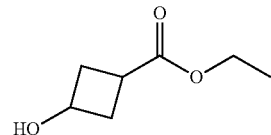

Sodium borohydride (319.35 mg, 8.44 mmol) was added in a solution of ethyl 3-carbonylcyclobutylformate (3.00 g, 21.10 mmol) in ethanol (20.00 mL). The reaction solution was stirred at 0° C. for 2 h, and TLC showed that the starting materials were completely reacted and a new product was formed. After completion of reaction, the system was added with 20 mL of water to quench the reaction, and then extracted with ethyl acetate (30 mL×3). The organic phase was combined and washed with 50 mL of saturated brine. The obtained organic phase was dried over anhydrous sodium sulfate, filtered under suction and evaporated under reduced pressure. The obtained crude compound was purified by column chromatography to give the compound of ethyl 3-hydroxycyclobutylformate (1.80 g, 12.49 mmol, yield of 59.17%) as a colorless liquid. $^1$H NMR (400 MHz, CHLOROFORM-d) δ=4.21-4.10 (m, 3H), 2.65-2.53 (m, 3H), 2.26-2.09 (m, 2H), 1.26 (t, J=7.2 Hz, 3H).

Example 58C: ethyl 3-[tert-butyl(dimethyl)silyl]oxycyclobutylformate

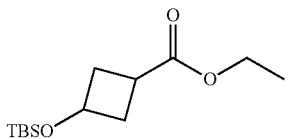 [SMILES: CCOC(=O)C1CC(O[Si](C)(C)C(C)(C)C)C1]

tert-Butyldimethylsilyl trifluoromethanesulfonate (3.96 g, 14.98 mmol, 3.44 mL) and 2,6-dimethylpyridine (2.01 g, 18.71 mmol, 2.18 mL) were added in a solution of ethyl 3-hydroxycyclobutylformate (1.80 g, 12.49 mmol) in dichloromethane (20.00 mL). The reaction solution was stirred at 25° C. for 2 h, and the system was added with 50 mL of water to quench the reaction, and then extracted with ethyl acetate (30 mL×3). The organic phase was combined and washed with 50 mL of saturated brine. The obtained organic phase was dried over anhydrous sodium sulfate, filtered under suction and evaporated under reduced pressure. The obtained crude compound was purified by column chromatography to give ethyl 3-[tert-butyl(dimethyl)silyl]oxycyclobutylformate (2.70 g, 10.45 mmol, yield of 83.65%) as a colorless liquid. $^1$H NMR (400 MHz, CHLOROFORM-d) δ=4.17-4.03 (m, 2H), 3.79 (dt, J=4.5, 9.8 Hz, 1H), 2.29 (ddd, J=3.6, 9.5, 12.2 Hz, 1H), 1.94-1.82 (m, 2H), 1.77-1.69 (m, 1H), 1.68-1.60 (m, 1H), 1.45 (dq, J=3.6, 12.7 Hz, 1H), 1.36-1.23 (m, 5H), 1.22-1.07 (m, 1H), 0.84 (s, 9H), 0.04 (s, 3H), 0.01 (s, 3H).

Example 58D: 3-[tert-butyl(dimethyl)silyl]oxycyclobutylmethanol

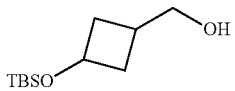 [SMILES: CC(C)(C)[Si](C)(C)OC1CC(CO)C1]

Lithium aluminum tetrahydride (366.98 mg, 9.67 mmol) was added in a solution of ethyl 3-[tert-butyl(dimethyl)silyl]oxycyclobutylformate (2.50 g, 9.67 mmol) in tetrahydrofuran (20.00 mL). The reaction solution was stirred at 0° C. for 2 h, and the system was added with 6 mL of water to quench the reaction and then filtered under suction, and the filtrate was extracted with ethyl acetate (30 mL×3). The organic phase was combined and washed with 50 mL of saturated brine. The obtained organic phase was dried over anhydrous sodium sulfate, filtered under suction and evaporated under reduced pressure. The obtained crude compound was purified by column chromatography to give 3-[tert-butyl(dimethyl)silyl]oxycyclobutylmethanol (1.30 g, 6.01 mmol, yield of 62.13%) as a colorless liquid. $^1$H NMR (400 MHz, CHLOROFORM-d) δ=4.15 (quin, J=7.3 Hz, 1H), 3.60 (d, J=6.3 Hz, 2H), 2.39-2.30 (m, 2H), 2.01-1.87 (m, 1H), 1.71-1.62 (m, 2H), 1.48-1.27 (m, 1H), 0.88 (s, 9H), 0.05-0.02 (m, 6H).

Example 58E: 3-[tert-butyl(dimethyl)silyl]oxycyclobutylcarboxaldehyde

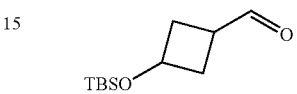

Oxalyl chloride (915.06 mg, 7.21 mmol, 631.08 μL) was added in a solution of dimethyl sulfoxide (938.76 mg, 12.02 mmol, 938.76 μL) in dichloromethane (30.00 mL). The reaction solution was stirred at −78° C. for 0.5 h, and then added with 3-[tert-butyl(dimethyl)silyl]oxycyclobutylmethanol (1.30 g, 6.01 mmol) with further stirring for 0.5 h. Triethylamine (3.04 g, 30.05 mmol, 4.17 mL) was then added thereto, and the reaction solution was stirred at −78° C. for 0.5 h. After completion of reaction, the system was added with 20 mL of water to quench the reaction, and filtered under suction. The filtrate was extracted with ethyl acetate (20 mL×3). The organic phase was combined and washed with 30 mL of saturated brine. The obtained organic phase was dried over anhydrous sodium sulfate, filtered under suction and evaporated under reduced pressure. The obtained crude compound was purified by column chromatography to give the compound of 3-[tert-butyl(dimethyl)silyl]oxycyclobutylcarboxaldehyde (750 mg, 3.50 mmol, yield of 58.21%) as a colorless liquid. $^1$H NMR (400 MHz, CHLOROFORM-d) δ=9.84-9.59 (m, 1H), 4.37-4.19 (m, 1H), 3.06-2.36 (m, 3H), 2.24-2.09 (m, 2H), 0.89-0.86 (m, 9H), 0.07-0.01 (m, 6H).

Example 58F: [3-[tert-butyl(dimethyl)silyl]oxycyclobutyl]-(3-iodo-2-thienyl)methanol

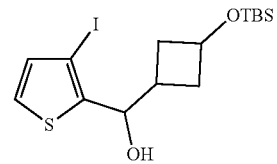 [SMILES: CC(C)(C)[Si](C)(C)OC1CC(C(O)c2sccc2I)C1]

A solution of n-butyllithium (2.5 mol/L, 1.57 mL) in n-hexane was slowly added dropwise to a solution of diisopropylamine (397.07 mg, 3.92 mmol, 551.49 μL) in diethyl ether (10.00 mL) at −78° C. over about 10 min, during which the temperature was controlled at −78° C. After completion of dropwise addition, the mixture was warmed up to 0° C. and stirred for 30 min. The system was cooled down to −78° C., and then added dropwise with 3-iodothiophene (824.20 mg, 3.92 mmol). After stirring for 1 h, 3-[tert-butyl(dimethyl)silyl]oxycyclobutylcarboxaldehyde (700.00 mg, 3.27 mmol) was added dropwise thereto and stirred at −78° C. for 2 h. The reaction was monitored by TLC. After completion of reaction, the system was added with 30 mL of saturated ammonium chloride solution, and then extracted with ethyl acetate (30 mL×3). The organic phase was combined and washed with 50 mL of saturated brine. The obtained organic phase was dried over anhydrous sodium sulfate, filtered under suction and evaporated under reduced pressure. The obtained crude compound was purified by column chromatography to give the compound of [3-[tert-butyl(dimethyl)silyl]oxycyclobutyl]-(3-iodo-2-thienyl)methanol (600.00 mg, 1.41 mmol, yield of 43.23%) as light yellow oil. $^1$H NMR (400 MHz, METHANOL-d4) δ=7.44-7.36 (m, 1H), 7.06-6.92 (m, 1H), 4.74-4.27 (m, 1H), 4.21-4.07 (m, 1H), 2.61-2.36 (m, 1H), 2.16-2.03 (m, 2H), 1.90-1.71 (m, 2H), 0.89 (s, 10H), 0.05 (d, J=1.0 Hz, 6H).

Example 58G: tert-butyl-[3-[imidazol-1-yl-(3-iodo-2-thienyl)methyl]cyclobutyl]-dimethyl-silane

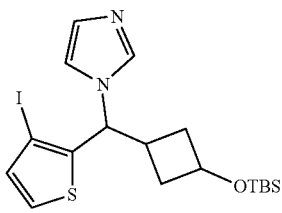 [SMILES: CC(C)(C)[Si](C)(C)OC1CC(C(c2sccc2I)n2ccnc2)C1]

1,1-Carbonyldiimidazole (1.14 g, 7.05 mmol) was added in a solution of [3-[tert-butyl(dimethyl)silyl]oxycyclobutyl]-(3-iodo-2-thienyl)methanol (600.00 mg, 1.41 mmol) in acetonitrile (10.00 mL). The reaction solution was reacted at 70° C. for 4 h, and the reaction was monitored by LCMS. After completion of reaction, the reaction solution was added with 30 mL of water, and extracted with ethyl acetate (30 mL×3). The combined organic phase was washed with 50 mL of saturated brine, dried over anhydrous sodium sulfate, filtered under suction and evaporated under reduced pressure. The crude product was purified by column chromatography to give the compound of tert-butyl-[3-[imidazol-1-yl-(3-iodo-2-thienyl)methyl]cyclobutyl]-dimethyl-silane (450.00 mg, 1.07 mmol, yield of 79.31%) as colorless oil. $^1$H NMR (400 MHz, METHANOL-d4) δ=7.90-7.81 (m, 1H), 7.53 (d, J=5.5 Hz, 1H), 7.19-7.13 (m, 1H), 7.11 (d, J=5.3 Hz, 1H), 6.96 (s, 1H), 5.62-5.51 (m, 1H), 4.61 (s, 1H), 4.29-4.21 (m, 1H), 2.42-2.30 (m, 1H), 2.43-2.16 (m, 1H), 1.90-1.63 (m, 2H), 0.89 (s, 9H), 0.04 (s, 6H).

Example 58H: tert-butyl-dimethyl-[3-(8H-thieno[3,4]pyrrolo[1,5-a]imidazol-8-yl)cyclobutyloxy]silane

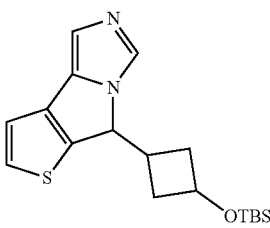 [SMILES: CC(C)(C)[Si](C)(C)OC1CC(C2c3sccc3-c3cncn32)C1]

Under protection of nitrogen gas, t-butyl-[3-[imidazol-1-yl-(3-iodo-2-thienyl)methyl]cyclobutyl]-dimethyl-silane (150.00 mg, 316.14 µmol), palladium acetate (7.10 mg, 31.61 µmol), tricyclohexylphosphine (17.73 mg, 63.23 µmol), potassium carbonate (87.39 mg, 632.28 µmol), and isopropylbenzene (2.00 mL) were successively added in a reaction flask, followed by reaction at 140° C. for 16 h. LC-MS showed the starting materials were completely reacted and the main peak was the MS peak of the desired product. After completion of reaction, the reaction solution was filtered under suction and washed with ethyl acetate (10 mL). The organic phase was added with 20 mL of water, and extracted with ethyl acetate (20 mL×3). The further organic phase combined was washed with 20 mL of saturated brine, dried over anhydrous sodium sulfate, filtered under suction and evaporated under reduced pressure. The crude product was purified by column chromatography to give tert-butyl-dimethyl-[3-(8H-thieno[3,4]pyrrolo[1,5-a]imidazol-8-yl)cyclobutyloxy]silane (120.00 mg, 346.26 µmol, yield of 54.76%). $^1$H NMR (400 MHz, CHLOROFORM-d) δ=7.68-7.60 (m, 1H), 7.35-7.31 (m, 1H), 7.15-7.10 (m, 1H), 6.93-6.90 (m, 1H), 5.60 (dd, J=1.9, 5.9 Hz, 1H), 5.21-5.07 (m, 1H), 3.97-3.92 (m, 1H), 3.97-3.92 (m, 1H), 2.63-2.41 (m, 2H), 2.40-2.22 (m, 1H), 1.97 (br s, 1H), 0.89-0.86 (m, 9H), 0.05-0.01 (m, 6H).

Example 58I: 3-(8H-thieno[3,4]pyrrolo[1,5-a]imidazol-8-yl)cyclobutanol

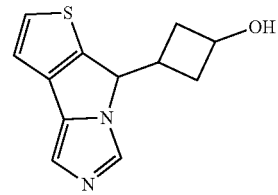 [SMILES: OC1CC(C2c3sccc3-c3cncn32)C1]

p-Toluenesulfonic acid monohydrate (164.66 mg, 865.65 µmol) was added in a solution of tert-butyl-dimethyl-[3-(8H-thieno[3,4]pyrrolo[1,5-a]imidazol-8-yl)cyclobutyloxy]silane (100 mg, 288.55 µmol) in dichloromethane (2.00 mL). The reaction solution was reacted at 20° C. for 16 h, and the reaction was monitored by TLC and LCMS. After completion of reaction, the reaction solution was added with 15 mL of saturated sodium hydrogen carbonate solution, and extracted with ethyl acetate (10 mL×3). The combined organic phase was washed with 15 mL of saturated brine, dried over anhydrous sodium sulfate, filtered under suction and evaporated under reduced pressure. The crude product was purified by column chromatography to give the compound of 3-(8H-thieno[3,4]pyrrolo[1,5-a]imidazol-8-yl)cyclobutanol (60.00 mg, 258.29 µmol, yield of 89.51%) as light yellow oil. $^1$H NMR (400 MHz, CHLOROFORM-d) δ=7.72-7.66 (m, 1H), 7.36-7.32 (m, 1H), 7.15-7.10 (m, 1H), 6.94-6.90 (m, 1H), 5.22-5.11 (m, 1H), 4.33-4.18 (m, 1H), 2.62-2.45 (m, 2H), 2.30-2.11 (m, 2H), 2.10-2.07 (m, 1H).

Preparation of the Title Compounds (Examples 58 to 61): 3-(8H-thieno[3,4]pyrrolo[1,5-a]imidazol-8-yl)cyclobutanol

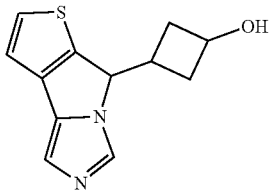 [SMILES: OC1CC(C2c3sccc3-c3cncn32)C1]

The crude compound of the racemate was purified by chiral SFC ("Column: Lux Cellulose-2 150×4.6 mm I.D., 3 μm; mobile phase: 40% of IPA (0.05% DEA) in CO$_2$; flow rate: 2.5 mL/min; column temperature: 40° C."), to finally give Example 58 (3 mg, 12.91 μmol, RT=3.195 min, ee=100%), Example 59 (3.00 mg, 12.91 μmol, RT=3.598 min, ee=92%), Example 60 (3.00 mg, 12.91 μmol, RT=4.428 min, ee=88%), and Example 61 (3.00 mg, 12.91 μmol, RT=5.424 min, ee=95%).

Example 58: $^1$H NMR (400 MHz, METHANOL-d4) δ=7.82 (s, 1H), 7.51 (d, J=5.0 Hz, 1H), 7.20 (d, J=5.0 Hz, 1H), 6.87 (s, 1H), 5.33 (d, J=7.3 Hz, 1H), 4.12 (quin, J=7.5 Hz, 1H), 2.53-2.44 (m, 1H), 2.43-2.31 (m, 1H), 2.26-2.11 (m, 1H), 1.93-1.75 (m, 2H).

Example 59: $^1$H NMR (400 MHz, METHANOL-d4)= 7.82 (s, 1H), 7.51 (d, J=4.8 Hz, 1H), 7.20 (d, J=5.0 Hz, 1H), 6.87 (s, 1H), 5.32 (d, J=7.3 Hz, 1H), 4.12 (quin, J=7.5 Hz, 1H), 2.54-2.34 (m, 2H), 2.26-2.13 (m, 1H), 1.94-1.73 (m, 2H).

Example 60: $^1$H NMR (400 MHz, METHANOL-d4)= 7.87 (s, 1H), 7.52 (d, J=5.0 Hz, 1H), 7.21 (d, J=5.0 Hz, 1H), 6.88 (s, 1H), 5.43 (d, J=7.5 Hz, 1H), 4.29 (quin, J=6.5 Hz, 1H), 2.84-2.72 (m, 1H), 2.48-2.35 (m, 1H), 2.29-2.17 (m, 2H), 2.14-2.02 (m, 1H).

Example 61: $^1$H NMR (400 MHz, METHANOL-d4) δ=7.87 (s, 1H), 7.52 (d, J=5.0 Hz, 1H), 7.21 (d, J=5.0 Hz, 1H), 6.88 (s, 1H), 5.43 (d, J=7.5 Hz, 1H), 4.29 (quin, J=6.5 Hz, 1H), 2.84-2.72 (m, 1H), 2.48-2.35 (m, 1H), 2.29-2.17 (m, 2H), 2.14-2.02 (m, 1H).

Examples 62 to 63: 8-[6,6-difluoro-3-bicyclo[3.1.0] cyclohexyl]-8H-thieno[3,4]pyrrolo[1,5-a]imidazole (trans)

Example 62A: methyl 6,6-difluoro-bicyclo[3.1.0] cyclohexyl-3-carboxylate

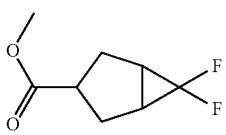

A 250 mL three-neck flask was fitted with a reflux condenser, a rubber stopper and a magnet, and then purged three times under a nitrogen atmosphere. KI (5.92 g, 35.67 mmol) was added thereto and dried. After cooling down to room temperature, methyl 3-cyclopentene-1-carboxylate (10.0 g, 79.27 mmol) and diglyme (1.10 mL) were added. An oil bath was heated up to 115-120° C., and TMSCl (17.22 g, 158.54 mmol) was added at the above temperature, followed by addition of methyl fluorosulfonyl difluoroacetate (30.46 g, 158.54 mmol). The reaction solution was reacted at 115° C. for 48 h, and quenched with water (100 mL), which was then extracted with ethyl acetate (50 mL×4). The combined organic phase was washed with brine (100 mL), dried over anhydrous sodium sulfate, filtered and concentrated. The residue was purified by column chromatography to give the title compound (yellow oil, trans: 6.80 g, yield of 48.70%; cis: 2.00 g, yield of 14.32%). The trans product: $^1$H NMR (400 MHz, CHLOROFORM-d) δ=3.69 (s, 3H), 2.90-2.76 (m, 1H), 2.40-2.16 (m, 4H), 2.09-1.93 (m, 2H); the cis product: $^1$H NMR (400 MHz, CHLOROFORM-d) δ=3.68 (s, 3H), 3.21-3.09 (m, 1H), 2.43-2.24 (m, 4H), 2.09-1.95 (m, 2H).

Example 62B: 6,6-difluoro-bicyclo[3.1.0]cyclo-hexyl-3-carboxaldehyde (trans)

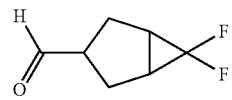

Under protection of nitrogen gas, DIBAlH (1 M, 46.83 mL) was slowly added to a solution of methyl 6,6-difluoro-bicyclo[3.1.0]cyclohexyl-3-carboxylate (trans) (5.50 g, 31.22 mmol) in dichloromethane (55.00 mL) at −78° C., and the reaction solution was stirred at −78° C. for 2 h. The reaction solution was quenched with saturated sodium potassium tartrate solution (50 mL), and extracted with dichloromethane (20 mL×4). The combined organic phase was washed with brine (50 mL), dried over anhydrous sodium sulfate, filtered and concentrated. The residue was purified by column chromatography to give the title compound (yellow oil, 2.50 g, yield of 54.80%). $^1$H NMR (400 MHz, CHLOROFORM-d) δ=9.67 (s, 1H), 2.93-2.77 (m, 1H), 2.31-2.14 (m, 4H), 2.11-2.08 (m, 1H), 2.06 (br s, 1H).

Example 62C: (3-bromo-2-thienyl)-6,6-difluoro-bicyclo[3.1.0]cyclohexyl-3-methanol (trans)

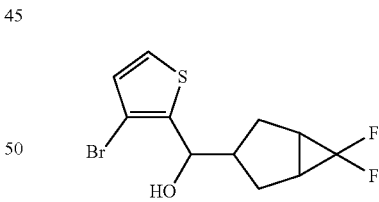

A solution of diisopropylamine (1.02 g, 10.12 mmol) in diethyl ether (10.00 mL) was cooled down to −78° C., and n-butyllithium (2.5 M, 4.05 mL) was slowly added thereto. After stirring at 0° C. for 0.5 h, 3-bromothiophene (1.50 g, 9.20 mmol) was added, with stirring at −78° C. for 1.5 h. 6,6-Difluoro-bicyclo[3.1.0]cyclohexyl-3-carboxaldehyde (trans) (1.48 g, 10.12 mmol) was added, and the reaction solution was stirred at −78° C. for 1.5 h. The reaction was quenched with ammonium chloride solution (10 mL), and the reaction solution was diluted with water (20 mL) and extracted with ethyl acetate (10 mL×4). The combined organic phase was washed with brine (30 mL), dried over anhydrous sodium sulfate, filtered and evaporated. The residue was purified by column chromatography to give the title compound (colorless oil, 800.00 mg, yield of 28.13%). ¹H NMR (400 MHz, CHLOROFORM-d) δ=7.30 (d, J=5.5 Hz, 1H), 6.94 (d, J=5.3 Hz, 1H), 4.90 (d, J=7.8 Hz, 1H), 2.55-2.45 (m, 1H), 2.30-2.22 (m, 1H), 2.19-2.07 (m, 2H), 2.06-1.94 (m, 2H), 1.92-1.82 (m, 2H).

Example 62D: 1-[(3-bromo-2-thienyl)-6,6-difluoro-bicyclo[3.1.0]cyclohexyl]methyl]imidazole (trans)

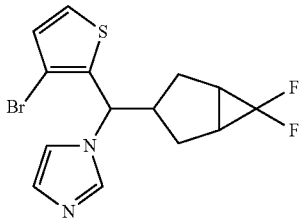 [SMILES: FC1(F)C2CC(C(c3sccc3Br)n3ccnc3)CC21]

CDI (2.62 g, 16.15 mmol) was added into a solution of (3-bromo-2-thienyl)-6,6-difluoro-bicyclo[3.1.0]cyclohexyl-3-methanol (trans) (1.00 g, 3.23 mmol) in acetonitrile (20.00 mL), and the reaction solution was stirred at 80° C. for 16 h. The reaction solution was then added with saturated ammonium chloride solution (10 mL), diluted with 20 mL of water, and extracted with ethyl acetate (15 mL×3). The combined organic phase was washed with brine (30 mL), dried over anhydrous sodium sulfate, filtered and evaporated. The residue was purified by column chromatography to give the title compound (colorless oil, 550.00 mg, yield of 47.40%). ¹H NMR (400 MHz, CHLOROFORM-d) δ=7.67 (s, 1H), 7.33 (d, J=5.3 Hz, 1H), 7.10-7.05 (m, 2H), 6.94 (d, J=5.3 Hz, 1H), 5.26 (d, J=11.3 Hz, 1H), 3.01-2.81 (m, 1H), 2.13-2.06 (m, 1H), 2.04-1.95 (m, 3H), 1.83-1.71 (m, 2H).

Example 62E: 8-[6,6-difluoro-3-bicyclo[3.1.0]cyclohexyl]-8H-thieno[3,4]pyrrolo[1,5-a]imidazole (trans) (racemate)

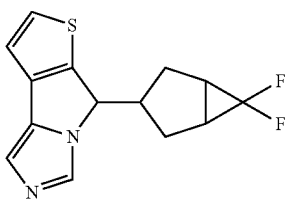 [SMILES: FC1(F)C2CC(C3c4sccc4-c4cncn43)CC21]

A solution of 1-[(3-bromo-2-thienyl)-6,6-difluoro-bicyclo[3.1.0]cyclohexyl]methyl]imidazole (100.00 mg, 278.37 μmol), palladium acetate (6.25 mg, 27.84 μmol), tricyclohexylphosphine (15.61 mg, 55.67 μmol) and potassium carbonate (76.95 mg, 556.74 μmol) in o-xylene (2.00 mL) was purged with N₂ three times, followed by stirring at 115° C. for 16 h. The reaction solution was diluted with water (20 mL), and extracted with ethyl acetate (10 mL×4). The combined organic phase was washed with brine (30 mL), dried over anhydrous sodium sulfate, filtered and concentrated. The residue was purified by column chromatography to give the title compound (30.00 mg, yield of 38.72%). ¹H NMR (400 MHz, CHLOROFORM-d) δ=7.59 (s, 1H), 7.28 (d, J=5.0 Hz, 1H), 7.07 (d, J=5.0 Hz, 1H), 6.86 (s, 1H), 5.06 (d, J=6.3 Hz, 1H), 2.60-2.45 (m, 1H), 2.25 (br dd, J=7.9, 12.9 Hz, 1H), 2.10-1.98 (m, 3H), 1.36 (br dd, J=4.4, 7.2 Hz, 2H).

Preparation of the Title Compounds (Examples 62 to 63)

8-[6,6-difluoro-3-bicyclo[3.1.0]cyclohexyl]-8H-thieno[3,4]pyrrolo[1,5-a]imidazole (trans)

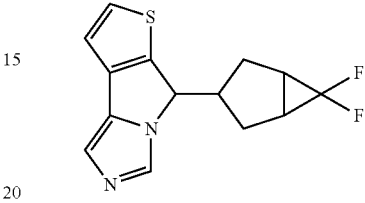

The racemate was subjected to chiral separation (column: Chiralpak AD-3 150×4.6 mm I.D., 3 μm; mobile phase: A: CO₂ B: ethanol (0.05% DEA); gradient: from 5% to 40% of B in 5 min and hold 40% for 2.5 min, then 5% of B for 2.5 min; flow rate: 2.5 mL/min; column temperature: 35° C.), to give two components. Component I was purified by preparative HPLC (water (10 mM NH₄HCO₃)-ACN) to give Example 62 (30.00 mg, yield of 42.26%; SFC retention time: 3.781 min). Component II was Example 63 (25.00 mg, yield of 35.57%; SFC retention time: 4.762 min).

Example 62: ¹H NMR (400 MHz, METHANOL-d4) δ=7.92 (br s, 1H), 7.52 (d, J=5.0 Hz, 1H), 7.21 (d, J=5.0 Hz, 1H), 7.02-6.72 (m, 1H), 5.37 (d, J=6.0 Hz, 1H), 2.67-2.52 (m, 1H), 2.26 (br dd, J=7.9, 13.4 Hz, 1H), 2.12-1.93 (m, 4H), 1.85-1.68 (m, 1H).

Example 63: ¹H NMR (400 MHz, METHANOL-d4) δ=7.96 (br s, 1H), 7.55 (d, J=5.0 Hz, 1H), 7.23 (d, J=5.0 Hz, 1H), 6.95 (br s, 1H), 5.39 (d, J=6.0 Hz, 1H), 2.72-2.57 (m, 1H), 2.28 (br dd, J=7.9, 13.2 Hz, 1H), 2.15-1.96 (m, 4H), 1.86-1.72 (m, 1H).

Examples 64 to 71: 3-(8H-thieno[3',2':3,4]pyrrolo[1,2-c]imidazol-8-yl)cyclohexanol Example 64A: ethyl 3-hydroxycyclohexanecarboxylate

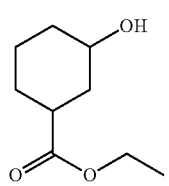

Sodium borohydride (1.00 g, 26.44 mmol) was added portionwise into a solution of ethyl 3-ketocyclohexanecarboxylate (9.00 g, 52.88 mmol) in methanol (100.00 mL) at 0° C. The mixture was stirred at 0° C. for 2 h. The reaction solution was quenched with 1M hydrochloric acid solution (30 mL), diluted with water (100 mL), and extracted with ethyl acetate (100 mL×3). The combined organic phase was washed with brine (100 mL×3), dried over anhydrous sodium sulfate, filtered and evaporated. The residue was purified by column chromatography to give the title compound (colorless oil, 6.8 g, yield of 74.67%). ¹H NMR (400 MHz, CHLOROFORM-d) δ=4.14-4.05 (m, 2H), 3.59 (tt, J=4.3, 10.4 Hz, 1H), 2.38-2.27 (m, 1H), 2.20-2.09 (m, 2H), 1.96-1.89 (m, 1H), 1.88-1.76 (m, 2H), 1.44-1.26 (m, 3H), 1.22 (t, J=7.2 Hz, 3H).

Example 64B: ethyl 3-[tert-butyl(dimethyl)silyl]oxycyclohexanecarboxylate

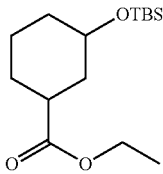 [SMILES: CCOC(=O)C1CCCC(O[Si](C)(C)C(C)(C)C)C1]

2,6-Dimethylpyridine (6.91 g, 64.46 mmol, 7.51 mL) and TBSOTf (13.63 g, 51.56 mmol, 11.85 mL) were added into a solution of ethyl 3-hydroxycyclohexanecarboxylate (7.40 g, 42.97 mmol) in dichloromethane (80.00 mL), and the mixture was stirred at 24° C. for 16 h. The reaction solution was dispersed in dichloromethane (150 mL) and water (150 mL). The organic phase was separated, washed with water (150 mL×3), dried over anhydrous sodium sulfate, filtered and evaporated. The residue was purified by preparative chromatography to give the title compound (colorless oil, 11.00 g, yield of 89.36%). ¹H NMR (400 MHz, CHLOROFORM-d) δ=4.11 (q, J=7.0 Hz, 2H), 3.60-3.50 (m, 1H), 2.35-2.23 (m, 1H), 2.11-2.02 (m, 1H), 1.88-1.76 (m, 3H), 1.46-1.37 (m, 1H), 1.31-1.21 (m, 6H), 0.87 (s, 9H), 0.05 (s, 6H).

Example 64C: 3-[tert-butyl(dimethyl)silyl]oxycyclohexylcarboxaldehyde

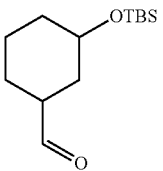

Under protection of nitrogen gas, DIBAL-H (1 M, 52.36 mL) was slowly added into a solution of ethyl 3-[tert-butyl(dimethyl)silyl]oxycyclohexanecarboxylate (10.00 g, 34.91 mmol) in tetrahydrofuran (100.00 mL) at −78° C., and then the reaction solution was stirred at −78° C. for 2 h. The reaction solution was quenched with saturated sodium potassium tartrate (100 mL), diluted with water (50 mL) and extracted with ethyl acetate (100 mL×3). The combined organic phase was washed with brine (100 mL×3), dried over anhydrous sodium sulfate, filtered and evaporated. The residue was purified by column chromatography to give the title compound (colorless oil, 7.45 g, yield of 80.02%). ¹H NMR (400 MHz, CHLOROFORM-d) δ=9.65-9.59 (m, 1H), 3.79-3.65 (m, 1H), 2.29-2.20 (m, 1H), 2.03 (td, J=3.8, 12.9 Hz, 1H), 1.87-1.82 (m, 1H), 1.79-1.71 (m, 2H), 1.59-1.44 (m, 2H), 1.38-1.30 (m, 2H), 0.88-0.87 (m, 9H), 0.05 (d, J=2.3 Hz, 6H).

Example 64D: (3-bromo-2-thienyl)-[3-[tert-butyl(dimethyl)silyl]oxycyclohexyl]methanol

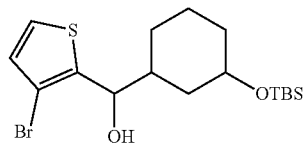 [SMILES: CC(C)(C)[Si](C)(C)OC1CCCC(C(O)c2sccc2Br)C1]

A solution of diisopropylamine (3.72 g, 36.80 mmol) in diethyl ether (50.00 mL) was cooled down to −78° C., and n-butyllithium (2.5 M, 13.49 mL) was slowly added thereto. After 1 hour, 3-bromothiophene (5.00 g, 30.67 mmol) was added and stirred at −78° C. for 1 h. 3-[Tert-butyl(dimethyl)silyl]oxycyclohexylcarboxaldehyde (7.43 g, 30.67 mmol) was further added, and the reaction solution was stirred at −78° C. for 1 h. The reaction solution was quenched by adding ammonium chloride solution (50 mL), diluted with water (50 mL) and extracted with ethyl acetate (50 mL×3). The organic phase was washed with brine (50 mL×3), dried over anhydrous sodium sulfate, filtered and evaporated. The residue was purified by column chromatography to give the title compound (colorless oil, 7.10 g, yield of 57.09%). ¹H NMR (400 MHz, CHLOROFORM-d) δ=7.22-7.18 (m, 1H), 6.88-6.83 (m, 1H), 4.82-4.67 (m, 1H), 3.60-3.42 (m, 1H), 2.33-2.16 (m, 1H), 1.77-1.68 (m, 2H), 1.62-1.50 (m, 1H), 1.34-1.23 (m, 1H), 1.22-1.05 (m, 3H), 1.01-0.88 (m, 1H), 0.83 (s, 4H), 0.81-0.77 (m, 5H), 0.02--0.02 (m, 3H), 0.05--0.13 (m, 3H).

Example 64E: [3-[(3-bromo-2-thienyl)-imidazol-1-yl-methyl]cyclohexyloxy]-tert-butyl-dimethyl-silane

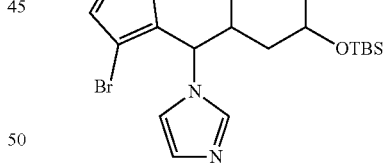

CDI (14.20 g, 87.55 mmol) was added into a solution of (3-bromo-2-thienyl)-[3-[tert-butyl(dimethyl)silyl]oxycyclohexyl]methanol (7.10 g, 17.51 mmol) in acetonitrile (70.00 mL), and the reaction solution was stirred at 80° C. for 16 h. The reaction solution was dispersed in ethyl acetate (100 mL) and water (100 mL). The organic phase was separated, washed with brine (100 mL×3), dried over anhydrous sodium sulfate, filtered and evaporated. The residue was purified by column chromatography to give the title compound (colorless oil, 6.40 g, yield of 80.24%). ¹H NMR (400 MHz, CHLOROFORM-d) δ=7.69-7.63 (m, 1H), 7.35 (dd, J=5.3, 10.0 Hz, 1H), 7.08 (br t, J=8.0 Hz, 2H), 7.00-6.93 (m, 1H), 5.35-5.16 (m, 1H), 4.10-3.52 (m, 1H), 2.24-2.13 (m, 1H), 1.92 (br s, 1H), 1.83-1.34 (m, 4H), 1.15-0.90 (m, 4H), 0.87 (d, J=1.5 Hz, 7H), 0.04--0.02 (m, 6H).

Example 64F: tert-butyl-dimethyl-[3-(8H-thieno[3,4]pyrrolo[1,5-a]imidazol-8-yl)cyclohexyloxy]silane

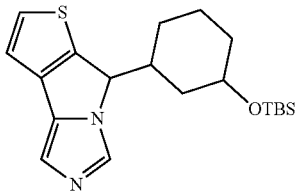 [SMILES: CC(C)(C)[Si](C)(C)OC1CCCC(C2c3sccc3-c3cncn32)C1]

Under protection of nitrogen gas, a mixture solution of [3-[(3-bromo-2-thienyl)-imidazol-1-yl-methyl]cyclohexyloxy]-tert-butyl-dimethyl-silane (6.40 g, 14.05 mmol), palladium acetate (315.44 mg, 1.41 mmol), tricyclohexylphosphine (788.01 mg, 2.81 mmol), potassium carbonate (3.88 g, 28.10 mmol) in o-xylene (65.00 mL) was stirred at 140° C. for 16 h. The reaction solution was dispersed in ethyl acetate (100 mL) and water (100 mL). The organic phase was separated, washed with brine (100 mL×3), dried over anhydrous sodium sulfate, filtered and evaporated. The residue was purified by column chromatography to give the title compound (brown oil, 3.80 g, yield of 72.20%). $^1$H NMR (400 MHz, CHLOROFORM-d) δ=7.61-7.53 (m, 1H), 7.29-7.24 (m, 1H), 7.09-7.06 (m, 1H), 6.87 (d, J=3.3 Hz, 1H), 5.01 (br d, J=3.5 Hz, 1H), 3.62-3.43 (m, 1H), 1.95-1.87 (m, 1H), 1.85-1.70 (m, 2H), 1.69-1.53 (m, 2H), 1.30-1.22 (m, 1H), 1.15-0.87 (m, 3H), 0.83 (t, J=3.9 Hz, 6H), 0.78 (s, 3H), 0.01--0.07 (m, 6H).

Preparation of the Title Compounds (Examples 64 to 71): 3-(8H-thieno[3,4]pyrrolo[1,5-a]imidazol-8-yl)cyclohexanol

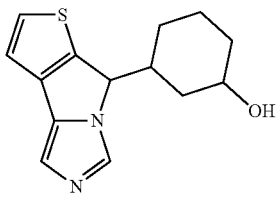 [SMILES: OC1CCCC(C2c3sccc3-c3cncn32)C1]

TsOH.H$_2$O (5.79 g, 30.42 mmol) was added into a solution of tert-butyl-dimethyl-[3-(8H-thieno[3,4]pyrrolo[1,5-a]imidazol-8-yl)cyclohexyloxy]silane (3.80 g, 10.14 mmol) in dichloromethane (40.00 mL), and the mixture was stirred at 22° C. for 16 h. The reaction solution was dispersed in dichloromethane (50 mL) and water (50 mL). The organic phase was separated, washed with water (50 mL×3), dried over anhydrous sodium sulfate, filtered and evaporated. The residue was purified by column chromatography to give the title compound (1.80 g, yield of 68.18%). 800 mg of the compound was purified by preparative chromatography, to give Peak1 (170 mg), Peak 2 (180 mg), Peak 3 (70 mg) and Peak 4 (60 mg). Peak 1 (170.00 mg, 652.97 μmol) was subjected to chiral separation (column: OJ-3, mobile phase: A: carbon dioxide B: ethanol (0.05% diethylamine)), to give Example 64 (68.00 mg, yield of 80.00%) (retention time: 3.267 min) and Example 65 (72.00 mg, yield of 84.71%) (retention time: 3.657 min).

Example 64: $^1$H NMR (400 MHz, METHANOL-d4) δ=7.87-7.80 (m, 1H), 7.83 (s, 1H), 7.49 (d, J=5.0 Hz, 1H), 7.17 (d, J=5.0 Hz, 1H), 6.86 (s, 1H), 5.24 (d, J=3.8 Hz, 1H), 3.63-3.52 (m, 1H), 2.19 (dt, J=3.0, 12.3 Hz, 1H), 2.03-1.86 (m, 2H), 1.74-1.63 (m, 1H), 1.32-1.17 (m, 2H), 1.15-0.99 (m, 2H), 0.70 (dq, J=3.3, 12.6 Hz, 1H).

Example 65: $^1$H NMR (400 MHz, METHANOL-d4) δ=7.72 (s, 1H), 7.38 (d, J=4.8 Hz, 1H), 7.06 (d, J=4.8 Hz, 1H), 6.75 (s, 1H), 5.12 (d, J=3.8 Hz, 1H), 3.53-3.41 (m, 1H), 2.13-2.02 (m, 1H), 1.92-1.75 (m, 2H), 1.62-1.52 (m, 1H), 1.19-1.06 (m, 2H), 1.04-0.88 (m, 2H), 0.59 (dq, J=3.5, 12.7 Hz, 1H).

Peak 2 (180.00 mg, 691.38 μmol) was subjected to chiral separation (column: Chiralpak AD-3 100×4.6 mm I.D., 3 μm; mobile phase: A: carbon dioxide B: ethanol (0.05% diethylamine)), to give Example 66 (64.00 mg, yield of 70.47%) (retention time: 5.251 min) and Example 67 (62.00 mg, yield of 68.82%) (retention time: 6.512 min).

Example 66: $^1$H NMR (400 MHz, METHANOL-d4) δ=7.76 (s, 1H), 7.42 (d, J=5.0 Hz, 1H), 7.11 (d, J=5.0 Hz, 1H), 6.78 (s, 1H), 5.24 (d, J=3.8 Hz, 1H), 3.39 (tt, J=4.1, 11.0 Hz, 1H), 2.24-2.06 (m, 1H), 1.86-1.73 (m, 2H), 1.70 (br d, J=12.3 Hz, 1H), 1.38-1.24 (m, 2H), 1.12-0.90 (m, 2H), 0.58 (q, J=12.0 Hz, 1H).

Example 67: $^1$H NMR (400 MHz, METHANOL-d4) δ=7.76 (s, 1H), 7.42 (d, J=5.0 Hz, 1H), 7.11 (d, J=5.0 Hz, 1H), 6.78 (s, 1H), 5.24 (d, J=4.0 Hz, 1H), 3.39 (tt, J=4.1, 10.9 Hz, 1H), 2.21-2.09 (m, 1H), 1.85-1.74 (m, 2H), 1.70 (br d, J=12.3 Hz, 1H), 1.38-1.25 (m, 2H), 1.12-0.90 (m, 2H), 0.58 (q, J=12.0 Hz, 1H).

Peak 3 (70.00 mg, 268.87 μmol) was subjected to chiral separation (column: Chiralpak AD-3 100×4.6 mm I.D., 3 μm; mobile phase: A: carbon dioxide B: isopropanol (0.05% diethylamine)), to give Example 68 (31.00 mg, yield of 84.28%) (retention time: 5.162 min) and Example 69 (28.00 mg, yield of 77.36%) (retention time: 6.033 min).

Example 68: $^1$H NMR (400 MHz, METHANOL-d4) δ=7.89 (s, 1H), 7.54 (d, J=5.0 Hz, 1H), 7.23 (d, J=4.8 Hz, 1H), 6.90 (s, 1H), 5.27 (d, J=4.0 Hz, 1H), 4.15 (br d, J=2.8 Hz, 1H), 2.64-2.53 (m, 1H), 1.85 (br d, J=13.1 Hz, 1H), 1.80-1.64 (m, 2H), 1.51-1.30 (m, 4H), 0.88 (dq, J=3.9, 12.7 Hz, 1H).

Example 69: $^1$H NMR (400 MHz, METHANOL-d4) δ=7.76 (s, 1H), 7.42 (d, J=5.0 Hz, 1H), 7.11 (d, J=5.0 Hz, 1H), 6.77 (s, 1H), 5.15 (d, J=4.0 Hz, 1H), 4.03 (br s, 1H), 2.47 (ddd, J=3.6, 8.9, 16.1 Hz, 1H), 1.79-1.49 (m, 3H), 1.40-1.18 (m, 4H), 0.76 (dq, J=3.5, 12.6 Hz, 1H).

Peak 4 (60.00 mg, 230.46 μmol) was subjected to chiral separation (column: Chiralpak AD-3 100×4.6 mm I.D., 3 μm; mobile phase: A: carbon dioxide B: isopropanol (0.05% diethylamine)), to give Example 70 (26.00 mg, yield of 84.87%) (retention time: 4.555 min) and Example 71 (24.00 mg, yield of 78.96%) (retention time: 5.865 min).

Example 70: $^1$H NMR (400 MHz, METHANOL-d4) δ=7.86 (s, 1H), 7.53 (d, J=5.0 Hz, 1H), 7.23 (d, J=5.0 Hz, 1H), 6.88 (s, 1H), 5.31 (d, J=4.0 Hz, 1H), 4.01 (br s, 1H), 2.63 (ddd, J=3.4, 9.1, 15.9 Hz, 1H), 1.89-1.72 (m, 3H), 1.66-1.57 (m, 1H), 1.41-1.22 (m, 3H), 1.00 (dt, J=2.5, 13.1 Hz, 1H).

Example 71: $^1$H NMR (400 MHz, METHANOL-d4) δ=7.75 (s, 1H), 7.42 (d, J=5.0 Hz, 1H), 7.11 (d, J=5.0 Hz, 1H), 6.77 (s, 1H), 5.19 (d, J=3.8 Hz, 1H), 3.89 (br d, J=2.8 Hz, 1H), 2.56-2.45 (m, 1H), 1.76-1.60 (m, 3H), 1.54-1.45 (m, 1H), 1.29-1.12 (m, 3H), 0.88 (dt, J=2.5, 13.1 Hz, 1H).

Examples 72 to 73: 8-cycloheptyl-8H-thieno[3',2':3,4]pyrrolo[1,2-c]imidazole

Example 72A:
N-methoxy-N-methyl-cycloheptanecarboxamide

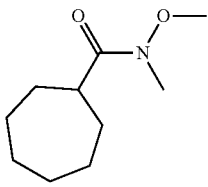

Triethylamine (10.67 g, 105.48 mmol, 14.62 mL), N-methoxymethylamine (3.60 g, 36.92 mmol) and HBTU (14.67 g, 38.68 mmol) were added into a solution of cycloheptylcarboxylic acid (5.00 g, 35.16 mmol) in DMF (50 mL) at 25° C., and the mixture was stirred for 16 h. The reaction solution was diluted with water (200 mL), and extracted with ethyl acetate (50 mL×6). The organic phase was combined, washed with brine (100 mL), dried over anhydrous sodium sulfate, filtered and concentrated. The residue was purified by column chromatography to give the title compound (colorless oil, 5.50 g, yield of 84.44%). $^1$H NMR (400 MHz, CHLOROFORM-d) δ=3.71 (d, J=1.5 Hz, 3H), 3.19 (s, 3H), 2.85 (br s, 1H), 1.88-1.61 (m, 9H), 1.49 (br s, 3H).

Example 72B:
(3-bromo-2-thienyl)-cycloheptyl-methanone

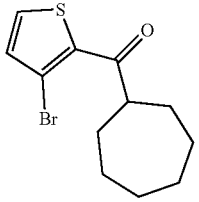 [SMILES: O=C(c1sccc1Br)C1CCCCCC1]

A solution of diisopropylamine (928.92 mg, 9.18 mmol) in diethyl ether (20.00 mL) was cooled down to −78° C., and n-butyllithium (2.5 M, 3.67 mL) was slowly added thereto. After addition, stirring was conducted at 0° C. for 30 min. The mixture was re-cooled down to −78° C., then added with 3-bromothiophene (1.32 g, 8.10 mmol), and maintained at −78° C. with stirring for 1 h. N-methoxy-N-methyl-cycloheptanecarboxamide (1.00 g, 5.40 mmol) was further added, and the reaction solution was stirred at −78° C. for 1 h. The reaction was quenched by adding ammonium chloride solution (20 mL), followed by extraction with ethyl acetate (10 mL×3). The organic phase was combined, washed with brine (20 mL), dried over anhydrous sodium sulfate, filtered and concentrated. The residue was purified by column chromatography to give the title compound (colorless oil, 300 mg, yield of 19.34%). $^1$H NMR (400 MHz, CHLOROFORM-d) δ=7.49 (d, J=5.3 Hz, 1H), 7.11 (d, J=5.3 Hz, 1H), 3.53 (tt, J=3.9, 9.5 Hz, 1H), 2.06-1.96 (m, 2H), 1.86-1.76 (m, 2H), 1.75-1.60 (m, 6H), 1.58-1.50 (m, 2H).

Example 72C:
(3-bromo-2-thienyl)-cycloheptyl-methanol

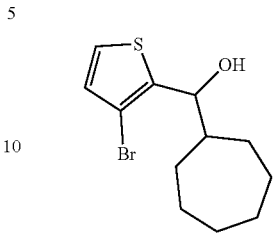

A solution of (3-bromo-2-thienyl)-cycloheptyl-methanone (300 mg, 1.04 mmol) in methanol (5.00 mL) was cooled down to 0° C., added with sodium borohydride (39.35 mg, 1.04 mmol), and maintained at 0° C. with stirring for 1 hour. Ammonium chloride solution (20 mL) was then added to quench, followed by extraction with ethyl acetate (10 mL×3). The organic phase was washed with brine (20 mL×3), dried over anhydrous sodium sulfate, filtered and concentrated to give the crude title compound (colorless oil, 300 mg). $^1$H NMR (400 MHz, CHLOROFORM-d) δ=7.18 (s, 1H), 6.85 (d, J=5.3 Hz, 1H), 4.79 (dd, J=3.5, 7.5 Hz, 1H), 2.01 (d, J=3.8 Hz, 1H), 1.97-1.85 (m, 2H), 1.63-1.54 (m, 2H), 1.49-1.36 (m, 7H), 1.26-1.20 (m, 1H).

Example 72D: 1-[(3-bromo-2-thienyl)-cycloheptyl-methyl]imidazole

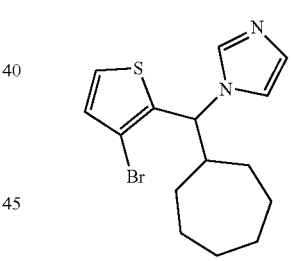

CDI (700.78 mg, 4.32 mmol) was added into a solution of (3-bromo-2-thienyl)-cycloheptylmethanol (250 mg, 864.36 μmol) in acetonitrile (5.00 mL). The reaction was stirred at 80° C. for 16 h. The reaction solution was added with water (20 mL) to quench, and extracted with ethyl acetate (10 mL×3). The organic phase was combined, washed with brine (20 mL), dried over anhydrous sodium sulfate, filtered and evaporated. The residue was purified by column chromatography to give the title compound (colorless oil, 250 mg, yield of 85.25%). $^1$H NMR (400 MHz, CHLOROFORM-d) δ=7.65 (s, 1H), 7.31 (d, J=5.8 Hz, 1H), 7.06 (s, 2H), 6.94 (d, J=5.3 Hz, 1H), 5.28 (d, J=11.0 Hz, 1H), 2.42-2.30 (m, 1H), 1.73-1.66 (m, 2H), 1.62-1.36 (m, 8H), 1.35-1.28 (m, 1H), 1.25-1.16 (m, 1H).

Example 72E: 8-cycloheptyl-8H-thieno[3,4]pyrrolo[1,5-a]imidazole

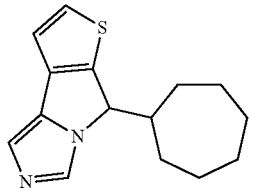 [SMILES: c1cc2c(s1)C(C1CCCCCC1)n1cncc1-2]

Under protection of nitrogen gas, a mixture solution of 1-[(3-bromo-2-thienyl)-cycloheptyl-methyl]imidazole (200 mg, 589.47 μmol), palladium acetate (13.23 mg, 58.95 μmol), tricyclohexylphosphine (33.06 mg, 117.89 μmol), potassium carbonate (162.94 mg, 1.18 mmol) in o-xylene (3.00 mL) was stirred at 140° C. for 16 h. The reaction solution was dispersed in ethyl acetate (10 mL) and water (10 mL), and extracted with ethyl acetate (10 mL×3). The organic phase was combined, washed with brine (20 mL), dried over anhydrous sodium sulfate, filtered and concentrated. The residue was purified by silica gel column to give the title compound (80 mg, yield of 49.37%).

Preparation of the Title Compounds (Examples 72 to 73): 8-cycloheptyl-8H-thieno[3,4]pyrrolo[1,5-a]imidazole

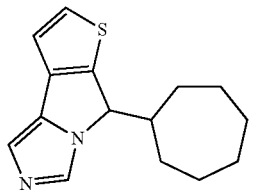 [SMILES: c1cc2c(s1)C(C1CCCCCC1)n1cncc1-2]

8-Cycloheptyl-8H-thieno[3,4]pyrrolo[1,5-a]imidazole was subjected to chiral separation (column: Lux Cellulose-2 150×4.6 mm I.D., 3 μm; mobile phase: A: $CO_2$ B: methanol (0.05% DEA); gradient: from 5% to 40% of B in 5.5 min and hold 40% for 3 min, then 5% of B for 1.5 min; flow rate: 2.5 mL/min; column temperature: 40° C.), to give Example 72 (35.00 mg, yield of 43.53%) (retention time: 6.739 min) and Example 73 (30.00 mg, yield of 36.49%) (retention time: 8.223 min).

Example 72: $^1$H NMR (400 MHz, METHANOL-d4) δ=7.87 (s, 1H), 7.52 (d, J=5.0 Hz, 1H), 7.22 (d, J=5.0 Hz, 1H), 6.88 (s, 1H), 5.34 (d, J=3.8 Hz, 1H), 2.38 (qt, J=3.5, 10.5 Hz, 1H), 1.95-1.75 (m, 2H), 1.70-1.42 (m, 7H), 1.40-1.29 (m, 1H), 1.26-1.16 (m, 1H), 0.97 (dtd, J=3.3, 10.4, 13.8 Hz, 1H).

Example 73: $^1$H NMR (400 MHz, METHANOL-d4) δ=7.87 (s, 1H), 7.52 (d, J=5.0 Hz, 1H), 7.22 (d, J=5.0 Hz, 1H), 6.88 (s, 1H), 5.34 (d, J=3.8 Hz, 1H), 2.44-2.31 (m, 1H), 1.94-1.76 (m, 2H), 1.70-1.44 (m, 7H), 1.38-1.30 (m, 1H), 1.25-1.16 (m, 1H), 1.02-0.91 (m, 1H).

Examples 74 to 75: 8-cyclopentyl-8H-thieno[3,4]pyrrolo[1,5-a]imidazole

Example 74A: cyclopentyl-(3-bromo-2-thienyl)methanol

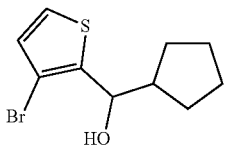 [SMILES: OC(c1sccc1Br)C1CCCC1]

At −78° C., a solution of n-butyllithium (2.5 mol/L, 22.42 mL) in n-hexane was slowly added dropwise into a solution of diisopropylamine (5.67 g, 56.05 mmol, 7.88 mL) in diethyl ether (30.00 mL) over about 10 min, during which the temperature was controlled at −78° C. After completion of dropwise addition, the mixture was warmed up to 0° C. and stirred for 30 min. The system was cooled down to −78° C., and then added dropwise with 3-bromothiophene (9.97 g, 61.14 mmol, 5.73 mL). After stirring for 1 h, cyclopentyl-carboxaldehyde (5.00 g, 50.95 mmol) was added dropwise, with stirring at −78° C. for another 2 h. After completion of reaction, the system was added with 50 mL of saturated ammonium chloride solution, and extracted with ethyl acetate (50 mL×3). The organic phase was combined, washed with 50 mL of saturated brine, dried over anhydrous sodium sulfate, filtered under suction and evaporated under reduced pressure. The obtained crude compound was purified by column chromatography to give the compound of cyclopentyl-(3-bromo-2-thienyl)methanol (8.0 g, crude) as a colorless liquid. $^1$H NMR (400 MHz, CHLOROFORM-d) δ=7.27 (s, 1H), 6.92 (d, J=5.3 Hz, 1H), 4.86 (d, J=8.5 Hz, 1H), 2.40-2.30 (m, 1H), 2.14 (br s, 1H), 1.96-1.85 (m, 1H), 1.76-1.65 (m, 2H), 1.60-1.49 (m, 4H).

Example 74 B: 1-[cyclopentyl-(3-bromo-2-thienyl)methyl]imidazole 1,1-Carbonyldiimidazole (6.21 g, 38.30 mmol) was added into a solution of cyclopentyl-(3-bromo-2-thienyl)methanol (2.00 g, 7.66 mmol) in acetonitrile (40.00 mL). The reaction solution was reacted at 70° C. for 16 h, then added with 20 mL of water, and extracted with ethyl acetate (10 mL×3). The combined organic phase was washed with 30 mL of saturated brine, dried over anhydrous sodium sulfate, filtered under suction and evaporated under reduced pressure. The crude product was purified by column chromatography to give the compound of 1-[cyclopentyl-(3-bromo-2-thienyl)methyl]imidazole (1.6 g, 5.14 mmol, yield of 67.10) as a colorless oil. $^1$H NMR (400 MHz, CHLOROFORM-d) δ=7.66 (s, 1H), 7.29 (d, J=5.5 Hz, 1H), 7.07-7.02 (m, 2H), 6.92 (d, J=5.3 Hz, 1H), 5.23 (d, J=11.3 Hz, 1H), 2.78 (quind, J=7.6, 11.3 Hz, 1H), 1.80-1.73 (m, 1H), 1.65-1.55 (m, 3H), 1.33-1.20 (m, 2H).

Preparation of the Title Compounds (Examples 74 to 75): 8-cyclopentyl-8H-thieno[3,4]pyrrolo[1,5-a]imidazole

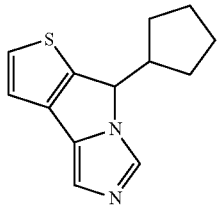 [SMILES: c1cc2c(s1)C(C1CCCC1)n1cncc1-2]

Under protection of nitrogen gas, 1-[cyclopentyl-(3-bromo-2-thienyl)methyl]imidazole (800.00 mg, 2.57 mmol), palladium acetate (57.71 mg, 257.00 µmol), tricyclohexylphosphine (144.16 mg, 518.00 µmol), potassium carbonate (1.07 mg, 7.71 mmol), o-xylene (15.00 mL) were successively added in a reaction flask, followed by reaction at 140° C. for 16 h. After completion of reaction, the reaction solution was filtered under suction, and washed with ethyl acetate (5 mL). The organic phase was added with 30 mL of water, and extracted with ethyl acetate (20 mL×3). The further organic phase combined was washed with 20 mL of saturated brine, dried over anhydrous sodium sulfate, filtered under suction and evaporated under reduced pressure. The crude product was purified by column chromatography to give 8-cyclopentyl-8H-thieno[3,4]pyrrolo[1,5-a]imidazole (300.00 mg, 1.30 mmol, yield of 50.68%). The racemate was subjected to chiral separation (column: Lux Cellulose-2 150×4.6 mm I.D., 3 µm; mobile phase: A: $CO_2$ B: Methanol (0.05% DEA); gradient: from 5% to 40% of B in 5.5 min and hold 40% for 3 min, then 5% of B for 1.5 min; flow rate: 2.5 mL/min; column temperature: 40° C.), to finally give Example 74 (140.00 mg, yield of 46.67%, RT=6.638 min, ee=98.8%) and Example 75 (140.00 mg, yield of 46.67%, RT=7.982 min, ee=98.3%).

Example 74: $^1$H NMR (400 MHz, METHANOL-d4) δ=7.86 (s, 1H), 7.50 (d, J=5.0 Hz, 1H), 7.20 (d, J=5.0 Hz, 1H), 6.86 (s, 1H), 5.36 (d, J=6.5 Hz, 1H), 2.61-2.44 (m, 1H), 2.06-1.96 (m, 1H), 1.78-1.47 (m, 6H), 1.27-1.16 (m, 1H).

Example 75: $^1$H NMR (400 MHz, METHANOL-d4) δ=7.87 (s, 1H), 7.50 (d, J=5.0 Hz, 1H), 7.20 (d, J=5.0 Hz, 1H), 6.87 (s, 1H), 5.36 (d, J=6.5 Hz, 1H), 2.57-2.45 (m, 1H), 2.05-1.95 (m, 1H), 1.78-1.63 (m, 3H), 1.61-1.45 (m, 3H), 1.27-1.15 (m, 1H).

Examples 76 to 77: 8-(6,6-difluoro-3-bicyclo[3.1.0]cyclohexyl)-8H-thieno[3,4]pyrrolo[1,5-a]imidazole (cis)

Example 76A: (3-bromothiophen-2-yl)(6,6-difluoro-bicyclo[3.1.0]cyclohexan-3-yl)methanol (cis)

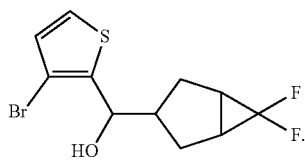 [SMILES: OC(c1sccc1Br)C1CC2C(C1)C2(F)F]

A solution of diisopropylamine (163.85 mg, 1.62 mmol) in diethyl ether (5.00 mL) was cooled down to −78° C., and n-butyllithium (2.5 M, 0.594 mL) was slowly added thereto. After 1 hour, 3-bromothiophene (220.10 mg, 1.35 mmol) was added and stirred at −78° C. for 1 h. 6,6-Difluorobicyclo[3.1.0]cyclohexane-3-carboxaldehyde (197.28 mg, 1.35 mmol) (obtained by reduction of methyl cis-6,6-difluorobicyclo[3.1.0]cyclohexane-3-formate) was then added, and the reaction solution was stirred at −78° C. for 1 h. The reaction was quenched by addition of ammonium chloride solution (5 mL), followed by dilution with water (10 mL) and extraction with ethyl acetate (10 mL×3). The organic phase was washed with brine (10 mL×3), dried over anhydrous sodium sulfate, filtered and evaporated. The residue was purified by column chromatography to give the title compound (colorless oil, 180.00 mg, yield of 43.13%). $^1$H NMR (400 MHz, CHLOROFORM-d) δ=7.19 (br d, J=4.5 Hz, 1H), 6.84 (br d, J=5.3 Hz, 1H), 4.79 (br d, J=8.8 Hz, 1H), 2.42-2.13 (m, 2H), 2.04-1.90 (m, 2H), 1.88-1.76 (m, 2H), 1.55-1.38 (m, 1H).

Example 76B: 1-[(3-bromo-2-thienyl)-(6,6-difluoro-3-bicyclo[3.1.0]cyclohexyl)methyl]imidazole (cis)

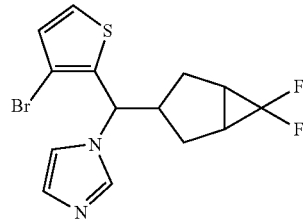 [SMILES: FC1(F)C2CC(C(c3sccc3Br)n3ccnc3)CC21]

CDI (472.02 mg, 2.91 mmol) was added into a solution of (3-bromothiophen-2-yl) (6,6-difluorobicyclo[3.1.0]cyclohexan-3-yl)methanol (cis) (180 mg, 582.20 µmol) in acetonitrile (5.00 mL), and the reaction solution was stirred at 80° C. for 16 h. The reaction solution was dispersed in ethyl acetate (30 mL) and water (30 mL). The organic phase was separated, washed with brine (30 mL×3), dried over anhydrous sodium sulfate, filtered and evaporated. The residue was purified by column chromatography to give the title compound (colorless oil, 160.00 mg, yield of 76.50%). MS-ESI (m/z): 359/361 (M+H)$^+$(Acq Method: 5-95 AB_1.5 min; Rt: 0.690 min). $^1$H NMR (400 MHz, CHLOROFORM-d) δ=7.59 (s, 1H), 7.24 (d, J=5.3 Hz, 1H), 7.19 (s, 1H), 6.97 (s, 1H), 6.86 (d, J=5.3 Hz, 1H), 5.26 (d, J=11.5 Hz, 1H), 2.11 (br d, J=7.3 Hz, 1H), 2.01-1.96 (m, 2H), 1.70 (br d, J=4.8 Hz, 2H), 1.54-1.44 (m, 2H).

Preparation of the Title Compounds (Examples 76 to 77)

8-(6,6-difluoro-3-bicyclo[3.1.0]cyclohexyl)-8H-thieno[3,4]pyrrolo[1,5-a]imidazole (cis)

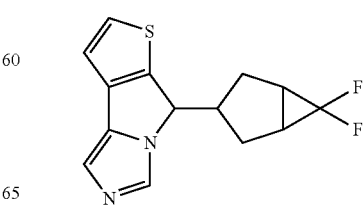

Under protection of nitrogen gas, a mixture solution of 1-[(3-bromo-2-thienyl)-(6,6-difluoro-3-bicyclo[3.1.0]cyclohexyl)methyl]imidazole (140.00 mg, 389.72 μmol), palladium acetate (8.75 mg, 38.97 μmol), tricyclohexylphosphine (21.86 mg, 77.94 μmol), potassium carbonate (107.73 mg, 779.44 μmol) in o-xylene (5.00 mL) was stirred at 120° C. for 48 h. The reaction solution was dispersed in ethyl acetate (30 mL) and water (30 mL). The organic phase was separated, washed with brine (30 mL×3), dried over anhydrous sodium sulfate, filtered and evaporated. The residue was purified by column chromatography to give the title compound (yellow oil, 80.00 mg, yield of 59.78%). MS-ESI (m/z): 279 (M+H)$^+$(Acq Method: 5-95 AB_1.5 min; Rt: 0.851 min). The racemate (80.00 mg, 287.44 μmol) was subjected to chiral separation (column: Chiralpak AD-3 100×4.6 mm I.D., 3 μm; mobile phase: A: carbon dioxide B: ethanol (0.05% diethylamine)), to give Example 76 (21.00 mg, yield of 35.79%, retention time: 3.429 min) and Example 77 (18.00 mg, yield of 31.92%, retention time: 4.489 min).

Example 76: $^1$H NMR (400 MHz, METHANOL-d4) δ=9.22 (s, 1H), 7.74 (d, J=5.3 Hz, 1H), 7.54 (s, 1H), 7.38 (d, J=5.0 Hz, 1H), 5.77 (d, J=6.3 Hz, 1H), 3.26-3.13 (m, 1H), 2.43-2.32 (m, 1H), 2.29-2.17 (m, 3H), 1.75-1.65 (m, 1H), 1.59 (br t, J=11.2 Hz, 1H).

Example 77: $^1$H NMR (400 MHz, METHANOL-d4) δ=9.22 (s, 1H), 7.74 (d, J=5.0 Hz, 1H), 7.54 (s, 1H), 7.38 (d, J=5.0 Hz, 1H), 5.77 (d, J=6.3 Hz, 1H), 3.27-3.10 (m, 1H), 2.44-2.32 (m, 1H), 2.30-2.16 (m, 3H), 1.76-1.66 (m, 1H), 1.59 (br t, J=11.2 Hz, 1H).

Examples 78 to 81: 8-(2,2-dimethyltetrahydropyran-4-yl)-8H-thieno[3,4]pyrrolo[1,5-a]imidazole Example 78A: (2,2-dimethytetrahydropyran-4-yl)-(3-iodo-2-thienyl)methanol

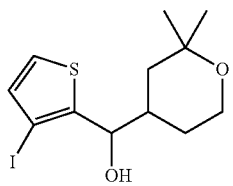 [SMILES: CC1(C)CC(C(O)c2sccc2I)CCO1]

A solution of n-butyllithium (2.5 mol/L, 3.09 mL) in n-hexane was slowly added dropwise to a solution of diisopropylamine (782.76 mg, 7.74 mmol, 1.09 mL) in diethyl ether (10.00 mL) at −78° C. over about 10 min, during which the temperature was controlled at −78° C. After completion of dropwise addition, the mixture was warmed up to 0° C. and stirred for 30 min. The system was cooled down to −78° C., and added dropwise with 3-iodothiophene (1.77 g, 8.44 mmol). After stirring for 1 h, 2,2-dimethyltetrahydropyran-4-carboxaldehyde (1.00 g, 7.03 mmol) was added dropwise thereto, and stirred at −78° C. for 2 h. TLC showed that the starting materials were completely reacted and a new product was formed. After completion of reaction, the system was added with 50 mL of saturated ammonium chloride solution, and then extracted with ethyl acetate (30 mL×3). The combined organic phase was washed with 50 mL of saturated brine, dried over anhydrous sodium sulfate, filtered under suction and evaporated under reduced pressure. The obtained crude product was purified by column chromatography to give the compound of (2,2-dimethyltetrahydropyran-4-yl)-(3-iodo-2-thienyl)methanol (1.35 g, 3.83 mmol, yield of 54.52%) as light yellow oil. $^1$H NMR (400 MHz, CHLOROFORM-d) δ=7.30 (d, J=5.3 Hz, 1H), 7.01 (d, J=5.3 Hz, 1H), 4.70 (br d, J=8.0 Hz, 1H), 3.74-3.67 (m, 1H), 3.64-3.56 (m, 1H), 2.29-2.22 (m, 1H), 2.14 (tdt, J=3.8, 8.2, 12.2 Hz, 1H), 1.98-1.91 (m, 1H), 1.39-1.28 (m, 2H), 1.26 (s, 3H), 1.22 (s, 3H).

Example 78B: 1-[(2,2-dimethyltetrahydropyran-4-yl)-(3-iodo-2-thienyl)methyl]imidazole

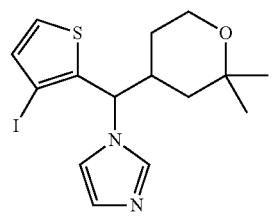 [SMILES: CC1(C)CC(C(c2sccc2I)n2ccnc2)CCO1]

1,1-Carbonyldiimidazole (3.11 g, 19.16 mmol) was added into a solution of (2,2-dimethyltetrahydropyran-4-yl)-(3-iodo-2-thienyl)methanol (1.35 g, 3.83 mmol) in acetonitrile (20.00 mL). The reaction solution was reacted at 70° C. for 4 h, and LC-MS showed that the starting materials were completely reacted and the main peak was the MS peak of the desired product. After completion of reaction, the reaction solution was added with 100 mL of water, and extracted with ethyl acetate (50 mL×3). The combined organic phase was washed with 50 mL of saturated brine, dried over anhydrous sodium sulfate, filtered under suction and evaporated under reduced pressure. The crude product was purified by column chromatography to give the compound of 1-[(2,2-dimethyltetrahydropyran-4-yl)-(3-iodo-2-thienyl)methyl]imidazole (1.50 g, 3.73 mmol, yield of 97.35%). $^1$H NMR (400 MHz, CHLOROFORM-d) δ=7.67 (d, J=4.0 Hz, 1H), 7.38-7.32 (m, 1H), 7.07 (d, J=3.8 Hz, 2H), 7.03 (dd, J=5.3, 7.3 Hz, 1H), 5.14-5.05 (m, 1H), 3.77-3.70 (m, 1H), 3.68-3.56 (m, 1H), 2.63-2.43 (m, 1H), 1.44 (br d, J=13.1 Hz, 1H), 1.34-1.25 (m, 1H), 1.20-1.17 (m, 6H), 1.16-1.10 (m, 1H).

Preparation of the Title Compounds (Examples 78 to 81): 8-(2,2-dimethyltetrahydropyran-4-yl)-8H-thieno[3,4]pyrrolo[1,5-a]imidazole

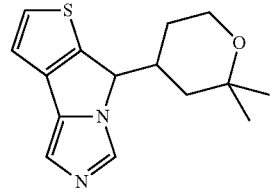 [SMILES: CC1(C)CC(C2c3sccc3-c3cncn32)CCO1]

Under protection of nitrogen gas, 1-[(2,2-dimethyltetrahydropyran-4-yl)-(3-iodo-2-thienyl)methyl]imidazole (400.00 g, 994.31 mmol), palladium acetate (22.32 mg, 99.43 μmol), tricyclohexylphosphine (55.77 mg, 198.86 μmol), potassium carbonate (417.27 mg, 2.98 mmol) and pivalic acid (30.46 mg, 298.29 μmol), N-methylpyrrolidone (4.00 mL) were successively added in a reaction flask, and then reacted at 180° C. for 10 min. TLC showed that the starting materials were completely reacted and a new product was formed. After completion of reaction, the reaction mixture was filtered under suction, and washed with ethyl acetate (5 mL). The organic phase was added with 50 mL of water and extracted with ethyl acetate (30 mL×3). The further organic phase combined was washed with 50 mL of saturated brine, dried over anhydrous sodium sulfate, filtered under suction and evaporated under reduced pressure. The crude product was purified by column chromatography to give a racemate (400.00 mg). The racemate was purified by chiral separation (column: Chiralcel OJ-3 150×4.6 mm I.D., 3 um; mobile phase: A: $CO_2$ B: ethanol (0.05% DEA); gradient: from 5% to 40% of B in 5 min and hold 40% for 2.5 min, then 5% of B for 2.5 min; flow rate: 2.5 mL/min; column temperature: 35° C.) and preparative chromatography, to finally give Example 78 (15.00 mg, 83.25 μmol, RT=2.527 min, ee=94.88%), Example 79 (10.00 mg, 36.45 μmol, RT=2.775 min, ee=75.82%), Example 80 (5.00 mg, 17.87 μmol, RT=2.880 min, ee=97.02%) and Example 81 (15.00 mg, 38.62 μmol, RT=2.918 min, ee=90.00%).

Example 78: $^1$H NMR (400 MHz, METHANOL-d4) δ=9.25 (s, 1H), 7.73 (d, J=5.0 Hz, 1H), 7.53 (d, J=0.8 Hz, 1H), 7.39 (d, J=5.0 Hz, 1H), 5.74 (d, J=4.5 Hz, 1H), 3.84-3.76 (m, 2H), 2.85-2.72 (m, 1H), 1.81-1.71 (m, 1H), 1.54-1.41 (m, 1H), 1.22 (s, 3H), 1.21-1.18 (m, 1H), 1.11 (s, 3H), 0.97 (t, J=12.8 Hz, 1H).

Example 79: $^1$H NMR (400 MHz, METHANOL-d4) δ=7.94 (s, 1H), 7.54 (d, J=5.0 Hz, 1H), 7.23 (d, J=5.0 Hz, 1H), 6.90 (s, 1H), 5.30 (br d, J=3.8 Hz, 1H), 3.73-3.58 (m, 2H), 2.70-2.57 (m, 1H), 1.66 (br d, J=12.5 Hz, 1H), 1.36-1.29 (m, 1H), 1.27 (s, 3H), 1.22 (s, 3H), 1.17 (br s, 1H), 1.10-0.97 (m, 1H).

Example 80: $^1$H NMR (400 MHz, METHANOL-d4) δ=7.89 (s, 1H), 7.54 (d, J=5.0 Hz, 1H), 7.23 (d, J=5.0 Hz, 1H), 6.89 (s, 1H), 5.32 (d, J=4.3 Hz, 1H), 3.76 (dd, J=1.8, 8.8 Hz, 2H), 2.67-2.54 (m, 1H), 1.76-1.68 (m, 1H), 1.44 (tt, J=8.8, 12.5 Hz, 1H), 1.20 (s, 3H), 1.17-1.11 (m, 1H), 1.09 (s, 3H), 0.94 (t, J=12.8 Hz, 1H).

Example 81: $^1$H NMR (400 MHz, METHANOL-d4) δ=7.91 (s, 1H), 7.53 (d, J=5.0 Hz, 1H), 7.22 (d, J=5.0 Hz, 1H), 6.89 (s, 1H), 5.28 (br d, J=3.8 Hz, 1H), 3.72-3.59 (m, 2H), 2.69-2.53 (m, 1H), 1.65 (br d, J=12.8 Hz, 1H), 1.34-1.29 (m, 1H), 1.27 (s, 3H), 1.21 (s, 3H), 1.18 (br d, J-12.0 Hz, 1H), 1.10-1.00 (m, 1H).

Examples 82 to 85: [2-(8H-thieno[3,4]pyrrolo[1,5-a]imidazol-8-yl)cyclohexanol Example 82A: ethyl 2-hydroxycyclohexanecarboxylate

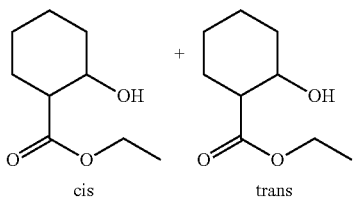

Sodium borohydride (889.00 mg, 23.50 mmol) was slowly added to a solution of ethyl 2-cyclohexanonecarboxylate (10.00 g, 58.75 mmol, 8.43 mL) in ethanol (100.00 mL) at 0° C., and the reaction solution was stirred at 0° C. for 4 h. The reaction was monitored by TLC. After completion, the reaction system was added with 50 mL of water at room temperature to quench the reaction, with extracted with ethyl acetate (30 mL×3). The organic phase was combined, washed with 50 mL of saturated brine, dried over anhydrous sodium sulfate, filtered under suction and evaporated under reduced pressure. The obtained crude compound was purified by column chromatography to give a colorless liquid, ethyl cis-2-hydroxycyclohexanecarboxylate (4.80 g, 27.87 mmol, yield of 47.44%). $^1$H NMR (400 MHz, CHLOROFORM-d) δ=4.19-4.08 (m, 3H), 3.20 (br s, 1H), 2.50-2.42 (m, 1H), 1.94-1.81 (m, 2H), 1.75-1.62 (m, 3H), 1.51-1.37 (m, 2H), 1.26 (t, J=7.2 Hz, 4H). ethyl trans-2-hydroxycyclohexanecarboxylate (2.60 g, 15.10 mmol, yield of 25.70%). $^1$H NMR (400 MHz, CHLOROFORM-d) δ=4.17 (q, J=7.3 Hz, 2H), 3.76 (dt, J=4.5, 10.2 Hz, 1H), 2.85 (br s, 1H), 2.24 (ddd, J=3.8, 9.8, 12.3 Hz, 1H), 2.08-2.05 (m, 1H), 2.04-1.99 (m, 1H), 1.82-1.68 (m, 2H), 1.40-1.31 (m, 1H), 1.29-1.22 (m, 6H).

Example 82B: ethyl trans-2-[tert-butyl(dimethyl)silyl]oxycyclohexanecarboxylate

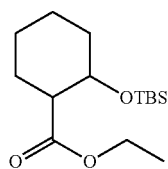 [SMILES: CCOC(=O)C1CCCCC1O[Si](C)(C)C(C)(C)C]

t-Butyldimethylsilyl trifluoromethanesulfonate (15.10 g, 57.13 mmol, 13.13 mL) and 2,6-dimethylpyridine (7.65 g, 71.42 mmol, 8.32 mL) were slowly added dropwise into a solution of ethyl trans-2-hydroxycyclohexanecarboxylate (8.20 g, 47.61 mmol) in dichloromethane (80.00 mL). The reaction solution was stirred at 25° C. for 2 h. The reaction system was added with 200 mL of water at room temperature to quench the reaction, and extracted with ethyl acetate (50 mL×3). The organic phase was combined, washed with 50 mL of saturated brine, dried over anhydrous sodium sulfate, filtered under suction and evaporated under reduced pressure. The obtained crude compound was purified by column chromatography to give ethyl trans-2-[tert-butyl(dimethyl)silyl]oxycyclohexanecarboxylate (12.00 g, 41.89 mmol, yield of 87.98%) as a colorless liquid. $^1$H NMR (400 MHz, CHLOROFORM-d) δ=4.13-4.04 (m, 2H), 3.79 (dt, J=4.5, 9.8 Hz, 1H), 2.36-2.25 (m, 1H), 1.91-1.84 (m, 2H), 1.79-1.63 (m, 3H), 1.51-1.33 (m, 2H), 1.26-1.22 (m, 3H), 1.21-1.12 (m, 1H), 0.84 (s, 9H), 0.04 (s, 3H), 0.01 (s, 3H).

Example 82C: {2-[tert-butyl(dimethyl)silyl]oxycyclohexyl}carboxaldehyde

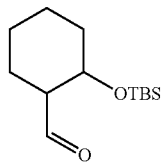 [SMILES: CC(C)(C)[Si](C)(C)OC1CCCCC1C=O]

A solution of diisobutylaluminum hydride in 1M toluene (1 mol/L, 62.84 mL) was slowly added dropwise into a solution of ethyl 2-[tert-butyl(dimethyl)silyl]oxycyclohexanecarboxylate (12.00 g, 41.89 mmol) in dichloromethane (80.00 mL). The reaction solution was stirred at −78° C. for 2 h. The reaction system was added with 50 mL of saturated sodium potassium tartrate solution at room temperature to quench the reaction, and extracted with dichloromethane (30 mL×3). The organic phase was combined, washed with 50 mL of saturated brine, dried over anhydrous sodium sulfate, filtered under suction and evaporated under reduced pressure. The obtained crude compound was purified by column chromatography to give {2-[tert-butyl(dimethyl)silyl]oxycyclohexyl}carboxaldehyde (6.00 g, 24.75 mmol, yield of 59.08%) as a colorless liquid. ¹H NMR (400 MHz, CHLOROFORM-d) δ=9.75 (d, J=2.8 Hz, 1H), 3.86-3.81 (m, 1H), 2.38-2.31 (m, 1H), 1.92 (br d, J=2.5 Hz, 1H), 1.79-1.69 (m, 5H), 1.40-1.33 (m, 2H), 0.84 (s, 9H), 0.06 (s, 3H), 0.04 (s, 3H).

Example 82D: {2-[tert-butyl(dimethyl)silyl]oxycyclohexyl}-(3-bromo-2-thienyl)methanol

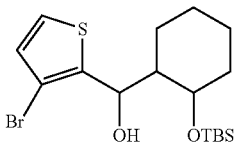 [SMILES: CC(C)(C)[Si](C)(C)OC1CCCCC1C(O)c1sccc1Br]

A solution of n-butyllithium (2.5 mol/L, 10.89 mL) in n-hexane was slowly added dropwise to a solution of diisopropylamine (2.75 g, 27.23 mmol, 3.83 mL) in diethyl ether (40.00 mL) at −78° C. over about 10 min, during which the temperature was controlled at −78° C. After completion of dropwise addition, the mixture was warmed up to 0° C. and stirred for 30 min. The system was cooled to −78° C., and added dropwise with 3-bromothiophene (4.84 g, 29.70 mmol, 2.78 mL). After stirring for 1 h, {2-[tert-butyl(dimethyl)silyl]oxycyclohexyl}carboxaldehyde (6.00 g, 24.75 mmol) was added dropwise thereto, and stirred at −78° C. for 2 h. After completion of reaction, the reaction system was added with 50 mL of saturated ammonium chloride solution, and then extracted with ethyl acetate (30 mL×3). The organic phases were combined, washed with 50 mL of saturated brine, dried over anhydrous sodium sulfate, filtered under suction and evaporated under reduced pressure. The crude compound was purified by column chromatography to give the compound of {2-[tert-butyl(dimethyl)silyl]oxycyclohexyl}-(3-bromo-2-thienyl)methanol (1.5 g, 3.70 mmol, yield of 14.95%) as a colorless oil. ¹H NMR (400 MHz, CHLOROFORM-d) δ=7.23 (d, J=5.3 Hz, 1H), 6.93 (d, J=5.3 Hz, 1H), 5.49 (dd, J=2.8, 5.3 Hz, 1H), 3.78 (dt, J=4.5, 10.0 Hz, 1H), 2.90 (d, J=5.3 Hz, 1H), 2.01-1.92 (m, 1H), 1.88-1.79 (m, 1H), 1.74-1.60 (m, 4H), 1.38-1.33 (m, 1H), 1.13-1.04 (m, 1H), 0.94 (s, 9H), 0.15 (s, 3H), 0.13 (s, 3H).

Example 82E: tert-butyl-{([2-imidazolyl(3-bromothienyl)methyl]cyclohexyl}-dimethylsilane

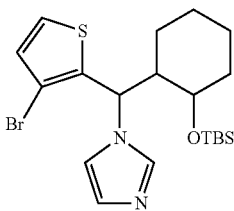 [SMILES: CC(C)(C)[Si](C)(C)OC1CCCCC1C(c1sccc1Br)n1ccnc1]

1,1-Carbonyldiimidazole (3.00 g, 18.50 mmol) was added into a solution of {2-[tert-butyl(dimethyl)silyl]oxycyclohexyl}-(3-bromo-2-thienyl)methanol (1.50 g, 3.70 mmol) in acetonitrile (30.00 mL). The reaction solution was reacted at 70° C. for 3 h. After completion of reaction, the reaction solution was added with 50 mL of water, and extracted with ethyl acetate (30 mL×3). The combined organic phase was washed with 50 mL of saturated brine, dried over anhydrous sodium sulfate, filtered under suction, and evaporated under reduced pressure. The crude product was purified by column chromatography to give the compound of tert-butyl-{[2-imidazolyl(3-bromothienyl)methyl]cyclohexyl}-dimethylsilane (1.20 g, 2.63 mmol, yield of 71.20%) as a colorless oil. ¹H NMR (400 MHz, CHLOROFORM-d) δ=7.58 (s, 1H), 7.30 (d, J=5.3 Hz, 1H), 7.03 (s, 1H), 6.98-6.94 (m, 2H), 6.11 (d, J=5.8 Hz, 1H), 3.47 (dt, J=3.8, 7.8 Hz, 1H), 2.21-2.12 (m, 1H), 1.94-1.84 (m, 1H), 1.76-1.68 (m, 1H), 1.61-1.52 (m, 1H), 1.45-1.28 (m, 3H), 0.93 (s, 9H), 0.92-0.83 (m, 2H), 0.10 (s, 3H), 0.05 (s, 3H).

Example 82F: tert-butyl-methyl-[2-(8H-thieno[3,4]pyrrolo[1,5-a]imidazol-8-yl)cyclohexylsilane

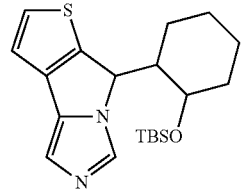 [SMILES: CC(C)(C)[Si](C)(C)OC1CCCCC1C1c2sccc2-c2cncn21]

Under protection of nitrogen gas, t-butyl-{[2-imidazolyl(3-bromothienyl)methyl]cyclohexyl}-dimethylsilane (1.20 g, 2.63 mmol), palladium acetate (59.05 mg, 263.00 µmol), tricyclohexylphosphine (147.51 mg, 526.00 mmol), potassium carbonate (1726.98 mg, 5.26 mmol), o-xylene (30.00 mL) were successively added in a reaction flask, followed by reaction at 140° C. for 16 h. After completion of reaction, the reaction solution was filtered under suction, and washed with ethyl acetate (30 mL). The organic phase was added with 50 mL of water, and extracted with ethyl acetate (30 mL×3). The further combined organic phase was washed with 50 mL of saturated brine, dried over anhydrous sodium sulfate, filtered under suction, and evaporated under reduced pressure. The crude product was purified by column chromatography to give isomer I (light yellow oil, 500.00 mg, 1.33 mmol, yield of 50.75%) and isomer II (light yellow oil, 160.00 mg, 427.00 mmol, yield of 16.24%).

Isomer I: ¹H NMR (400 MHz, CHLOROFORM-d) δ=7.62 (s, 1H), 7.35 (d, J=5.0 Hz, 1H), 7.11 (d, J=5.0 Hz, 1H), 6.94 (s, 1H), 5.78 (s, 1H), 3.81 (dt, J=4.3, 10.3 Hz, 1H), 2.14-2.06 (m, 1H), 1.96-1.88 (m, 1H), 1.52-1.32 (m, 3H)), 1.19-1.00 (m, 3H), 0.93 (s, 9H), 0.42 (dq, J=3.6, 12.8 Hz, 1H), 0.19 (d, J=2.5 Hz, 6H).

Isomer II: ¹H NMR (400 MHz, CHLOROFORM-d) δ=7.65 (s, 1H), 7.33 (d, J=5.0 Hz, 1H), 7.15 (d, J=4.8 Hz, 1H), 6.94 (s, 1H), 5.72 (d, J=3.5 Hz, 1H), 3.76 (dt, J=4.5, 10.2 Hz, 1H), 2.18-2.06 (m, 2H), 1.75-1.67 (m, 1H), 1.51-1.33 (m, 5H), 0.93 (s, 8H), 0.93-0.92 (m, 1H), 0.44 (dq, J=3.4, 12.9 Hz, 1H), 0.21 (s, 3H), 0.19 (s, 3H).

Preparation of the Title Compounds (Examples 82 to 83): [2-(8H-thieno[3,4]pyrrolo[1,5-a]imidazol-8-yl)cyclohexanol

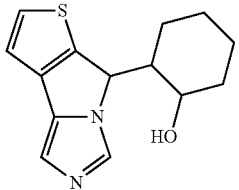 [SMILES: OC1CCCCC1C1c2sccc2-c2cncn21]

p-Toluenesulfonic acid monohydrate (758.98 mg, 3.99 mmol) was added into a solution of tert-butyl-methyl-[2-(8H-thieno[3,4]pyrrolo[1,5-a]imidazol-8-yl)cyclohexylsilane (Isomer I of Example 82F, 500 mg, 1.33 mmol) in 1,2-dichloroethane (5.00 mL). The reaction solution was reacted at 85° C. for 16 h, and the reaction was monitored by LCMS. After completion of reaction, the reaction solution was added with 15 mL of saturated sodium hydrogen carbonate solution, and extracted with ethyl acetate (10 mL×3). The combined organic phase was washed with 15 mL of saturated brine, dried over anhydrous sodium sulfate, filtered under suction, and evaporated under reduced pressure. The crude product was purified by column chromatography to give [2-(8H-thieno[3,4]pyrrolo[1,5-a]imidazol-8-yl)cyclohexanol (300 mg) as a light yellow liquid. The racemate was separated by chiral separation ("OD_3_EtOH_DEA_5_40_25 ML Vial: 1:F, 2 Channel Name: PDA Ch1 220 nm@4.8 nm—Compens. Injection Volume: 3.00 µL Proc. Chnl. Descr.: PDA Ch1 220 nm@4.8 nm—Compens. Run Time: 10.0 min"), and purified by acidic preparative chromatography, to finally give Example 82 (trifluoroacetate, 80 mg, 213.69 µmol, RT=3.24 min, ee=99%) and Example 83 (trifluoroacetate, 80 mg, 213.69 µmol, RT=3.745 min, ee=99.3%).

Example 82: $^1$H NMR (400 MHz, METHANOL-d4) δ=9.06 (s, 1H), 7.72 (d, J=5.0 Hz, 1H), 7.48 (s, 1H), 7.37 (d, J=5.0 Hz, 1H), 5.97 (d, J=2.3 Hz, 1H), 3.40 (dt, J=4.1, 10.4 Hz, 1H), 2.25 (tdd, J=3.0, 10.1, 12.8 Hz, 1H), 2.00-1.93 (m, 1H), 1.78-1.67 (m, 2H), 1.57-1.50 (m, 1H), 1.41-1.21 (m, 3H), 0.99-0.86 (m, 1H).

Example 83: $^1$H NMR (400 MHz, METHANOL-d4) δ=9.05 (s, 1H), 7.72 (d, J=5.5 Hz, 1H), 7.48 (d, J=1.0 Hz, 1H), 7.37 (d, J=5.0 Hz, 1H), 5.97 (d, J=2.8 Hz, 1H), 3.51-3.36 (m, 1H), 2.30-2.19 (m, 1H), 1.97 (br d, J=12.0 Hz, 1H), 1.79-1.66 (m, 2H), 1.54 (br d, J=13.3 Hz, 1H), 1.40-1.23 (m, 3H), 1.00-0.85 (m, 1H).

Preparation of the Title Compounds (Examples 84 to 85): [2-(8H-thieno[3,4]pyrrolo[1,5-a]imidazol-8-yl)cyclohexanol

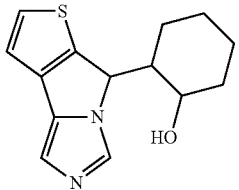 [SMILES: OC1CCCCC1C1c2sccc2-c2cncn21]

p-Toluenesulfonic acid monohydrate (274.20 mg, 1.44 mmol) was added into a solution of tert-butyl-methyl-[2-(8H-thieno[3,4]pyrrolo[1,5-a]imidazol-8-yl)cyclohexylsilane (Isomer II of Example 82F, 180 mg, 480.50 µmol) in 1,2-dichloroethane (2.00 mL). The reaction solution was reacted at 85° C. for 16 h. After completion of reaction, the reaction solution was added with 15 mL of saturated sodium hydrogen carbonate solution, and extracted with ethyl acetate (10 mL×3). The combined organic phase was washed with 15 mL of saturated brine, dried over anhydrous sodium sulfate, filtered under suction, and evaporated under reduced pressure. The crude product was purified by column chromatography to give [2-(8H-thieno[3,4]pyrrolo[1,5-a]imidazol-8-yl)cyclohexanol (100 mg). The racemate was separated by chiral separation ("OD_3_EtOH_DEA_5_40_25 ML Vial: 1:F, 2 Channel Name: PDA Ch1 220 nm@4.8 nm—Compens. Injection Volume: 3.00 µL Proc. Chnl. Descr.: PDA Ch1 220 nm@4.8 nm—Compens. Run Time: 10.0 min"), and purified by acidic preparative chromatography, to give Example 84 (trifluoroacetate, 15 mg, 40.07 µmol, RT=2.667 min, ee=97%) and Example 85 (trifluoroacetate, 15 mg, 40.07 µmol, RT=3.184 min, ee=94%).

Example 84: $^1$H NMR (400 MHz, METHANOL-d4) δ=9.17 (s, 1H), 7.72 (d, J=5.0 Hz, 1H), 7.52 (s, 1H), 7.39 (d, J=5.0 Hz, 1H), 6.19 (d, J=4.0 Hz, 1H), 3.72 (dt, J=4.4, 10.5 Hz, 1H), 2.41-2.29 (m, 1H), 2.17-2.07 (m, 1H), 1.83-1.72 (m, 1H), 1.59-1.51 (m, 1H), 1.50-1.37 (m, 1H), 1.29-1.09 (m, 2H), 0.97-0.88 (m, 1H), 0.51 (dq, J=3.6, 12.7 Hz, 1H).

Example 85: $^1$H NMR (400 MHz, METHANOL-d4) δ=9.17 (s, 1H), 7.72 (d, J=5.0 Hz, 1H), 7.52 (s, 1H), 7.39 (d, J=5.0 Hz, 1H), 6.19 (d, J=4.0 Hz, 1H), 3.72 (dt, J=4.3, 10.5 Hz, 1H), 2.43-2.30 (m, 1H), 2.17-2.07 (m, 1H), 1.80-1.71 (m, 1H), 1.59-1.51 (m, 1H), 1.51-1.39 (m, 1H), 1.30-1.09 (m, 2H), 0.93 (br dd, J=2.8, 13.3 Hz, 1H), 0.58-0.44 (m, 1H).

Examples 86 to 87: 8-(1-phenylpiperidin-4-yl)-8H-thieno[3',2':3,4]pyrrolo[1,2-c]imidazole Example 86A: ethyl-1-phenylpiperidine-4-carboxylate

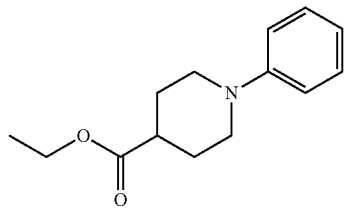 [SMILES: CCOC(=O)C1CCN(c2ccccc2)CC1]

Iodobenzene (1.95 g, 9.54 mmol, 1.06 mL), palladium tri-tert-butylphosphine (325.03 mg, 636.00 µL) and potassium phosphate ((2.70 g, 12.72 mmol) were added into a solution of ethyl-piperidine-4-carboxylate (1.00 g, 6.36 mmol, 980.39 µL) in DME (30.00 mL) at 23° C. The reaction solution was heated to 100° C. and stirred for 16 h. The reaction solution was filtered, and the filtrate was diluted with water (30 mL) and extracted with ethyl acetate (20 mL×3). The combined organic layers were washed with brine (30 mL×1), dried over anhydrous sodium sulfate, filtered, and evaporated under reduced pressure. The obtained residue was purified by column chromatography to give the title compound (yellow oil, 910.00 mg, yield of 61.33%). ¹H NMR (400 MHz, CHLOROFORM-d) δ=7.28-7.24 (m, 2H), 6.94 (d, J=8.0 Hz, 2H), 6.85 (t, J=7.3 Hz, 1H), 4.16 (q, J=7.0 Hz, 2H), 3.65 (td, J=3.3, 12.7 Hz, 2H), 2.79 (dt, J=2.5, 11.9 Hz, 2H), 2.43 (tt, J=4.0, 11.2 Hz, 1H), 2.03 (br dd, J=3.1, 13.4 Hz, 2H), 1.94-1.82 (m, 2H), 1.27 (t, J=7.2 Hz, 3H).

Example 86B: 1-phenylpiperidine-4-carboxaldehyde

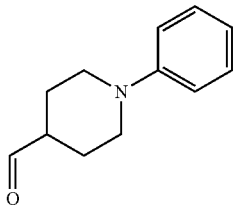 [SMILES: O=CC1CCN(c2ccccc2)CC1]

Diisobutylaluminum hydride (1 M, 28.42 mL) was slowly added into a solution of ethyl-1-phenylpiperidine-4-carboxylate (5.10 g, 21.86 mmol) in dichloromethane (200.00 mL) at −78° C., and the reaction solution was stirred at −78° C. for 1 h. The reaction was quenched with saturated ammonium chloride solution (100 mL) at −78° C., followed by extraction with dichloromethane (200.00 mL×2). The combined organic phase was washed with brine (200 mL×1), dried over anhydrous sodium sulfate, filtered, and evaporated under reduced pressure to give a residue. The residue was purified by column chromatography to give the title compound (black oil, 3.10 g, 16.38 mmol, yield of 74.93%). ¹H NMR (400 MHz, CHLOROFORM-d) δ=9.71 (s, 1H), 7.30-7.23 (m, 2H), 6.95 (d, J=8.0 Hz, 2H), 6.87 (t, J=7.4 Hz, 1H), 3.63 (td, J=3.8, 12.7 Hz, 2H), 2.92-2.82 (m, 2H), 2.46-2.35 (m, 1H), 2.07-1.99 (m, 2H), 1.88-1.74 (m, 2H).

Example 86C: (3-bromothiophen-2-yl)(1-phenylpiperidin-4-yl)methanol

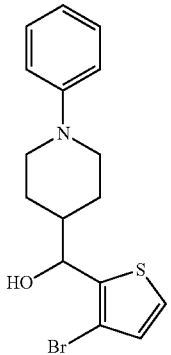

n-Butyllithium (2.5 M, 7.21 mL) was slowly added into a solution of diisopropylamine (1.99 g, 19.66 mmol, 2.76 mL) in diethyl ether (30.00 mL) at −65° C., and then tribromothiophene (2.67 g, 16.38 mmol, 1.53 mL) was injected thereto after one hour, with stirring at −65° C. for 1 h. 1-Phenylpiperidine-4-carboxaldehyde (3.10 g, 16.38 mmol) was then added, and the reaction mixture was stirred at −65° C. for another 1 h. The reaction solution was quenched with ammonium chloride (30 mL), then diluted with water (30 mL), and extracted with ethyl acetate (20 mL×3). The combined organic phase was washed with brine (20 mL×3), dried over anhydrous sodium sulfate, filtered and evaporated. The residue was purified by column chromatography to give the title compound (yellow oil, 3.00 g, 7.00 mmol, yield of 42.74%). ¹H NMR (400 MHz, CHLOROFORM-d) δ=7.30 (d, J=5.3 Hz, 1H), 7.27-7.22 (m, 2H), 6.98-6.91 (m, 3H), 6.84 (t, J=7.3 Hz, 1H), 4.89 (d, J=8.0 Hz, 1H), 3.75 (br d, J=12.3 Hz, 1H), 3.66 (br d, J=13.1 Hz, 1H), 2.75-2.61 (m, 2H), 1.94-1.81 (m, 1H), 1.61-1.47 (m, 4H), 1.27 (t, J=7.2 Hz, 1H).

Example 86D: 4-((3-bromothiophen-2-yl)(1H-imidazol-1-yl)methyl)-1-phenylpiperidine

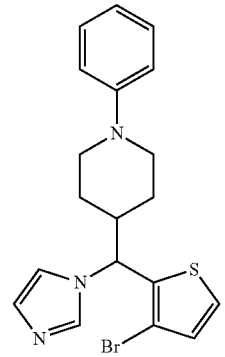 [SMILES: Brc1ccsc1C(C1CCN(c2ccccc2)CC1)n1ccnc1]

Carbonyldiimidazole (5.69 g, 35.10 mmol) was added into a solution of (3-bromothiophen-2-yl)(1-phenylpiperidin-4-yl)methanol (3.00 g, 7.02 mmol) in acetonitrile (30.00 mL). The reaction solution was refluxed with stirring at 80° C. for 16 h. After cooling down to room temperature, the reaction solution was allowed to separate with ethyl acetate (50.00 mL) and water (50.00 mL). The organic phase was washed with brine (30 mL×3), dried over anhydrous sodium sulfate, filtered and evaporated. The residue was purified by column chromatography to give the title compound (yellow oil, 1.35 g, 3.26 mmol, yield of 46.38%). ¹H NMR (400 MHz, CHLOROFORM-d) δ=7.70 (s, 1H), 7.38 (d, J=5.3 Hz, 1H), 7.33-7.27 (m, 2H), 7.13 (s, 2H), 7.00 (d, J=5.3 Hz, 1H), 6.95 (d, J=8.0 Hz, 2H), 6.89 (t, J=7.3 Hz, 1H), 5.34-5.31 (m, 1H), 3.70 (td, J=3.6, 8.8 Hz, 2H), 2.80-2.67 (m, 2H), 2.36-2.23 (m, 1H), 1.75 (br dd, J=2.4, 12.9 Hz, 1H), 1.50 (dd, J=3.8, 8.0 Hz, 2H), 1.30 (t, J=7.2 Hz, 1H).

Preparation of the Title Compounds (Examples 86 to 87): 8-(1-phenylpiperidin-4-yl)-8H-thieno[3',2':3,4]pyrrolo[1,2-c]imidazole

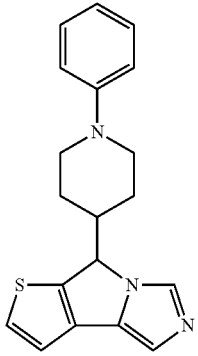 [SMILES: c1ccc(N2CCC(C3c4sccc4-c4cncn43)CC2)cc1]

Palladium acetate (72.97 mg, 325.00 μmol), tricyclohexylphosphine (182.16 mg, 650.00 μmol) and potassium carbonate (898.37 mg, 6.50 mmol) were added into a solution of 4-((3-bromothiophen-2-yl)(1H-imidazol-1-yl)methyl)-1-phenylpiperidine (1.35 g, 3.25 mmol) in o-xylene (20.00 mL), and then the reaction solution was purged with nitrogen gas three times. The mixture was refluxed with stirring at 140° C. for 16 h. After cooling down to room temperature, the reaction solution was filtered, and the filtrate was washed with brine (30 mL×3). The aqueous phase was extracted with ethyl acetate (20 mL×3). The combined organic phase was dried over anhydrous sodium sulfate, filtered and evaporated under reduced pressure to give a residue. The residue was purified by column chromatography to give the title compound (450.00 mg, 1.36 mmol, yield of 41.85%). $^1$H NMR (400 MHz, CHLOROFORM-d) δ=7.70 (s, 1H), 7.37 (d, J=5.0 Hz, 1H), 7.27-7.22 (m, 2H), 7.16 (d, J=5.0 Hz, 1H), 6.96 (s, 1H), 6.91 (d, J=8.0 Hz, 2H), 6.85 (t, J=7.3 Hz, 1H), 5.16 (d, J=4.5 Hz, 1H), 3.82-3.75 (m, 1H), 3.67 (br d, J=12.3 Hz, 1H), 2.78-2.61 (m, 2H), 2.17-2.08 (m, 1H), 1.54 (td, J=2.8, 12.7 Hz, 1H), 1.48-1.30 (m, 2H), 1.29-1.25 (m, 1H).

The racemate (450.00 mg, 1.36 mmol) was subjected to chiral separation (column: Chiralcel OD-3 100×4.6 mm I.D., 3 μm; mobile phase: A: carbon dioxide B: ethanol (0.05% diethylamine); gradient: 40% B in A; flow rate: 2.8 mL/min; column temperature: 40° C.), to give Example 86 (110.00 mg, 340.53 μmol, yield of 25.04%, retention time: 1.932 min) and Example 87 (110.00 mg, 337.45 μmol, yield of 24.81%, retention time: 3.479 min).

Example 86: $^1$H NMR (400 MHz, METHANOL-d$_4$) δ=9.25 (s, 1H), 7.80 (d, J=5.3 Hz, 1H), 7.60 (d, J=0.8 Hz, 1H), 7.52-7.42 (m, 5H), 7.37-7.32 (m, 1H), 5.93 (d, J=3.8 Hz, 1H), 3.87-3.80 (m, 1H), 3.69 (br d, J=12.5 Hz, 1H), 3.48 (dt, J=2.9, 12.5 Hz, 1H), 3.43-3.35 (m, 1H), 2.78 (tdd, J=4.0, 8.2, 12.1 Hz, 1H), 2.16 (br d, J=11.3 Hz, 1H), 2.02-1.90 (m, 1H), 1.70-1.54 (m, 2H).

Example 87: $^1$H NMR (WXFL10310289_001, 400 MHz, METHANOL-d$_4$) δ=7.91 (s, 1H), 7.54 (d, J=5.0 Hz, 1H), 7.25-7.18 (m, 3H), 6.95 (d, J=7.8 Hz, 2H), 6.91 (s, 1H), 6.82 (t, J=7.3 Hz, 1H), 5.39 (d, J=4.0 Hz, 1H), 3.76 (br d, J=12.3 Hz, 1H), 3.64 (br d, J=12.0 Hz, 1H), 2.79-2.61 (m, 2H), 2.35-2.25 (m, 1H), 1.95-1.88 (m, 2H), 1.65 (dq, J=4.3, 12.4 Hz, 1H), 1.40 (br d, J=12.8 Hz, 1H).

Examples 88 to 89: 8-(4-phenylcyclohexyl)-8H-thieno[3',2':3,4]pyrrolo[1,2-c]imidazole Example 88A: (4-(methoxymethylene)cyclohexyl)benzene

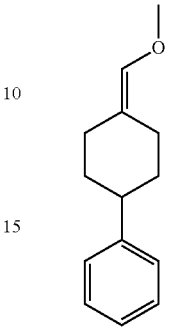

Potassium t-butoxide (1M, 23.25 mL) was slowly added dropwise to a solution of methoxymethyl triphenylphosphonium chloride (7.97 g, 23.25 mmol) in tetrahydrofuran (80.00 mL) with rapidly stirring at 23° C. The reaction solution was further stirred at 23° C. for 45 min, and then slowly added with a solution of 4-phenylcyclohexanone (3.00 g, 17.22 mmol) in tetrahydrofuran (30.00 mL). The reaction solution was further stirred for 12 h. The solvent was evaporated under reduced pressure, followed by dilution with petroleum ether (20 mL) and then washing in turn with water (100 mL) and saturated brine (100 mL). The organic phase was dried over anhydrous sodium sulfate, filtered and evaporated. The residue was purified by column chromatography to give the title compound (colorless oil, 2.05 g, yield of 58.83%). $^1$H NMR (400 MHz, CHLOROFORM-d) δ=7.24-7.13 (m, 2H), 7.12-7.01 (m, 3H), 5.71 (s, 1H), 3.46 (s, 3H), 2.87-2.74 (m, 1H), 2.52 (tt, J=3.3, 12.2 Hz, 1H), 2.13-2.01 (m, 1H), 2.01-1.90 (m, 1H), 1.87-1.78 (m, 2H), 1.74-1.60 (m, 1H), 1.42-1.33 (m, 2H), 1.31 (br d, J=4.0 Hz, 1H).

Example 88B: 4-phenylcyclohexylcarboxaldehyde

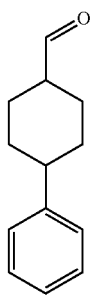

Hydrochloric acid (3 M, 15.00 mL) was slowly added to a solution of 4-phenylcyclohexylcarboxaldehyde (2.00 g, 9.89 mmol) in tetrahydrofuran (20.00 mL), and the reaction solution was stirred at 80° C. for 60 h. The reaction solution was then cooled down to 25° C., diluted with water (20.00 mL), and extracted with ethyl acetate (20 mL×3). The combined organic phase was evaporated under reduced pressure to give a residue, and the residue was further purified by column chromatography to give the title compound (yellow oil, 550 mg, yield of 29.52%). $^1$H NMR (400

MHz, CHLOROFORM-d) δ=9.73 (d, J=1.3 Hz, 1H), 7.38-7.30 (m, 3H), 7.26-7.22 (m, 2H), 2.57-2.51 (m, 1H), 2.40-2.33 (m, 1H), 2.22-2.14 (m, 2H), 2.13-2.06 (m, 2H), 1.58-1.45 (m, 4H).

Example 88C:
(3-bromothiophen-2-yl)(4-phenylcyclohexyl)methanol

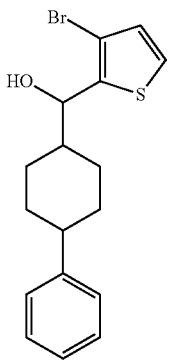

n-Butyllithium (2.5 M, 1.28 mL) was slowly added into a solution of diisopropylamine (354.57 mg, 3.50 mmol, 492.46 μL) in diethyl ether (7.00 mL) at −65° C., and then tribromothiophene (476.29 mg, 2.92 mmol, 273.73 μL) was injected thereto after 1 h. After stirring at −65° C. for 1 h, 4-phenylcyclohexylcarboxaldehyde (550.00 mg, 2.92 mmol) was then added, and the reaction solution was further stirred at −65° C. for 1 h.

The reaction solution was quenched with ammonium chloride (20 mL), diluted with water (20 mL), and extracted with ethyl acetate (20 mL×3). The combined organic phase was washed with brine (20 mL×3), dried over anhydrous sodium sulfate, filtered and evaporated. The residue was purified by column chromatography to give the title compound (colorless oil, 350.00 mg, yield of 34.12%). $^1$H NMR (400 MHz, CHLOROFORM-d) δ=7.23-7.18 (m, 4H), 7.14-7.10 (m, 3H), 6.88-6.84 (m, 1H), 5.24-4.76 (m, 1H), 2.47-2.36 (m, 1H), 2.47-2.36 (m, 1H), 2.22-2.15 (m, 1H), 1.95-1.79 (m, 3H), 1.74 (td, J=3.9, 7.8 Hz, 1H), 1.47-1.38 (m, 2H), 1.26-1.20 (m, 2H).

Example 88D: 1-((3-bromothiophen-2-yl)(4-phenyl-cyclohexyl)methyl)-1H-imidazole

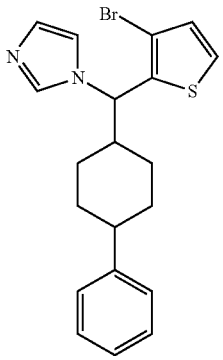 [SMILES: Brc1ccsc1C(C1CCC(c2ccccc2)CC1)n1ccnc1]

Carbonyldiimidazole (807.75 mg, 4.98 mmol) was added into a solution of (3-bromothiophen-2-yl)(4-phenylcyclohexyl)methanol (350 mg, 996.30 μmol) in acetonitrile (10.00 mL), and the reaction solution was refluxed with stirring at 80° C. for 16 h. After cooling down to room temperature, the reaction solution was allowed to separated with ethyl acetate (10.00 mL) and water (10.00 mL). The organic phase was washed with brine (10 mL×3), dried over anhydrous sodium sulfate, filtered and evaporated. The residue was purified by column chromatography to give the title compound (yellow oil, 250.00 mg, yield of 62.52%). $^1$H NMR (400 MHz, CHLOROFORM-d) δ=7.73-7.68 (m, 1H), 7.37-7.33 (m, 2H), 7.32-7.28 (m, 2H), 7.23-7.20 (m, 2H), 7.10 (d, J=5.8 Hz, 2H), 6.98-6.95 (m, 1H), 5.27 (d, J=10.8 Hz, 1H), 2.52 (tt, J=3.3, 12.2 Hz, 1H), 2.21 (tq, J=3.3, 11.4 Hz, 1H), 1.99-1.91 (m, 2H), 1.85-1.76 (m, 2H), 1.61-1.52 (m, 2H), 1.28 (t, J=7.2 Hz, 2H).

Preparation of the Title Compounds (Examples 88 to 89): 8-(4-phenylcyclohexyl)-8H-thieno[3',2':3,4]pyrrolo[1,2-c]imidazole

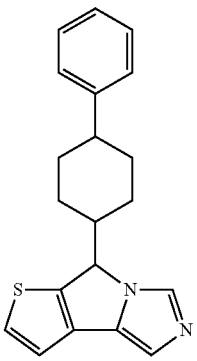 [SMILES: c1ccc(C2CCC(C3c4sccc4-c4cncn43)CC2)cc1]

Palladium acetate (11.19 mg, 49.83 μmol), tricyclohexylphosphine (27.95 mg, 99.66 μmol) and potassium carbonate (137.74 mg, 996.62 μmol) were added into a solution of 1-((3-bromothiophen-2-yl)(4-phenylcyclohexyl)methyl)-1H-imidazole (200 mg, 498.31 μmol) in o-xylene (4.00 mL), and then the reaction solution was purged with nitrogen gas three times. The mixture solution was refluxed with stirring at 140° C. for 16 h. After cooling down to room temperature, the reaction solution was filtered, and the filtrate was washed with brine (10 mL×3). The aqueous phase was extracted with ethyl acetate (10 mL×3), and the resulting organic phase combined was dried over anhydrous sodium sulfate, filtered and evaporated under reduced pressure to give a residue. The residue was purified by column chromatography to give the title compound (120 mg, yield of 61.04%). $^1$H NMR (400 MHz, CHLOROFORM-d) δ=7.72-7.64 (m, 1H), 7.40-7.35 (m, 1H), 7.32-7.28 (m, 2H), 7.21-7.15 (m, 4H), 6.98-6.93 (m, 1H), 5.21-5.14 (m, 1H), 2.46 (br t, J=12.0 Hz, 1H), 2.18-2.12 (m, 1H), 2.05-1.87 (m, 4H), 1.53-1.39 (m, 2H), 1.30-1.24 (m, 2H).

The racemate (40.00 mg, 124.82 μmol) was subjected to chiral separation (column: ChiralCel OD-3 100×4.6 mm I.D., 3 μm; mobile phase: A: carbon dioxide B: ethanol (0.05% diethylamine); gradient: from 5% to 40% of B for 4.5 min and hold 40% for 2.5 min, then 5% of B for 1 min; flow rate: 2.8 mL/min; column temperature: 40° C.), to give Example 88 (13.00 mg, yield of 32.17%, retention time: 3.862 min) and Example 89 (9.00 mg, yield of 22.23%, retention time: 4.721 min).

Example 88: ¹H NMR (400 MHz, CHLOROFORM-d) δ=7.63 (s, 1H), 7.29 (d, J=5.0 Hz, 1H), 7.20 (d, J=8.5 Hz, 2H), 7.14-7.07 (m, 4H), 6.88 (s, 1H), 5.07 (d, J=4.0 Hz, 1H), 2.42-2.33 (m, 1H), 2.05 (ddd, J=3.6, 8.4, 15.8 Hz, 1H), 1.97-1.80 (m, 3H), 1.54-1.45 (m, 2H), 1.42-1.30 (m, 2H), 1.02 (dq, J=3.6, 12.6 Hz, 1H).

Example 89: ¹H NMR (400 MHz, CHLOROFORM-d) δ=7.71 (s, 1H), 7.37 (d, J=5.0 Hz, 1H), 7.32-7.28 (m, 2H), 7.22-7.15 (m, 4H), 6.96 (s, 1H), 5.16 (d, J=4.0 Hz, 1H), 2.46 (br t, J=12.3 Hz, 1H), 2.19-2.08 (m, 1H), 2.07-1.88 (m, 3H)), 1.55-1.35 (m, 4H), 1.16-1.04 (m, 1H).

Examples 90 to 91: 8-cyclohexyl-2-dimethyl-8H-thieno[3',2':3,4]pyrrolo[1,2-c]imidazole Example 90A: (3-bromo-5-methylthiophen-2-yl)(cyclohexyl)methanol

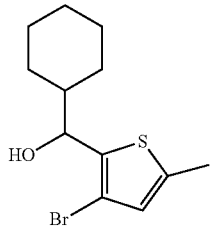

n-Butyllithium (2.5 M, 3.92 mL) was added into a solution of diisopropylamine (1.08 g, 10.70 mmol, 1.50 mL) in tetrahydrofuran (10.00 mL) at −65° C. After stirring for 1 h, 4-bromo-2-methyl-thiophene (1.58 g, 8.92 mmol) was slowly added thereto with a syringe, and the reaction solution was further stirred at −65° C. for 1 h, followed by addition of cyclohexylcarboxaldehyde (1.00 g, 8.92 mmol, 1.08 mL) with a syringe. The reaction solution was stirred at −65° C. for another 1 hour. The reaction solution was quenched with saturated ammonium chloride solution (20.00 mL) at −65° C., diluted with water (20.00 mL) and then extracted with ethyl acetate (20 mL×3). The combined organic layers were washed with brine (20 mL×3), dried over anhydrous sodium sulfate, filtered and evaporated under reduced pressure to give a residue. The residue was purified by column chromatography to give the title compound (colorless oil, 1.30 g, 4.49 mmol, yield of 50.34%). ¹H NMR (400 MHz, CHLOROFORM-d) δ=6.58 (d, J=1.0 Hz, 1H), 4.71 (dd, J=1.8, 8.0 Hz, 1H), 2.45 (d, J=1.0 Hz, 3H), 1.84-1.75 (m, 1H), 1.73-1.61 (m, 3H), 1.51-1.42 (m, 1H), 1.31-0.96 (m, 6H).

Example 90B: 1-((3-bromo-5-methylthiophen-2-yl)(cyclohexyl)methyl)-1H-imidazole

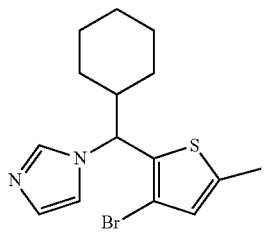 [SMILES: Cc1cc(Br)c(C(C2CCCCC2)n2ccnc2)s1]

A mixture solution of (3-bromo-5-methylthiophen-2-yl)(cyclohexyl)methanol (1.30 g, 4.49 mmol) and carbonyldiimidazole (3.64 g, 22.45 mmol) in acetonitrile (15 mL) was purged with nitrogen gas three times, and then heated to 80° C. to reflux for 16 h. The reaction solution was allowed to separate with ethyl acetate (20 mL) and water (20 mL). The organic phase was washed with brine (10 mL×3), dried, filtered and evaporated under reduced pressure to give a residue. The residue was purified by column chromatography to give the title compound (black oil, 470.00 mg, 1.39 mmol, yield of 30.85%). ¹H NMR (400 MHz, CHLOROFORM-d) δ=7.61 (s, 1H), 7.05 (d, J=5.8 Hz, 2H), 6.59 (s, 1H), 5.14 (d, J=11.0 Hz, 1H), 2.45 (s, 3H), 1.79-1.63 (m, 5H), 1.31-1.12 (m, 4H), 1.07-0.88 (m, 2H).

Preparation of the Title Compounds (Examples 90 to 91): 8-cyclohexyl-2-dimethyl-8H-thieno[3',2':3,4]pyrrolo[1,2-c]imidazole

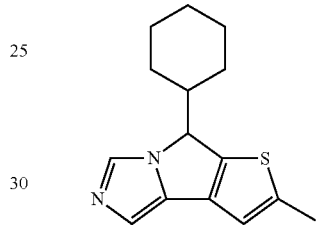

A mixture solution of 1-((3-bromo-5-methylthiophen-2-yl)(cyclohexyl)methyl)-1H-imidazole (470.00 mg, 1.39 mmol), palladium acetate (31.21 mg, 139.00 μmol), tricyclohexylphosphine (77.96 mg, 278.00 μmol) and potassium carbonate (384.22 mg, 2.78 mmol) in o-xylene (5.00 mL) was purged with nitrogen gas three times, and then heated to 140° C. with stirring for 16 h. The reaction solution was filtered, and the filtrate was washed with brine (10.00 mL×3). The aqueous phase thereof was extracted with ethyl acetate (10.00 mL×3), and the resulting organic phase combined was dried over anhydrous sodium sulfate, filtered and evaporated. The residue was purified by column chromatography to give the title compound (120.00 mg, 449.57 μmol, yield of 32.34%). ¹H NMR (400 MHz, CHLOROFORM-d) δ=7.63 (s, 1H), 6.86 (s, 1H), 6.82 (s, 1H), 4.99 (d, J=4.3 Hz, 1H), 2.54 (s, 3H), 1.97 (ddd, J=3.6, 8.3, 15.6 Hz, 1H), 1.86-1.65 (m, 5H), 1.33-1.07 (m, 5H).

The racemate (120.00 mg, 464.43 μmol) was subjected to chiral separation (column: Chiralpak AD-3 150×4.6 mm I.D., 3 μm; mobile phase: A: carbon dioxide B: ethanol (0.05% diethylamine); gradient: from 5% to 40% of B for 5 min and then hold for 2.5 min, then 5% of B for 2.5 min; flow rate: 2.5 mL/min; column temperature: 35° C.), to give Example 90 (30.00 mg, 115.96 μmol, yield of 24.97%, retention time: 4.469 min) and Example 91 (30.00 mg, 115.60 μmol, yield of 24.89%, retention time: 5.123 min).

Example 90: ¹H NMR (WXFL10310290_001, 400 MHz, METHANOL-d₄) δ=7.83 (s, 1H), 6.92 (s, 1H), 6.81 (s, 1H), 5.20 (d, J=3.5 Hz, 1H), 2.56 (s, 3H), 2.19-2.06 (m, 1H), 1.83 (br s, 2H), 1.71 (br d, J=11.0 Hz, 2H), 1.44-1.34 (m, 1H), 1.29-1.11 (m, 4H), 0.89-0.76 (m, 1H).

Example 91: ¹H NMR (WXFL10310291_001,400 MHz, METHANOL-d₄) δ=7.84 (br s, 1H), 6.92 (s, 1H), 6.81 (br s, 1H), 5.20 (d, J=3.8 Hz, 1H), 2.56 (s, 3H), 2.18-2.06 (m, 1H), 1.83 (br s, 2H), 1.71 (br d, J=10.5 Hz, 2H), 1.38 (br d, J=13.1 Hz, 1H), 1.29-1.11 (m, 4H), 0.89-0.77 (m, 1H).

Examples 92 to 96: 5-(4-(quinolin-4-yl)cyclohexyl)-5H-thieno[3',2':3,4]pyrrolo[1,2-a]imidazole and 5-(4-(quinolin-4-yl)cyclohexyl)-5H-thieno[3',2':3,4]pyrrolo[1,2-a]imidazole Example 92A: ethyl 4-(trifluoromethanesulfonyloxy)cyclohex-3-ene-1-carboxylate

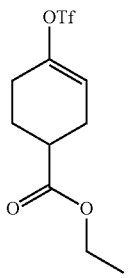

[Bis(trimethylsilyl)amide]lithium (1M, 176.25 mL) was slowly added dropwise to a solution of ethyl 4-oxycyclohexylcarboxylate (30.00 g, 176.25 mmol, 28.04 mL) in tetrahydrofuran (600.00 mL) at −65° C. After stirring for 1 h, a solution of 1,1,1-trifluoro-N-phenyl-N-(trifluoromethanesulfonyl)methanesulfonamide (69.26 g, 193.88 mmol) in tetrahydrofuran (150 mL) was added dropwise. The ice bath was removed at 30 min after completion of dropwise addition, and the reaction solution was further stirred at 30° C. for 12 h. The reaction solution was quenched with 1M aqueous ammonium chloride solution (200 mL) and separated. The organic layer was in turn washed with 0.5 M aqueous sodium hydroxide solution (500 mL×2), 200 mL of saturated ammonium chloride solution and 200 mL of brine, dried, and concentrated under reduced pressure to give a residue. The residue was purified by column chromatography to give the title compound (colorless oil, 36.00 g, 119.10 mmol, yield of 67.57%). ¹H NMR (400 MHz, CHLOROFORM-d) δ=5.70-5.64 (m, 1H), 4.06 (q, J=7.2 Hz, 2H), 2.54-2.45 (m, 1H), 2.39-2.26 (m, 4H), 2.08-1.99 (m, 1H), 1.88-1.76 (m, 1H), 1.18-1.14 (m, 3H).

Example 92B: ethyl 4-(4,4,5,5-tetramethyl-1,3,2-dioxaborolan-2-yl)cyclohex-3-ene-1-carboxylate

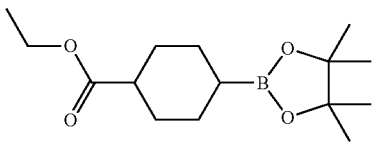 [SMILES: CCOC(=O)C1CCC(B2OC(C)(C)C(C)(C)O2)CC1]

A solution of ethyl 4-(trifluoromethanesulfonyloxy)cyclohex-3-ene-1-carboxylate (36.00 g, 119.10 mmol), 4,4,5,5-tetramethyl-2-(4,4,5,5-tetramethyl-1,3,2-dioxaborolan-2-yl)-1,3,2-dioxaborolane (45.37 g, 178.65 mmol), ferrocene dichloride palladium (8.71 g, 11.91 mmol) and potassium acetate (46.75 g, 476.40 mmol) in dioxane (400 mL) was heated to 110° C. to reflux for 15 h under protection of nitrogen gas. After cooling, ethyl acetate (200 mL) and sodium hydrogen carbonate (200 mL) were added. The aqueous phase was extracted with ethyl acetate, and the resulting organic phase combined was washed with brine, dried and concentrated under reduced pressure to give a residue. The residue was purified by column chromatography to give the title compound (yellow oil, 28.00 g, 89.84 mmol, yield of 75.43%). ¹H NMR (400 MHz, CHLOROFORM-d) δ=6.54 (br d, J=1.3 Hz, 1H), 4.16-4.10 (m, 2H), 2.55-2.45 (m, 1H), 2.36-2.22 (m, 3H), 2.17-2.06 (m, 1H), 2.04-1.97 (m, 1H), 1.66-1.53 (m, 1H), 1.25 (s, 15H).

Example 92C: ethyl 4-(4-quinoline)cyclohex-3-ene-1-carboxylate

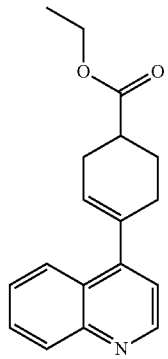 [SMILES: CCOC(=O)C1CC=C(c2ccnc3ccccc23)CC1]

A solution of ethyl 4-(4,4,5,5-tetramethyl-1,3,2-dioxaborolan-2-yl)cyclohex-3-ene-1-carboxylate (28.00 g, 89.84 mmol), 4-bromoquinoline (18.69 g, 89.84 mmol), ferrocene palladium dichloride (6.57 g, 8.98 mmol) and potassium carbonate (24.83 g, 179.68 mmol) in tetrahydrofuran (300 mL) and water (75 mL) was heated to reflux at 80° C. for 16 h under nitrogen gas. After cooling, the reaction solution was added with ethyl acetate-(400 mL) and sodium hydrogen carbonate (400 mL), and allowed to separate. The aqueous phase was extracted with ethyl acetate, and the resulting organic phase combined was washed with brine, dried over anhydrous sodium sulfate, filtered and evaporated to give a residue. The residue was purified by column chromatography to give the title compound (yellow oil, 15.50 g, 55.09 mmol, yield of 61.32%). ¹H NMR (400 MHz, CHLOROFORM-d) δ=8.83 (d, J=4.5 Hz, 1H), 8.11 (d, J=8.3 Hz, 1H), 7.97 (dd, J=0.8, 8.3 Hz, 1H), 7.68 (ddd, J=1.5, 7.0, 8.3 Hz, 1H), 7.51 (ddd, J=1.1, 6.9, 8.3 Hz, 1H), 7.16 (d, J=4.3 Hz, 1H), 5.84 (dd, J=1.8, 3.5 Hz, 1H), 4.21 (q, J=7.2 Hz, 2H), 2.81-2.72 (m, 1H), 2.55 (td, J=2.4, 5.0 Hz, 2H), 2.51-2.44 (m, 2H), 2.25-2.17 (m, 1H), 2.03-1.94 (m, 1H), 1.30 (t, J=7.2 Hz, 3H).

Example 92D: ethyl 4-(4-quinoline)cyclohexylcarboxylate

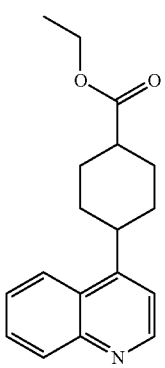

A solution of ethyl 4-(4-quinoline)cyclohex-3-ene-1-carboxylate (15.50 g, 55.09 mmol) and Pd/C (1.50 g, purity of 10%) in methanol (200 mL) was purged with argon gas three times, and then stirred under hydrogen stream (50 psi) at 25° C. for 15 h. The reaction solution was filtered and concentrated under reduced pressure, and the residue was purified by column chromatography to give the title compound (yellow oil, 14.50 g, 51.17 mmol, yield of 92.88%). $^1$H NMR (400 MHz, CHLOROFORM-d) δ=8.86-8.81 (m, 1H), 8.10 (dd, J=8.4, 17.7 Hz, 2H), 7.73-7.66 (m, 1H), 7.59-7.53 (m, 1H), 7.27-7.24 (m, 1H), 4.21 (q, J=7.3 Hz, 2H), 3.41-3.31 (m, 1H), 2.48-2.31 (m, 2H), 2.24-2.08 (m, 1H), 1.94-1.58 (m, 6H), 1.33-1.28 (m, 3H).

Example 92E: [4-(4-quinolyl)cyclohexyl]methanol

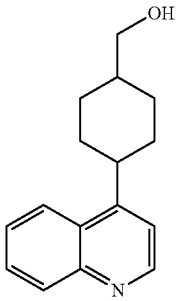 [SMILES: OCC1CCC(c2ccnc3ccccc23)CC1]

Lithium aluminium hydride (1.74 g, 45.88 mmol) was added into a solution of ethyl 4-(4-quinoline)cyclohexylcarboxylate (13.00 g, 45.88 mmol) in tetrahydrofuran (200 mL) at 0° C. The mixture solution was stirred at 0° C. for 1 h. The reaction solution was quenched with water (1.5 mL), 10% sodium hydroxide solution (3 mL) and water (4.5 mL) at 0° C., and then filtered. The filtrate was extracted with ethyl acetate, and the combined organic phase was dried over anhydrous sodium sulfate, filtered and evaporated under reduced pressure, to give the residue (8.7 g, 36.05 mmol, yield of 78.58%). $^1$H NMR (400 MHz, CHLOROFORM-d) δ=8.77-8.73 (m, 1H), 8.03 (dd, J=8.5, 18.6 Hz, 2H), 7.65-7.59 (m, 1H), 7.52-7.45 (m, 1H), 7.21-7.17 (m, 1H), 3.70 (d, J=7.5 Hz, 2H), 3.51 (d, J=6.0 Hz, 1H), 3.38-3.26 (m, 1H), 2.04-1.82 (m, 4H), 1.79-1.59 (m, 3H), 1.67-1.59 (m, 2H).

Example 92F: 4-(4-quinolyl)cyclohexylcarboxaldehyde

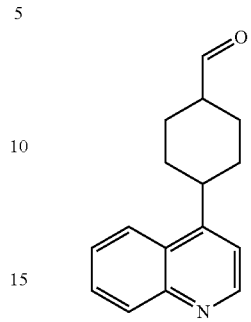

Dess-martin periodinane (21.62 g, 50.97 mmol)) was added into a solution of [4-(4-quinolyl)cyclohexyl]methanol (8.20 g, 33.98 mmol) in dichloromethane (100 mL) at 0° C. The reaction solution was stirred at 0° C. for 3 h. The reaction solution was quenched with sodium thiosulfate (250 mL) and filtered, and the filtrate was extracted with dichloromethane. The combined organic phase was dried over anhydrous sodium sulfate, filtered and evaporated under reduced pressure to give a residue. The residue was purified by column chromatography to give the title compound (yellow oil, 4.95 g, 20.68 mmol, yield of 60.87%).

Example 92G: (3-bromo-2-thienyl)-[4-(4 quinolyl)cyclohexyl]methanol

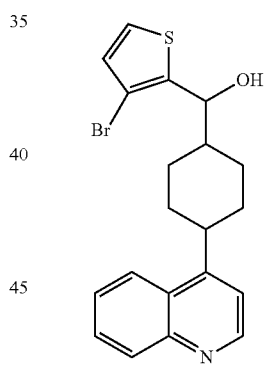

n-Butyllithium (2.5 M, 9.47 mL) was added dropwise into a solution of diisopropylamine (2.61 g, 25.82 mmol, 3.63 mL) in diethyl ether (60 mL) at −65° C. After 1 hour, 3-bromothiophene (3.51 g, 21.52 mmol, 2.02 mL) was added. After another 1 hour, 4-(4-quinolyl)cyclohexylcarboxaldehyde (5.15 g, 21.52 mmol) was added. The reaction mixture was then stirred at −65° C. for 1 h. The reaction solution was quenched with saturated ammonium chloride solution (200 mL), and allowed to separate. The aqueous phase was extracted with ethyl acetate, and the resulting organic phase combined was dried over anhydrous sodium sulfate, filtered and evaporated under reduced pressure to give a residue. The residue was purified by column chromatography to give the title compound (a yellow gum, 2.15 g, 5.34 mmol, yield of 24.83%). $^1$H NMR (400 MHz, METHANOL-d$_4$) δ=8.80-8.76 (m, 1H), 8.76-8.71 (m, 1H), 8.22 (t, J=8.0 Hz, 2H), 8.02 (t, J=6.9 Hz, 2H), 7.78-7.71 (m, 2H), 7.67-7.61 (m, 2H), 7.50 (d, J=4.8 Hz, 1H), 7.48-7.45

(m, 1H), 7.43 (dd, J=3.5, 5.0 Hz, 2H), 6.95 (dd, J=2.5, 5.3 Hz, 2H), 5.34 (d, J=10.3 Hz, 1H), 4.60 (s, 2H), 3.59-3.48 (m, 1H), 3.46-3.35 (m, 1H), 2.43 (br d, J=13.1 Hz, 1H), 2.34-2.25 (m, 1H), 2.15-2.03 (m, 3H), 2.00-1.94 (m, 2H), 1.93-1.82 (m, 3H), 1.79-1.69 (m, 2H), 1.68-1.42 (m, 6H), 1.26-1.18 (m, 2H).

Example 92H: 4-[4-[(3-bromo-2-thienyl)-imidazol-1-yl-methyl]cyclohexyl]quinoline

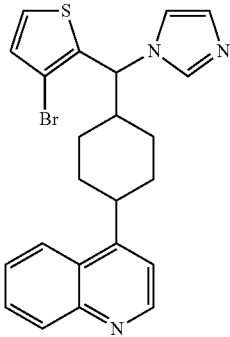 [SMILES: Brc1ccsc1C(C1CCC(c2ccnc3ccccc23)CC1)n1ccnc1]

A solution of (3-bromo-2-thienyl)-[4-(4-quinolyl)cyclohexyl]methanol (2.15 g, 5.34 mmol) and N,N-carbonyldiimidazole (4.33 g, 26.70 mmol) in acetonitrile (30.00 mL) was stirred at 80° C. for 16 h. After cooling, the reaction mixture was washed with water. The organic phase was dried over anhydrous sodium sulfate, filtered and evaporated under reduced pressure to give a residue. The residue was purified by column chromatography to give the title compound (1.50 g, 3.32 mmol, yield of 62.09%). $^1$H NMR (400 MHz, CHLOROFORM-d) δ=8.92 (d, J=4.5 Hz, 1H), 8.85 (d, J=4.5 Hz, 1H), 8.16-8.10 (m, 2H), 8.05 (dd, J=2.5, 8.3 Hz, 2H), 7.76-7.76 (m, 1H), 7.76-7.70 (m, 4H), 7.60-7.55 (m, 2H), 7.41-7.35 (m, 3H), 7.26 (s, 1H), 7.16-7.13 (m, 2H), 7.10 (br d, J=3.5 Hz, 2H), 6.97 (dd, J=4.0, 5.3 Hz, 2H), 5.95 (d, J=12.0 Hz, 1H), 5.35 (d, J=10.8 Hz, 1H), 3.47 (br s, 1H), 3.36 (br t, J=11.8 Hz, 1H), 2.74 (br d, J=12.3 Hz, 1H), 2.36-2.24 (m, 1H), 2.14-2.06 (m, 2H), 1.95-1.85 (m, 5H), 1.83-1.72 (m, 3H), 1.70-1.57 (m, 3H), 1.50 (br d, J=8.8 Hz, 1H), 1.46-1.31 (m, 2H).

Example 92I: 8-(4-(quinolin-4-yl)cyclohexyl)-8H-thieno[3',2':3,4]pyrrolo[1,2-c]imidazole

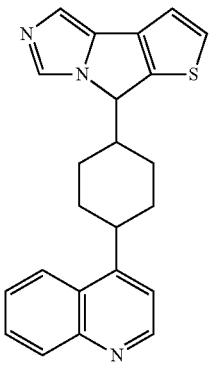 [SMILES: c1ccc2c(C3CCC(C4c5sccc5-c5cncn54)CC3)ccnc2c1]

Preparation of the Title Compounds (Examples 92 to 95): 5-(4-(quinolin-4-yl)cyclohexyl)-8H-thieno[3',2':3,4]pyrrolo[1,2-c]imidazole

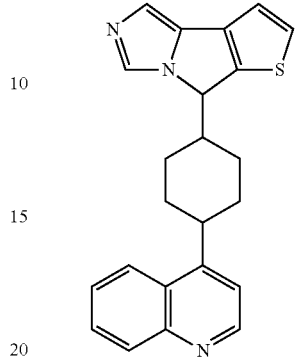

The racemate of 5-(4-(quinolin-4-yl)cyclohexyl)-8H-thieno[3',2':3,4]pyrrolo[1,2-c]imidazole (200.00 mg, 538.36 μmol) was subjected to chiral separation (chiral column: OD-3 100×4.6 mm I.D., 3 μm; mobile phase: A: carbon dioxide B: ethanol (0.05% diethylamine); gradient: from 5% to 40% of B for 4.5 or 4 min and hold 40% for 2.5 min, then 5% of B for 1 min; flow rate: 2.8 mL/min; column temperature: 40° C.), to give Example 92 (12.00 mg, 31.48 μmol, yield of 5.85%, retention time=1.674 min), Example 93 (5.00 mg, 13.31 μmol, yield of 2.47%, retention time=2.263 min), Example 94 (2.00 mg, 5.33 μmol, yield of 0.99%, retention time=3.164 min) and Example 95 (10.00 mg, 26.25 μmol, yield of 4.88%, retention time=5.596 min).

Example 92: $^1$H NMR (WXFL10310293_001, 400 MHz, METHANOL-d$_4$) δ=8.75 (d, J=4.5 Hz, 1H), 8.17 (d, J=8.3 Hz, 1H), 8.03 (d, J=8.0 Hz, 1H), 7.96 (s, 1H), 7.75 (dt, J=1.3, 7.7 Hz, 1H), 7.66-7.60 (m, 1H), 7.58 (d, J=5.0 Hz, 1H), 7.44 (d, J=4.8 Hz, 1H), 7.26 (d, 1=5.0 Hz, 1H), 6.93 (s, 1H), 5.40 (d, J=4.0 Hz, 1H), 3.40-3.34 (m, 1H), 2.40-2.31 (m, 1H), 2.15-1.95 (m, 3H), 1.82-1.52 (m, 4H), 1.32-1.19 (m, 1H).

Example 93: $^1$H NMR (WXFL10310294_001, 400 MHz, METHANOL-d$_4$) 5=8.65 (d, J=4.8 Hz, 1H), 8.08 (d, J=8.5 Hz, 1H), 7.92 (d, J=8.0 Hz, 1H), 7.85 (s, 1H), 7.67-7.61 (m, 1H), 7.56-7.50 (m, 1H), 7.47 (d, J=5.0 Hz, 1H), 7.35 (d, J=4.8 Hz, 1H), 7.15 (d, J=5.0 Hz, 1H), 6.82 (s, 1H), 5.32 (d, J=4.0 Hz, 1H), 3.32-3.24 (m, 1H), 2.26 (dt, J=3.6, 12.1 Hz, 1H), 2.07-1.99 (m, 1H), 1.99-1.87 (m, 2H), 1.73-1.42 (m, 4H), 1.22-1.16 (m, 1H).

Example 94: $^1$H NMR (WXFL10310295_001, 400 MHz, METHANOL-d$_4$)=8.73 (d, J=4.5 Hz, 1H), 8.20 (br d, J=8.0 Hz, 1H), 8.02 (d, J=8.3 Hz, 1H), 7.89 (s, 1H), 7.74 (br t, J=7.5 Hz, 1H), 7.63 (br t, J=7.5 Hz, 1H), 7.56-7.49 (m, 2H), 7.21 (br d, J=4.5 Hz, 1H), 6.89 (s, 1H), 5.53-5.47 (m, 1H), 3.79 (br s, 1H), 2.28-1.84 (m, 7H), 1.76-1.56 (m, 2H).

Example 95: $^1$H NMR (WXFL10310296_001, 400 MHz, METHANOL-d$_4$) δ=8.64 (d, J=4.8 Hz, 1H), 8.11 (d, J=8.3 Hz, 1H), 7.93 (d, J=7.8 Hz, 1H), 7.80 (s, 1H), 7.67-7.61 (m, 1H), 7.54 (dt, J=1.1, 7.7 Hz, 1H), 7.45 (d, J=4.8 Hz, 1H), 7.42 (d, J=5.0 Hz, 1H), 7.11 (d, J=5.0 Hz, 1H), 6.79 (s, 1H), 5.43 (d, J=7.3 Hz, 1H), 3.71 (quin, J=5.7 Hz, 1H), 2.20-2.10 (m, 1H), 2.09-2.01 (m, 2H), 2.00-1.78 (m, 4H), 1.67-1.48 (m, 2H).

Preparation of the Title Compound (Example 96): 5-(4-(quinolin-4-yl)cyclohexyl)-5H-thieno[3',2':3,4]pyrrolo[1,2-a]imidazole

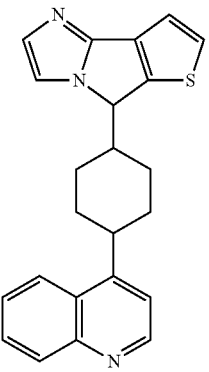 [SMILES: c1ccc2c(C3CCC(C4c5sccc5-c5nccn54)CC3)ccnc2c1]

A solution of 4-[4-[(3-bromo-2-thienyl)-imidazol-1-yl-methyl]cyclohexyl]quinoline (440.00 mg, 972.57 μmol), tricyclohexylphosphine (54.55 mg, 194.51 μmol), palladium acetate (21.84 mg, 97.26 μmol) and potassium carbonate (268.84 mg, 1.95 mmol) in o-xylene (15 mL) was purged with nitrogen gas three times, and then stirred at 140° C. for 16 h. The reaction solution was filtered, and the filtrate was washed with brine. The organic layer was dried over anhydrous sodium sulfate, filtered and evaporated under reduced pressure to give a residue. The residue was purified by column chromatography to give Example 96 (70.00 mg, 188.43 μmol, yield of 19.37%) and Example 92I (200.00 mg, 538.36 μmol, yield of 55.35%).

Example 96: $^1$H NMR (400 MHz, METHANOL-$d_4$) δ=8.74 (d, J=4.8 Hz, 1H), 8.14 (d, J=8.5 Hz, 1H), 8.01 (d, J=8.5 Hz, 1H), 7.73 (t, J=7.7 Hz, 1H), 7.65-7.57 (m, 2H), 7.46-7.40 (m, 2H), 7.32 (d, J=4.8 Hz, 1H), 7.10 (s, 1H), 5.25 (d, J=4.0 Hz, 1H), 2.34 (dt, J=3.5, 12.2 Hz, 1H), 2.10 (br d, J=12.5 Hz, 1H), 2.06-1.92 (m, 2H), 1.75 (dq, J=2.9, 12.4 Hz, 1H), 1.68-1.55 (m, 2H), 1.47 (br d, J=13.3 Hz, 1H), 1.30-1.24 (m, 1H), 1.16 (dq, J=3.3, 12.6 Hz, 1H).

Examples 97 to 104: 3-(8H-thieno[3,4]pyrrolo[1,5-a]imidazol-8-yl)cyclohexylcarboxylic Acid Example 97A: ethyl 3-(methoxymethylene)cyclohexanecarboxylate

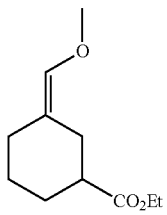

A solution of potassium tert-butoxide (1 mol/L, 88.13 mL) in tetrahydrofuran was slowly added dropwise to a solution of methoxymethyl triphenylphosphonium chloride (30.21 g, 88.13 mmol) in tetrahydrofuran (20.00 mL) at 0° C., and the temperature was controlled at 0° C. with stirring for 30 min. A solution of ethyl 3-carbonylcyclohexanecarboxylate (10.00 g, 58.75 mmol) in tetrahydrofuran (10 mL) was then added dropwise to the system. After completion of dropwise addition, the system was warmed up to 28° C. and stirred for 16 h. TLC showed that the starting materials were completely reacted and a new product was formed. After completion of reaction, the reaction system was added with 30 mL of water, and this reaction system was then directly used in the next step.

Example 97B: ethyl 3-formylcyclohexanecarboxylate

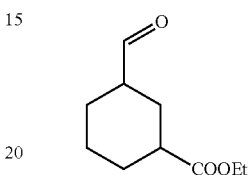

Water (20 mL) and dilute hydrochloric acid (6 mol/L, 10 mL) were slowly added dropwise to the crude product obtained from the last step at 0° C., and the reaction solution was reacted at 28° C. for 1 h, and the reaction was monitored by TLC. After completion of reaction, the reaction solution was added with a saturated sodium hydrogen carbonate solution to pH=7, and extracted with ethyl acetate (20 mL×3). The combined organic phase was washed with 50 mL of saturated brine, dried over anhydrous sodium sulfate, filtered under suction, and evaporated under reduced pressure. The crude product was purified by column chromatography to give ethyl 3-formylcyclohexanecarboxylate (10.00 g, 54.28 mmol, yield of 92.38%) as a colorless liquid.

Example 97C: ethyl 3-[(3-bromo-2-thienyl)-hydroxy-methyl]cyclohexanecarboxylate

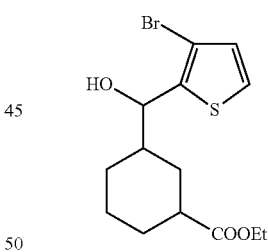

A solution of n-butyllithium (2.5 mol/L, 25.79 mL) in n-hexane was slowly added dropwise to a solution of diisopropylamine (6.52 g, 64.48 mmol, 9.06 mL) in diethyl ether (100.00 mL) at −78° C. over about 10 min, during which the temperature was controlled at −78° C. After completion of dropwise addition, the mixture was warmed up to 0° C. and stirred for 30 min. The system was cooled down to −78° C., and then added dropwise with 3-bromo-thiophene (11.47 g, 70.34 mmol, 6.59 mL). After stirring for 1 h, ethyl 3-formylcyclohexanecarboxylate (10.80 g, 58.62 mmol) was further added dropwise, and stirred at −78° C. for another 2 h. After completion of reaction, the system was added with 100 mL of saturated ammonium chloride solution, and then extracted with ethyl acetate (50 mL×3). The organic phase was combined, washed with 100 mL of saturated brine, dried over anhydrous sodium sulfate, filtered under suction, and evaporated under reduced pressure. The obtained crude product was purified by column chromatography to give the compound of ethyl 3-[(3-bromo-2-thienyl)-hydroxy-methyl]cyclohexanecarboxylate (9.00 g, 25.92 mmol, yield of 44.22%) as a colorless oil. $^1$H NMR (400 MHz, CHLOROFORM-d) δ=7.28 (s, 1H), 6.94-6.90 (m, 1H), 4.83 (ddd, J=3.3, 7.6, 10.5 Hz, 1H), 4.12 (q, J=7.0 Hz, 2H), 2.42-2.20 (m, 2H), 2.14 (br dd, J=3.4, 9.9 Hz, 1H), 2.01-1.90 (m, 2H), 1.86-1.70 (m, 2H), 1.44-1.42 (m, 1H), 1.37-1.31 (m, 1H), 1.28-1.24 (m, 3H), 1.17-1.05 (m, 1H).

Example 97D: ethyl 3-[(3-bromo-2-thienyl)-imidazol-1-yl-methyl]cyclohexanecarboxylate

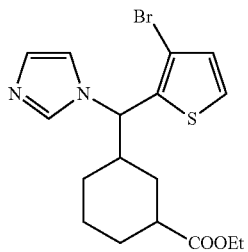 [SMILES: CCOC(=O)C1CCCC(C(c2sccc2Br)n2ccnc2)C1]

1,1-Carbonyldiimidazole (21.01 g, 129.60 mmol) was added into a solution of ethyl (3-[(3-bromo-2-thienyl)-hydroxy-methyl]cyclohexanecarboxylate (9.00 g, 25.92 mmol) in acetonitrile (100.00 mL). The reaction solution was reacted at 80° C. for 12 h, and the reaction was monitored by TLC and LCMS. After completion of reaction, the reaction solution was added with 100 mL of water at 25° C., and extracted with ethyl acetate (30 mL×3). The combined organic phase was washed with 100 mL of saturated brine, dried over anhydrous sodium sulfate, filtered under suction and evaporated under reduced pressure. The crude product was purified by column chromatography to give ethyl 3-[(3-bromo-2-thienyl)-imidazol-1-yl-methyl]cyclohexanecarboxylate (5.40 g, 13.59 mmol, yield of 52.43%). $^1$H NMR (400 MHz, CHLOROFORM-d) δ=7.68-7.61 (m, 1H), 7.35-7.28 (m, 1H), 7.26 (s, 1H), 7.14-7.02 (m, 2H), 6.96-6.90 (m, 1H), 5.32-5.19 (m, 1H), 4.16-4.05 (m, 2H), 2.76-2.10 (m, 2H), 2.03-1.94 (m, 1H), 1.92-1.81 (m, 1H), 1.66 (br s, 1H), 1.60-1.45 (m, 1H), 1.42-1.28 (m, 3H), 1.27-1.22 (m, 3H), 1.09-0.89 (m, 1H).

Example 97E: ethyl 3-(8H-thieno[3,4]pyrrolo[1,5-a]imidazol-8-yl)cyclohexanecarboxylate

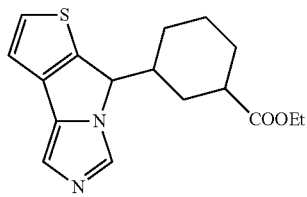 [SMILES: CCOC(=O)C1CCCC(C2c3sccc3-c3cncn32)C1]

Under protection of nitrogen gas, ethyl 3-[(3-bromo-2-thienyl)-imidazol-1-yl-methyl]cyclohexanecarboxylate (5.20 g, 13.09 mmol), palladium acetate (293.82 mg, 1.31 mmol), tricyclohexylphosphine (734.02 mg, 2.62 mmol), potassium carbonate (3.62 g, 26.18 mmol), and o-xylene (100.00 mL) were successively added in a reaction flask, and reacted at 140° C. for 16 h. After completion of reaction, the reaction solution was filtered under suction, and washed with ethyl acetate (30 mL). The organic phase was added with 100 mL of water, and extracted with ethyl acetate (100 mL×3). The resulting organic phase combined was washed with 100 mL of saturated brine, dried over anhydrous sodium sulfate, filtered under suction, and evaporated under reduced pressure. The crude product was purified by column chromatography to give ethyl 3-(8H-thieno[3,4]pyrrolo[1,5-a]imidazol-8-yl)cyclohexanecarboxylate (2.20 g, 6.95 mmol, yield of 53.12%). $^1$H NMR (400 MHz, CHLOROFORM-d) δ=7.67-7.64 (m, 1H), 7.34 (dd, J=1.8, 5.0 Hz, 1H), 7.14 (d, J=5.0 Hz, 1H), 6.94 (s, 1H), 5.16-5.06 (m, 1H), 4.20-3.99 (m, 2H), 3.78-3.71 (m, 2H), 2.44-2.23 (m, 1H), 2.16-1.96 (m, 2H), 1.84-1.71 (m, 2H), 1.47-1.35 (m, 2H), 1.30-1.24 (m, 3H), 1.13-0.82 (m, 1H).

Preparation of the Title Compounds (Examples 97 to 104): 3-(8H-thieno[3,4]pyrrolo[1,5-a]imidazol-8-yl) cyclohexylcarboxylic acid

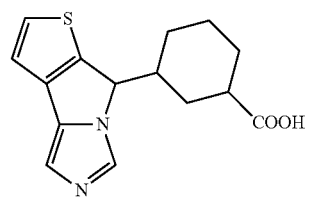 [SMILES: O=C(O)C1CCCC(C2c3sccc3-c3cncn32)C1]

Lithium hydroxide (60.55 mg, 2.53 mmol) was added into a solution of ethyl 3-(8H-thieno[3,4]pyrrolo[1,5-a]imidazol-8-yl) cyclohexanecarboxylate (200.00 mg, 1.33 mmol) in tetrahydrofuran (2.00 mL) and water (2.00 mL). The reaction solution was reacted at 65° C. for 16 h. After completion of reaction, the reaction solution was added with dilute hydrochloric acid (1 mol/L) to pH=5, and 100 mL of water was added thereto, followed by extraction with 50% dichloromethane/isopropanol (50 mL×3). The organic phase was dried over anhydrous sodium sulfate, filtered under suction, and evaporated under reduced pressure. The crude product was purified by column chromatography to give 3-(8H-thieno[3,4]pyrrolo[1,5-a]imidazol-8-yl)cyclohexanecarboxylic acid (100 mg, 339.85 μmol, yield of 53.77%). $^1$H NMR (400 MHz, METHANOL-d4) δ=8.54-8.41 (m, 1H), 7.62 (d, J=5.0 Hz, 1H), 7.33-7.26 (m, 1H), 7.18 (br s, 1H), 5.59-5.42 (m, 1H), 3.93 (spt, J=6.1 Hz, 1H), 2.89-2.62 (m, 1H), 2.55-2.29 (m, 2H), 2.10-1.74 (m, 4H), 1.00-0.89 (m, 2H).

The racemate was purified by preparative chromatography (acidic conditions) to give four components, including component I (trifluoroacetate, 160 mg, 554.86 μmol, yield of 24.66%, HPLC RT=1.71 min); component II (trifluoroacetate, 160 mg, 554.86 μmol, yield of 24.66%, HPLC RT=1.75 min); component III (trifluoroacetate, 100 mg, 341.69 μmol, yield of 15.19%, HPLC RT=1.79 min); and component IV (trifluoroacetate, 100 mg, 341.69 μmol, yield of 15.19%, HPLC RT=1.80 min).

Component I was separated by chiral separation (column: ChiralCel OJ-H 150×4.6 mm I.D., 5 μm; mobile phase: A: CO$_2$ B: ethanol (0.05% DEA); gradient: from 5% to 40% of B in 5.5 min and hold 40% for 3 min, then 5% of B for 1.5 min; flow rate: 2.5 mL/min; column temperature: 40° C.), and then purified by acidic preparative chromatography, to finally give Example 97 (trifluoroacetate, 20.00 mg, 49.55

µmol, SFC RT=3.914 min, ee=80%), and Example 98 (trifluoroacetate, 30.00 mg, 73.98 µmol, SFC RT=4.306 min, ee=85%).

Example 97: ¹H NMR (400 MHz, METHANOL-d4) δ=9.20 (s, 1H), 7.72 (d, J=5.0 Hz, 1H), 7.53 (s, 1H), 7.38 (d, J=5.0 Hz, 1H), 5.75 (d, J=3.5 Hz, 1H), 2.51-2.38 (m, 2H), 2.10 (br d, J=12.5 Hz, 1H), 2.01 (br d, J=12.5 Hz, 1H), 1.81 (br d, J=13.3 Hz, 1H), 1.44-1.28 (m, 3H), 1.27-1.18 (m, 1H), 0.88-0.74 (m, 1H).

Example 98: ¹H NMR (400 MHz, METHANOL-d4) δ=9.19 (s, 1H), 7.71 (d, J=5.0 Hz, 1H), 7.53 (s, 1H), 7.38 (d, J=5.3 Hz, 1H), 5.75 (d, J=3.5 Hz, 1H), 2.50-2.38 (m, 2H), 2.09 (br d, J=12.3 Hz, 1H), 2.01 (br d, J=12.5 Hz, 1H), 1.85-1.76 (m, 1H), 1.44-1.17 (m, 4H), 0.80 (dq, J=3.4, 12.6 Hz, 1H).

Component II was separated by chiral separation ("AD_3_EtOH_DEA_5_40_25 ML Vial: 1:D, 8, Channel Name: PDA Ch1 220 nm@4.8 nm—Compens. Injection Volume: 1.00 µL, Proc. Chnl. Descr.: PDA Ch1 220 nm@ 4.8 nm—Compens. Run Time: 10.0 min"), and purified by acidic preparative chromatography, to finally give Example 99 (trifluoroacetate, 25.00 mg, 61.23 µmol, SFC RT=4.811 min, ee=80%), and Example 100 (trifluoroacetate, 28.00 mg, 69.09 µmol, SFC RT=5.635 min, ee=96%).

Example 99: ¹H NMR (400 MHz, METHANOL-d4) δ=9.18 (s, 1H), 7.72 (d, J=5.0 Hz, 1H), 7.52 (s, 1H), 7.39 (d, J=5.0 Hz, 1H), 5.76 (d, J=3.5 Hz, 1H), 2.46 (ddd, J=3.3, 9.0, 15.6 Hz, 1H), 2.33 (tt, J=3.3, 12.1 Hz, 1H), 2.06-1.88 (m, 3H), 1.57-1.42 (m, 2H), 1.34-1.17 (m, 2H), 0.87 (q, J=12.5 Hz, 1H).

Example 100: ¹H NMR (400 MHz, METHANOL-d4) δ=9.19 (s, 1H), 7.75-7.68 (m, 1H), 7.53 (s, 1H), 7.43-7.34 (m, 1H), 5.76 (d, J=3.5 Hz, 1H), 2.47 (dt, J=3.1, 12.2 Hz, 1H), 2.39-2.28 (m, 1H), 2.07-1.88 (m, 3H), 1.57-1.41 (m, 2H), 1.34-1.18 (m, 2H), 0.87 (dq, J=2.9, 12.4 Hz, 1H).

Component III was separated by chiral separation ("AD_3_EtOH_DEA_5_40_25 ML Vial: 1:D, 8, Channel Name: PDA Ch1 220 nm@4.8 nm—Compens. Injection Volume: 1.00 µL, Proc. Chnl. Descr.: PDA Ch1 220 nm@ 4.8 nm—Compens. Run Time: 10.0 min"), and purified by acidic preparative chromatography, to finally give Example 101 (trifluoroacetate, 8.00 mg, 19.56 µmol, SFC RT=4.674 min, ee=99.08%), and Example 102 (trifluoroacetate, 9.00 mg, 22.04 µmol, SFC RT=5.193 min, ee=98.5%).

Example 101: ¹H NMR (400 MHz, METHANOL-d4) δ=9.20 (s, 1H), 7.72 (d, J=5.0 Hz, 1H), 7.52 (s, 1H), 7.38 (d, J=5.0 Hz, 1H), 5.72 (d, J=3.8 Hz, 1H), 2.86 (br s, 1H), 2.59 (dt, J=3.1, 12.4 Hz, 1H), 2.28-2.09 (m, 2H), 1.69-1.57 (m, 1H), 1.51-1.29 (m, 4H), 0.89 (dq, J=4.1, 12.2 Hz, 1H).

Example 102: ¹H NMR (400 MHz, METHANOL-d4) δ=9.20 (s, 1H), 7.72 (d, J=5.0 Hz, 1H), 7.52 (s, 1H), 7.38 (d, J=5.0 Hz, 1H), 5.72 (d, J=3.8 Hz, 1H), 2.86 (br s, 1H), 2.59 (ddd, J=3.5, 8.8, 15.7 Hz, 1H), 2.28-2.10 (m, 2H), 1.68-1.55 (m, 1H), 1.52-1.29 (m, 4H), 0.89 (dq, J=4.1, 12.1 Hz, 1H).

Component IV was separated by chiral separation ("AD_3_EtOH_DEA_5_40_25 ML Vial: 1:D, 8, Channel Name: PDA Ch1 220 nm@4.8 nm—Compens. Injection Volume: 1.00 µL, Proc. Chnl. Descr.: PDA Ch1 220 nm@ 4.8 nm—Compens. Run Time: 10.0 min"), and purified by acidic preparative chromatography, to finally give Example 103 (trifluoroacetate, 12.00 mg, 29.67 µmol, SFC RT=5.037 min, ee=67.24%), and Example 104 (trifluoroacetate, 12.00 mg, 29.67 µmol, RT=5.626 min, ee=96.00%).

Example 103: ¹H NMR (400 MHz, METHANOL-d4) δ=9.17 (s, 1H), 7.72 (d, J=5.0 Hz, 1H), 7.53 (s, 1H), 7.39 (d, J=5.0 Hz, 1H), 5.72 (d, J=3.8 Hz, 1H), 2.72-2.57 (m, 2H), 2.17 (br d, J=13.1 Hz, 1H), 1.94 (br d, J=12.0 Hz, 1H), 1.85-1.74 (m, 1H), 1.61-1.27 (m, 4H), 0.92 (dt, J=4.8, 12.7 Hz, 1H).

Example 104: ¹H NMR (400 MHz, METHANOL-d4) δ=9.16 (s, 1H), 7.72 (d, J=5.0 Hz, 1H), 7.53 (s, 1H), 7.38 (d, J=5.0 Hz, 1H), 5.71 (d, J=3.8 Hz, 1H), 2.72-2.53 (m, 2H), 2.17 (br d, J=13.1 Hz, 1H), 1.94 (br d, J=12.0 Hz, 1H), 1.84-1.75 (m, 1H), 1.57-1.31 (m, 4H), 0.92 (dt, J=4.8, 12.7 Hz, 1H).

Examples 105 to 106: 8-[2-(4-fluorotetrahydropyran-4-yl)ethyl]-8H-thieno[3,4]pyrrolo[1,5-a]imidazole

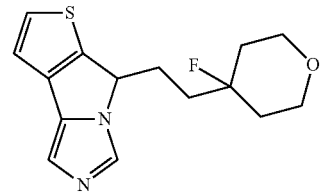 [SMILES: FC1(CCC2c3sccc3-c3cncn32)CCOCC1]

A solution of the racemic mixture (100.00 mg, 344.38 µmol) of Example 28 and Example 29 in dichloromethane (1 mL) was slowly added dropwise to a solution of (diethylamino)difluorosulfide tetrafluoroborate (473.18 mg, 2.07 mmol) in dichloromethane (1.00 mL), and then triethylamine hydrogen fluoride (166.55 mg, 1.03 mmol) was added thereto. After the reaction solution was stirred at 20° C. for 16 h, the reaction solution was added with 20 mL of water and extracted with dichloromethane (20 mL×3). The combined organic phase was washed with 50 mL of saturated brine, dried over anhydrous sodium sulfate, filtered under suction, and evaporated under reduced pressure. The crude product was purified by column chromatography to give the title compound (28.00 mg, 95.77 µmol, yield of 27.81%). ¹H NMR (400 MHz, METHANOL-d4) δ=8.14 (br s, 1H), 7.57 (d, J=4.8 Hz, 1H), 7.24 (d, J=4.8 Hz, 1H), 7.00 (br s, 1H), 5.53 (br t, J=5.5 Hz, 1H), 3.79-3.61 (m, 4H), 2.39-2.27 (m, 1H), 2.20-2.10 (m, 1H), 1.77-1.70 (m, 3H), 1.69-1.44 (m, 3H).

The racemate was subjected to chiral separation (mobile phase: A: CO₂ B: ethanol (0.05% DEA); gradient: from 5% to 40% of B in 4.5 min and hold 40%, for 2.5 min, then 5% of B for 1 min; flow rate: 2.8 mL/min; column temperature: 40° C.), to finally give Example 105 (0.11 g, 369.29 µmol, SFC RT=3.131 min, ee=98.1%) and Example 106 (0.1 g, 337.51 µmol, SFC RT=3.488 min, ee=99.3%).

Example 105: ¹H NMR (400 MHz, METHANOL-d4) δ=7.91 (s, 1H), 7.54 (d, J=5.0 Hz, 1H), 7.21 (d, J=5.0 Hz, 1H), 6.89 (s, 1H), 5.47 (t, J=5.6 Hz, 1H), 3.79-3.72 (m, 2H), 3.71-3.63 (m, 2H), 2.35-2.24 (m, 1H), 2.19-2.07 (m, 1H), 1.77-1.70 (m, 3H), 1.69-1.41 (m, 3H).

Example 106: ¹H NMR (400 MHz, METHANOL-d4) δ=8.02 (s, 1H), 7.55 (d, J=5.0 Hz, 1H), 7.22 (d, J=5.0 Hz, 1H), 6.94 (s, 1H), 5.50 (t, J=5.6 Hz, 1H), 3.78-3.71 (m, 2H), 3.70-3.57 (m, 2H), 2.31 (tdd, J=4.9, 11.8, 13.7 Hz, 1H), 2.19-2.08 (m, 1H), 1.77-1.69 (m, 3H), 1.69-1.42 (m, 3H).

Examples 107 to 110: (trans)-2-(-8H-thieno[3',2':3,4]pyrrolo[1,2-c]imidazol-8-yl)cyclopentanol Example 107A: ethyl (trans)-2-hydroxycyclopentanecarboxylate, ethyl (cis)-2-hydroxycyclopentanecarboxylate

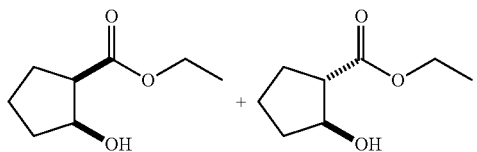

Sodium borohydride (6.06 g, 160.07 mmol) was added portionwise into a solution of ethyl 2-cyclopentanonecarboxylate (50.00 g, 320.14 mmol) in ethanol (500 mL) at 0° C., and stirred at 0° C. for 1 hour. The reaction solution was quenched with water (200 mL) at 0° C. and allowed to separate. The aqueous layer was extracted with dichloromethane, and the resulting organic layers combined were washed with brine, dried and concentrated under reduced pressure to give a residue. The residue was purified by column chromatography to give the title compounds of cis-Example 107A (colorless oil, 17.00 g, 107.47 mmol, yield of 33.57%) and trans-Example 107A (colorless oil, 17.00 g, 107.47 mmol, yield of 33.57%).

Cis-Example 107A: $^1$H NMR (400 MHz, CHLOROFORM-d) δ=5.30 (s, 1H), 4.43 (quin, J=3.5 Hz, 1H), 4.22-4.14 (m, 2H), 3.12 (d, J=2.8 Hz, 1H), 2.67 (dt, J=4.4, 9.3 Hz, 1H), 2.05-1.86 (m, 3H), 1.82-1.73 (m, 2H), 1.69-1.56 (m, 1H), 1.32-1.23 (m, 3H).

Trans-Example 107A: $^1$H NMR (400 MHz, CHLOROFORM-d) δ=4.40-4.32 (m, 1H), 4.15 (q, J=7.3 Hz, 2H), 2.65 (dt, J=6.4, 8.6 Hz, 1H), 2.37 (s, 1H), 2.09-1.93 (m, 2H), 1.86-1.56 (m, 4H), 1.26 (t, J=7.2 Hz, 3H).

Example 107B: ethyl (trans)-2-((tert-butyldimethylsilyl)oxy)cyclopentanecarboxylate

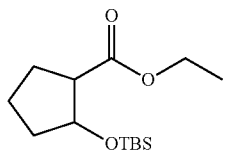 [SMILES: CCOC(=O)C1CCCC1O[Si](C)(C)C(C)(C)C]

At 0° C., 2,6-dimethylpyridine (9.14 g, 85.34 mmol, 9.93 mL) and tert-butyldimethylsily trifluoromethylsulfonate (18.05 g, 68.27 mmol, 15.70 mL) were successively added dropwise into a solution of ethyl (trans)-2-hydroxycyclopentanecarboxylate (9.00 g, 56.89 mmol) in dichloromethane (100 mL), and the reaction solution was stirred at room temperature for 2 h. The reaction solution was washed with water, dried and concentrated under reduced pressure to give a residue. The residue was purified by column chromatography to give the title compound (yellow oil, 13.50 g, 49.55 mmol, yield of 87.10%). $^1$H NMR (400 MHz, CHLOROFORM-d) δ=4.39 (q, J=5.8 Hz, 1H), 4.13 (q, J=7.2 Hz, 2H), 2.66 (dt, J=5.5, 8.3 Hz, 1H), 2.07-1.94 (m, 1H), 1.92-1.82 (m, 1H), 1.82-1.63 (m, 3H), 1.62-1.52 (m, 1H), 1.27 (t, J=7.2 Hz, 3H), 0.90-0.85 (m, 9H), 0.06-0.02 (m, 6H).

Example 107C: (trans)-2-((tert-butyldimethylsilyl)oxy)cyclopentanecarboxaldehyde

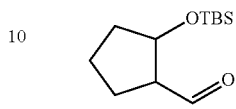

Diisobutylaluminum hydride (1 M, 74.69 mL) was added dropwise into a solution of ethyl (trans)-2-((tert-butyldimethylsilyl)oxy)cyclopentanecarboxylate (18.50 g, 67.90 mmol) in dichloromethane (200 mL) at −65° C. The reaction solution was stirred at −65° C. for 2 h. The reaction solution was quenched with saturated sodium potassium tartrate solution (100 mL) at 0° C., and separated. The aqueous layer was extracted with ethyl acetate, and the resulting organic phase combined was dried over anhydrous sodium sulfate, filtered and evaporated to give a residue. The residue was purified by column chromatography to give the title compound (colorless oil, 11.00 g, 48.16 mmol, yield of 70.93%). $^1$H NMR (400 MHz, METHANOL-d$_4$) δ=9.64 (d, J=2.3 Hz, 1H), 4.50 (q, J=5.4 Hz, 1H), 2.74-2.65 (m, 1H), 1.99-1.88 (m, 1H), 1.88-1.74 (rm, 3H), 1.69-1.55 (m, 2H), 0.91-0.87 (m, 9H), 0.08 (d, J=3.3 Hz, 6H).

Example 107D: (trans)-(3-bromothiophen-2-yl)(2-((tert-butyldimethylsilyl)oxy)cyclopentyl)methanol

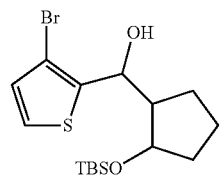 [SMILES: CC(C)(C)[Si](C)(C)OC1CCCC1C(O)c1sccc1Br]

n-Butyllithium (2.5 M, 21.19 mL) was added dropwise into a solution of diisopropylamine (5.85 g, 57.79 mmol, 8.13 mL) in methyl tert-butyl ether (100 mL) at 0° C. After 1 hour, 3-bromothiophene (8.64 g, 52.98 mmol, 4.97 mL) and (trans)-2-((tert-butyldimethylsilyl)oxy)cyclopentanecarboxaldehyde (11.00 g, 48.16 mmol) were added. The reaction mixture was stirred at 0° C. for an additional 1 hour. The reaction solution was quenched with saturated ammonium chloride solution (100 mL) and separated. The aqueous layer was extracted with ethyl acetate, and the resulting organic layers combined were dried, filtered and concentrated under reduced pressure. The residue was purified by column chromatography to give the title compound (brown oil, 8.50 g, 21.71 mmol, yield of 45.09%). $^1$H NMR (400 MHz, METHANOL-d$_4$) δ=7.36 (d, J=5.3 Hz, 1H), 6.91 (d, J=5.3 Hz, 1H), 4.97 (d, J=5.8 Hz, 1H), 4.10 (q, J=5.3 Hz, 1H), 2.20-2.11 (m, 1H), 1.89-1.79 (m, 1H), 1.78-1.59 (m, 4H), 1.58-1.49 (m, 1H), 0.90-0.84 (m, 9H), −0.02 (d, J=8.0 Hz, 5H).

187

Example 107E: (trans)-1-((3-bromothiophen-2-yl) (2-((tert-butyldimethylsilyl)oxy) cyclopentyl) methyl)-1H-imidazole

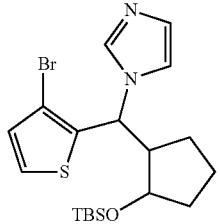 [SMILES: CC(C)(C)[Si](C)(C)OC1CCCC1C(c1sccc1Br)n1ccnc1]

(Trans)-(3-bromothiophen-2-yl)(2-((tert-butyldimethylsilyl)oxy)cyclopentyl)methanol (9.20 g, 23.50 mmol), N,N-carbonyldiimidazole (7.62 g, 47.01 mmol) and imidazole (4.8 g, 70.51 mmol) were dissolved in acetonitrile, and the reaction mixture was stirred at 85° C. for 12 h. The reaction mixture was filtered, washed with brine, dried over anhydrous sodium sulfate, filtered, and concentrated under reduced pressure to give a residue. The residue was purified by column chromatography to give the title compound (8.20 g, 18.57 mmol, yield of 79.03%). ¹H NMR (400 MHz, METHANOL-d₄) δ=7.84 (s, 1H), 7.53 (d, J=5.5 Hz, 1H), 7.28 (s, 1H), 7.02-6.99 (m, 1H), 6.98-6.95 (m, 1H), 5.44 (d, J=11.5 Hz, 1H), 3.98 (td, J=3.0, 5.7 Hz, 1H), 2.88-2.79 (m, 1H), 1.97-1.87 (m, 1H), 1.87-1.76 (m, 2H), 1.74-1.62 (m, 2H), 1.23-1.15 (m, 1H), 0.82 (s, 8H), −0.05--0.10 (m, 3H), −0.21 (s, 3H).

Example 107F: (trans)-8-(2-((tert-butyldimethylsilyl)oxy)cyclopentyl)-8H-thieno[3',2':3,4]pyrrolo[1,2-c]imidazole

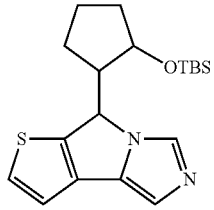 [SMILES: CC(C)(C)[Si](C)(C)OC1CCCC1C1c2sccc2-c2cncn21]

A mixture solution of (trans)-1-((3-bromothiophen-2-yl) (2-((tert-butyldimethylsilyl)oxy)cyclopentyl)methyl)-1H-imidazole (8.20 g, 18.57 mmol), palladium acetate (416.98 mg, 1.86 mmol), potassium carbonate (5.13 g, 37.14 mmol) and bis(1-adamantyl)-butyl-phosphine (1.33 g, 3.71 mmol) in toluene (100.00 mL) was heated to 115° C. with stirring for 16 h. The reaction mixture solution was filtered and concentrated under reduced pressure to remove toluene. The residue was washed with brine, dried over anhydrous sodium sulfate, filtered, and concentrated under reduced pressure to give a residue. The residue was purified by column chromatography to give the title compound (5.50 g, 15.10 mmol, yield of 81.31%). ¹H NMR (400 MHz, METHANOL-d₄) δ=7.85 (s, 1H), 7.52 (d, J=5.0 Hz, 1H), 7.23 (d, J=4.8 Hz, 1H), 6.88 (s, 1H), 5.46 (d, J=4.0 Hz, 1H), 3.72 (q, J=5.0 Hz, 1H), 2.74 (tt, J=4.5, 9.0 Hz, 1H), 2.11-2.03 (m, 1H), 1.92-1.72 (m, 2H), 1.72-1.56 (m, 3H), 0.84-0.79 (m, 9H), −0.08--0.14 (m, 3H), −0.19--0.26 (m, 3H).

188

Preparation of the Title Compounds (Examples 107 to 110): (trans)-2-(8H-thieno[3',2':3,4]pyrrolo[1,2-c] imidazol-8-yl)cyclopentanol (Trans)-8-(2-((tert-butyldimethylsilyl)oxy)cyclopentyl)-8H-thieno[3',2':3,4]pyrrolo[1,2-c]imidazole (5.50 g, 15.25 mmol) and p-toluenesulfonic acid monohydrate (8.70 g, 45.76 mmol) were dissolved in 1,2-dichloroethane (100 mL), and the reaction mixture solution was stirred at 85° C. for 12 h. The reaction solution was quenched with saturated sodium hydrogen carbonate solution (100 mL). The reaction solution was allowed to separate, and the aqueous layer was extracted with ethyl acetate. The resulting organic phase combined was dried over anhydrous sodium sulfate, filtered, and concentrated under reduced pressure to give a residue. The residue was purified by column chromatography to give the title compound (2.10 g, 8.46 mmol, yield of 55.48%). ¹H NMR (400 MHz, DMSO-d₆) δ=7.91-7.81 (m, 1H), 7.65-7.60 (m, 1H), 7.28-7.21 (m, 1H), 6.85-6.81 (m, 1H), 5.50 (d, J=4.8 Hz, 1H), 4.78 (br d, J=4.5 Hz, 1H), 3.92-3.85 (m, 1H), 2.38-2.28 (m, 1H), 1.70-1.53 (m, 3H), 1.51-1.39 (m, 2H), 1.06-0.96 (m, 1H).

The racemate (900.00 mg, 3.65 mmol) was subjected to chiral separation (chiral column: Lux Cellulose-2 150×4.6 mm I.D., 3 μm; mobile phase: A: carbon dioxide B: methanol (0.05% diethylamine); gradient: from 5% to 40% of B for 5.5 min and hold for 40% for 3 min, then 5% of B for 1.5 min; flow rate: 2.5 mL/min; column temperature: 40° C.), to give Example 107 (300.00 mg, 1.19 mmol, yield of 32.51%, retention time=6.106 min), Example 108 (300.00 mg, 1.21 mmol, yield of 33.06%, retention time=6.470 min), Example 109 (100.00 mg, 404.58 μmol, yield of 11.08%, retention time=6.838 min) and Example 110 (100.00 mg, 398.69 μmol, yield of 10.92%, retention time=8.760 min).

Example 107: ¹H NMR (WXFL10310308_001, 400 MHz, DMSO-d₆) δ=7.83 (s, 1H), 7.62 (d, J=5.0 Hz, 1H), 7.23 (d, =5.0 Hz, 1H), 6.84 (s, 1H), 5.50 (d, J=4.8 Hz, 1H), 4.79 (d, J=4.8 Hz, 1H), 3.88 (quin, J=5.3 Hz, 1H), 2.37-2.29 (m, 1H), 1.69-1.53 (m, 3H), 1.52-1.41 (m, 2H), 1.06-0.94 (m, 1H).

Example 108: ¹H NMR (WXFL10310309_001, 400 MHz, DMSO-d₆) δ=7.83 (s, 1H), 7.63 (d, J=5.3 Hz, 1H), 7.23 (d, J=5.0 Hz, 1H), 6.84 (s, 1H), 5.51 (d, J=5.0 Hz, 1H), 4.79 (d, J=4.8 Hz, 1H), 3.88 (quin, J=5.3 Hz, 1H), 2.38-2.30 (m, 1H), 1.70-1.55 (m, 3H), 1.52-1.42 (m, 2H), 1.06-0.96 (m, 1H).

Example 109: ¹H NMR (WXFL10310310_001, 400 MHz, DMSO-d₆) δ=7.90 (s, 1H), 7.64 (d, J=4.8 Hz, 1H), 7.27 (d, J=5.0 Hz, 1H), 6.82 (s, 1H), 5.51 (d, J=5.5 Hz, 1H), 5.10 (d, J=4.8 Hz, 1H), 4.14-4.06 (m, 1H), 2.45-2.37 (m, 1H), 1.84-1.76 (m, 1H), 1.60-1.48 (m, 2H), 1.46-1.32 (m, 2H), 0.85-0.75 (m, 1H).

Example 110: ¹H NMR (WXFL10310311_001, 400 MHz, DMSO-d₆) δ=7.90 (s, 1H), 7.64 (d, J=5.0 Hz, 1H), 7.26 (d, J=5.0 Hz, 1H), 6.82 (s, 1H), 5.51 (d, J=5.5 Hz, 1H), 5.10 (d, J=4.8 Hz, 1H), 4.13-4.06 (m, 1H), 2.46-2.38 (m, 1H), 1.84-1.76 (m, 1H), 1.60-1.49 (m, 2H), 1.46-1.33 (m, 2H), 0.86-0.74 (m, 1H).

Examples 111 to 114: 1-(3,3-difluorocyclobutyl)-2-(8H-thieno[3',2':3,4] pyrrolo[1,2-c]imidazol-8-yl)ethanol Example 111A: 3,3-difluoro-N-methoxy-N-methyl-cyclobutylcarboxamide

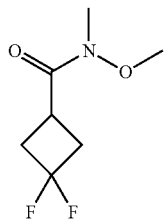

HOBt (59.57 g, 440.85 mmol), EDCl (14.09 g, 73.48 mmol) and triethylamine (178.44 g, 1.76 mmol, 244.44 mL) were added portionwise to a solution of 3,3-difluorocyclobutylcarboxylic acid (40.00 g, 293.90 mmol) in dichloromethane (50 mL). The reaction solution was stirred at 20° C. for half an hour. N-methoxymethylamine (43.00 g, 440.85 mmol, hydrochloride) was then added slowly. The reaction solution was stirred at 20° C. for 12 h. The reaction was quenched with saturated brine (600 mL), and the organic phase was dried over anhydrous sodium sulfate, filtered and distilled. The residue was purified by column chromatography to give the title compound (38.00 g, yield of 72.17%), as a yellow liquid. $^1$H NMR (400 MHz, CHLOROFORM-d) δ=3.70 (s, 3H), 3.28 (br d, J=7.8 Hz, 1H), 3.23 (s, 3H), 3.02-2.81 (m, 1H), 3.02-2.81 (m, 1H), 2.80-2.63 (m, 2H).

Example 111B: 1-(3,3-difluorocyclobutyl)but-3-en-1-one

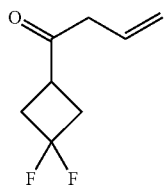

Under protection of nitrogen gas, 3,3-difluoro-N-methoxy-N-methylcyclobutylcarboxamide (15 g, 83.72 mmol) was dissolved in tetrahydrofuran (150 mL), which was added with allylmagnesium bromide (1 mol/L, 167.44 mL) at −70° C. The reaction mixture was stirred at −70° C. for 1 h. The reaction solution was quenched with water (150 mL), and extracted with ethyl acetate (100 mL×3). The combined organic phase was dried over anhydrous sodium sulfate, filtered and distilled to give a residue. The residue was purified by column chromatography to give the title compound (13 g, yield of 97%), as a yellow liquid. $^1$H NMR (400 MHz, CHLOROFORM-d) δ=5.90 (tdd, J=7.0, 10.2, 17.2 Hz, 1H), 5.27-5.18 (m, 2H), 3.26-3.19 (m, 2H), 3.14 (dquin, J=2.4, 8.6 Hz, 1H), 2.90-2.62 (m, 1H), 2.90-2.62 (m, 3H).

Example 111C: 1-(3,3-difluorocyclobutyl)but-3-en-1-ol

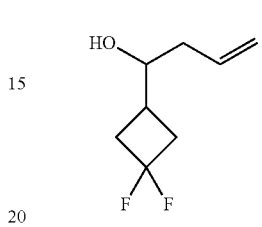

1-(3,3-Difluorocyclobutyl)but-3-en-1-one (1.7 g, 10.61 mmol) was dissolved in methanol (10 mL), and sodium borohydride (401.4 mg, 10.61 mmol) was slowly added thereto. The reaction mixture was stirred at 20° C. for 15 min. The reaction solution was quenched with water (50 mL), and extracted with ethyl acetate (30 mL×3). The combined organic phase was washed with saturated brine (50 mL), dried over anhydrous sodium sulfate and filtered. The organic phase was further concentrated to give the title compound (1.5 g, crude), as yellow oil, which was directly used in the next step without further purification. $^1$H NMR (400 MHz, CHLOROFORM-d) δ=5.73 (dddd, J=6.4, 8.0, 10.4, 16.8 Hz, 1H), 5.17-5.02 (m, 2H), 3.56 (tt, J=3.6, 7.4 Hz, 1H), 2.59-2.41 (m, 3H), 2.40-2.07 (m, 3H), 2.05-1.94 (m, 1H), 1.60 (d, J=4.0 Hz, 1H).

Example 111D: tert-butyl((1-(3,3-difluorocyclobutyl)but-3-en-1-yl)oxy)dimethylsilane

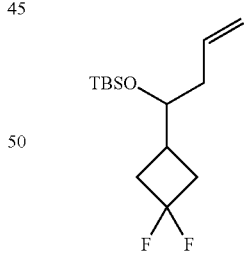

1-(3,3-Difluorocyclobutyl)but-3-en-1-ol (1.5 g, 9.25 mmol) was dissolved in dichloromethane (30 mL), which was added with 2,6-dimethylpyridine (1.49 g, 13.87 mmol). TBSOTf (2.93 g, 11.1 mmol) was added at 0° C. After stirring at 20° C. for 2 h, the reaction solution was concentrated. The residue was purified by column chromatography to give the title compound (2 g, 7.23 mmol), as a yellow liquid. $^1$H NMR (400 MHz, CHLOROFORM-d) δ=5.97-5.51 (m, 1H), 5.11-4.84 (m, 2H), 3.81-3.48 (m, 1H), 2.59-2.00 (m, 8H), 0.84 (s, 9H), 0.01 (d, J=7.3 Hz, 6H).

Example 111E: 3-((tert-butyldimethylsilyl)oxy)-3-(3,3-difluorocyclobutyl)propionaldehyde

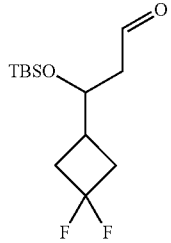

tert-Butyl((1-(3,3-difluorocyclobutyl)but-3-en-1-yl)oxy)dimethylsilane (2 g, 7.23 mmol) was dissolved in dichloromethane (10 mL) and methanol (10 mL), and ozone was introduced at −70° C. and 15 Psi until the reaction solution turned blue. Nitrogen gas was then introduced for another 5 min. Dimethyl sulfide (4.49 g, 72.3 mmol) was added at −70° C., followed by stirring at 20° C. for 16 h. The reaction mixture was concentrated, and the residue was purified by column chromatography to give the title compound (1.78 g, yield of 88.43%), as a yellow liquid. $^1$H NMR (400 MHz, CHLOROFORM-d) δ=9.72 (t, J=2.1 Hz, 1H), 4.20-4.00 (m, 1H), 2.68-2.01 (m, 8H), 0.82 (s, 9H), 0.01 (d, J=7.5 Hz, 6H).

Example 111F: 1-(3-bromothiophen-2-yl)-3-((tert-butyldimethylsilyl)oxy)-3-(3,3-difluorocyclobutyl)propan-1-ol

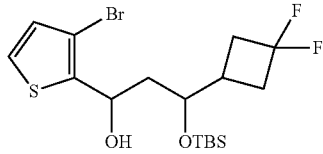 [SMILES: CC(C)(C)[Si](C)(C)OC(CC(O)c1sccc1Br)C1CC(F)(F)C1]

Under protection of nitrogen gas, n-butyllithium (2.5 mol/L, 2.81 mL) was slowly added dropwise to a solution of diisopropylamine (775.92 mg, 7.67 mmol) in tert-butyl methyl ether (10 mL) at −70° C. After stirring at 0° C. for 1 h, tribromothiophene (1.04 g, 6.39 mmol) was dissolved in tert-butyl methyl ether (10 mL), which was then slowly added to the reaction solution. After stirring at 0° C. for 1 h, a sultion of 3-((tert-butyldimethylsilyl)oxy)-3-(3,3-difluorocyclobutyl)propionaldehyde (1.78 g, 6.39 mmol) in tert-butyl methyl ether (10 mL) was further added to the reaction mixture. After stirring at 0° C. for 1 h, the reaction mixture was quenched with aqueous ammonium chloride solution (100 mL), and extracted with ethyl acetate (50 mL) three times. After washing once with saturated brine (100 mL), the combined organic phase was dried, filtered, and concentrated to give the title compound (2.8 g, crude) as yellow oil, which was used directly in the next step without further purification. $^1$H NMR (400 MHz, CHLOROFORM-d) δ=7.25 (dd, J=3.8, 5.3 Hz, 1H), 6.97-6.90 (m, 1H), 5.38-5.06 (m, 1H), 4.07-3.92 (m, 1H), 2.76-2.40 (m, 5H), 2.01-1.75 (m, 2H), 0.97-0.92 (m, 9H), 0.22-0.09 (m, 6H).

Example 111G: 1-(1-(3-bromothiophen-2-yl)-3-((tert-butyldimethylsilyl)oxy)-3-(3,3-difluorocyclobutyl)propyl)-1H-imidazole

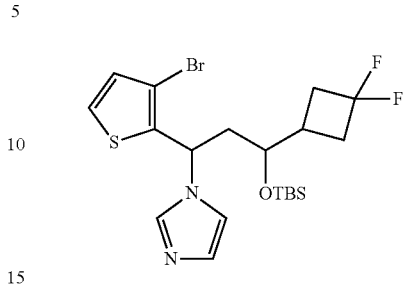

1-(3-Bromothiophen-2-yl)-3-((tert-butyldimethylsilyl)oxy)-3-(3,3-difluorocyclobutyl)propan-1-ol (2.8 g, 6.34 mmol) was dissolved in acetonitrile (30 mL), and imidazole (1.29 g, 19.02 mmol) and carbonyldiimidazole (2.06 g, 12.68 mmol) were added thereto. After stirred at 90° C. for 16 h, the reaction was quenched with water (100 mL). The organic phase was dried, filtered and concentrated. The concentrate was purified by column chromatography to give the title compound (2 g, yield of 64.18%), as yellow oil. $^1$H NMR (400 MHz, CHLOROFORM-d) δ=7.65 (d, J=11.8 Hz, 1H), 7.31 (t, J=5.1 Hz, 1H), 7.10 (s, 1H), 7.05-6.90 (m, 2H), 5.83-5.62 (m, 1H), 3.59 (t, J=5.8 Hz, 1H), 2.62-2.08 (m, 7H), 0.94 (d, J=3.8 Hz, 9H), 0.14--0.02 (m, 6H).

Example 111H: 8-(2-((tert-butyldimethylsilyl)oxy)-2-(3,3-difluorocyclobutyl)ethyl)-8H-thieno[3',2':3,4]pyrrolo[1,2-c]imidazole

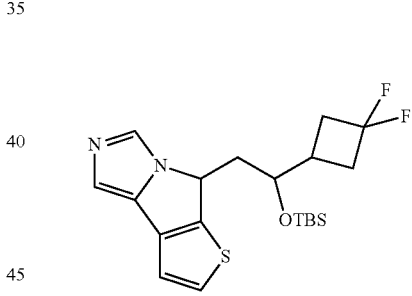

1-(1-(3-Bromothiophen-2-yl)-3-((tert-butyldimethylsilyl)oxy)-3-(3,3-difluorocyclobutyl)propyl)-1H-imidazole (2 g, 4.07 mmol), palladium acetate (91.38 mg, 407.00 μmol), bis(1-adamantyl)-butyl-phosphate (291.85 mg, 814.00 μmol) and potassium carbonate (1.13 g, 8.14 mmol) were added to xylene (40 mL). Under protection of nitrogen gas, the solution was warmed up to 140° C. with stirring for 16 h. The reaction solution was concentrated, quenched with water (100 mL) and extracted with ethyl acetate (100 mL×3). The combined organic phase was washed with brine (100 mL), dried, filtered and concentrated. The concentrate was purified by column chromatography to give the title compound (1.3 g, yield of 77.89%). $^1$H NMR (400 MHz, CHLOROFORM-d) δ=7.67 (d, J=7.5 Hz, 1H), 7.41-7.34 (m, 1H), 7.16 (dd, J=5.0, 10.0 Hz, 1H), 6.97 (s, 1H), 5.29-5.19 (m, 1H), 4.08-3.96 (m, 1H), 2.68-2.13 (m, 7H), 2.10-1.92 (m, 2H), 1.79 (ddd, J=3.5, 9.7, 13.6 Hz, 1H), 0.94 (d, J=6.3 Hz, 9H), 0.22-0.09 (m, 6H).

Preparation of the Title Compounds (Examples 111 to 114): 1-(3,3-difluorocyclobutyl)-2-(8H-thieno[3', 2':3,4]pyrrolo[1,2-c]imidazol-8-yl)ethanol

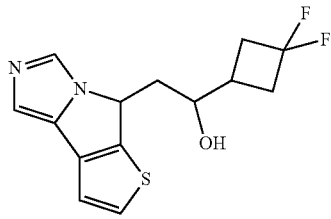 [SMILES: OC(CC1c2sccc2-c2cncn21)C1CC(F)(F)C1]

8-(2-((tert-Butyldimethylsilyl)oxy)-2-(3,3-difluorocyclobutyl)ethyl)-8H-thieno[3',2':3,4]pyrrolo[1,2-c]imidazole (1.3 g, 3.17 mmol) was dissolved in dichloromethane (20 mL) and p-toluenesulfonic acid monohydrate (1.81 g, 9.51 mmol) was added thereto. The reaction solution was stirred at 30° C. for 16 h. The reaction solution was adjusted to pH 9 with aqueous sodium carbonate solution, and then extracted with dichloromethane (30 mL×3). The combined organic phase was washed with brine (100 mL), dried, filtered and concentrated. The concentrate was purified by column chromatography to give the title compound (0.8 g, yield of 85.16%).

The racemate was subjected to chiral separation (column OD-3 100×4.6 mm I.D., 3 μm; mobile phase: A: carbon dioxide B: ethanol (0.05% diethanolamine); gradient: from 5% to 40% of B in 4.5 min and hold 40% for 2.5 min, then 5% of B for 1 min; flow rate: 2.8 mL/min; column temperature: 40° C.), to give Example 111 (85 mg, retention time=2.249 min), Example 112 (90 mg, retention time=2.367 min), Example 113 (100 mg, retention time=2.529 min) and Example 114 (110 mg, retention time=2.775 min).

Example 111: $^1$H NMR (400 MHz, DMSO-$d_6$) δ=7.88 (s, 1H), 7.61 (d, J=5.0 Hz, 1H), 7.22 (d, J=5.0 Hz, 1H), 6.84 (s, 1H), 5.53-5.31 (m, 2H), 3.89 (br dd, J=4.1, 9.7 Hz, 1H), 2.56 (br s, 2H), 2.48-2.31 (m, 2H), 2.16 (br d, J=4.0 Hz, 1H), 1.94-1.76 (m, 2H).

Example 112: $^1$H NMR (400 MHz, DMSO-$d_6$) δ=7.89 (s, 1H), 7.61 (d, J=5.0 Hz, 1H), 7.21 (d, J=4.8 Hz, 1H), 6.84 (s, 1H), 5.53-5.34 (m, 2H), 3.89 (br dd, J=4.0, 9.5 Hz, 1H), 2.55 (br s, 2H), 2.41 (br d, J=7.5 Hz, 2H), 2.16 (br d, J=4.8 Hz, 1H), 1.92-1.75 (m, 2H).

Example 113: $^1$H NMR (400 MHz, DMSO-$d_6$) δ=7.90 (s, 1H), 7.64 (d, J=5.0 Hz, 1H), 7.26 (d, J=5.0 Hz, 1H), 6.84 (s, 1H), 5.53-5.36 (m, 2H), 3.79 (br s, 1H), 2.53-2.53 (m, 1H), 2.63-2.52 (m, 1H), 2.45 (br s, 2H), 2.24-2.06 (m, 2H), 1.61 (ddd, J=2.6, 10.0, 13.2 Hz, 1H).

Example 114: $^1$H NMR (400 MHz, DMSO-$d_6$) δ=7.90 (s, 1H), 7.64 (d, J=4.8 Hz, 1H), 7.26 (d, J=5.0 Hz, 1H), 6.84 (s, 1H), 5.50-5.37 (m, 2H), 3.80 (br dd, J=3.0, 9.5 Hz, 1H), 2.64-2.52 (m, 2H), 2.46-2.28 (m, 2H), 2.24-2.07 (m, 2H), 1.61 (ddd, J=2.8, 10.0, 13.1 Hz, 1H).

Examples 115 to 118: 4-(8H-thieno[3,4]pyrrolo[1,5-a]imidazol-8-yl)cyclohexylmethanol Example 115A: ethyl 4-[tert-butyldimethylsilyl]oxy-cyclohexanecarboxylate

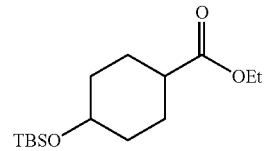 [SMILES: CCOC(=O)C1CCC(O[Si](C)(C)C(C)(C)C)CC1]

2,6-Dimethylpyridine (6.97 g, 65.03 mmol) and TBSOTf (12.89 g, 48.77 mmol) were added to a solution of ethyl 4-hydroxycyclohexanecarboxylate (5.60 g, 32.52 mmol) in DCM (50.00 mL) at 0° C. The mixture was stirred at 0° C. for 2 h. The reaction solution was diluted with DCM (200 mL), washed with water (30 mL×3) and brine (200 mL), dried over anhydrous sodium sulfate, filtered and evaporated. The residue was purified by column chromatography to give the title compound (colorless oil, 9.00 g, yield of 96.60%). $^1$H NMR (400 MHz, CHLOROFORM-d) δ=4.06 (dq, J=5.1, 7.2 Hz, 2H), 3.84 (br s, 0.5H), 3.56-3.45 (m, 0.5H), 2.28-2.11 (m, 1H), 1.98-1.79 (m, 3H), 1.64-1.54 (m, 2H), 1.48-1.36 (m, 2H), 1.31-1.24 (m, 1H), 1.20 (dt, J=3.0, 7.2 Hz, 3H), 0.83 (d, J=1.5 Hz, 9H), −0.01 (d, J=8.5 Hz, 6H).

Example 115B: 4-[tert-butyldimethylsilyl]oxy-cyclohexanecarboxaldehyde

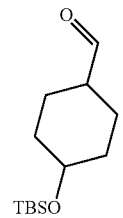

Under protection of nitrogen gas, DIBAL-H (1 M, 83.79 mL) was slowly added to a solution of ethyl 4-[tert-butyldimethylsilyl]oxy-cyclohexanecarboxylate (8.00 g, 27.93 mmol) in DCM (80.00 mL) at −78° C. The reaction solution was then stirred at −78° C. for 3 h. The reaction solution was quenched with saturated sodium potassium tartrate solution (100 mL), and extracted with DCM (50.00 mL×4). The combined organic phase was washed with brine (200 mL), dried over anhydrous sodium sulfate, filtered and concentrated. The concentrate was purified by column chromatography to give the title compound (colorless oil, 3.00 g, yield of 40.28%). $^1$H NMR (400 MHz, CHLOROFORM-d) δ=9.58 (d, J=8.0 Hz, 1H), 3.91-3.46 (m, 1H), 2.20-2.07 (m, 1H), 2.02-1.91 (m, 1H), 1.88-1.75 (m, 2H), 1.57-1.43 (m, 2H), 1.38-1.17 (m, 3H), 0.83 (d, J=3.0 Hz, 9H), 0.04-−0.06 (m, 6H).

Example 115C: 4-[tert-butyldimethylsilyl]oxy-cyclohexyl-(3-iodo-2-thienyl)methanol

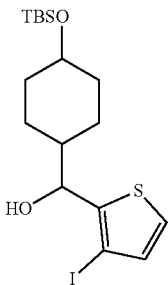

A solution of diisopropylamine (1.59 g, 15.71 mmol) in diethyl ether (15.00 mL) was cooled down to −78° C., then slowly added with n-butyllithium (2.5 M, 6.28 mL). After stirring at 0° C. for 30 min, 3-iodothiophene (3.00 g, 14.28 mmol) was added thereto at −78° C., with stirring at −78° C. for an additional 1.5 h. 4-[tert-Butyldimethylsilyl]oxy-cyclohexanecarboxaldehyde (3.00 g, 12.37 mmol) was further added, and the reaction mixture was stirred at −78° C. for 3 h. The reaction solution was added with ammonium chloride solution (30 mL) to quench, and then extracted with ethyl acetate (20 mL×4). The organic phase was washed with brine (50 mL), dried over anhydrous sodium sulfate, filtered and evaporated. The residue was purified by column chromatography to give the title compound (colorless oil, 2.50 g, yield of 38.69%). $^1$H NMR (400 MHz, CHLOROFORM-d) δ=7.24 (br d, J=4.8 Hz, 1H), 6.96 (d, J=5.0 Hz, 1H), 4.75-4.66 (m, 1H), 3.93-3.45 (m, 1H), 2.12-2.05 (m, 1H), 1.91-1.58 (m, 6H), 1.35-1.27 (m, 1H), 1.17-1.06 (m, 2H), 0.85-0.81 (m, 9H), 0.01--0.02 (m, 6H).

Example 115D: tert-butyl-[4-[imidazol-1-yl-(3-iodo-2-thienyl)methyl]cyclohexyloxy]-2-methylsilane

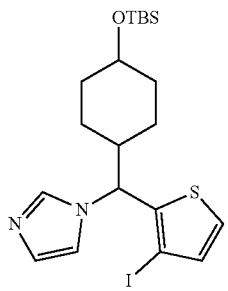 [SMILES: CC(C)(C)[Si](C)(C)OC1CCC(C(c2sccc2I)n2ccnc2)CC1]

CDI (4.48 g, 27.65 mmol) was added into a solution of 4-[tert-butyldimethylsilyl]oxy-cyclohexyl-(3-iodo-2-thienyl)methanol (2.50 g, 5.53 mmol) in acetonitrile (50.00 mL), and the reaction was stirred at 80° C. for 16 h. The reaction solution was added with ammonium chloride solution (30 mL) to quench, and extracted with ethyl acetate (20 mL×4). The combined organic phase was washed with brine (50 mL), dried over anhydrous sodium sulfate, filtered and evaporated. The residue was purified by column chromatography to give the title compound (yellow oil, 2.00 g, yield of 71.97%). $^1$H NMR (400 MHz, CHLOROFORM-d) δ=7.64 (d, J=13.6 Hz, 1H), 7.29 (t, J=5.0 Hz, 1H), 7.06-7.01 (m, 2H), 6.98 (dd, J=2.1, 5.1 Hz, 1H), 5.21-5.06 (m, 1H), 3.96-3.47 (m, 1H), 2.14-2.03 (m, 1H), 1.87-1.77 (m, 1H), 1.67-1.56 (m, 2H), 1.50-1.33 (m, 3H), 1.14-0.95 (m, 2H), 0.85 (d, J=13.6 Hz, 9H), 0.00 (d, J=1.5 Hz, 6H).

Example 115E: tert-butyl-dimethyl-[4-(8H-thieno[3,4]pyrrolo[1,5-a]imidazol-8-yl)-cyclohexyloxy]silane

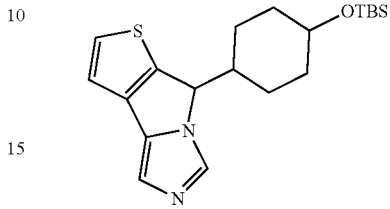

A mixture solution of tert-butyl-[4-[imidazol-1-yl-(3-iodo-2-thienyl)methyl]cyclohexyloxy]-2-methylsilane (1.80 g, 3.58 mmol), palladium acetate (80.42 mg, 358.19 μmol), tricyclohexylphosphine (200.89 mg, 716.38 μmol) and potassium carbonate (990.10 mg, 7.16 mmol) in o-xylene (5.00 mL) was purged with nitrogen gas three times, followed by stirring at 140° C. for 16 h. The reaction solution was diluted with water (30 mL) and filtered, and the filtrate was extracted with ethyl acetate (20 mL×4). The combined organic phase was washed with brine (50 mL), dried over anhydrous sodium sulfate, filtered and concentrated. The residue was purified by column chromatography to give the title compound (700.00 mg, yield of 52.21%). $^1$H NMR (400 MHz, CHLOROFORM-d) δ=7.64 (d, J=2.8 Hz, 1H), 7.32 (t, J=5.3 Hz, 1H), 7.11 (dd, J=1.5, 5.0 Hz, 1H), 6.91 (d, J=3.3 Hz, 1H), 5.05 (dd, J=4.3, 16.3 Hz, 1H), 4.00-3.38 (m, 1H), 1.99-1.71 (m, 4H), 1.51-1.05 (m, 5H), 0.99-0.80 (m, 9H), 0.04-0.07 (m, 6H).

Preparation of the Title Compounds (Examples 115 to 118): 4-(8H-thieno[3,4]pyrrolo[1,5-a]imidazol-8-yl)-cyclohexanol

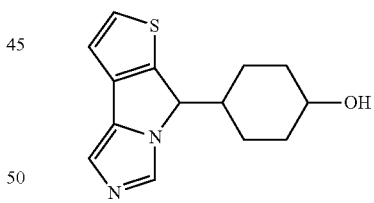

TsOH.H$_2$O (966.04 mg, 5.61 mmol) was added into a solution of tert-butyl-dimethyl-[4-(8H-thieno[3,4]pyrrolo[1,5-a]imidazol-8-yl)-cyclohexyloxy]silane (700.00 mg, 1.87 mmol) in dichloromethane (5.00 mL), and the mixture was stirred at 20° C. for 16 h. The reaction solution was diluted with dichloromethane (50 mL), washed with saturated NaHCO$_3$ solution (5 mL×3) and brine (30 mL), dried over anhydrous sodium sulfate, filtered and concentrated. The residue was purified by column chromatography to give the title compound (400.00 mg, yield of 74.64%). The racemate was subjected to chiral separation (column: Lux Cellulose-2 150×4.6 mm I.D., 3 μm; mobile phase: A: CO$_2$ B: methanol (0.05% DEA); gradient: from 5% to 40% of B in 5.5 min and hold 40% for 3 min, then 5% of B for 1.5 min; flow rate: 2.5 mL/min; column temperature: 40° C.), to give Example 115

(50.00 mg, yield of 12.41%) (retention time: 6.309 min), Example 116 (60.00 mg, yield of 14.96%) (retention time: 6.632 min), Example 117 (50.00 mg, yield of 12.45%) (retention time: 7.509 min) and Example 118 (50.00 mg, yield of 12.45%) (retention time: 7.935 min).

Example 115: $^1$H NMR (400 MHz, METHANOL-d4) δ=7.87 (s, 1H), 7.53 (d, J=5.0 Hz, 1H), 7.22 (d, J=5.0 Hz, 1H), 6.89 (s, 1H), 5.30 (d, J=4.3 Hz, 1H), 3.99 (br s, 1H), 2.24-2.10 (m, 1H), 1.95-1.83 (m, 1H), 1.78-1.45 (m, 5H), 1.33 (dq, J=3.9, 12.8 Hz, 1H), 1.07 (br d, J=13.3 Hz, 1H).

Example 116: $^1$H NMR (400 MHz, METHANOL-d4) δ=7.87 (s, 1H), 7.53 (d, J=5.0 Hz, 1H), 7.22 (d, J=5.0 Hz, 1H), 6.89 (s, 1H), 5.30 (d, J=4.3 Hz, 1H), 4.00 (br s, 1H), 2.24-2.10 (m, 1H), 1.95-1.83 (m, 1H), 1.78-1.45 (m, 5H), 1.33 (dq, J=3.9, 12.8 Hz, 1H), 1.07 (br d, J=13.3 Hz, 1H).

Example 117: $^1$H NMR (400 MHz, METHANOL-d4) δ=7.77 (s, 1H), 7.41 (d, J=5.0 Hz, 1H), 7.10 (d, J=5.0 Hz, 1H), 6.77 (s, 1H), 5.21 (d, J=4.0 Hz, 1H), 3.46-3.38 (m, 1H), 1.90-2.09 (m, 2H), 1.84-1.75 (m, 2H), 1.27-1.18 (m, 4H), 0.86-0.74 (m, 1H).

Example 118: $^1$H NMR (400 MHz, METHANOL-d4) δ=7.88 (s, 1H), 7.53 (d, J=5.0 Hz, 1H), 7.23 (d, J=5.0 Hz, 1H), 6.89 (s, 1H), 5.33 (d, J=4.0 Hz, 1H), 3.48-3.37 (m, 1H), 2.18-1.99 (m, 2H), 1.94-1.80 (m, 2H), 1.38-1.18 (m, 4H), 0.97-0.84 (m, 1H).

Examples 119 to 120: 1-cyclohexyl-2-methyl-2-(8H-thieno[3,4]pyrrolo[1,5-a]imidazol-8-yl)-propan-1-ol Example 119A: methyl 3-cyclohexyl-3-hydroxy-2,2-dimethyl-propionate

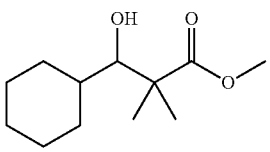

A solution of diisopropylamine (32.75 g, 323.63 mmol) in tetrahydrofuran (300.00 mL) was cooled down to −78° C., and then slowly added with n-butyllithium (2.5 M, 117.68 mL), followed by stirring at 0° C. for 30 min. Methyl 2-methylpropionate (30.05 g, 294.21 mmol) was then added thereto at −20° C., with stirring for 2.5 h. Cyclohexylcarboxaldehyde (11.00 g, 98.07 mmol) was further added, followed by stirring at 5° C. for 3 h. The reaction solution was added with ammonium chloride solution (200 mL) to quench, and extracted with ethyl acetate (100 mL×3). The combined organic phase was washed with brine (300 mL), dried over anhydrous sodium sulfate, filtered and evaporated. The residue was purified by column chromatography to give the title compound (colorless oil, 20.00 g, yield of 95.16%). $^1$H NMR (400 MHz, CHLOROFORM-d) δ=3.62 (s, 3H), 3.27 (dd, J=3.1, 8.7 Hz, 1H), 2.76 (d, J=8.8 Hz, 1H), 1.66 (br d, J=12.0 Hz, 2H), 1.56 (br d, J=11.8 Hz, 1H), 1.47-1.34 (m, 3H), 1.33-1.23 (m, 1H), 1.20 (s, 3H), 1.18-1.13 (m, 1H), 1.11 (s, 3H), 1.09-0.94 (m, 3H).

Example 119B: methyl 3-[tert-butyldimethylsilyl]oxy-3-cyclohexyl-3-hydroxy-2,2-dimethyl-propionate

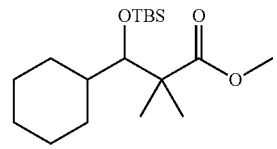 [SMILES: COC(=O)C(C)(C)C(O[Si](C)(C)C(C)(C)C)C1CCCCC1]

2,6-Dimethylpyridine (20.00 g, 186.66 mmol) and TBSOTf (37.01 g, 139.99 mmol) were added into a solution of methyl 3-cyclohexyl-3-hydroxy-2,2-dimethyl-propionate (20.00 g, 93.33 mmol) in DCM (200 mL), and the reaction solution was stirred at 0° C. for 2 h. The mixture solution was diluted with DCM (300 mL), washed with water (100 mL×3) and brine (200 mL), dried over anhydrous sodium sulfate, filtered and evaporated. The residue was purified by column chromatography to give the title compound (colorless oil, 27.00 g, yield of 88.05%). $^1$H NMR (400 MHz, CHLOROFORM-d) δ=3.66 (d, J=2.3 Hz, 1H), 3.62 (s, 3H), 1.70-1.55 (m, 4H), 1.46 (br d, J=9.3 Hz, 1H), 1.30-1.14 (m, 3H), 1.10 (d, J=15.3 Hz, 9H), 0.87 (s, 9H), 0.08 (s, 3H), 0.00 (s, 3H).

Example 119C: 3-[tert-butyldimethylsilyl]oxy-3-cyclohexyl-2,2-dimethyl-propan-1-ol

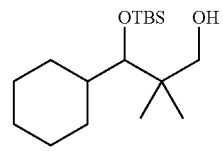 [SMILES: CC(C)(CO)C(O[Si](C)(C)C(C)(C)C)C1CCCCC1]

Under protection of nitrogen gas, DIBAL-H (1 M, 30.44 mL) was slowly added into a solution of methyl 3-[tert-butyldimethylsilyl]oxy-3-cyclohexyl-3-hydroxy-2,2-dimethyl-propionate (5.00 g, 27.93 mmol) in DCM (50.00 mL) at −78° C., and the reaction solution was stirred at −78° C. for 2 h. The reaction solution was quenched with saturated sodium potassium tartrate solution (50 mL) at −78° C., and extracted with ethyl acetate (30.00 mL×4). The combined organic phase was washed with brine (50 mL), dried over anhydrous sodium sulfate, filtered and concentrated. The residue was purified by column chromatography to give the title compound (colorless oil, 4.30 g, yield of 94.00%). $^1$H NMR (400 MHz, CHLOROFORM-d) δ=3.67 (d, J=10.8 Hz, 1H), 3.19-3.08 (m, 2H), 2.89 (br s, 1H), 1.71-1.59 (m, 3H), 1.59-1.42 (m, 3H), 1.38-1.09 (m, 5H), 0.97 (s, 3H), 0.83 (s, 9H), 0.68 (s, 3H), 0.02 (d, J=13.8 Hz, 6H).

Example 119D: 3-[tert-butyldimethylsilyl]oxy-3-cyclohexyl-2,2-dimethyl-propionaldehyde

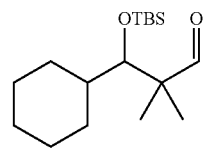

Under protection of nitrogen gas, a solution of (COCl)₂ (3.38 g, 26.62 mmol) in DCM (50.00 mL) was added into a solution of DMSO (4.16 g, 53.24 mmol) in DCM (50.00 mL) at −78° C. After stirring for 30 min, a solution of 3-[tert-butyldimethylsilyl]oxy-3-cyclohexyl-2,2-dimethyl-propan-1-ol (4.00 g, 13.31 mmol) in DCM (100.00 mL) was added thereto with stirring for 60 min, followed by adding triethylamine (12.12 g, 119.79 mmol). After stirring for 1 h, the reaction solution was quenched with water (200 mL) at −78° C. and extracted with DCM (50.00 mL×3). The combined organic phase was washed with water (100 mL×3) and brine (50 mL), dried over anhydrous sodium sulfate, filtered and concentrated. The residue was purified by column chromatography to give the title compound (colorless oil, 3.50 g, yield of 88.09%). ¹H NMR (400 MHz, CHLOROFORM-d) δ=9.60 (s, 1H), 3.51 (d, J=2.0 Hz, 1H), 1.73-1.62 (m, 2H), 1.57 (br d, J=12.0 Hz, 1H), 1.45-1.37 (m, 2H), 1.28-1.05 (m, 5H), 1.04-0.95 (m, 7H), 0.85 (s, 9H), 0.10-0.03 (m, 6H).

Example 119E: 3-[tert-butyldimethylsilyl]oxy-3-cyclohexyl-1-(3-iodo-2-thienyl)-2,2-dimethyl-propan-1-ol

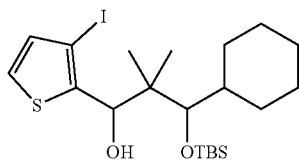 [SMILES: CC(C)(C(O)c1sccc1I)C(O[Si](C)(C)C(C)(C)C)C1CCCCC1]

A solution of diisopropylamine (1.59 g, 15.71 mmol) in diethyl ether (15.00 mL) was cooled down to −78° C., and slowly added with n-butyllithium (2.5 M, 6.28 mL), followed by stirring at 0° C. for 30 min. 3-Iodothiophene (3.00 g, 14.28 mmol) was then added thereto at −78° C., with stirring at −78° C. for 1.5 h. 3-[tert-Butyldimethylsilyl]oxy-3-cyclohexyl-2,2-dimethyl-propionaldehyde (3.41 g, 11.43 mmol) was further added, and the reaction mixture was stirred at −78° C. for 3 h. The reaction solution was added with ammonium chloride solution (50 mL) to quench, and extracted with ethyl acetate (20 mL×4). The organic phase was washed with brine (50 mL), dried over anhydrous sodium sulfate, filtered and concentrated. The residue was purified by column chromatography to give the title compound (colorless oil, 3.30 g, yield of 45.44%). ¹H NMR (400 MHz, CHLOROFORM-d) δ=7.30 (d, J=5.3 Hz, 1H), 7.04-6.89 (m, 1H), 5.43-5.06 (m, 1H), 3.58-3.30 (m, 1H), 2.07-1.62 (m, 6H), 1.53-1.22 (m, 6H), 1.18-1.12 (m, 3H), 1.02-0.96 (m, 9H), 0.80-0.66 (m, 3H), 0.27-0.13 (m, 6H).

Example 119F: tert-butyl-[1-cyclohexyl-3-imidazol-1-yl-3-(3-iodo-2-thienyl)-2,2-dimethyl-propoxy]-dimethyl-silane

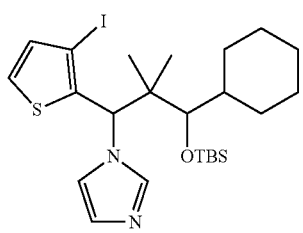 [SMILES: CC(C)(C(O[Si](C)(C)C(C)(C)C)C1CCCCC1)C(c1sccc1I)n1ccnc1]

CDI (5.26 g, 32.45 mmol) was added into a solution of 3-[tert-butyldimethylsilyl]oxy-3-cyclohexyl-1-(3-iodo-2-thienyl)-2,2-dimethyl-propan-1-ol (3.30 g, 6.49 mmol) in acetonitrile (50.00 mL), and the reaction was stirred at 80° C. for 16 h. The reaction solution was added with ammonium chloride solution (50 mL) to quenched, concentrated and then extracted with ethyl acetate (50 mL×3). The combined organic phase was washed with brine (100 mL), dried over anhydrous sodium sulfate, filtered and concentrated. The residue was purified by column chromatography to give the title compound (isomer 1, colorless oil, 1.20 g, yield of 33.13%; isomer 2, colorless oil, 1.15 g, yield of 31.74%).

Isomer 1: ¹H NMR (400 MHz, CHLOROFORM-d) δ=7.56 (s, 1H), 7.26 (d, J=5.3 Hz, 1H), 7.07-7.04 (m, 1H), 6.97-6.93 (m, 2H), 5.87 (s, 1H), 3.11 (d, J=1.3 Hz, 1H), 1.68 (br s, 3H), 1.58 (br s, 1H), 1.39-1.33 (m, 1H), 1.28-1.20 (m, 5H), 1.16-1.03 (m, 4H), 0.89-0.86 (m, 12H), 0.00 (s, 3H), −0.14 (s, 3H).

Isomer 2: ¹H NMR (400 MHz, CHLOROFORM-d) δ=7.57 (s, 1H), 7.33 (d, J=5.5 Hz, 1H), 7.01 (d, J=5.5 Hz, 1H), 6.97-6.91 (m, 2H), 5.64 (s, 1H), 3.31 (s, 1H), 1.66 (br d, J=8.5 Hz, 3H), 1.49-1.26 (m, 3H), 1.16 (s, 3H), 1.07-0.99 (m, 5H), 0.93 (s, 3H), 0.86 (s, 9H), 0.00 (s, 6H).

Example 119G: tert-butyl-[1-cyclohexyl-2-methyl-2-(8H-thieno[3,4]pyrrolo[1,5-a]imidazol 8 yl)]-dimethyl-silane

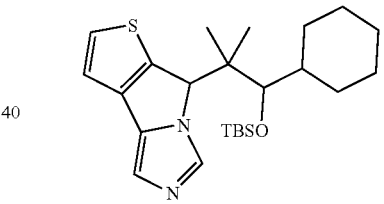

Palladium acetate (40.19 mg, 179.00 μmol), tricyclohexylphosphine (100.40 mg, 358.00 μmol), potassium carbonate (990.10 mg, 7.16 mmol) were added into a mixture solution of tert-butyl-[1-cyclohexyl-3-imidazol-1-yl-3-(3-iodo-2-thienyl)-2,2-dimethyl-propoxy]-dimethyl-silane (isomer 1) (1.00 g, 1.79 mmol) in o-xylene (15.00 mL), which was purged with nitrogen gas three times and then stirred at 140° C. for 16 h. The reaction solution was diluted with water (50 mL) and filtered, and the filtrate was extracted with ethyl acetate (20 mL×4). The combined organic phase was washed with brine (50 mL), dried over anhydrous sodium sulfate, filtered, and concentrated. The residue was purified by column chromatography to give the title compound (500 mg, yield of 54.00%). ¹H NMR (400 MHz, CHLOROFORM-d) δ=7.57 (br s, 1H), 7.23 (d, J=5.0 Hz, 1H), 7.04 (d, J=5.0 Hz, 1H), 6.86 (br s, 1H), 5.14 (s, 1H), 3.61 (s, 1H), 1.67 (br d, J=10.0 Hz, 4H), 1.42-1.28 (m, 3H), 1.14-1.00 (m, 4H), 0.97 (s, 3H), 0.86 (s, 9H), 0.69 (s, 3H), 0.10 (s, 3H), 0.00 (s, 3H), −0.05-−0.07 (m, 1H).

Preparation of the Title Compounds (Examples 119 to 120): 1-cyclohexyl-2-methyl-2-(8H-thieno[3,4]pyrrolo[1,5-a]imidazol-8-yl)-propan-1-ol

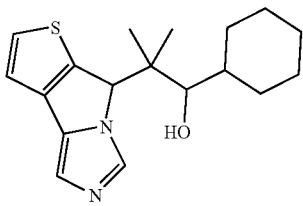 [SMILES: CC(C)(C(O)C1CCCCC1)C1c2sccc2-c2cncn21]

TsOH.H$_2$O (599.26 mg, 3.48 mmol) was added to a solution of tert-butyl-[1-cyclohexyl-2-methyl-2-(8H-thieno[3,4]pyrrolo[1,5-a]imidazol-8-yl)]-dimethyl-silane (500.00 mg, 1.16 mmol) in dichloromethane (5.00 mL), and the mixture was stirred at 20° C. for 24 h. Additional TsOH.H$_2$O (599.26 mg, 3.48 mmol) and 1,2-dichloroethane (5.00 mL) was added thereto, and the mixture was stirred at 60° C. for 24 h. The reaction solution was diluted with dichloromethane (50 mL), washed with saturated NaHCO$_3$ solution (10 mL×4) and brine (30 mL), dried over anhydrous sodium sulfate, filtered and concentrated. The residue was purified by column chromatography to give the title compound (150.00 mg, yield of 30.65%).

The racemate was subjected to chiral separation (column: Chiralpak AD-3 150×4.6 mm I.D., 3 μm; mobile phase: 40% of iso-propanol (0.05% DEA) in CO$_2$; flow rate: 2.5 mL/min; column temperature: 35° C.) to give two components. Component 1 was purified by preparative HPLC ([wateR (0.1% TFA)-ACN]; B %: 25%-55%, 8 min) to give Example 119 (40.00 mg, yield of 19.60%, TFA salt; SFC retention time: 2.553 min); and component 2 was Example 120 (40.00 mg, yield of 26.67%, retention time: 6.267 min).

Example 119: $^1$H NMR (400 MHz, METHANOL-d4) δ=9.19 (s, 1H), 7.70 (d, J=5.3 Hz, 1H), 7.54 (s, 1H), 7.36 (d, J=5.3 Hz, 1H), 5.85 (s, 1H), 3.61 (d, J=2.8 Hz, 1H), 1.90 (br d, J=7.0 Hz, 1H), 1.86-1.74 (m, 2H), 1.70 (br d, J=12.3 Hz, 1H), 1.65-1.51 (m, 2H), 1.49-1.18 (m, 8H), 0.54 (s, 3H).

Example 120: $^1$H NMR (400 MHz, METHANOL-d4) δ=7.88 (s, 1H), 7.52 (d, J=5.0 Hz, 1H), 7.21 (d, J=5.0 Hz, 1H), 6.91 (s, 1H), 5.47 (s, 1H), 3.60 (d, J=2.3 Hz, 1H), 1.93-1.65 (m, 4H), 1.60-1.28 (m, 9H), 1.26-1.18 (m, 1H), 0.51 (s, 3H).

Examples 121 to 122: 1-cyclohexyl-2-methyl-2-(8H-thieno[3,4]pyrrolo[1,5-a]imidazol-8-yl)-propan-1-ol

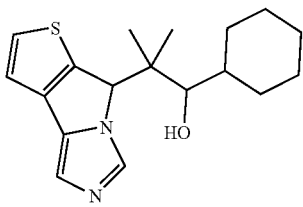 [SMILES: CC(C)(C(O)C1CCCCC1)C1c2sccc2-c2cncn21]

A racemate, obtained from tert-butyl-[1-cyclohexyl-3-imidazol-1-yl-3-(3-iodo-2-thienyl)-2,2-dimethyl-propoxy]-dimethyl-silane (isomer 2) (1.15 g, 2.06 mmol) according to the method in Example 119, was subjected to chiral separation (column: Chiralpak AS-3 150×4.6 mm I.D., 3 μm; mobile phase: A: CO$_2$ B: iso-propanol (0.05% DEA); gradient: from 5% to 40% of B in 5 min and hold 40% for 2.5 min, then 5% of B for 2.5 min; flow rate: 2.5 mL/min; column temperature: 35° C.), to give Example 121 (50.00 mg, yield of 24.88%, SFC retention time: 3.415 min); and component 2 was Example 122 (48.00 mg, yield of 23.21%, SFC retention time: 4.561 min).

Example 121: $^1$H NMR (400 MHz, METHANOL-d4) δ=7.89 (s, 1H), 7.52 (d, J=5.0 Hz, 1H), 7.23 (d, J=5.0 Hz, 1H), 6.89 (s, 1H), 5.48 (s, 1H), 3.47 (d, J=2.5 Hz, 1H), 1.96-1.54 (m, 6H), 1.47-1.29 (m, 5H), 1.16 (s, 3H), 0.55 (s, 3H).

Example 122: $^1$H NMR (400 MHz, METHANOL-d4) δ=9.05 (s, 1H), 7.70 (d, J=5.0 Hz, 1H), 7.52 (s, 1H), 7.39 (d, J=5.0 Hz, 1H), 5.81 (s, 1H), 1.97-1.87 (m, 1H), 1.86-1.74 (m, 2H), 1.73-1.55 (m, 3H), 1.48-1.15 (m, 9H), 0.68 (s, 3H).

Experimental Example 1: In Vitro hIDO1 Enzyme Activity Test

Experimental Objective

The change of NFK production was detected by using the NFK Green™ fluorescent molecule, which is the metabolite of the IDO1 enzyme, and the IC$_{50}$ value of the compound was used as an index, to evaluate the inhibitory effect of the compound on the recombinant human IDO1 enzyme.

Experimental Materials

IDO1 Enzyme Activity Assay Kit, NTRC # NTRC-hIDO-10K;
384-well enzyme reaction plate, PerkinElmer #6007279;
384-well plate for compounds, Greiner #781280;
Sealing film, PerkinElmer #6050185;
Envision Multimode Plate Reader, PerkinElmer;
Bravo automated liquid handling platform, Agilent.

Experiment Steps and Methods

1. Compound Loading:
The compound was diluted to 1 mM in DMSO, and then diluted 3-fold in duplicate wells, with 10 gradients. 48 μL of 50 mM phosphate buffer (pH 6.5) was transferred to the compound plate via Bravo automated liquid handling platform. 2 μL of the diluted solution of the compound in DMSO was then added and mixed, followed by transferring 10 μL therein to an enzyme reaction plate.

2. IDO1 Enzyme Activity Assay:
The IDO1 enzyme was diluted to 20 nM in the reaction buffer (50 mM phosphate buffer pH 6.5, 0.1% Tween-20, 2% glycerol, 20 mM ascorbic acid, 20 μg/mL catalase and 20 μM methylene blue), and 20 μL of the solution was transferred to an enzyme reaction plate and incubated at 23° C. for 30 min. The reaction was started by adding 10 μL of 400 μM L-type tryptophan substrate and incubated at 23° C. for 90 min. 10 μL of NFK Green™ fluorescent dye was added, and the plate was sealed with the sealing film, incubated at 37° C. for 4 h, and then read on Envision Multimode Plate Reader (Ex 400 nm/Em 510 nm).

3. Data Analysis:
The control wells with the IDO1 enzyme but no compound was set as 0% inhibition, and the control wells without the IDO1 enzyme was set as 100% inhibition, and the IC50 value of the compound was calculated by analyzing the data with XLFit 5.

Experimental Example 2: hIDO1 Cytological Activity Assay

Experimental Objective

The change of kynurenine in Hela cells was detected by the LC-MS method, and the IC50 value of the compound was used as an index, to evaluate the inhibitory effect of the compound on IDO1 enzyme.

Experimental Materials

Cell line: Hela cells;
Medium: RPMI 1640 phenol red free, Invitrogen #11835030
10% fetal bovine serum, Gibco #10099141
1× Penicillin-Streptomycin, Gibco #15140-122;
Precipitant: 4 µM L-kynurenine-d4, dissolved in 100% acetonitrile, CacheSyn #CSTK008002;
Trypsin, Invitrogen #25200-072;
DPBS, Hyclone #5H$_{30028.01}$B;
Recombinant human γ-interferon, Invitrogen #PHC4033;
5% (w/v) trichloroacetic acid, Alfa Aesar # A11156;
96-well cell plate, Corning #3357;
96-well plate for compounds, Greiner #781280;
96-well V-bottom plate, Axygen #WIPP02280;
$CO_2$ incubator, Thermo#371;
Centrifuge, Eppendorf #5810R;
Vi-cell cell counter, Beckman Coulter;
Labcyte FLIPR, Molecular Device.

Experiment Steps and Methods

1. Hela Cell Inoculation:
A medium, trypsin and DPBS were pre-heated in a 37° C. water bath. The medium for cell culture was sucked out and washed with 10 mL of DPBS; then the pre-heated trypsin was added into the culture flask, and the flask was rotated to allow the trypsin to uniformly cover it, and then placed in a 37° C., 5% $CO_2$ incubator and digested for 1-2 min; in each T150, cells were dispersed with 10-15 mL of medium, centrifuged at 800 rpm for 5 min, and then resuspended in 10 mL of medium; 1 mL of cell suspension was pipetted and the cells were counted with Vi-cell; Hela cells were diluted with medium to 5×10$^5$/mL, 80 µL of the solution was added to a 96-cell plate, and cultured at 37° C. for 5-6 h in a 5% $CO_2$ incubator.

2. Loading Compound:
The compound was diluted to 1 mM in DMSO, and then diluted 3-fold in duplicate wells, with 9 gradients. 5 µL of the diluted solution of the compound in DMSO was added to the compound plate containing 95 µL of the medium, and mixed, followed by transferring 10 µL of the mixture to a cell plate.

3. Cytological Activity Assay:
10 µL of recombinant human γ-interferon was added at a final concentration of 100 ng/mL to induce IDO1 expression. The cells were incubated at 37° C. for 20 h in a 5% $CO_2$ incubator. 4 µL of 5% (w/v) trichloroacetic acid was added thereto, mixed and incubated at 50° C. for 30 min. After centrifugation at 2400 rpm for 10 min, 40 µL of the supernatant was taken and placed in a 96-well V-bottom plate, and then a precipitant was added in the plate. After mixing, the mixture was centrifuged at 4000 rpm for 10 min. 100 µL of the supernatant was transferred to a new 96-well V-bottom plate. The content of kynurenine was determined by LC-MS.

4. Data Analysis:
The control wells having γ-interferon but no compound was set as 0% inhibition, and the control wells without Hela cell was set as 100% inhibition, and the $IC_{50}$ value of the compound was calculated by analyzing the data with XLFit 5.
The experimental results were shown in Table 1:

TABLE 1

$IC_{50}$ results of hIDO1 enzyme activity in vitro

| Tested samples (the title compounds) | hIDO1 Enzyme activity (nM) | Cytoactive (nM) |
|---|---|---|
| Example 1 | >10000 | — |
| Example 2 | >10000 | — |
| Example 3 | >10000 | — |
| Example 4 | 83.61 | 612.7 |
| Example 5 | 5026.17 | — |
| Example 6 | 9670.83 | — |
| Example 7 | 7.22 | 5.08 |
| Example 8 | 64.8 | — |
| Example 9 | 55 | 17.5 |
| Example 10 | >10000 | >5000 |
| Example 11 | 5982 | — |
| Example 12 | 106 | — |
| Example 13 | >10000 | — |
| Example 14 | 65.89 | 219.58 |
| Example 15 | 5221.45 | — |
| Example 16 | 71.01 | 910.74 |
| Example 17 | 338.16 | — |
| Example 18 | >10000 | — |
| Example 19 | >10000 | — |
| Example 20 | 586.02 | — |
| Example 21 | 9159.59 | — |
| Example 22 | 23.06 | 212 |
| Example 23 | 5263.39 | — |
| Example 24 | 1027.05 | — |
| Example 25 | 8119.7 | — |
| Example 26 | >10000 | — |
| Example 27 | 869.36 | — |
| Example 28 | >10000 | >5000 |
| Example 29 | 51.6 | 117 |
| Example 30 | >10000 | — |
| Example 31 | >10000 | — |
| Example 32 | 806.69 | — |
| Example 33 | >10000 | — |
| Example 34 | >10000 | — |
| Example 35 | 2811.3 | — |
| Example 36 | 2430.25 | — |
| Example 37 | 2404.08 | — |
| Example 38 | >10000 | — |
| Example 39 | 46 | 90.45 |
| Example 40 | >10000 | — |
| Example 41 | 48.05 | 74.93 |
| Example 42 | 253 | 779 |
| Example 43 | >10000 | — |
| Example 44 | >10000 | — |
| Example 45 | 3827 | — |
| Example 46 | 11.4 | 28 |
| Example 47 | 1676 | — |
| Example 48 | 518 | — |
| Example 49 | >10000 | — |
| Example 50 | >10000 | — |
| Example 51 | >10000 | — |
| Example 52 | 676 | — |
| Example 53 | 161 | 377 |
| Example 54 | >10000 | — |
| Example 55 | >10000 | — |
| Example 56 | 851.48 | — |
| Example 57 | 886.16 | — |
| Example 58 | 2100.66 | — |
| Example 59 | >10000 | — |
| Example 60 | >10000 | — |
| Example 61 | 1203.49 | — |
| Example 62 | 199.39 | 445.69 |
| Example 63 | 8799.61 | >5000 |
| Example 64 | >10000 | — |

TABLE 1-continued

IC$_{50}$ results of hIDO1 enzyme activity in vitro

| Tested samples (the title compounds) | hIDO1 Enzyme activity (nM) | Cytoactive (nM) |
|---|---|---|
| Example 65 | 5525.91 | — |
| Example 66 | >10000 | — |
| Example 67 | 161.77 | — |
| Example 68 | 1834.46 | — |
| Example 69 | 2322.4 | — |
| Example 70 | 1089.8 | — |
| Example 71 | >10000 | — |
| Example 72 | 99.88 | 222.67 |
| Example 73 | >10000 | >5000 |
| Example 74 | 256.9 | — |
| Example 75 | >10000 | — |
| Example 76 | 882.56 | — |
| Example 77 | 37.03 | 124.90 |
| Example 78 | >10000 | — |
| Example 79 | >10000 | — |
| Example 80 | 5045.31 | — |
| Example 81 | 8269.8 | — |
| Example 82 | 1550.99 | — |
| Example 83 | 1266.37 | — |
| Example 84 | 454.25 | — |
| Example 85 | 27.16 | 159.11 |
| Example 86 | 545.5 | — |
| Example 87 | >10000 | — |
| Example 88 | 477.63 | — |
| Example 89 | >10000 | — |
| Example 90 | >10000 | — |
| Example 91 | 6746.15 | — |
| Example 92 | 685.65 | — |
| Example 93 | >10000 | — |
| Example 94 | 1460.65 | — |
| Example 95 | >10000 | — |
| Example 96 | >10000 | — |
| Example 97 | >10000 | — |
| Example 98 | >10000 | — |
| Example 99 | >10000 | — |
| Example 100 | 6767.43 | — |
| Example 101 | >10000 | — |
| Example 102 | >10000 | — |
| Example 103 | >10000 | — |
| Example 104 | >10000 | — |
| Example 105 | | |
| Example 106 | | |
| Example 107 | 182.93 | — |
| Example 108 | >10000 | — |
| Example 109 | >10000 | — |
| Example 110 | >10000 | — |
| Example 111 | | |
| Example 112 | | |
| Example 113 | | |
| Example 114 | | |
| Example 115 | 3510.59 | — |
| Example 116 | >10000 | — |
| Example 117 | 215.11 | 891.04 |
| Example 118 | 7290.1 | — |
| Example 119 | 389.58 | 1975.26 |
| Example 120 | >10000 | — |
| Example 121 | 585.12 | — |
| Example 122 | >10000 | — |

Experimental Example 3: hIDO1 Efficacy Test In Vivo

Experimental Example 3A: Model Validation: LPS Induction Increased Kyn Level in Lung and Plasma of C57BL/6 Mice In the in vivo assay, chemical mediators that are able to induce inflammatory responses such as lipopolysaccharide (LPS) and interferon gamma (IFNg) were widely used to induce in vivo IDO1 expression. To verify this effect of LPS, this experiment was performed. Prior to the experiment, 60 mg/kg sodium pentobarbital was injected into the abdominal cavity of the animals for anesthetizing. Under deep anesthesia, 6 C57BL/6 mice (6-8 weeks, body weight of 18-20 g) were induced by intranasal administration (i.n.) of LPS (E. Coli O111: B4, Sigma-L2630). LPS was dissolved in PBS, and the dose is 25 μg/20 μL per animal. As a control, another 6 mice were received the same volume of PBS through the nasal cavity. Subsequently, the animals were housed as usual, and their plasma were collected at 25 h, 26 h, and 30 h after LPS/PBS induction, and the lung samples were collected at 26 h and 30 h (3 animals per a time point) and determined the kynurenine (Kyn) level. The determination of the Kyn level was performed by the LC/MS method using Shimadzu LCMS-8050 system.

The results of Experimental Example 3A were shown in FIG. 1. This experiment demonstrates that intranasal administration of O111:B4 E. coli-derived LPS can increase Kyn level in lung and plasma of C57BL/6 mice within 25-30 h after administration. Therefore, the LPS-induced C57BL/6 mouse model was an effective animal model for studying expression and activity of IDO1.

After induction by LPS, the Kyn level in lung and plasma of C57BL/6 mice were increased relative to the PBS-treated control group.

Experimental Example 3B

In Vivo Pharmacodynamics of IDO1: The Reduction of Kyn Level in Lung and Plasma of C57BL/6 Mice Induced by LPS Experimental Example 3A confirmed that the LPS-induced C57BL/6 mouse was an effective model for studying expression and activity of IDO1. In this model, the in vivo IDO1 inhibitory activities of Example 7 and the control compound (NLG919) were verified and compared. A total of three groups of C57BL/6 mice (6-8 weeks, body weight of 18-20 g) were induced by O111:B84 E. coli LPS at a dose of 25 μg/20 μL, 6 to 10 mice in each group. Each group received the following drug treatment at 0, 12 h, and 24 h after induction (administration volume was 5 mL/kg):

Group 1, 40% polyethylene glycol 400 (PEG400) aqueous solution orally as a solvent control;

Group 2, 50 mg/kg NLG919 orally, formulated in 40% PEG400 aqueous solution;

Group 3, 50 mg/kg WXFL10310138 orally, prepared in 40% PEG400 aqueous solution.

Plasma were collected at 1 h, 2 h, 4 h and 6 h after the end of the last administration, and lung samples were collected at 2 h and 6 h (3 to 5 animals per a time point) and determined the Kyn level by the LC/MS method.

Figure 2:
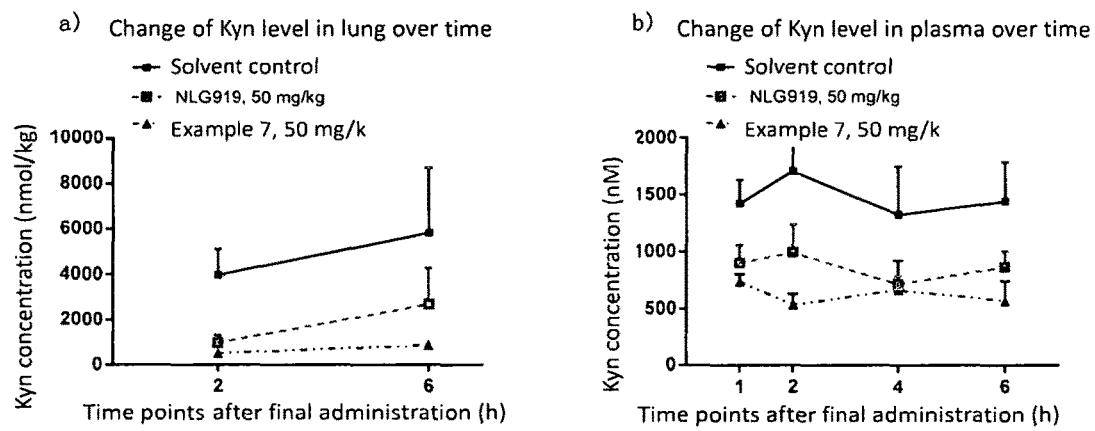
FIG. 2 shows experimental results of experimental Example 3B, and compared to NLG919, Example 7 significantly reduced the Kyn level in lung and plasma of LPS-induced C57BL/6 mice.

The experimental results were shown in FIG. 2, and in vivo pharmacodynamic experiments by using the LPS-induced mouse model showed that both Example 7 and NLG919 effectively inhibited in vivo activity of IDO1 and caused reduction of the Kyn level in lung and plasma. In addition, the degree of Kyn level reduction caused by Example 7 was more significant than that of NLG919.

Compared to NLG919, Example 7 significantly reduced Kyn level in lung and plasma of LPS-induced C57BL/6 mice, and the compounds of the present invention have significant inhibition of IDO1 receptors.

What is claimed is:

1. A compound of formula I:

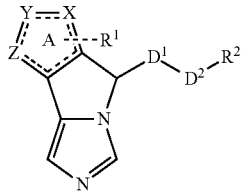

wherein,
ring A is a heteroaromatic ring, X, Y, and Z are each independently selected from C, O, N, or S atoms, and X, Y, Z are not C atoms at the same time, and ring A may be optionally substituted with 1 or 2 $R^1$ groups;

$D^1$ is $(CR^{A1}R^{B1})_p$;

$D^2$ is $(CR^{A2}R^{B2})_q$, $NR^3$, O, S, SO, $SO_2$, C(O), OC(O), C(O)O, $NR^3C(O)$, $C(O)NR^3$, $NR^3SO_2$, $SO_2NR^3$, $NR^3C(O)NR^4$ or $NR^3SO_2NR^4$;

$R^2$ is selected from H, OH, $NR^3R^4$, halogen, halogenated $C_{1-6}$ alkyl, hydroxy $C_{1-6}$ alkyl, $C_{1-6}$ alkyl, $C_{1-6}$ heteroalkyl, or 3- to 12-membered saturated, partially saturated or aromatic mono-, bi-, or tri-cyclic ring, wherein the ring group may optionally contain 1, 2 or 3 heteroatoms selected from O, N, or S, and the ring may be optionally substituted with 1, 2 or 3 R groups;

each of $R^1$ may be independently selected from OH, $NR^3R^4$, halogen, CN, COOH, halogenated $C_{1-6}$ alkyl, $C_{1-6}$ alkyl, $C_{2-6}$ alkenyl, $C_{2-6}$ alkynyl, $C_{1-6}$ heteroalkyl, $C_{3-6}$ cycloalkyl, halogenated $C_{3-6}$ cycloalkyl, phenyl, halogenated phenyl, 5- to 6-membered heteroaryl, or halogenated 5- to 6-membered heteroaryl;

each of R is independently selected from OH, $NR^3R^4$, halogen, oxo, CN, COOH, $C_{1-4}$ alkyl, $C_{2-4}$ alkenyl, $C_{2-4}$ alkynyl, or 6- to 12-membered aryl; said $C_{1-4}$ alkyl, $C_{2-4}$ alkenyl, $C_{2-4}$ alkynyl, or 6- to 12-membered aryl may be optionally substituted with 1 or 2 OH groups, halogen groups, $NH_2$ groups, CN groups, or COOH groups;

$R^3$ and $R^4$ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynl, $C_{1-6}$ heteroalkyl, halogenated $C_{1-6}$ heteroalkyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl;

$R^{A1}$, $R^{B1}$, $R^{A2}$, and $R^{B2}$ are each independently selected from H, OH, $NH_2$, halogen, halogenated $C_{1-3}$ alkyl, or $C_{1-4}$ alkyl;

p is 0, 1 or 2,
q is 0 or 1,
or a pharmaceutically acceptable salt thereof.

2. The compound or the pharmaceutically acceptable salt thereof according to claim 1, wherein ring A is a heteroaromatic ring, which may be optionally substituted with 1 or 2 $R^1$ groups; wherein:

Y and Z are selected from C, and X is selected from S; or
X and Y are selected from C, and Z is selected from S; or
X and Z are selected from C, and Y is selected from S; or
X and Y are selected from C, and Z is selected from O; or
X and Z are selected from C, and Y is selected from O; or
Y and Z are selected from C, and X is selected from O; or X and Y are selected from C, and Z is selected from N; or
X and Z are selected from C, and Y is selected from N; or
Y and Z are selected from C, and X is selected from N; or
X and Y are selected from N, and Z is selected from C; or
X and Z are selected from N, and Y is selected from C; or
Y and Z are selected from N, and X is selected from C; or
X, Y and Z are each selected from N; or
X is selected from C, Y is selected from N, and Z is selected from O; or
X is selected from C, Y is selected from O, and Z is selected from N; or
X is selected from N, Y is selected from C, and Z is selected from O; or
X is selected from N, Y is selected from O, and Z is selected from C; or
X is selected from O, Y is selected from N, and Z is selected from C; or
X is selected from O, Y is selected from C, and Z is selected from N; or
X is selected from C, Y is selected from N, and Z is selected from S; or
X is selected from C, Y is selected from S, and Z is selected from N; or
X is selected from N, Y is selected from C, and Z is selected from S; or
X is selected from N, Y is selected from S, and Z is selected from C; or
X is selected from S, Y is selected from N, and Z is selected from C; or
X is selected from S, Y is selected from C, and Z is selected from N.

3. The compound or the pharmaceutically acceptable salt thereof according to claim 1, wherein the compound has Formula II:

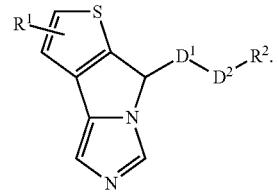

4. The compound or the pharmaceutically acceptable salt thereof according to claim 1, wherein each of R is independently selected from OH, $NR^3R^4$, halogen, oxo, CN, COOH, $C_{1-4}$ alkyl, $C_{2-4}$ alkenyl, $C_{2-4}$ alkynyl or 6- to 12-membered aryl; and said $C_{1-4}$ alkyl, $C_{2-4}$ alkenyl, $C_{2-4}$ alkynyl or 6- to 12-membered aryl may be optionally substituted with 1 or 2 OH groups, halogen groups, $NH_2$ groups, CN groups or COOH groups.

5. The compound or the pharmaceutically acceptable salt thereof according to claim 1, wherein $D^1$ is a single bond or $(CR^{A1}R^{B1})$.

6. The compound or the pharmaceutically acceptable salt thereof according to claim 1, wherein $D^2$ is a single bond, $-(CR^{A2}R^{B2})-$, $NR_3$, O, S, SO, $SO_2$ or C(O).

7. The compound or the pharmaceutically acceptable salt thereof according to claim 1, wherein $-D^1-D^2-$ is a single bond, $-(CHR^{A1})-$, $-(CR^{A1}R^{B1})-(CHR^{A2})-$, $-(CHR^{A1})-(CHR^{A2})$ or $-(CHR^{A1})-O-$.

8. The compound or the pharmaceutically acceptable salt thereof according to claim 1, wherein $R^2$ is selected from H; OH; methyl; ethyl; propyl; isopropyl; butyl; isobutyl; sec-butyl; tert-butyl; n-pentyl; isopentyl; neopentyl; adamantyl; cyclopropyl; cyclobutyl; cyclopentyl; cyclohexyl; cycloheptyl; cyclooctyl; or

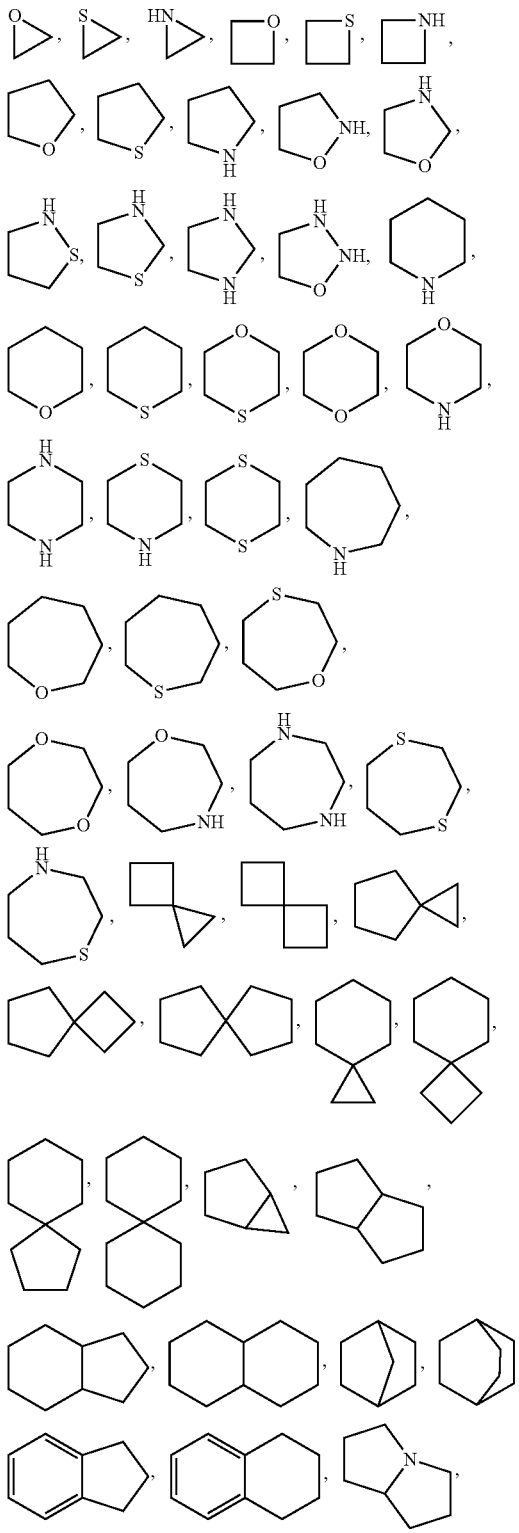

-continued

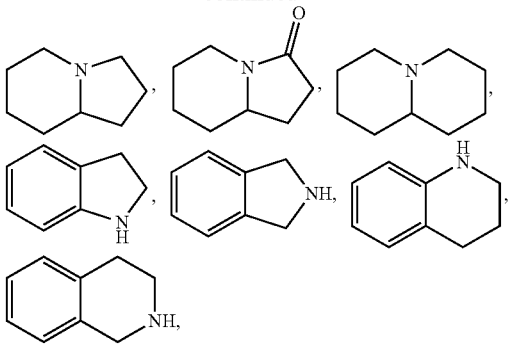

with a loss of one hydrogen atom at any position, wherein said rings may be optionally substituted with 1, 2 or 3 R groups.

9. The compound or the pharmaceutically acceptable salt thereof according to claim 1, wherein $R^1$ is independently selected from halogen, halogenated $C_{1-6}$ alkyl, $C_{1-6}$ alkyl, $C_{3-6}$ cycloalkyl, halogenated $C_{3-6}$ cycloalkyl, phenyl or halogenated phenyl.

10. The compound or the pharmaceutically acceptable salt thereof according to claim 1, wherein R is independently selected from OH, fluorine, chlorine, bromine, iodine, oxo, COOH, methyl, ethyl, propyl, isopropyl, butyl, isobutyl, sec-butyl, tert-butyl, phenyl or quinolyl, wherein methyl, ethyl, propyl, isopropyl, butyl, isobutyl, sec-butyl, tert-butyl, phenyl or quinolyl may be optionally substituted with OH.

11. The compound or the pharmaceutically acceptable salt thereof according to claim 1, wherein $R^3$ and $R^4$ are each independently selected from H, $C_{1-6}$ alkyl, halogenated $C_{1-6}$ alkyl, $C_{2-6}$ alkenyl, halogenated $C_{2-6}$ alkenyl, $C_{2-6}$ alkynyl, halogenated $C_{2-6}$ alkynyl, $C_{3-6}$ cycloalkyl, halogenated $C_{3-6}$ cycloalkyl, phenyl, halogenated phenyl, 5- to 6-membered heteroaryl or halogenated 5- to 6-membered heteroaryl.

12. The compound or the pharmaceutically acceptable salt thereof according to claim 1, wherein $R^{A1}$, $R^{B1}$, $R^{A2}$ and $R^{B2}$ are each independently selected from H, OH, $NH_2$, halogen, or $C_{1-4}$ alkyl.

13. The compound or the pharmaceutically acceptable salt thereof according to claim 1, wherein $R^{A2}$ and $R^{B2}$ are each independently selected from H, OH, $NH_2$ or $C_{1-4}$ alkyl.

14. The compound or the pharmaceutically acceptable salt thereof according to claim 1, selected from any one of the following compounds or the pharmaceutically acceptable salt thereof:

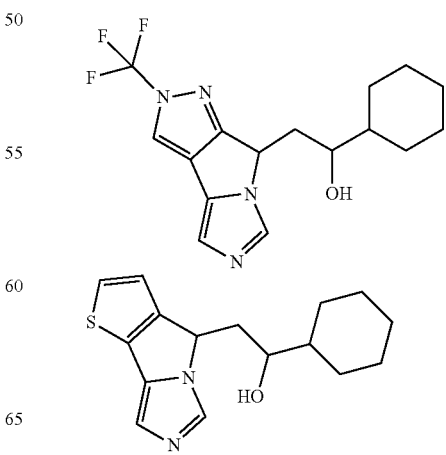

211
-continued
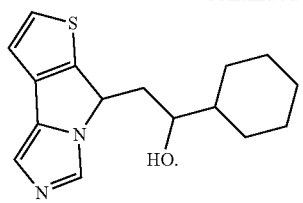
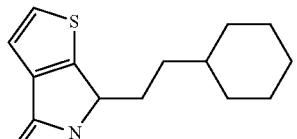
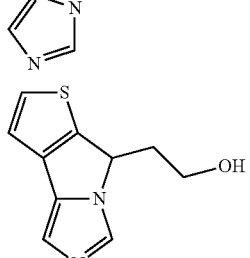
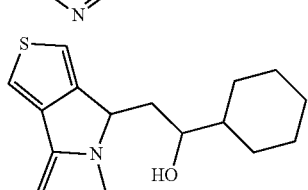
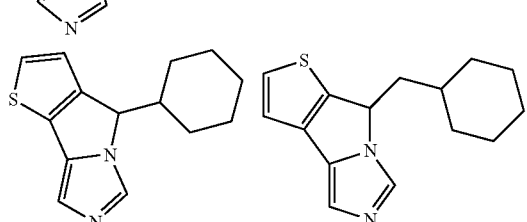
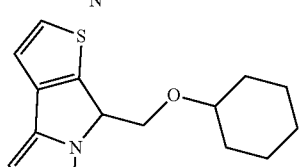
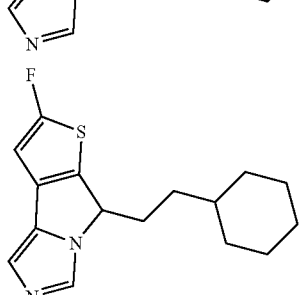
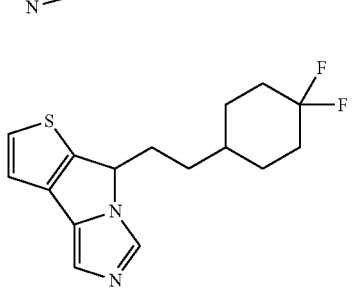
212
-continued
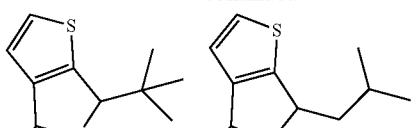
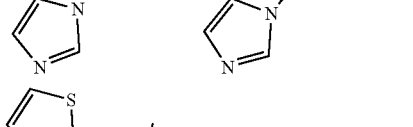
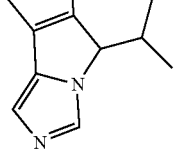
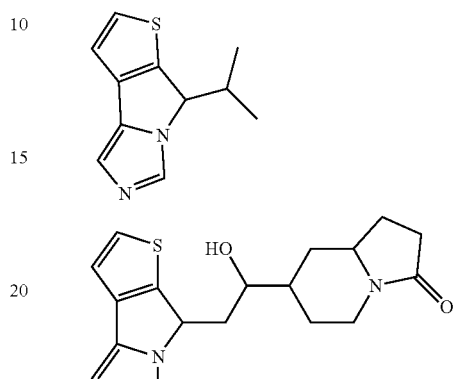
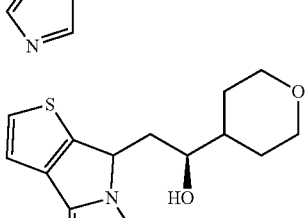
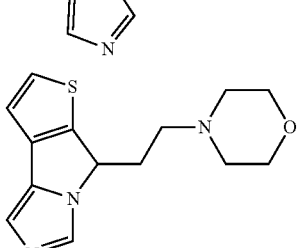
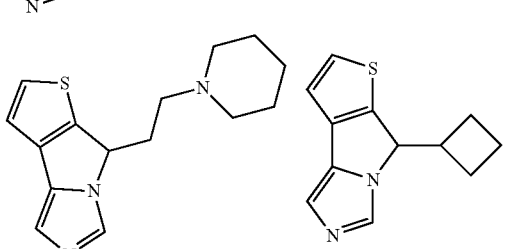
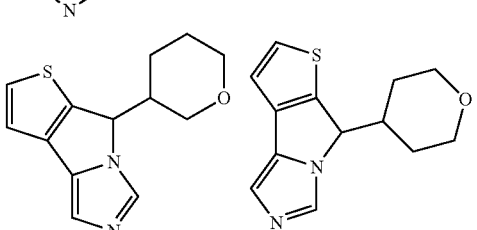
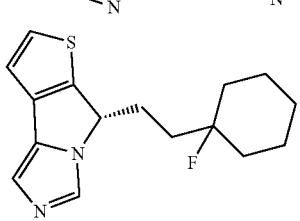

213
-continued
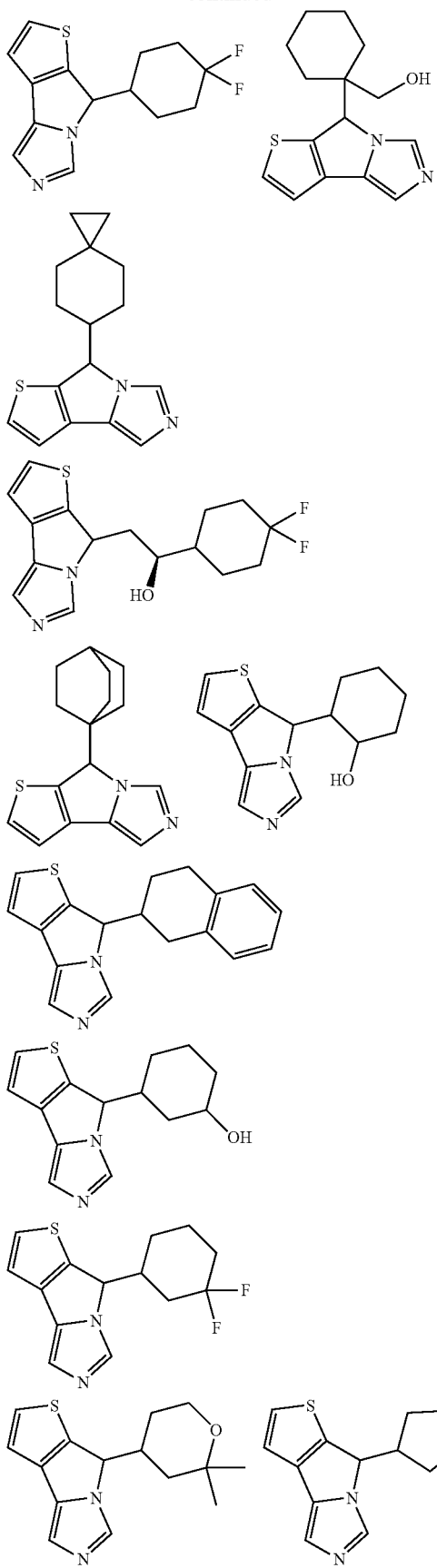
214
-continued
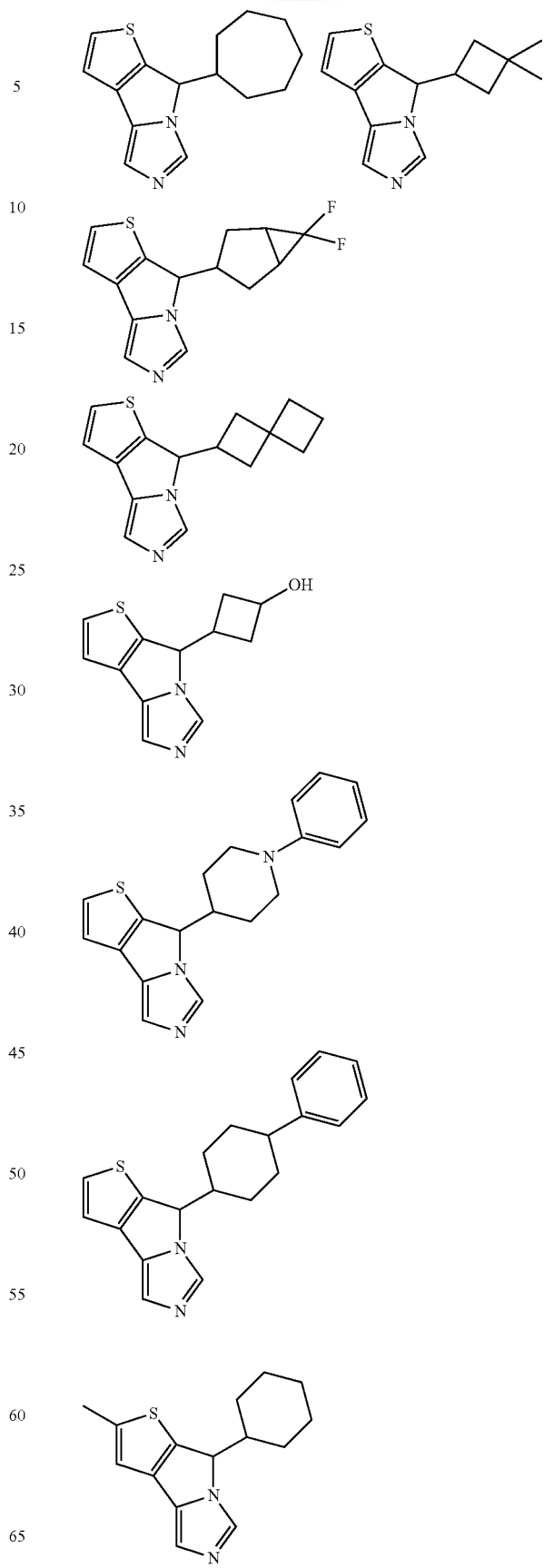

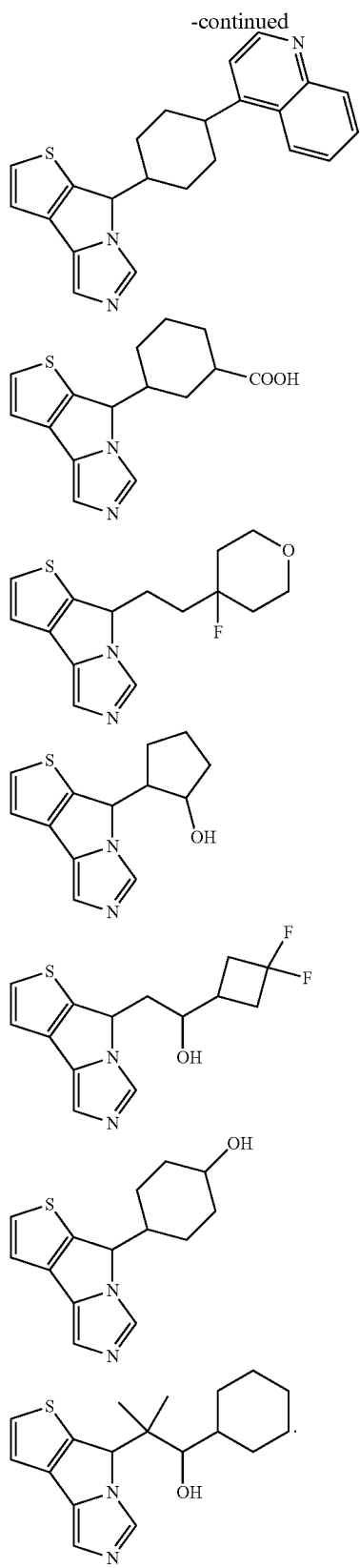
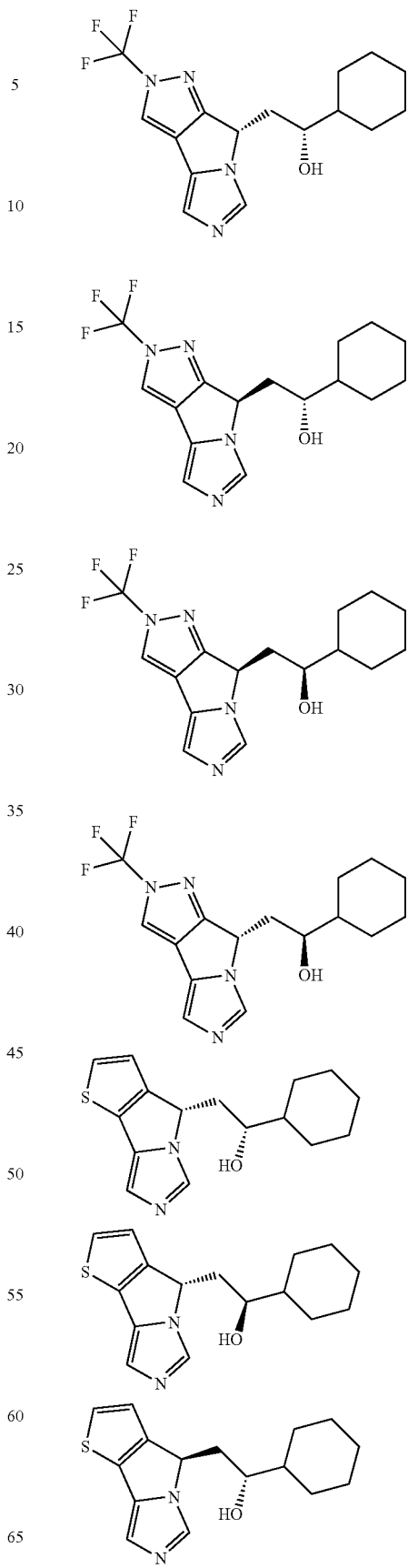
15. The compound or the pharmaceutically acceptable salt thereof according to claim 1, selected from any one of the following compounds or the pharmaceutically acceptable salt thereof:

217
-continued
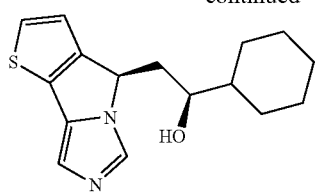
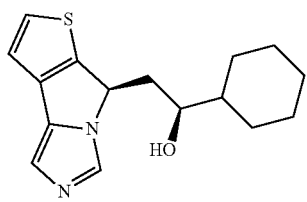
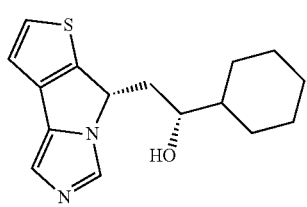
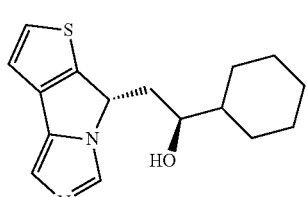
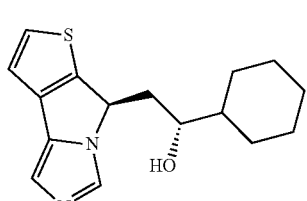
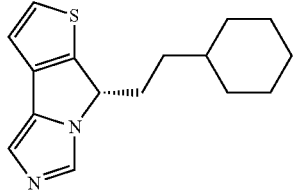
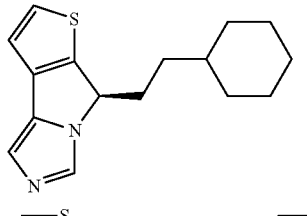
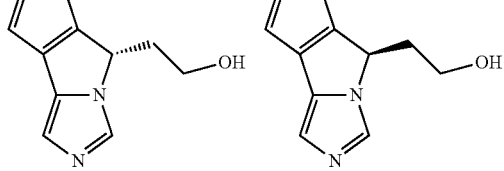
218
-continued
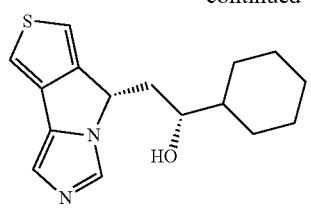
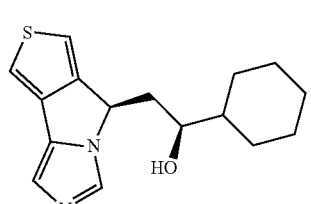
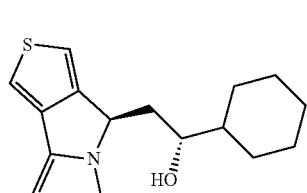
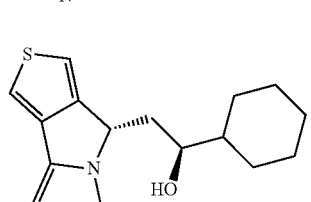
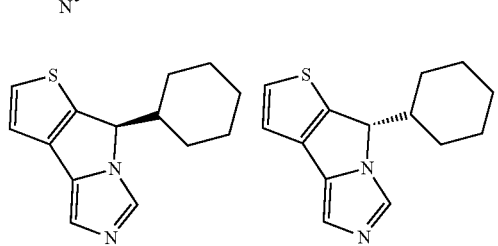
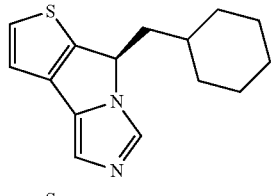
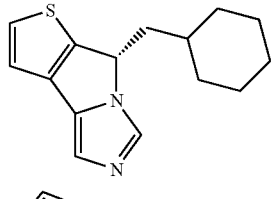
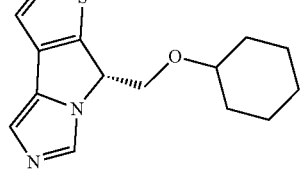

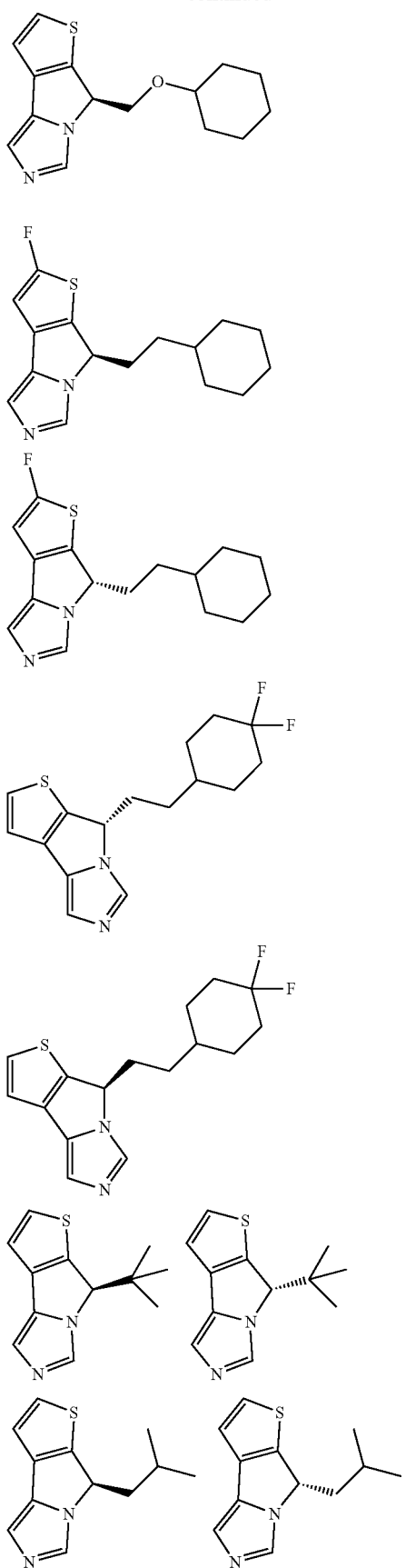
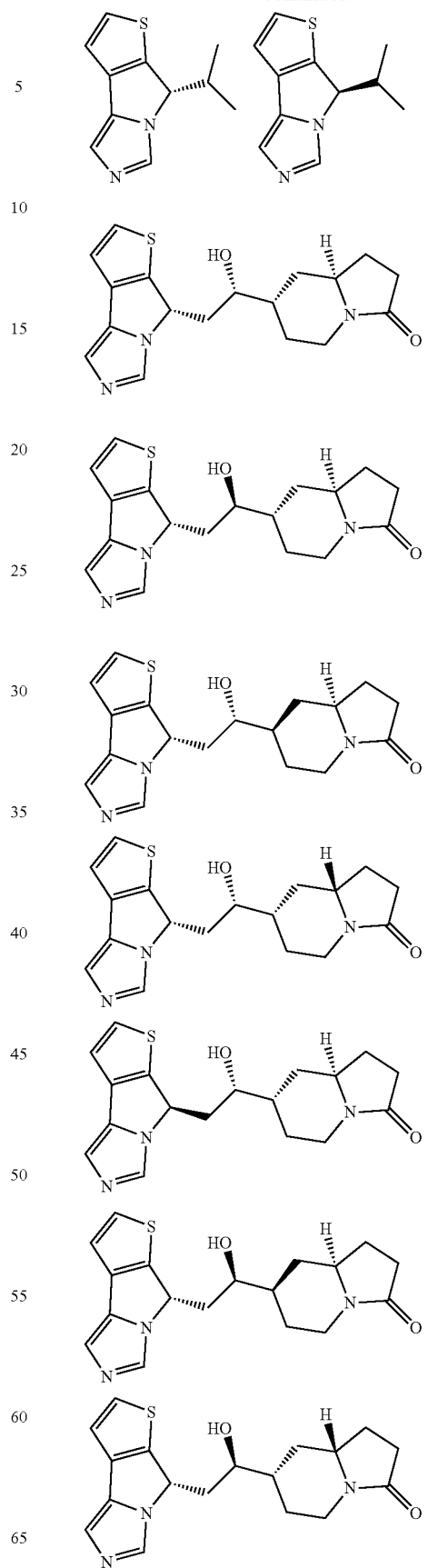

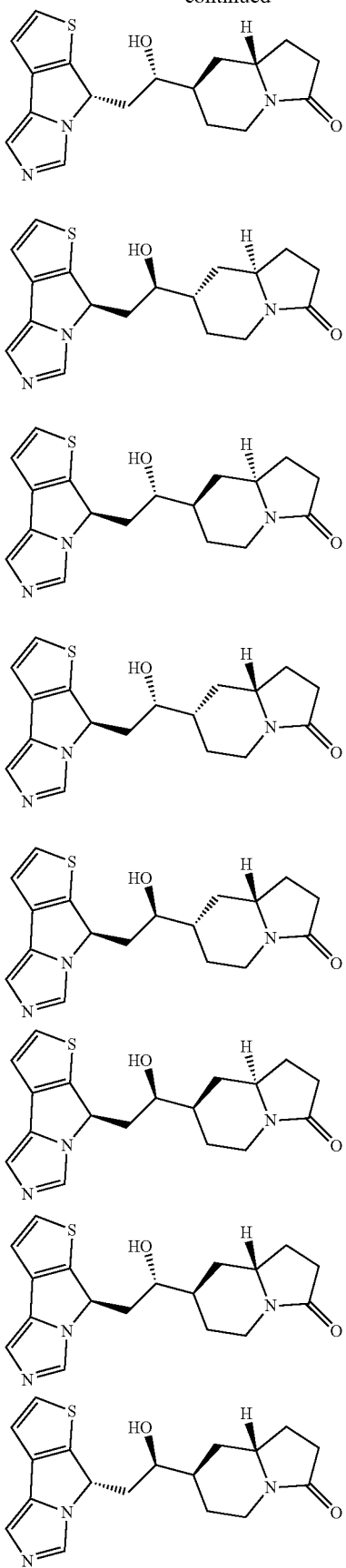
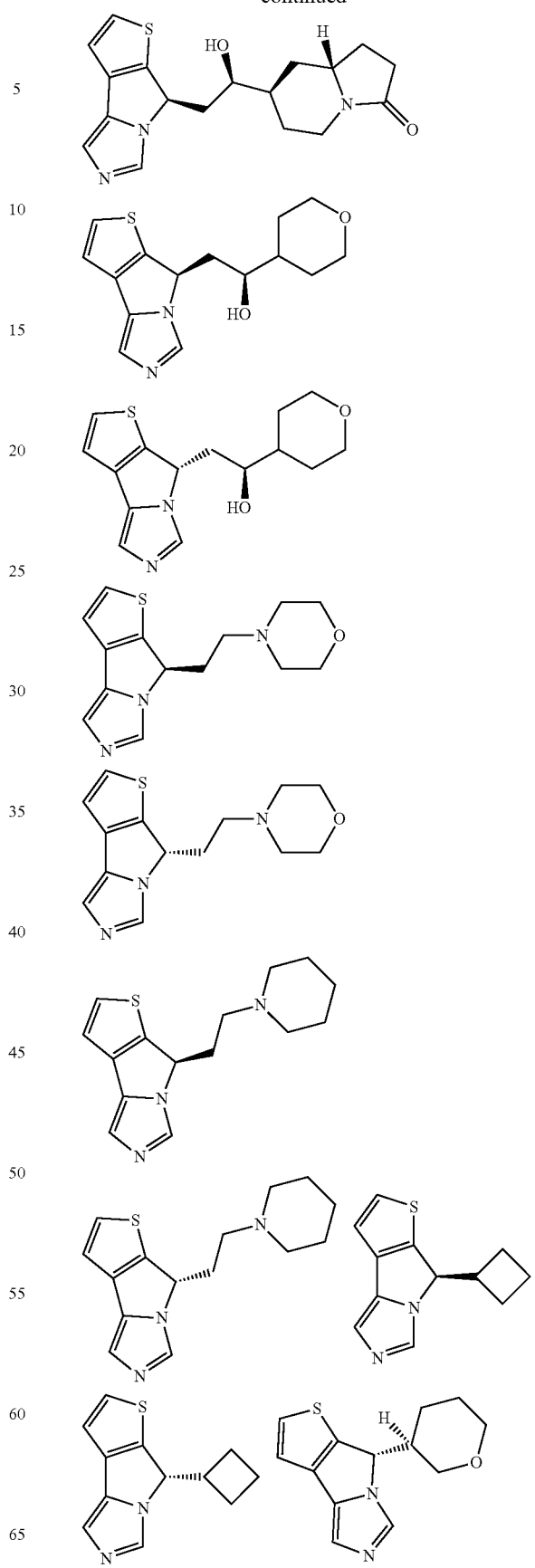

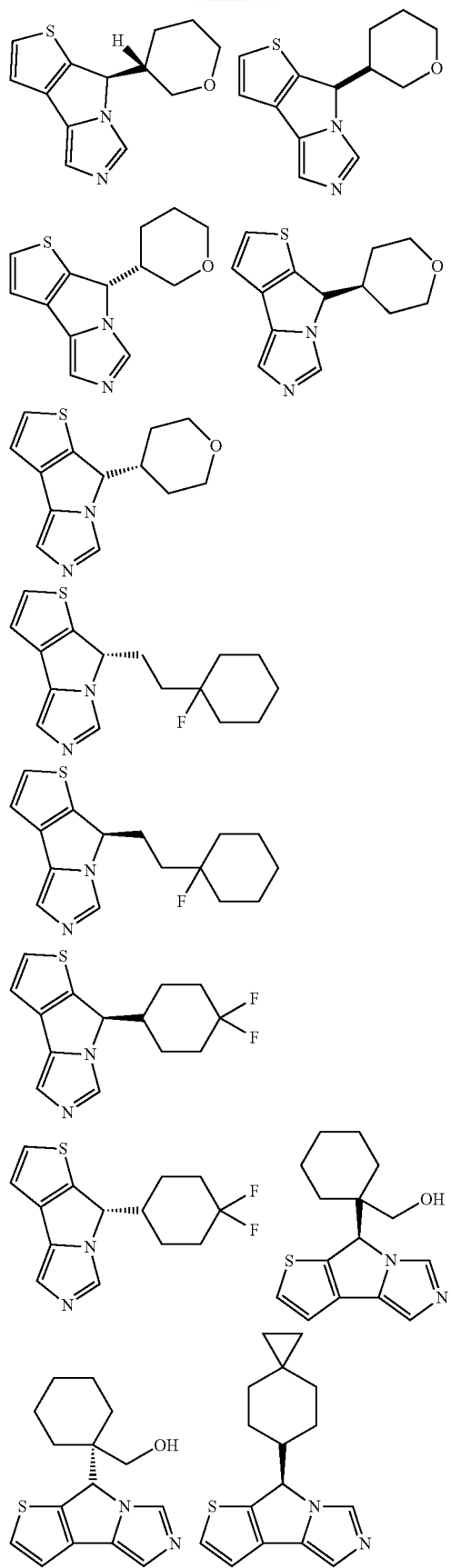
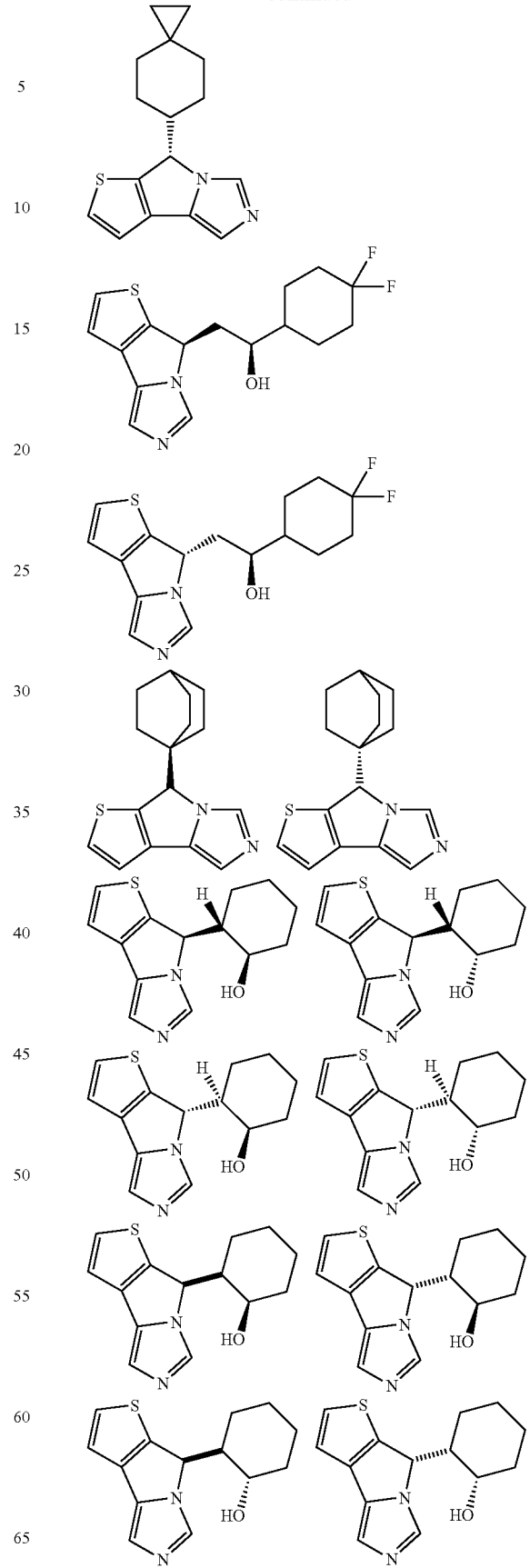

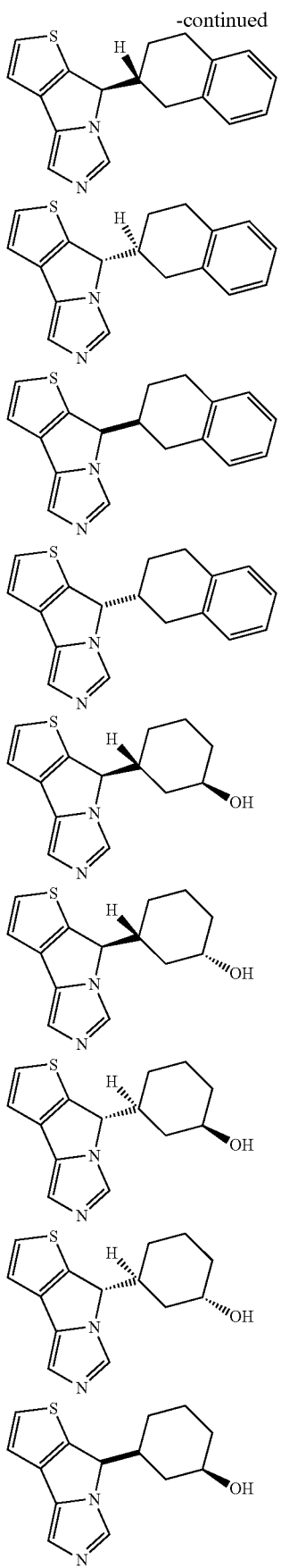
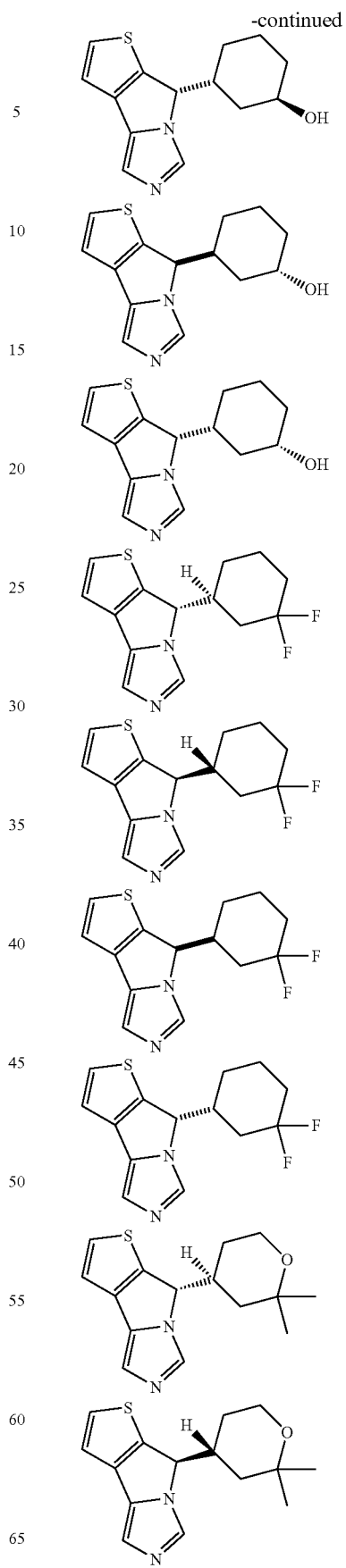

227
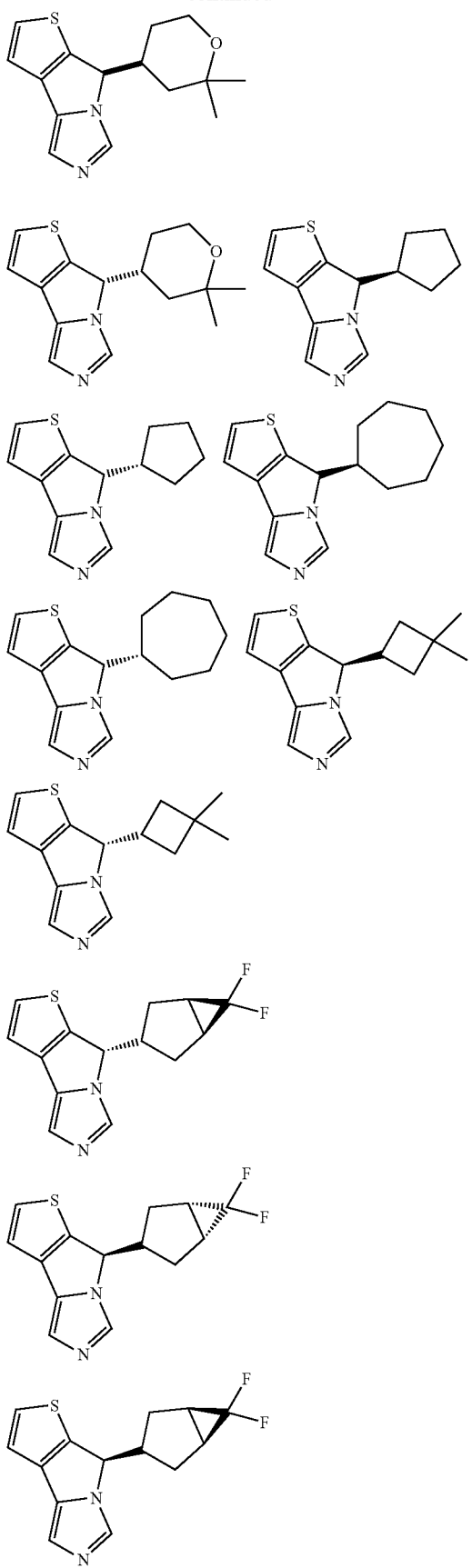
228
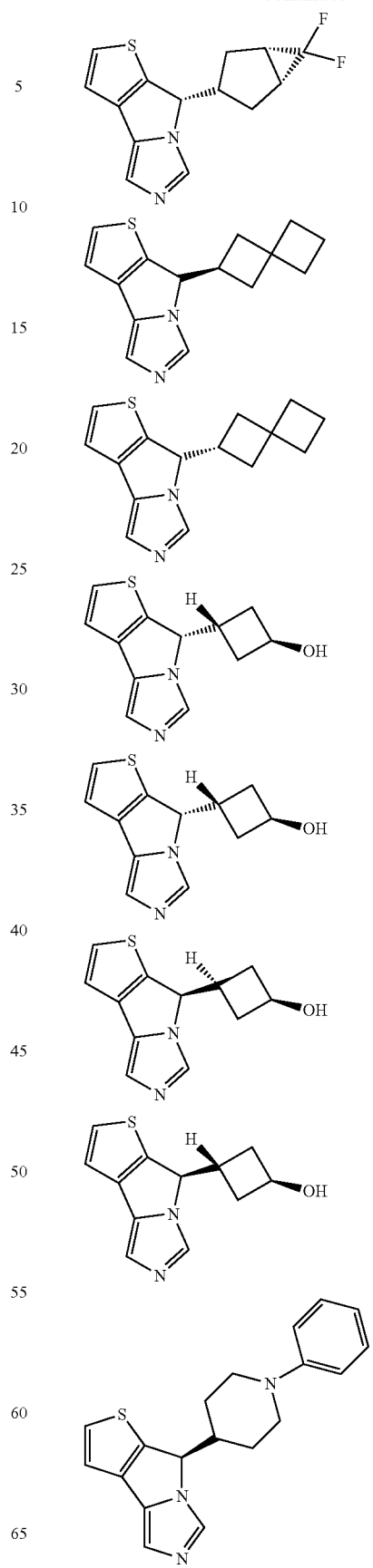

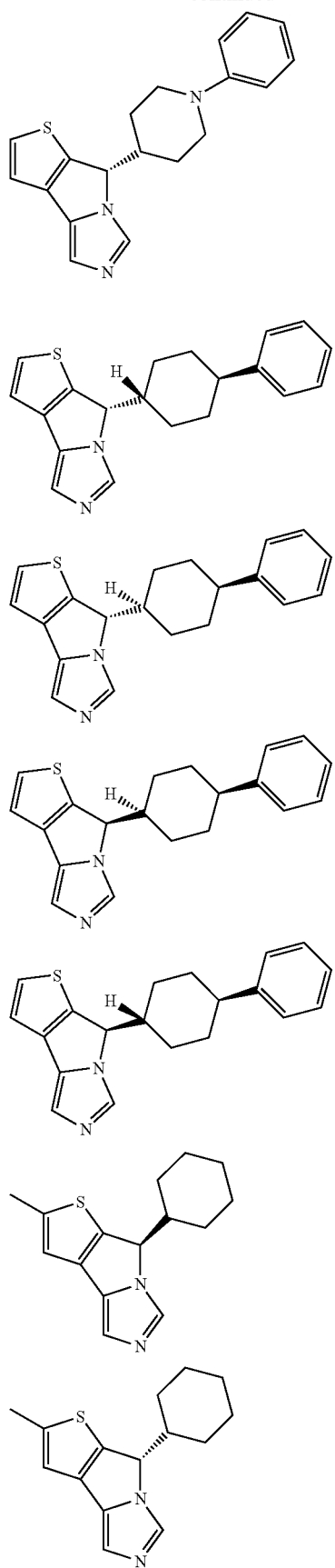
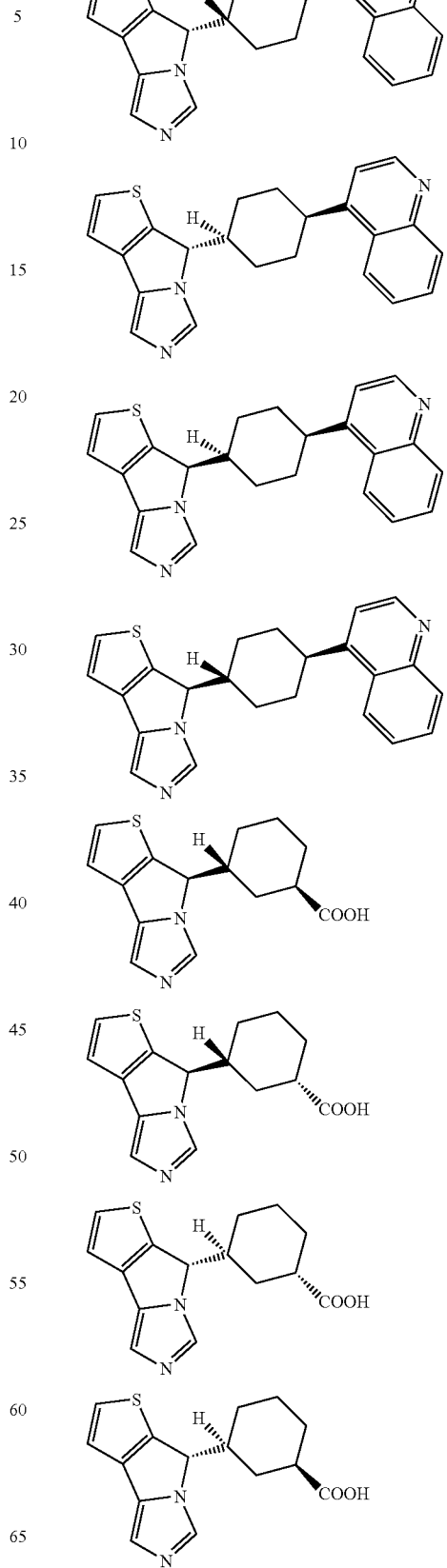

231
-continued
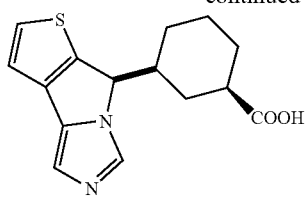
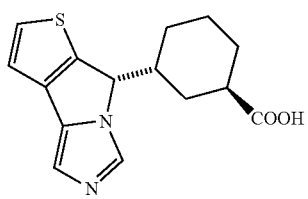
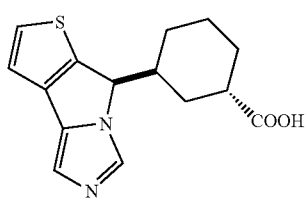
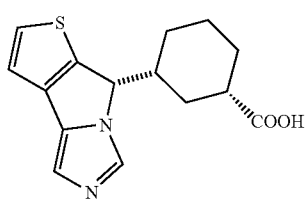
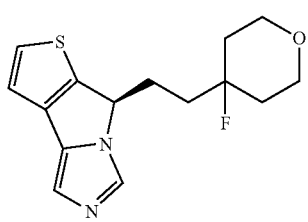
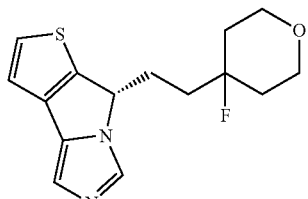
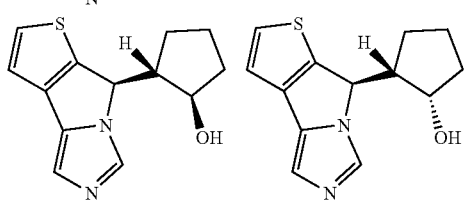
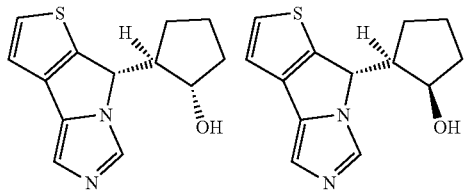
232
-continued
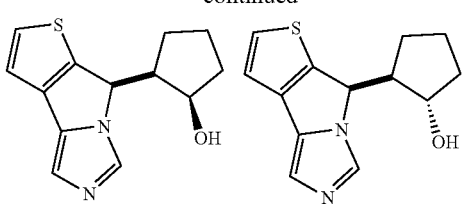
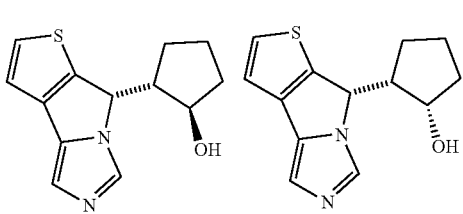
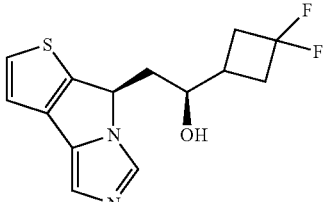
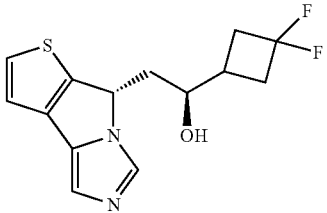
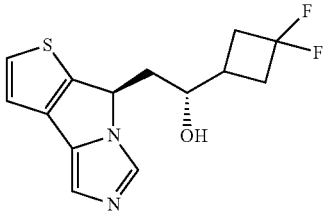
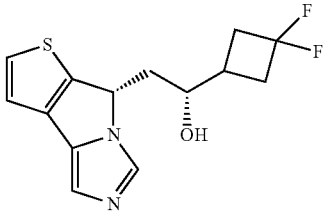
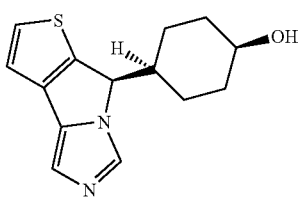
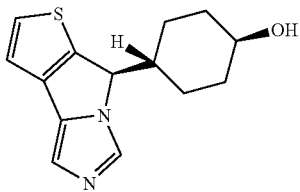

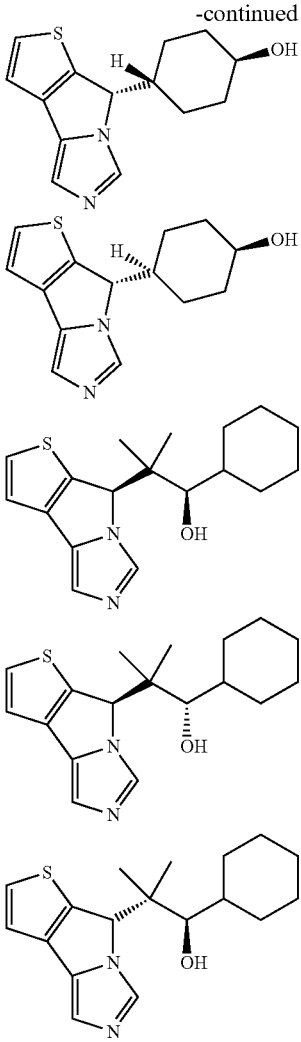

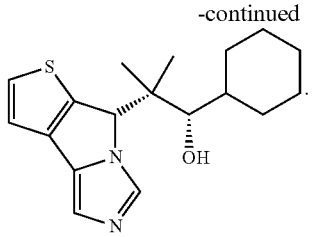

16. A pharmaceutical composition comprising a compound according to claim 1, or a pharmaceutically acceptable salt thereof, and one or more pharmaceutically acceptable carriers or excipients.

17. A method for inhibiting an immunosuppressive disease mediated by indol 2,3-dioxygenase (IDO), comprising administering a compound according to claim 1 or a pharmaceutically acceptable salt.

18. The method according to claim 17, wherein the immunosuppressive disease is associated with an infectious disease or cancer.

19. The method according to claim 17, wherein the infectious disease is selected from the following influenza, hepatitis C virus (HCV), human papilloma virus (HPV), cytomegalovirus (CMV), poliovirus, herpes zoster virus, human immunodeficiency virus (HIV), epstein-barr virus (EBV) or coxsackie virus; and wherein the cancer is selected from colon cancer, pancreatic cancer, breast cancer, prostate cancer, lung cancer, brain cancer, ovarian cancer, cervical cancer, testicular cancer, kidney cancer, head or neck cancer, lymphoma, leukemia or melanoma.

* * * * *

UNITED STATES PATENT AND TRADEMARK OFFICE
CERTIFICATE OF CORRECTION

PATENT NO. : 10,487,088 B2
APPLICATION NO. : 15/999075
DATED : November 26, 2019
INVENTOR(S) : Shilan Liu Page 1 of 1

It is certified that error appears in the above-identified patent and that said Letters Patent is hereby corrected as shown below:

On the Title Page

Column 1, Item (73), Line 2, under Assignees, delete "Beijing" and insert --Jiangsu--.

In the Claims

In Column 207, Line 46, Claim 1, delete "alkynl," and insert --alkynyl,--.

In Column 207, Line 54, Claim 1, delete "I or 2," and insert --1 or 2,--.

In Column 209, Lines 15-20, Claim 8, delete " " and insert -- 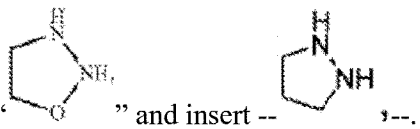 ,--.

In Column 211, Lines 1-10, Claim 14, delete

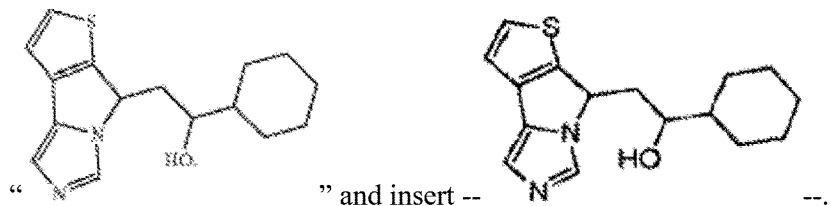

" " and insert -- --.

In Column 234, Lines 31 (Approx.), Claim 19, delete "immunodcficicncy" and insert --immunodeficiency--.

Signed and Sealed this
Nineteenth Day of May, 2020

Andrei Iancu
*Director of the United States Patent and Trademark Office*